United States Patent
Jamieson et al.

(10) Patent No.: US 9,611,330 B2
(45) Date of Patent: Apr. 4, 2017

(54) COMPOSITIONS AND METHODS FOR CANCER AND CANCER STEM CELL DETECTION AND ELIMINATION

(75) Inventors: Catriona H. Jamieson, La Jolla, CA (US); Qingfei Jiang, San Diego, CA (US); Kelly A. Frazer, San Diego, CA (US); Christian L. Barrett, San Diego, CA (US); Anil Sadarangani, La Jolla, CA (US); Angela Court, San Diego, CA (US); Leslie Crews Robertson, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 245 days.

(21) Appl. No.: 14/342,384

(22) PCT Filed: Sep. 7, 2012

(86) PCT No.: PCT/US2012/054307
§ 371 (c)(1),
(2), (4) Date: Jun. 27, 2014

(87) PCT Pub. No.: WO2013/036867
PCT Pub. Date: Mar. 14, 2013

(65) Prior Publication Data
US 2014/0302059 A1    Oct. 9, 2014

Related U.S. Application Data

(60) Provisional application No. 61/532,417, filed on Sep. 8, 2011, provisional application No. 61/537,185, filed on (Continued)

(51) Int. Cl.
*A61K 48/00* (2006.01)
*C12N 15/11* (2006.01)
(Continued)

(52) U.S. Cl.
CPC ............ *C07K 16/40* (2013.01); *A61K 31/713* (2013.01); *A61K 31/7105* (2013.01); *C07K 2/00* (2013.01);
(Continued)

(58) Field of Classification Search
USPC ....................................... 514/44, 2
See application file for complete search history.

(56) References Cited

U.S. PATENT DOCUMENTS

2003/0105041 A1 * 6/2003 Bennett ................ C12N 15/113
514/44 A
2007/0009530 A1    1/2007 Altaba et al.
(Continued)

OTHER PUBLICATIONS

Hartwig et al. The large form of ADAR 1 is responsible for enhanced hepatitis delta virus RNA editing in interferon-alpha-stimulated host cells. J Viral Hepatitis 13(3): 150-157, 2006.*
(Continued)

*Primary Examiner* — Terra C Gibbs
(74) *Attorney, Agent, or Firm* — Greer, Burns & Crain, Ltd.; Gregory P. Einhorn

(57) ABSTRACT

In alternative embodiments, the invention provides compositions and methods for inhibiting or ablating cancer stem cells. In alternative embodiments, the invention provides compositions and methods for inhibiting the action of double-stranded RNA-specific adenosine deaminases, or ADAR, enzymes. In alternative embodiments, the invention provides compositions and methods for treating, ameliorating or preventing diseases and conditions responsive to the inhibition of cell differentiation and/or self-renewal of dysfunctional cells, cancer cells, leukemia cells, hematopoietic stem cells or cancer stem cells, e.g., leukemia or Chronic Myeloid Leukemia (CML). In alternative embodiments, the invention provides compositions and methods for inhibiting a Sonic Hedgehog (Shh) pathway, e.g., by using a Smooth-
(Continued)

ened (SMO) protein inhibitor. In alternative embodiments, the invention provides compositions and methods for measuring or determining, or predicting, chronic myelogenous leukemia (CML) progression, Leukemic Stem Cell (LSC) generation and/or tyrosine kinase inhibitor resistance. In alternative embodiments, the invention provides compositions and methods for determining or measuring the effectiveness of a treatment, a drug, a therapy or a diet for eliminating, killing or reducing the amounts of a leukemic stem cell (LSC) or cells.

20 Claims, 25 Drawing Sheets

Related U.S. Application Data on Sep. 21, 2011, provisional application No. 61/537,161, filed on Sep. 21, 2011, provisional application No. 61/537,157, filed on Sep. 21, 2011.

(51) Int. Cl.
*C07H 21/02* (2006.01)
*C07H 21/04* (2006.01)
*C07K 16/40* (2006.01)
*A61K 31/7105* (2006.01)
*A61K 31/713* (2006.01)
*G01N 33/574* (2006.01)
*C12N 9/80* (2006.01)
*C07K 2/00* (2006.01)
*C12N 15/113* (2010.01)
*A61K 38/00* (2006.01)

(52) U.S. Cl.
CPC ............ *C12N 9/80* (2013.01); *C12N 15/1137* (2013.01); *C12Y 305/04004* (2013.01); *G01N 33/57426* (2013.01); *G01N 33/57484* (2013.01); *A61K 38/00* (2013.01); *G01N 2333/4703* (2013.01); *G01N 2800/52* (2013.01)

(56) References Cited

U.S. PATENT DOCUMENTS

2007/0059311 A1  3/2007  Xie
2011/0059448 A1  3/2011  Jamieson et al.

OTHER PUBLICATIONS

Casey et al. (Journal of Virology, 2002 vol. 76:12399-12404).*
Jiang et al. (PNAS, 2013 vol. 110:1041-1046).*
Lingfei Bai, International Preliminary Report on Patentability, PCT/US2012/054307, The International Bureau of WIPO, Date of Mailing: Mar. 20, 2014.
Choi, Sung Hee, International Search Report and Written Opinion, Korean Patent Office, PCT/US2012/054307, Date Mailed: Mar. 11, 2013.
Hartner et al., "ADAR1 is essential for maintenance of hematopoiesis and suppression of interferon signaling", Nat Immunol., Jan. 2009, 10(1): 109-115.
Kikuchi, M. et al., "High Ki67, Bax, and thymidylate synthase expression well correlates with response to chemoradiation therapy in locally advanced rectal cancers: proposal of a logistic model for prediction", British Journal of Cancer, 2009, vol. 101, pp. 116-123.
O'Toole, S.A. et al., "Hedgehog overexpression is associated with stromal interactions and predicts for poor outcome in breast cancer", Cancer Research, Jun. 1, 2011, vol. 71, No. 11, pp. 4002-4014.
Xufeng et al., "ADAR1 is required for hematopoietic progenitor cell survival via RNA editing", PNAS, Oct. 20, 2009, vol. 106, No. 42, pp. 17763-17768.

* cited by examiner

CML
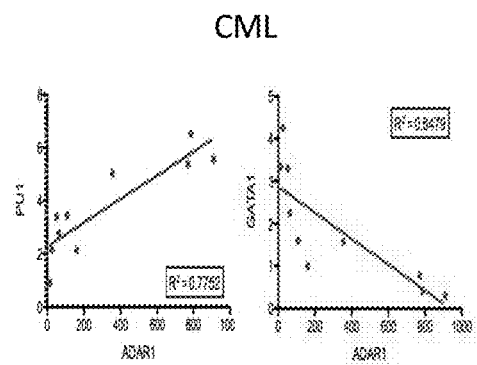
ADAR1 Transduced Cord
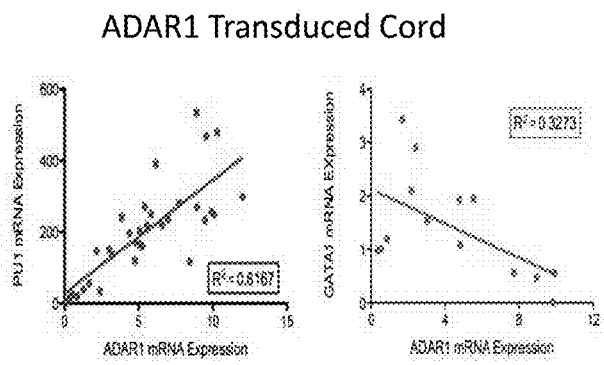
FIG. 7A
FIG. 7B

Blast Crisis LSC Activate Sonic Hedgehog Signaling in Selective Niches
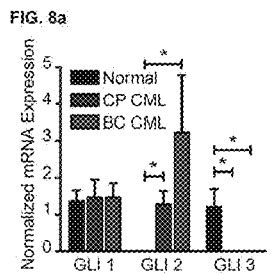
FIG. 8a
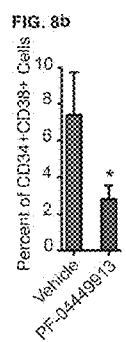
FIG. 8b
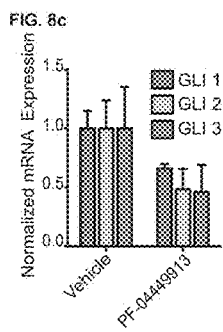
FIG. 8c
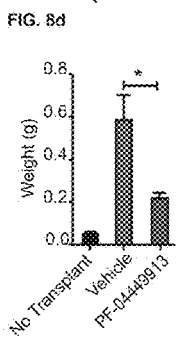
FIG. 8d
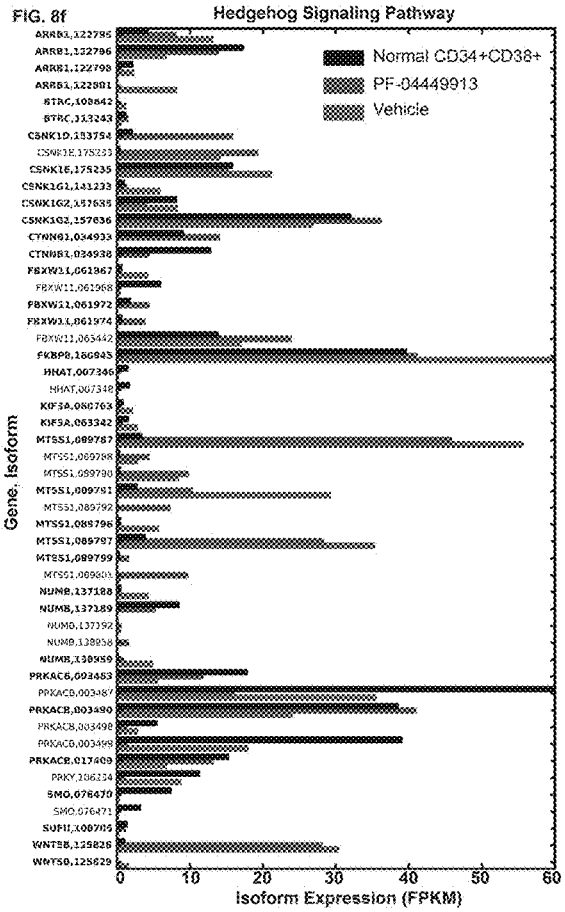
FIG. 8f
FIG. 8e
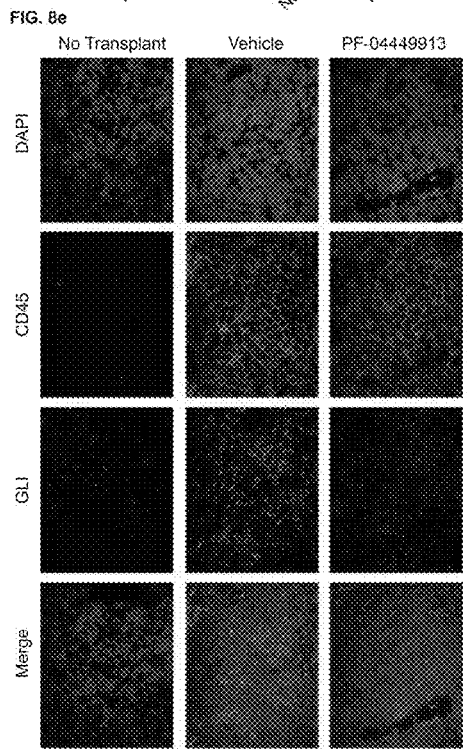
FIG. 8g
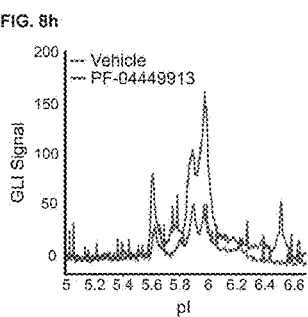
FIG. 8h
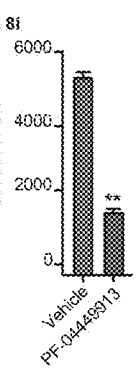
FIG. 8i

Dormant Blast Crisis LSC Activation with Sonic Hedgehog Inhibition
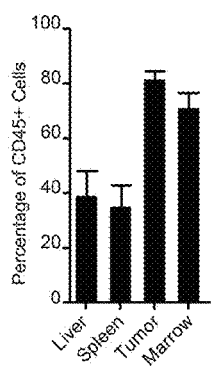
FIG. 9a
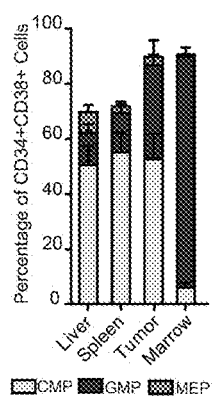
FIG. 9b
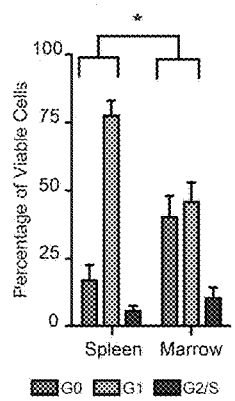
FIG. 9c
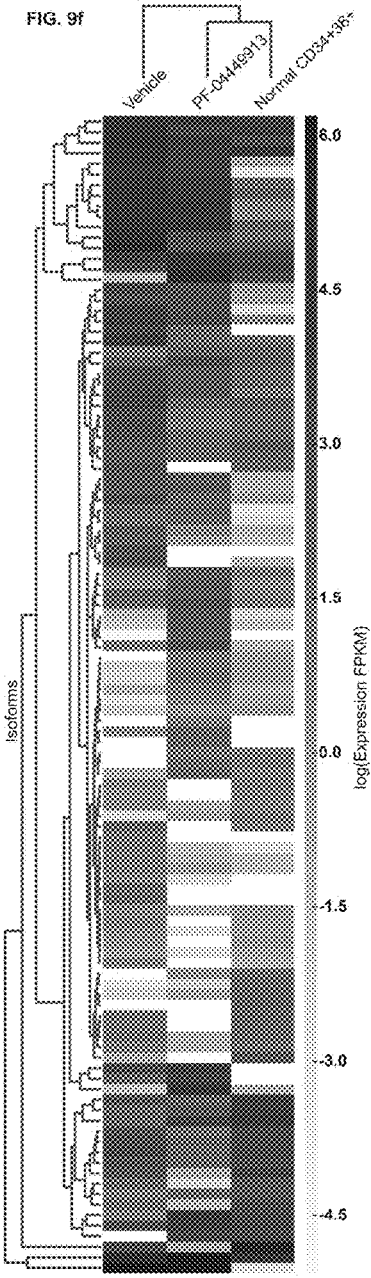
FIG. 9f
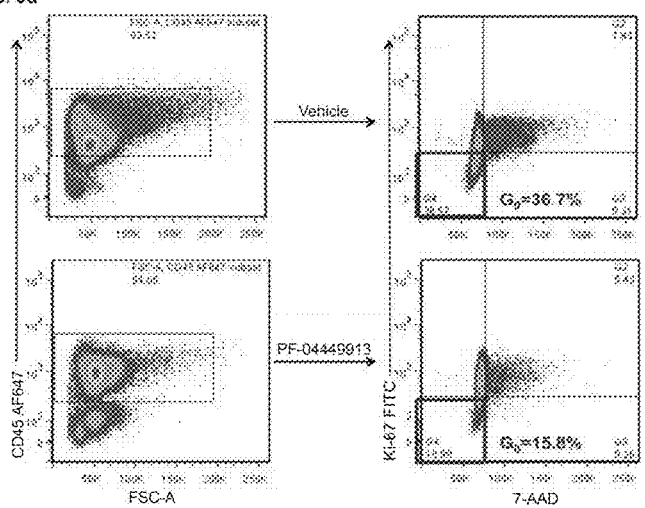
FIG. 9d
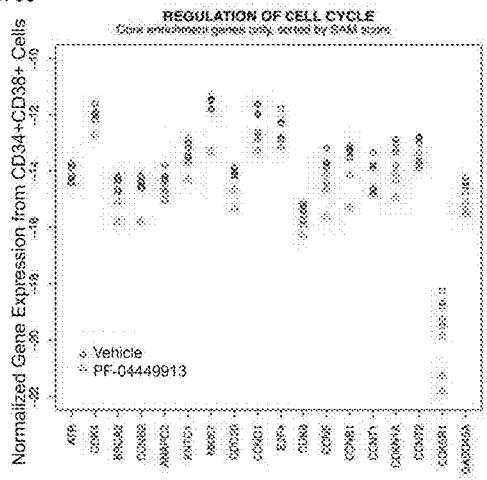
FIG. 9e
FIG. 9g
| Counts of Isoform Expression Relative to Vehicle | | Normal CD34+CD38+ | |
|---|---|---|---|
| | | Higher | Lower |
| PF-04449913 Treated | Higher | 50 | 18 |
| | Lower | 17 | 25 |
| P-value = 0.0006 | | | |

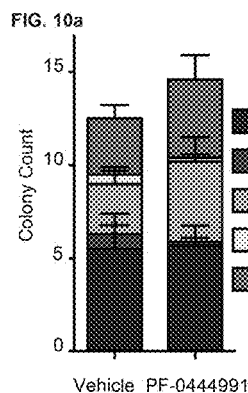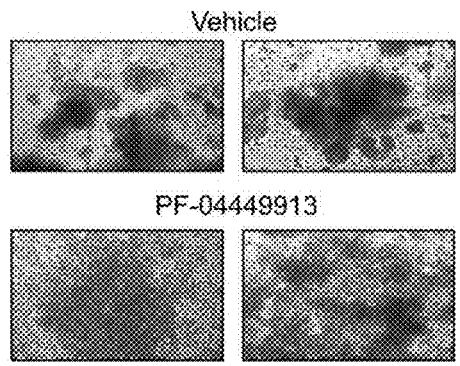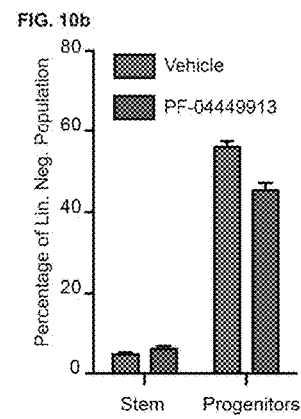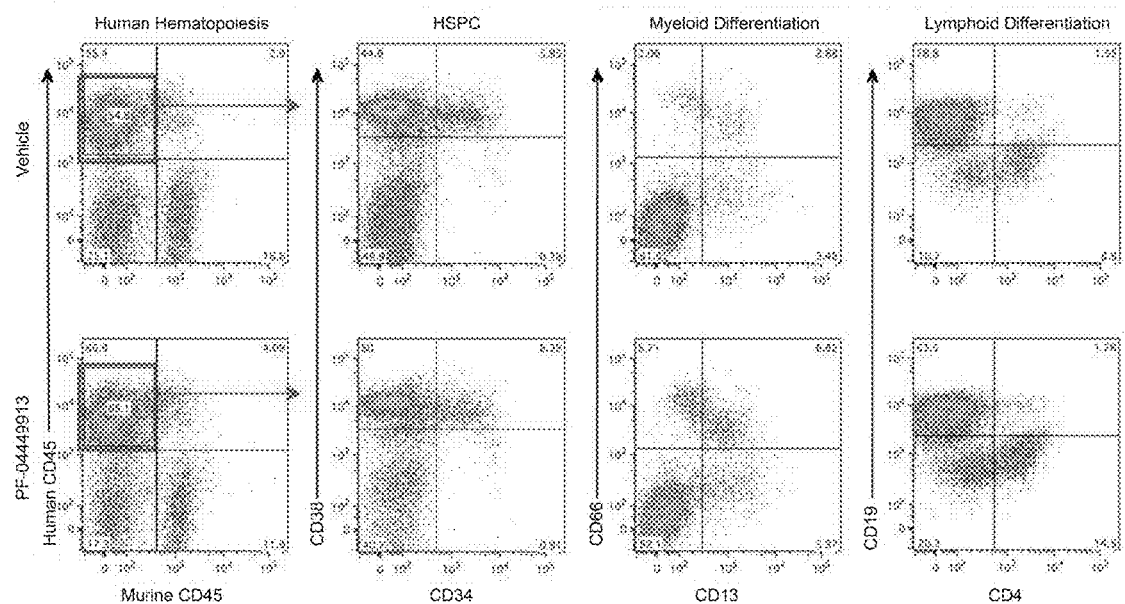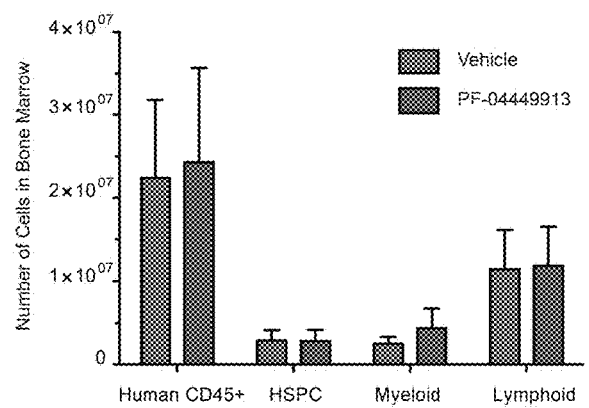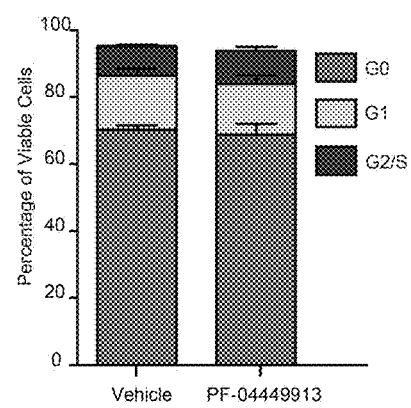

Combined BCR-ABL and Shh Inhibition Reduces LSC Survival in the Niche

PF-04449913 Structure and Chemical Properties

PF-04449913 Inhibits Shh Signaling in Ptch$^{+/-}$p53$^{+/-}$ Tumor Model

FIG. 13a
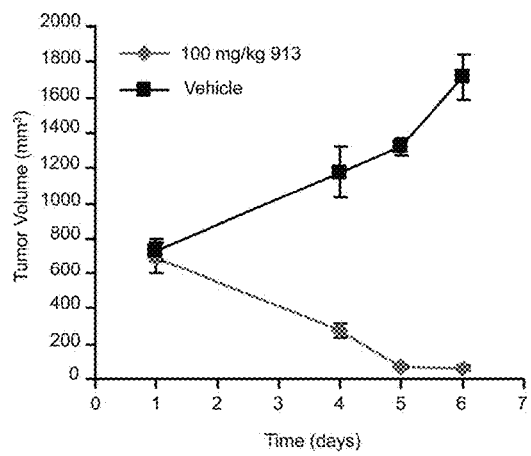

FIG. 13b
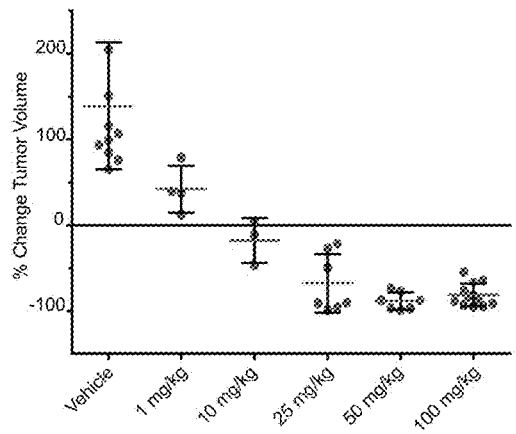

FIG. 13c
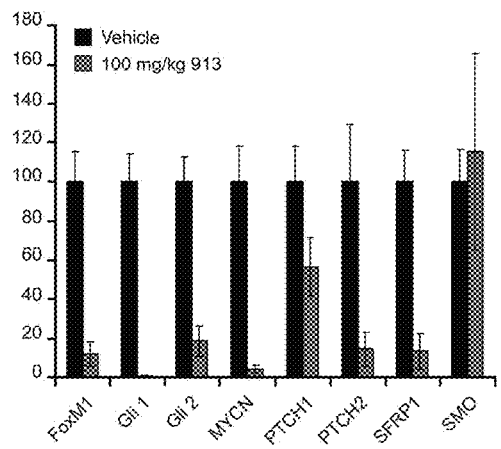

FIG. 13d
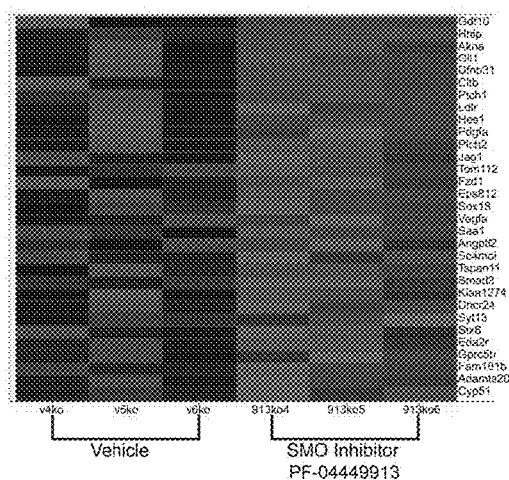

FIG. 13e

| Signature | Source | P-Val | Obs/Exp |
|---|---|---|---|
| Hedgehog Up | NetPath | 5.75E-10 | 114.42 |
| Hedgehog Signaling Pathway | NetPath | 7.26E-08 | 96.11 |
| Sonic Hedgehog Signaling | Ingenuity | 8.96E-08 | 91.53 |
| Basal Cell Carcinoma | KEGG | 9.00E-08 | 43.69 |
| Basal Cell Carcinoma Signaling | Ingenuity | 1.52E-07 | 39.39 |
| Shh Gli Targets Neural Patterning Chip2 Vokes | msigDB | 2.22E-07 | 73.93 |
| Hedgehog Signaling Pathway | KEGG | 4.18E-06 | 36.27 |
| Axonal Guidance Signaling | Ingenuity | 6.61E-06 | 9.48 |
| Signaling Events Mediated by the Hedgehog Family | PID | 1.22E-05 | 65.53 |
| Epidermis Development | GO | 1.51E-05 | 26.33 |
| Multicellular Organismal Development | GO | 1.71E-05 | 4.39 |
| Biosynthesis of Steroids | KEGG | 2.31E-05 | 53.39 |
| Regulation of Smoothened Signaling Pathway | GO | 4.17E-05 | 192.22 |
| Platelet-derived Growth Factor Receptor Signaling Pathway | GO | 6.25E-05 | 160.18 |
| Smoothened Signaling Pathway | GO | 6.25E-05 | 160.18 |

LSC Responses to Shh Inhibition Are Niche Dependent

Decreased Cell Cycle Regulator Expression Enhances LSC Cycling
FIG. 15a
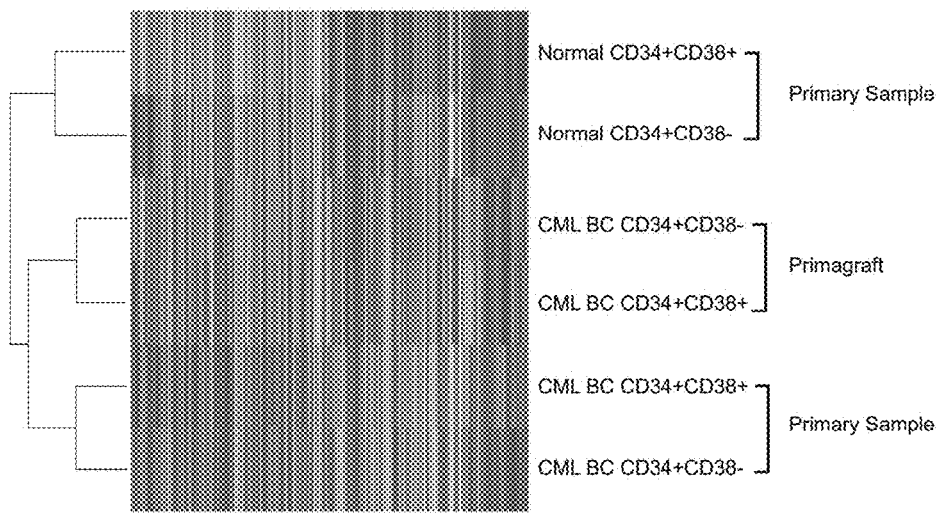
FIG. 15b
| Name | Size | NOM p-Val | FDR q-Val | FWER p-Val |
|---|---|---|---|---|
| Regulation of Cell Cycle | 41 | 9.76E-04 | 0.04004 | 0.0205 |
| G1 Phase and G1/S Transition | 12 | 0.142568 | 0.41387 | 0.387 |
| G2 Phase and G2/M Transition | 23 | 0.174927 | 0.40832 | 0.5205 |
| Kegg Cell Cycle | 121 | 0.110553 | 0.31768 | 0.5365 |
| Cell Cycle Checkpoint and Cell Cycle Arrest | 30 | 0.508577 | 0.72935 | 0.91 |
| S Phase and DNA Replication | 9 | 0.645545 | 0.82831 | 0.9715 |
| M Phase | 7 | 0.799209 | 0.84137 | 0.989 |
FIG. 15c
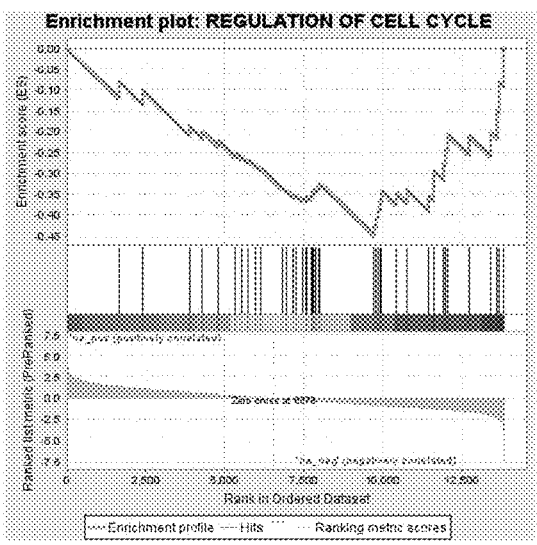
FIG. 15d
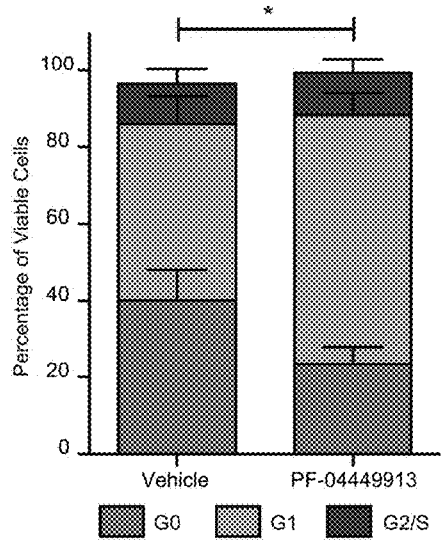

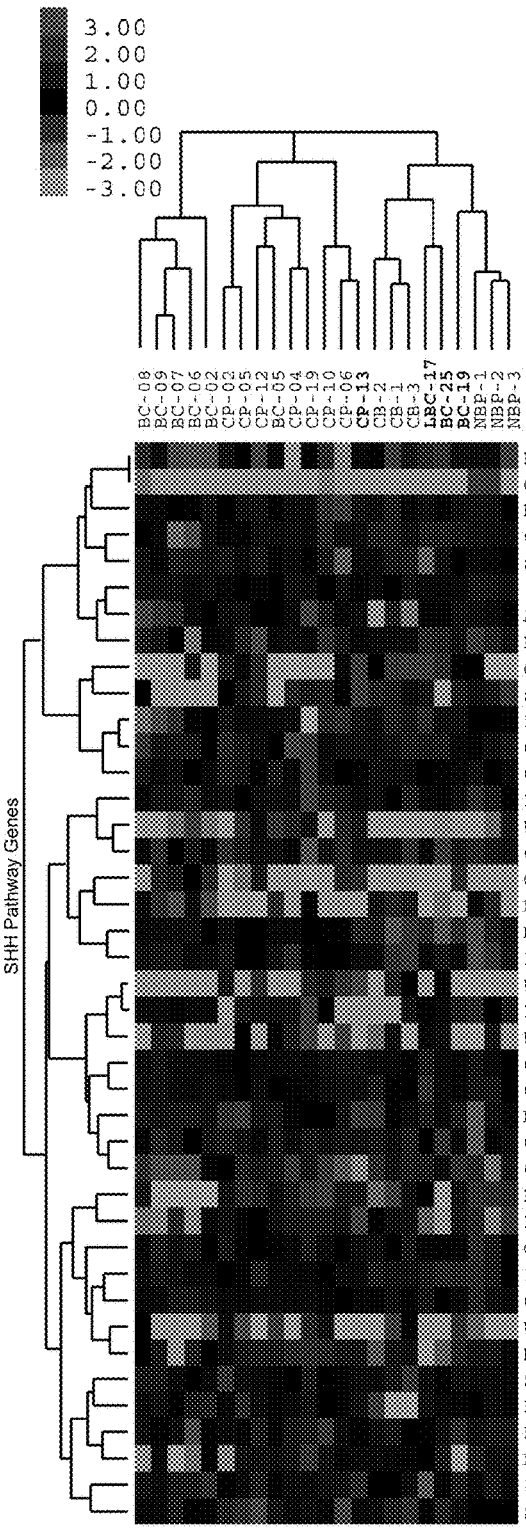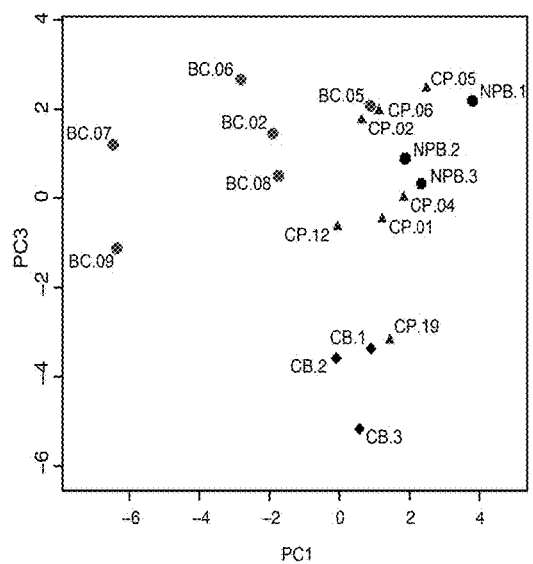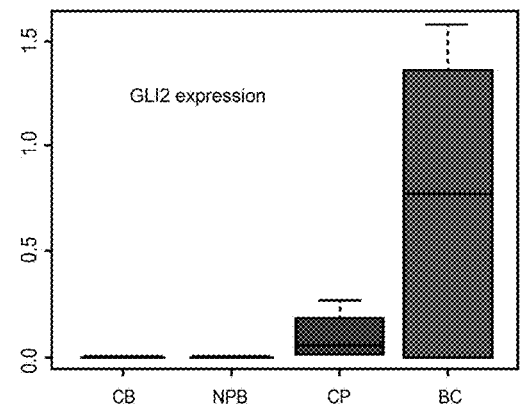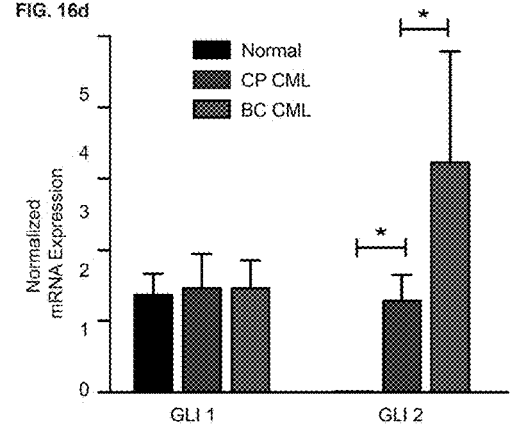

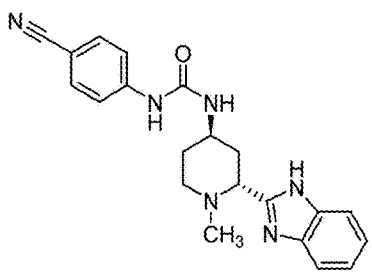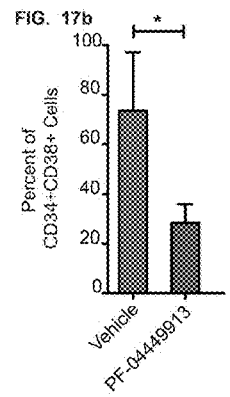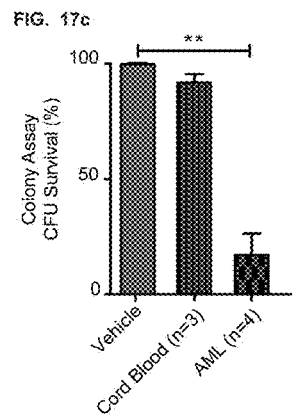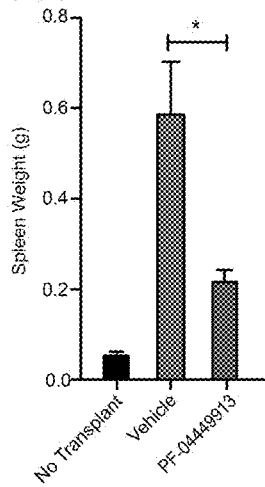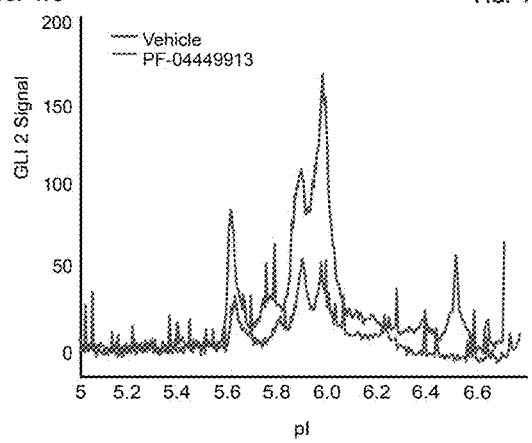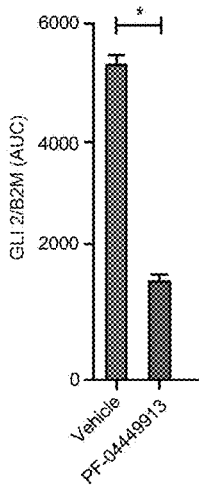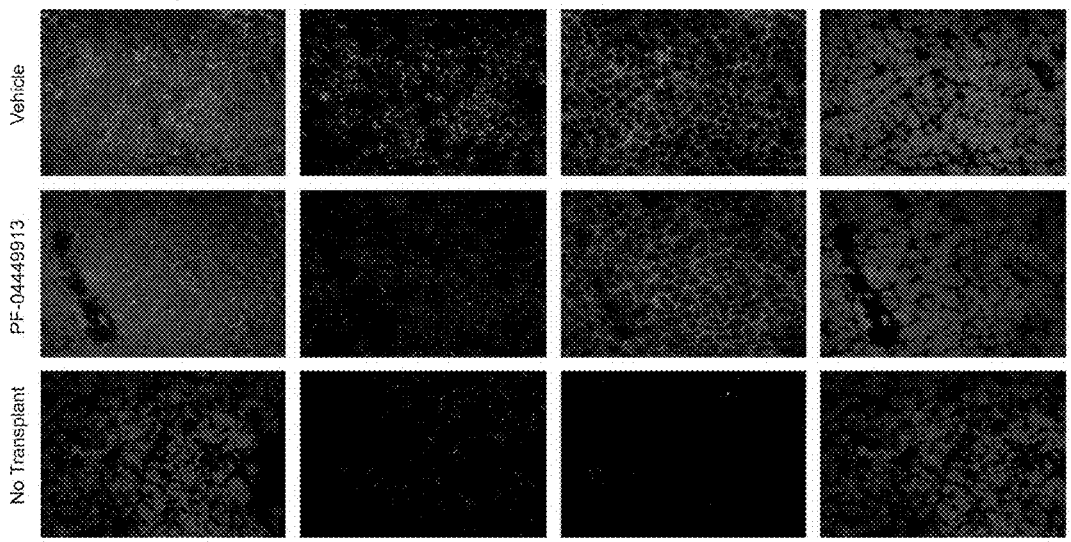

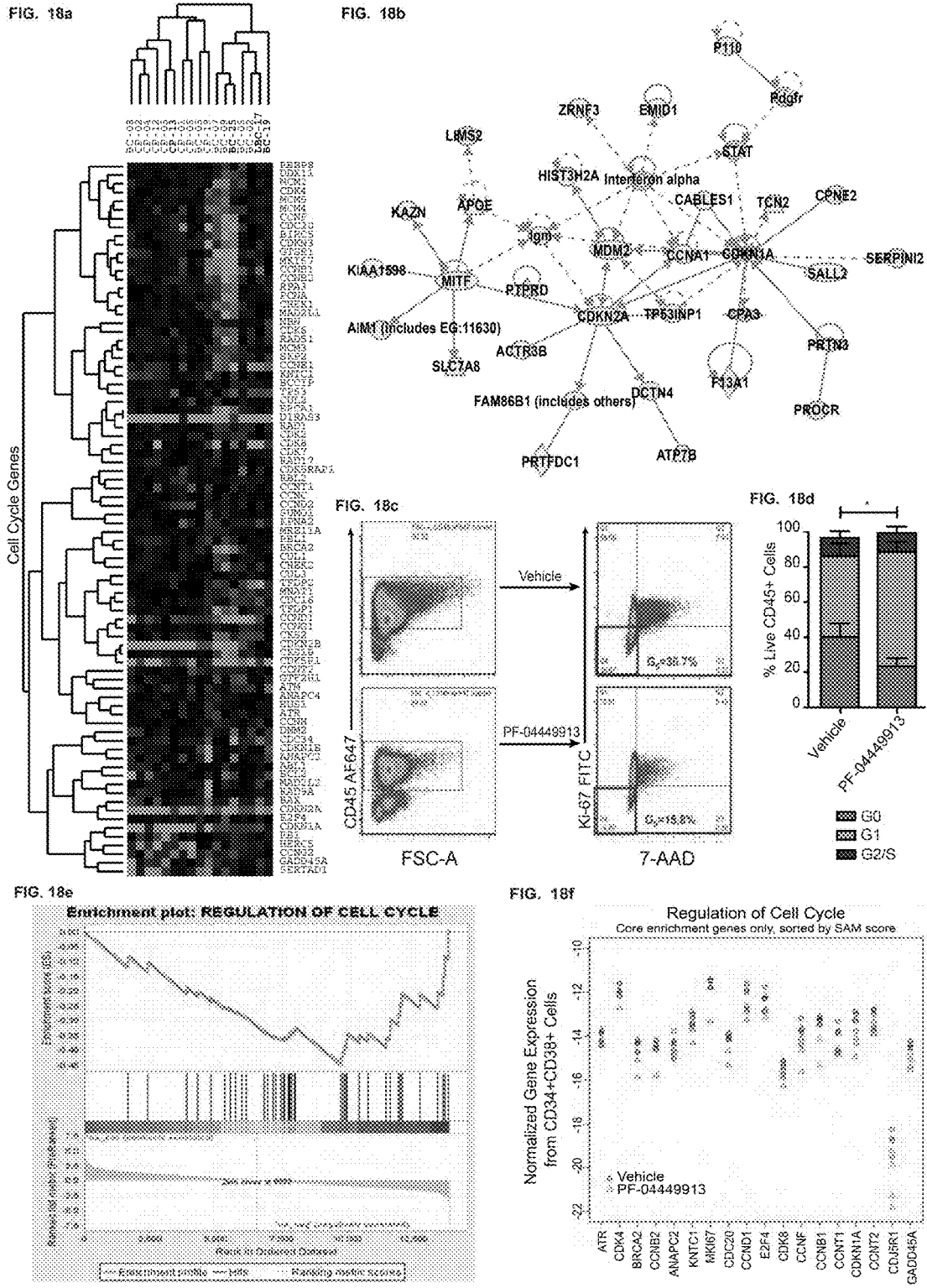

FIG. 19a

| Patient Characteristics | (N = 35) |
|---|---|
| Age, median (range) | 69 (35-79) |
| Gender, n (%) | |
| Female | 14 (40) |
| Male | 21 (60) |
| ECOG, n (%) | |
| 0 | 12 (34) |
| 1 | 18 (51) |
| 2 | 5 (14) |
| Malignancy, n (%) | |
| AML | 20 (57) |
| CML | 5 (14) |
| CMML | 1 (3) |
| MDS | 3 (9) |
| MF | 6 (17) |
| Prior therapy for primary diagnosis | |
| No[a] | 10 (29) |
| Yes | 25 (71) |

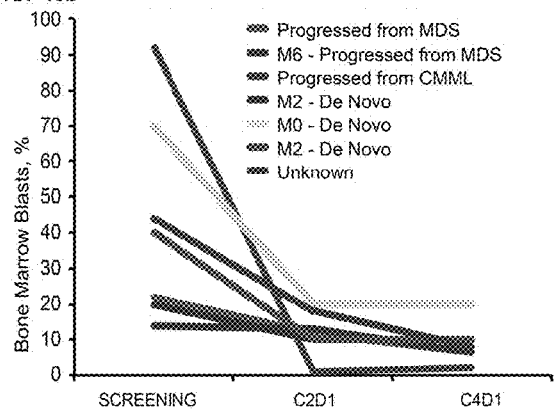

FIG. 19b

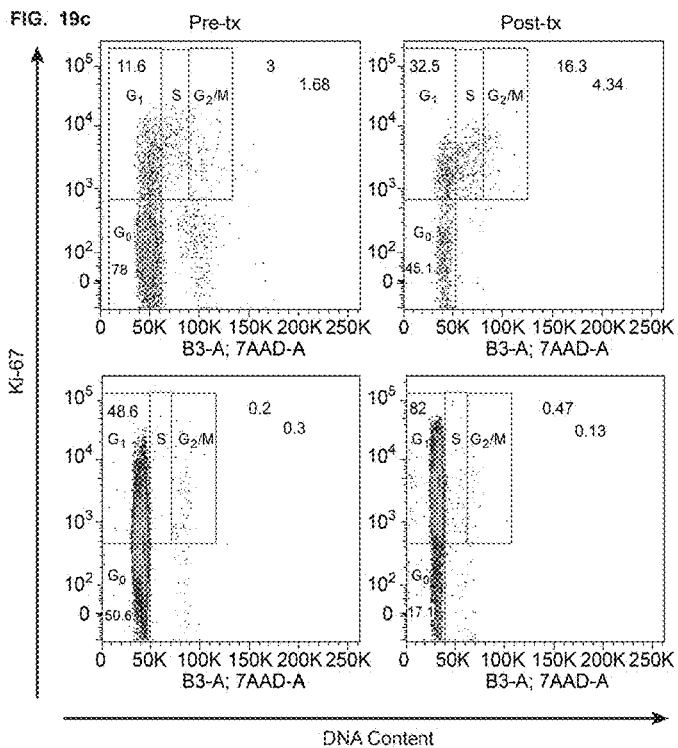

FIG. 19c

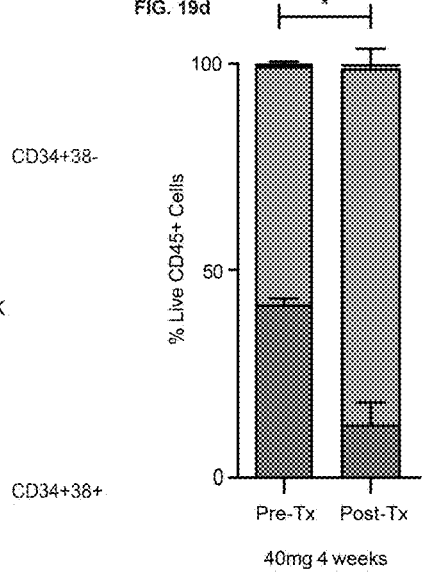

FIG. 19d

FIG. 19e  Cell Cycle Analyses Primary Patient Samples

| Patient | PF-04449913 | Diagnosis post Tx | % Change G0 CD34+ CD38+ | % Change G0 CD34+ CD38- | Clinical info. Pre-treatment | Clinical info. Post-treatment |
|---|---|---|---|---|---|---|
| Pt ID 1004-1008 | 120 mg | AML (4 weeks post Tx) | +27.5% | +12.4% | 49% BM blasts | 33% BM blasts |
| Pt ID 1004-1002 | 80 mg | PV-AML (4 weeks post Tx) | +0.4% | (-0.5%) | 43% BM blasts | 95% BM blasts |
| Pt ID 1004-1010 | 80 mg | MDS-AML (16 weeks post Tx) | (-5.9%) | (-23.7%) | 49% BM blasts | 18% BM blasts |
| Pt ID 1004-1005 | 40 mg | CML – no mutation (4 weeks post Tx) | (-5.3%) | (-28.7%) | BCR-ABL 12.08% | BCR-ABL 4.19% |
| Pt ID 1004-1003 | 180 mg | MDS (4 weeks post Tx) | (-8.9%) | +13.5% | 18% BM blasts | 14% BM blasts |
| Pt ID 1004-1004 | 40 mg | CML – no mutation (12 weeks post Tx) | +16.3% | ND (few cells) | BCR-ABL 9% | BCR-ABL 100% |
| Pt ID 1001-1007 | 80 → 40 mg | CMML-AML (4 weeks post Tx) | (-18.8%) | (-21.6%) | 92% BM blasts | 2% BM blasts |

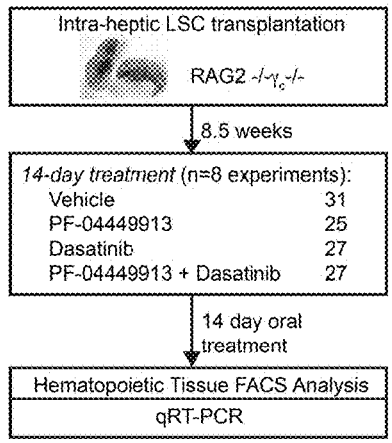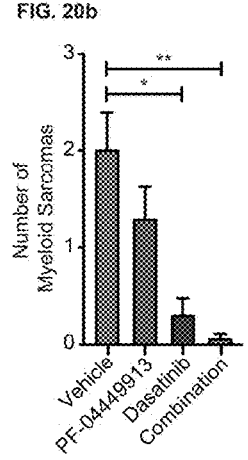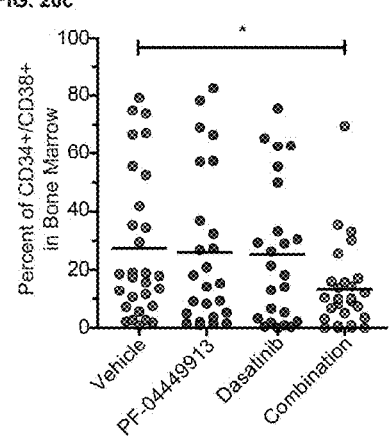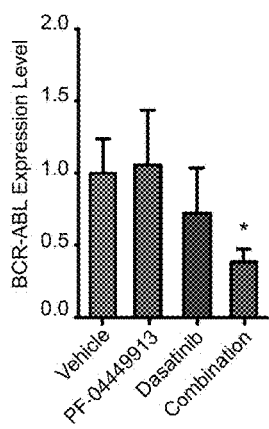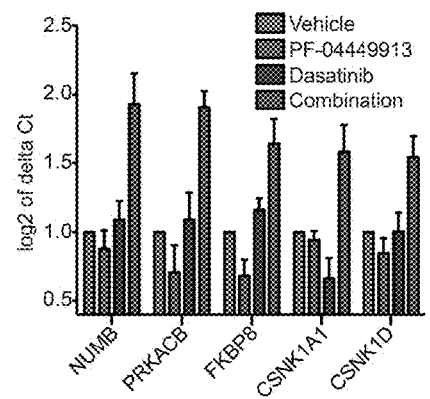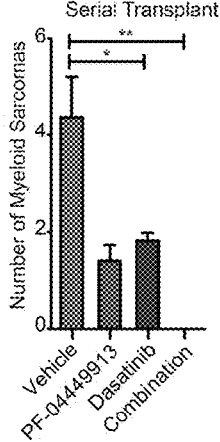

FIG. 21a

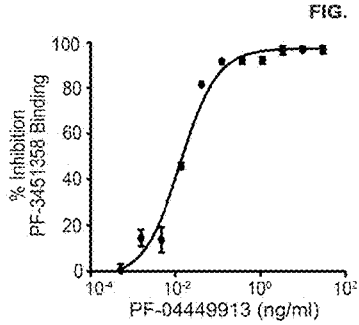

FIG. 21b

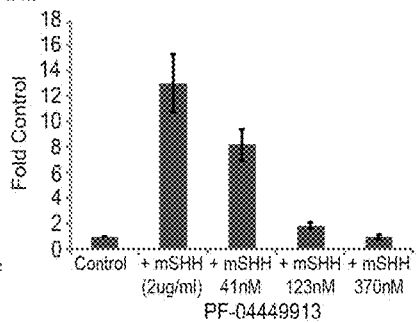

FIG. 21c

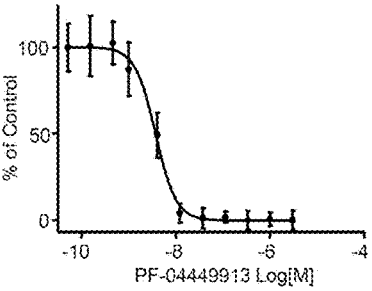

FIG. 21d

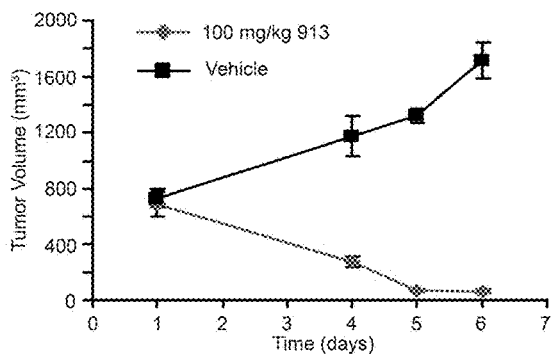

FIG. 21e

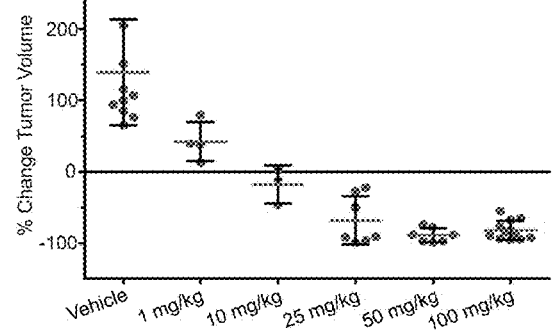

FIG. 21f

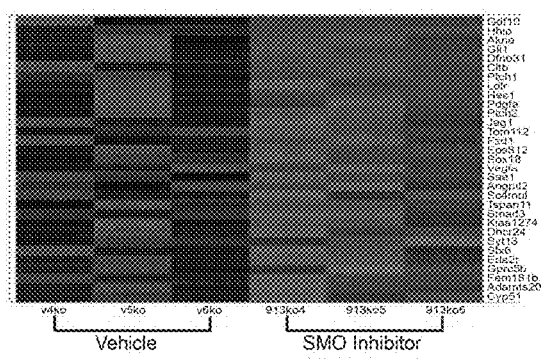

FIG. 21g

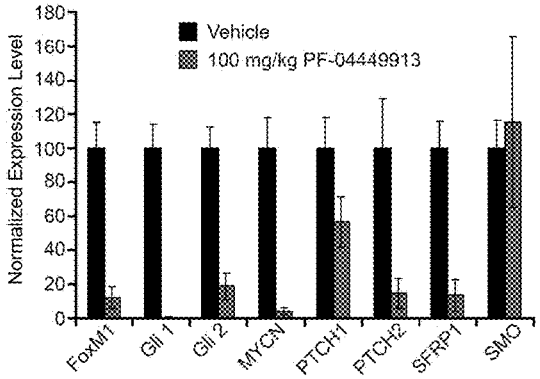

FIG. 21h

| Signature | Source | P-Val | Obs/Exp |
|---|---|---|---|
| Hedgehog Up | NetPath | 5.75E-10 | 114.42 |
| Hedgehog Signaling Pathway | NetPath | 7.26E-08 | 96.11 |
| Sonic Hedgehog Signaling | Ingenuity | 8.96E-08 | 91.53 |
| Basal Cell Carcinoma | KEGG | 9.00E-08 | 43.69 |
| Basal Cell Carcinoma Signaling | Ingenuity | 1.52E-07 | 39.39 |
| SHH Gli Targets Neural Patterning Chip2 Vokes | msigDB | 2.22E-07 | 73.93 |
| Hedgehog Signaling Pathway | KEGG | 4.18E-06 | 36.27 |
| Axonal Guidance Signaling | Ingenuity | 6.61E-06 | 9.48 |
| Signaling Events Mediated by the Hedgehog Family | PID | 1.22E-05 | 65.53 |
| Epidermis Development | GO | 1.51E-05 | 26.33 |
| Multicellular Organismal Development | GO | 1.71E-05 | 4.39 |
| Biosynthesis of Steroids | KEGG | 2.31E-05 | 53.29 |
| Regulation of Smoothened Signaling Pathway | GO | 4.17E-05 | 192.22 |
| Platelet-derived Growth Factor Receptor Signaling Pathway | GO | 6.25E-05 | 160.18 |
| Smoothened Signaling Pathway | GO | 6.25E-05 | 160.18 |

FIG. 22a

| NAME | SIZE | NOM p-val | FDR q-val | FWER p-val |
|---|---|---|---|---|
| REGULATION OF CELL CYCLE | 41 | 9.76E-04 | 0.040042 | 0.0205 |
| G1 PHASE AND G1/S TRANSITION | 12 | 0.142568 | 0.413871 | 0.387 |
| G2 PHASE AND G2/M TRANSITION | 23 | 0.174927 | 0.408327 | 0.5205 |
| KEGG_CELL_CYCLE | 121 | 0.110553 | 0.317688 | 0.5365 |
| CELL CYCLE CHECKPOINT AND CELL CYCLE ARREST | 30 | 0.508577 | 0.729359 | 0.91 |
| S PHASE AND DNA REPLICATION | 9 | 0.645545 | 0.828316 | 0.9715 |
| M PHASE | 7 | 0.799209 | 0.841371 | 0.989 |
| NEGATIVE REGULATION OF CELL CYCLE | 7 | 0.519 | 0.543 | 0.918 |

FIG. 22b  Cell Cycle analyses Primary Patient Samples

| Patient | PF-04449913 | Diagnosis | Clinical info. Pre-Tx | Clinical info. Post Tx |
|---|---|---|---|---|
| Pt ID 1003 1001 | 5 mg | AML | 26% - BM blasts<br>3100 - WBC<br>2% PB blasts | 90% - BM blasts<br>2200 – WBC<br>2% - PB blasts |
| Pt ID 1003 1002 | 10 mg | AML | 20% - BM blasts<br>12400 - WBC<br>8% PB blasts | 10% - BM blasts<br>25200 – WBC<br>0% - PB blasts |
| Pt ID 1003 1003 | 20 mg | CML | ND - BM blasts<br>2710 - WBC<br>0% PB blasts<br>BCR-ABL 26% | 99% - BM blasts<br>2400 – WBC<br>0% - PB blasts<br>BCR-ABL 37% |
| Pt ID 1003 1004 | 20 mg | AML | 35% - BM blasts<br>1880 - WBC<br>0% PB blasts | 35% - BM blasts<br>3100 – WBC<br>0% - PB blasts |
| Pt ID 1003 1006 | 80 mg | CML | ND - BM blasts<br>7200 - WBC<br>25% PB blasts<br>BCR-ABL 15% | ND – BM blasts<br>53200 – WBC<br>50% - PB blasts<br>BCR-ABL ND (pt stopped before C1D21, BioMol ND) |
| Pt ID 1003 1007 | 80 mg | AML | 70% - BM blasts<br>3400 - WBC<br>0% PB blasts | 20% - BM blasts<br>6400 – WBC<br>0% - PB blasts |
| Pt ID 1003 1008 | 80 mg | AML | 40% - BM blasts<br>1800 - WBC<br>26% PB blasts | 10% - BM blasts<br>24300 – WBC<br>2% - PB blasts |
| Pt ID 1003 1010 | 120 mg | MF | 0% - BM blasts<br>5100 - WBC<br>4% PB blasts | ND – BM blasts<br>13400 – WBC<br>4% - PB blasts |

FIG. 22c

| GSEA PATHWAY | ES | NOM p-val | FDR q-val |
|---|---|---|---|
| REACTOME_PACKAGING_OF_TELOMERE_ENDS | 29 | 2.9 | 0 |
| REACTOME_RNA_POLYMERASE_I_PROMOTER_OPENING | 33 | 2.88 | 0 |
| KEGG_SYSTEMIC_LUPUS_ERYTHEMATOSUS | 63 | 2.87 | 0 |
| REACTOME_RNA_POLYMERASE_I_PROMOTER_CLEARANCE | 52 | 2.82 | 0 |
| REACTOME_TELOMERE_MAINTENANCE | 56 | 2.68 | 0 |
| REACTOME_RNA_POLYMERASE_I_III_AND_MITOCHONDRIAL_TRANSCRIPTION | 84 | 2.41 | 0 |
| REACTOME_TRANSCRIPTION | 155 | 2.22 | 0 |
| REACTOME_RNA_POLYMERASE_I_CHAIN_ELONGATION | 24 | 2.02 | 0 |
| BIOCARTA_ATRBRCA_PATHWAY | 17 | 1.8 | 0.008 |
| REACTOME_MITOTIC_PROMETAPHASE | 71 | 1.79 | 0 |
| REACTOME_MRNA_3_END_PROCESSING | 33 | 1.76 | 0.004 |
| REACTOME_RNA_POLYMERASE_II_TRANSCRIPTION | 84 | 1.61 | 0.006 |
| KEGG_OLFACTORY_TRANSDUCTION | 19 | 1.61 | 0.025 |
| KEGG_NOD_LIKE_RECEPTOR_SIGNALING_PATHWAY | 42 | 1.6 | 0.024 |
| BIOCARTA_IGF1_PATHWAY | 16 | 1.58 | 0.035 |
| REACTOME_UNFOLDED_PROTEIN_RESPONSE | 19 | 1.54 | 0.044 |
| REACTOME_TRANSPORT_OF_MATURE_MRNA_DERIVED_FROM_AN_INTRON_CONTAINING_TRANSCRIPT | 47 | 1.53 | 0.023 |
| REACTOME_G2_M_CHECKPOINTS | 31 | 1.51 | 0.034 |
| A PRIORI ANALYSIS | | | |
| G2 PHASE AND G2/M TRANSITION | 18 | 0.044 | 0.048 |
| REGULATION OF CELL CYCLE | 34 | 0.056 | 0.082 |

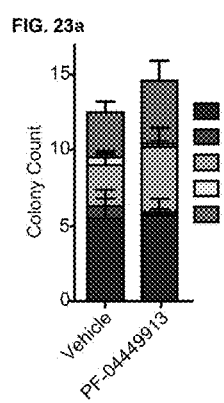
FIG. 23a
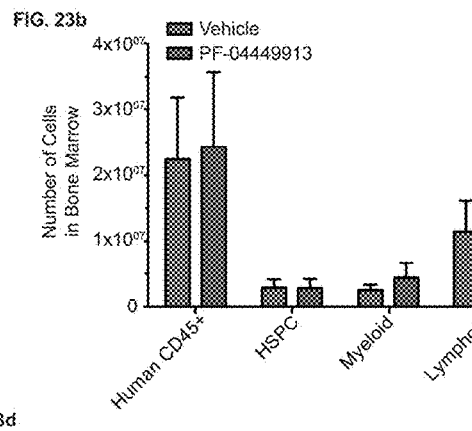
FIG. 23b
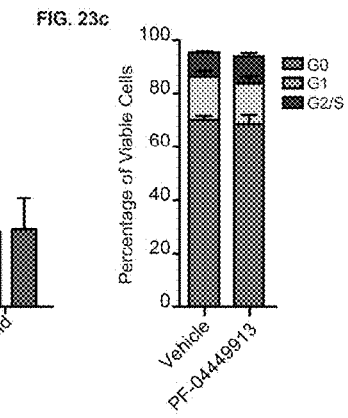
FIG. 23c
FIG. 23d

COMPOSITIONS AND METHODS FOR CANCER AND CANCER STEM CELL DETECTION AND ELIMINATION

CROSS-REFERENCE TO RELATED APPLICATIONS

This United States utility patent application is the §371 national phase of Patent Convention Treaty (PCT) International Application no. PCT/US2012/054307 having an international filing date of Sep. 7, 2012, which claims benefit of priority to U.S. Provisional Patent Application Ser. No. 61/532,417, filed Sep. 8, 2011; U.S. Ser. No. 61/537,157, filed Sep. 21, 2011; U.S. Ser. No. 61/537,161, filed Sep. 21, 2011; and U.S. Ser. No. 61/537,185, filed Sep. 21, 2011. The aforementioned applications are expressly incorporated herein by reference in their entirety and for all purposes.

TECHNICAL FIELD

This invention relates to oncology, cellular and developmental biology and drug discovery. In alternative embodiments, the invention provides compositions and methods for inhibiting or ablating cancer stem cells. In alternative embodiments, the invention provides compositions and methods for inhibiting the action of double-stranded RNA-specific adenosine deaminases, or ADAR, enzymes. In alternative embodiments, the invention provides compositions and methods for treating, ameliorating or preventing diseases and conditions responsive to the inhibition of cell differentiation and/or self-renewal of dysfunctional cells, cancer cells, leukemia cells, hematopoietic stem cells or cancer stem cells, e.g., leukemia or Chronic Myeloid Leukemia (CML).

In alternative embodiments, the invention provides compositions and methods for inhibiting a Sonic Hedgehog (Shh) pathway, e.g., by using a Smoothened (SMO) protein inhibitor. In alternative embodiments, the invention provides compositions and methods for inhibiting a Sonic Hedgehog (Shh) pathway, e.g., by using a Smoothened (SMO) protein inhibitor; to force, stimulate or initiate a dormant cell or a cancer stem cell (e.g., a Chronic Myelogenous Leukemia (CML) stem cell) to cycle so they the cell can more effectively targeted by a chemotherapy, a radiation therapy or a targeted tyrosine kinase inhibitor; as a biomarker of response to chemotherapy; and/or, as a target for drug development.

In alternative embodiments, the invention provides compositions and methods for measuring or determining, or predicting, chronic myelogenous leukemia (CML) progression, Leukemic Stem Cell (LSC) generation and/or tyrosine kinase inhibitor resistance comprising measuring or determining, individually or together, levels or amounts of GLI2 transcript and/or protein (increasing) and/or GLI3 transcript and/or protein (decreasing) as prognostic biomarkers of chronic myelogenous leukemia (CML) progression, Leukemic Stem Cell (LSC) generation and/or tyrosine kinase inhibitor resistance. In alternative embodiments, the invention provides compositions and methods for measuring or determining, or predicting, a response to an inhibitor or inhibitors of a Sonic Hedgehog (Shh) pathway, or a targeted Shh inhibition, or a selective Shh inhibition, comprising measuring or determining, individually or together, levels or amounts of GLI1 and/or GLI2 transcript and/or protein.

In alternative embodiments, the invention provides compositions and methods for determining or measuring the effectiveness of a treatment, a drug, a therapy or a diet for eliminating, killing or reducing the amounts of a leukemic stem cell (LSC) or cells. In alternative embodiments, the invention provides compositions and methods for determining or predicting a positive response or monitoring a response (predicting a negative or positive response) to a selective JAK2 inhibition therapy, drug or treatment.

BACKGROUND

RNA editing is a post-transcriptional processing mechanism that results in an RNA sequence that is different from that encoded by the genomic DNA and thereby diversifies the gene product and function. The type of RNA editing that is most prevalent in higher eukaryotes converts adenosine residues into inosine (A-to-I editing) in double-stranded RNA (dsRNA) through the action of double-stranded RNA-specific adenosine deaminases, or ADAR, enzymes.

ADAR is an enzyme that in humans is encoded by the ADAR gene (ADAR1 is an acronym for "adenosine deaminase acting on RNA 1"). ADAR1 RNA edits by site-specific deamination of adenosines. The ADAR1 enzyme destabilizes double stranded RNA through conversion of adenosine to inosine. The ADAR1 enzyme modifies cellular and viral RNAs, including coding and noncoding RNAs. ADAR1 is an RNA editing enzyme, required for hematopoiesis. ADAR1$^{+/-}$ chimeric embryos die before embryonic day 14 with defects in the hematopoietic system. Regulated levels of ADAR1 expression are critical for embryonic erythropoiesis in the liver. Mutations in the ADAR gene have been associated with dyschromatosis symmetrica hereditaria. Alternate transcriptional splice variants, encoding different isoforms, have been characterized.

Traditional CML treatment, such as hydroxyurea and imatinib, is a great financial burden on patients. Moreover, they are not efficient at eradicate leukemia cancer stem cells, which often leads to disease progression and relapse. New drugs that target at cancer stem cells are urgently needed for patient care.

Studies suggested that leukemia stem cells (LSC) promote therapeutic resistance, relapse and disease progression, the leading causes of leukemia mortality, as a result of enhanced survival and self-renewal combined with a propensity to become dormant in supportive microenvironments. Therapies capable of breaking LSC quiescence while sparing normal hematopoietic stem cell (HSC) function have remained elusive. In chronic myeloid leukemia (CML) mouse models, Sonic hedgehog (Shh) pathway activation promotes LSC maintenance. However, the comparative role of Shh signaling in human normal HSC and LSC quiescence induction and self-renewal had not been determined.

Signal transducer and activator of transcription 5A (STAT5a) is a protein that in humans is encoded by the STAT5A gene. The protein encoded by this gene is a member of the STAT family of transcription factors. In response to cytokines and growth factors, STAT family members are phosphorylated by the receptor associated kinases, and then form homo- or heterodimers that translocate to the cell nucleus where they act as transcription activators. This protein is activated by, and mediates the responses of many cell ligands, such as IL2, IL3, IL7 GM-CSF, erythropoietin, thrombopoietin, and different growth hormones. Activation of this protein in myeloma and lymphoma associated with a TEL/JAK2 gene fusion is independent of cell stimulus and has been shown to be essential for the tumorigenesis.

Janus kinase 2 (JAK2) is a human protein that has been implicated in signaling by members of the type II cytokine receptor family (e.g. interferon receptors), the GM-CSF receptor family, and the gp130 receptor family (e.g., IL-6R), and the single chain receptors such as Epo-R. JAK2 gene fusions with the TEL(ETV6) and PCMI genes have been found in leukemia patients. Mutations in JAK2 have been implicated in myeloproliferative disorders.

SUMMARY

RNA Editing as a Novel Cancer Stem Cell Target

In alternative embodiments, the invention provides methods for treating, ameliorating or preventing diseases and conditions responsive to the inhibition or slowing of cell differentiation and/or self-renewal (or self-renewal capacity) of dysfunctional cells, cancer cells, leukemia cells, hematopoietic stem cells or cancer stem cells, comprising, (a) providing a composition that inhibits or slows the expression of or the activity of: and ADAR1 gene (adenosine deaminase acting on RNA 1), and ADAR1 gene product, an ADAR1 transcript, and/or an ADAR1 polypeptide; and (b) administering a sufficient amount of the composition to an individual in need thereof, wherein a sufficient amount comprises the inhibition or slowing of cell differentiation and/or self-renewal of dysfunctional cells, cancer cells, leukemia cells, hematopoietic stem cells or cancer stem cells.

In alternative embodiments of the methods, the hematopoietic stem cell or cancer stem cell comprises a cancer stem cell, or a leukemia cell, or a Chronic Myeloid Leukemia (CML) cell, a leukemia stem cell, or a Chronic Myeloid Leukemia (CML) stem cell.

In alternative embodiments of the methods, the composition that inhibits or slows the expression of an ADAR1 gene, an ADAR1 gene product, an ADAR1 transcript, and/or an ADAR1 polypeptide comprises:

(a) an inhibitory nucleic acid molecule or an antisense oligonucleotide inhibitory to expression of the ADAR1 gene or ADAR1 gene transcript;

(b) a polypeptide, peptide or an antibody inhibitory to the expression of the ADAR1 gene or ADAR1 gene transcript, or activity or expression of the ADAR1 enzyme;

(c) the method of (a), wherein the inhibitory nucleic acid molecule or antisense oligonucleotide inhibitory to expression of the ADAR1 gene or ADAR1 gene transcript comprises: an RNAi inhibitory nucleic acid molecule, a double-stranded RNA (dsRNA) molecule, a small interfering RNA (siRNA), a microRNA (miRNA) and/or a short hairpin RNA (shRNA); or (d) the method of (a) or (c), wherein inhibitory nucleic acid molecule comprises a ribozyme.

In alternative embodiments of the methods, the inhibitory nucleic acid molecule or antisense oligonucleotide inhibitory to expression of the ADAR1 gene or ADAR1 gene transcript comprises a single or doublestranded and/or sense or antisense sequence or subsequence comprising SEQ ID NO:1, SEQ ID NO:2 or SEQ ID NO:3.

In alternative embodiments of the methods, the antibody inhibitory to the expression of the ADAR1 gene or ADAR1 gene transcript, or activity or expression of the ADAR1 enzyme comprises an antibody or antigen-binding fragment thereof that specifically binds to a protein as set forth in SEQ ID NO:3.

In alternative embodiments of the methods, the polypeptide or peptide inhibitory to the expression of the ADAR1 gene or ADAR1 gene transcript, or activity or expression of the ADAR1 enzyme comprises a peptide aptamer or an ADAR1-binding polypeptide or peptide.

In alternative embodiments of the methods, the composition that inhibits or slows the expression of or the activity of: an ADAR1 gene (adenosine deaminase acting on RNA 1), an ADAR1 gene product, an ADAR1 transcript, and/or an ADAR1 polypeptide is administered in vitro, ex vivo or in vivo.

In alternative embodiments, the invention provides compositions, pharmaceutical compositions or formulations, or equivalents, comprising a composition that inhibits or slows the expression of or the activity of: an ADAR1 gene (adenosine deaminase acting on RNA 1), and ADAR1 gene product, an ADAR1 transcript, and/or an ADAR1 polypeptide, wherein optionally the composition or formulation is formulated for administration in vitro, ex vivo or in vivo.

In alternative embodiments, the invention provides kits comprising: a composition used to practice a method of any of the invention, or a composition, a pharmaceutical composition or a formulation of the invention, and optionally comprising instructions for use thereof.

Compositions and Methods for Dormant Cancer Stem Cell Detection and Elimination

In alternative embodiments, the invention provides compositions and methods to detect dormant cancer stem cells, e.g., Chronic Myelogenous Leukemia (CML) stem cells. In alternative embodiments, the invention provides compositions and methods for use therapeutically to force dormant cancer stem cells, e.g., Chronic Myelogenous Leukemia (CML) stem cells, into cycle so they can be targeted by a therapeutic agent or procedure, e.g., chemotherapy, radiation therapy or targeted tyrosine kinase inhibitors.

In alternative embodiments, the invention provides methods for activating, stimulating or initiating in a cancer stem cell a transition from G0 to G1 of the cell cycle, or initiating cell cycling in a cancer stem cell, or breaking dormancy in a cancer stem cell, or inducing in a stem cell susceptibility to BCR-ABL inhibition, comprising:

(a) providing a composition that inhibits a Sonic Hedgehog (Shh), or providing a Smoothened (SMO) protein inhibitor (Smoothened (SMO) is an integral membrane protein mediator, a of Hedgehog signaling); and (b) administering an effective amount of the Sonic Hedgehog (Shh) inhibitor or the Smoothened (SMO) protein inhibitor to the cancer stem cell, thereby activating, stimulating or initiating in the cancer stem cell a transition from G0 to G1 of the cell cycle, or initiating cell cycling in the cancer stem cell, inducing in the stem cell susceptibility to BCR-ABL inhibition, or breaking dormancy in the stem cell.

In alternative embodiments, the invention provides methods for radiosensitization of a cancer stem cell, or sensitizing a cancer stem cell to a treatment or protocol that targets dividing cells, or sensitizing a cancer stem cell to a chemotherapy, a radiation therapy or a targeted tyrosine kinase inhibitor, comprising, (a) providing a composition that inhibits a Sonic Hedgehog (Shh), or providing a Smoothened (SMO) protein inhibitor; and (b) administering an effective amount of the Sonic Hedgehog (Shh) inhibitor or the Smoothened (SMO) protein inhibitor to the cancer stem cell, thereby radiosensitizing the cancer stem cell, or sensitizing the cancer stem cell to a treatment or protocol that targets dividing cells, or sensitizing the cancer stem cell to a chemotherapy, a radiation therapy or a targeted tyrosine kinase inhibitor.

In alternative embodiments of the methods, the cancer stem cell is a hematopoietic cancer stem cell, or the cancer stem cell is a leukemia stem cell, or a Chronic Myeloid Leukemia (CML) stem cell or a Chronic Myeloid Leukemia (CML) stem cell.

In alternative embodiments of the methods, the composition that inhibits or slows the expression of an Shh gene, an Shh gene product, an Shh transcript, and/or an Shh polypeptide comprises:

(a) an inhibitory nucleic acid molecule or an antisense oligonucleotide inhibitory to expression of a Shh gene or Shh gene transcript;

(b) a polypeptide, peptide or an antibody inhibitory to the expression of the Shh gene or Shh gene transcript, or activity or expression of the Shh polypeptide;

(c) the method of (a), wherein the inhibitory nucleic acid molecule or antisense oligonucleotide inhibitory to expression of the Shh gene or Shh gene transcript comprises: an RNAi inhibitory nucleic acid molecule, a double-stranded RNA (dsRNA) molecule, a small interfering RNA (siRNA), a microRNA (miRNA) and/or a short hairpin RNA (shRNA); or (d) the method of (a) or (c), wherein inhibitory nucleic acid molecule comprises a ribozyme.

In alternative embodiments of the methods, the composition that inhibits or slows the expression of a Shh gene, a Shh gene product, a Shh transcript, and/or a Shh polypeptide comprises a PF-04449913 (structure illustrated in FIG. 17a), or an equivalent thereof, or a bioisostere thereof.

In alternative embodiments of the methods, the antibody inhibitory to the expression of a Shh gene, a Shh gene product or a Shh transcript, or activity or expression of the Shh polypeptide, comprises an antibody or antigen-binding fragment thereof that specifically binds to a Shh protein.

In alternative embodiments of the methods, the polypeptide or peptide inhibitory to the expression of a Shh gene, a Shh gene product or a Shh transcript, or activity or expression of the Shh protein comprises a peptide aptamer or a Shh protein-binding polypeptide or peptide.

In alternative embodiments of the methods, the composition that inhibits or slows the expression of or the activity of: a Shh gene, a Shh gene product or a Shh transcript, and/or an Shh polypeptide is administered in vitro, ex vivo or in vivo.

The invention provides compositions, pharmaceutical compositions or formulations comprising a composition that inhibits or slows the expression of or the activity of: a Shh gene, a Shh gene product or a Shh transcript, and/or an Shh polypeptide, wherein optionally the composition or formulation is formulated for administration in vitro, ex vivo or in vivo. In alternative embodiments, the composition that inhibits or slows the expression of or the activity of: a Shh gene, a Shh gene product or a Shh transcript, and/or an Shh polypeptide comprises any composition used to practice a method of the invention, e.g., a PF-04449913 (structure illustrated in FIG. 17a), or an equivalent thereof, or a bioisostere thereof.

The invention provides arrays or kits comprising a cancer stem cell splice isoform and/or proteome detection platform, wherein the array or kit comprises a sufficient plurality of nucleic acids and/or proteins to detect a dormant cancer stem cell from a non-dormant stem cell or a cancer stem cell transitioning from G0 to G1 of the cell cycle.

The invention provides methods for determining the effectiveness of a test compound for: activating, stimulating or initiating in a cancer stem cell a transition from G0 to G1 of the cell cycle; or initiating cell cycling in a cancer stem cell; or breaking dormancy in a cancer stem cell; or radiosensitizing of a cancer stem cell; or sensitizing a cancer stem cell to a treatment or protocol that targets dividing cells; inducing in a stem cell susceptibility to BCR-ABL inhibition; or sensitizing a cancer stem cell to a chemotherapy, a radiation therapy or a targeted tyrosine kinase inhibitor, comprising analyzing the cancer stem cell transcript (RNA) splice isoform pattern and/or the proteome before and after contacting the test compound to the stem cell, wherein a change of the cancer stem cell to a non-dormant transcript (RNA) splice isoform pattern and/or the proteome pattern indicates that the test compound is effective for: activating, stimulating or initiating in a cancer stem cell a transition from G0 to G1 of the cell cycle; or initiating cell cycling in a cancer stem cell; or breaking dormancy in a cancer stem cell; or radiosensitizing of a cancer stem cell; or sensitizing a cancer stem cell to a treatment or protocol that targets dividing cells; inducing in a stem susceptibility to BCR-ABL inhibition; or sensitizing a cancer stem cell to a chemotherapy, a radiation therapy or a targeted tyrosine kinase inhibitor, wherein optionally the analyzing comprises use of an array or a kit of the invention.

The invention provides kits comprising: a composition used to practice a method of the invention, or a composition, a pharmaceutical composition or a formulation of the invention, and optionally comprising instructions for use thereof. Sonic Hedgehog Targets as Biomarkers of Prognosis and Response for Human Chronic Myelogenous Leukemia In alternative embodiments, the invention provides compositions and methods to detect dormant cancer stem cells, e.g., Chronic Myelogenous Leukemia (CML) stem cells. In alternative embodiments, the invention provides compositions and methods for use therapeutically to force dormant cancer stem cells, e.g., Chronic Myelogenous Leukemia (CML) stem cells, into cycle so they can be targeted by a therapeutic agent or procedure, e.g., chemotherapy, radiation therapy or targeted tyrosine kinase inhibitors.

In alternative embodiments, the invention provides compositions and methods for measuring or determining, or predicting, chronic myelogenous leukemia (CML) progression, Leukemic Stem Cell (LSC) generation and/or tyrosine kinase inhibitor resistance, comprising: measuring or determining, individually or together, levels or amounts of GLI2 transcript and/or protein (increasing) and/or GLI3 transcript and/or protein (decreasing) as prognostic biomarkers of chronic myelogenous leukemia (CML) progression, Leukemic Stem Cell (LSC) generation and/or tyrosine kinase inhibitor resistance, wherein increased or increasing levels of GLI2 transcript and/or protein and/or decreasing levels of GLI3 transcript and/or protein indicate and/or predict chronic myelogenous leukemia (CML) progression, Leukemic Stem Cell (LSC) generation and/or tyrosine kinase inhibitor resistance.

In alternative embodiments, the invention provides compositions and methods for measuring or determining, or predicting, a response to an inhibitor or inhibitors of a Sonic Hedgehog (Shh) pathway, or a targeted Shh inhibition, or a selective Shh inhibition, comprising:

measuring or determining, individually or together, levels or amounts of GLI1 and/or GLI2 transcript and/or protein, wherein the presence of one or both GLI1 and/or GLI2 transcript and/or protein, and/or increased or increasing levels of one or both GLI1 and/or GLI2 transcript and/or protein indicates a response to an inhibitor or inhibitors of a Sonic Hedgehog (Shh) pathway, or a targeted Shh inhibition, or a selective Shh inhibition.

In alternative embodiments, the invention provides compositions and methods for measuring or determining, or predicting, whether a cancer stem cell has or will transition from G0 to G1 of the cell cycle, or has or will initiate cell cycling, or has or will break dormancy, or has been induced to have a susceptibility to BCR-ABL inhibition, comprising:

measuring or determining, individually or together, levels or amounts of GLI1 and/or GLI2 transcript and/or protein, wherein the presence of one or both GLI1 and/or GLI2 transcript and/or protein, and/or increased or increasing levels of one or both GLI1 and/or GLI2 transcript and/or protein, indicates a response to an inhibitor or inhibitors of a Sonic Hedgehog (Shh) pathway, or a targeted Shh inhibition, or a selective Shh inhibition, thereby also indicating or predicting whether a cancer stem cell has or will transition from G0 to G1 of the cell cycle, or has or will initiate cell cycling, or has or will break dormancy, or has been induced to have a susceptibility to BCR-ABL inhibition.

In alternative embodiments, for methods of the invention, the presence, absence and/or amount of a GLI1, GLI2 and/or GLI3 transcript and/or protein is measured using an array, an immunoassay, an immunoprecipitation, a kit, a polymerase chain reaction (PCR), a qRT-PCR, a nanofluidic assay or device, a nanofluidic proteome assay, a chromatography, a nanoproteomics quantification, an isoelectric focusing assay, or a combination thereof.

In alternative embodiments, the invention provides compositions and methods for assessing the eradication of self-renewing cancer stem cells, or Leukemic Stem Cells (LSCs), comprising:

measuring or determining, individually or together, levels or amounts of GLI1 and/or GLI2 transcript and/or protein, wherein the absence of one or both GLI1 and/or GLI2 transcript and/or protein, and/or decreasing levels of one or both GLI1 and/or GLI2 transcript and/or protein, indicates a response to an inhibitor or inhibitors of a Sonic Hedgehog (Shh) pathway, or a targeted Shh inhibition, or a selective Shh inhibition, thereby also indicating or predicting an eradication or diminishment of self-renewing cancer stem cells, or Leukemic Stem Cells (LSCs).

In alternative embodiments, the invention provides arrays, immunoassays, kits and the like comprising nucleic acids, proteins or antibodies capable of determining or measuring the presence, absence and/or amount of a GLI1, GLI2 and/or GLI3 transcript and/or protein. In alternative embodiments, the arrays or kits comprise a composition used to practice a method of the invention, or a composition, and optionally comprising instructions for use thereof.

Spliced Isoform Biomarkers to Assess Responses to Cancer Stem Cell Targeted Therapies In alternative embodiments, the invention provides compositions and methods for determining or measuring the effectiveness of a treatment, a drug, a therapy or a diet for eliminating, killing or reducing the amounts of a leukemic stem cell (LSC) or cells, comprising:

(a) determining or measuring the amount of an alternatively spliced phosphoStat5a and/or a phospho-JAK2;

(b) determining or measuring the amount of an alternatively spliced Stat5a and/or a JAK2; or (c) determining or measuring the amount of an alternatively spliced Stat5a and/or a JAK2 transcript or message;

wherein a decrease in the amount of the alternatively spliced phosphoStat5a and/or a phospho-JAK2, or alternatively spliced Stat5a and/or a JAK2 transcript or message, or alternatively spliced Stat5a and/or a JAK2 transcript or message, determines or predicts that the treatment, drug, therapy or diet will be effective for the treatment, prevention or amelioration of a leukemic stem cell (LSC) or cells, or eliminating, killing or reducing the amounts of a leukemic stem cell (LSC) or cells.

In alternative embodiments, the invention provides compositions and methods for selecting a diet, a treatment, a drug or a therapy; to treat or ameliorate a leukemic stem cell (LSC), or, for eliminating, killing or reducing the amounts of a leukemic stem cell (LSC) or cells, comprising:

(a) applying, contacting or administering a diet, a treatment, a drug or a therapy to a LSC cell or a cell population or subpopulation, and (b)(i) determining or measuring the amount of an alternatively spliced phosphoStat5a and/or a phospho-JAK2;

(ii) determining or measuring the amount of an alternatively spliced Stat5a and/or a JAK2; or (iii) determining or measuring the amount of an alternatively spliced Stat5a and/or a JAK2 transcript or message;

wherein a decrease in the amount of the alternatively spliced phosphoStat5a and/or a phospho-JAK2, or alternatively spliced Stat5a and/or a JAK2 transcript or message, or alternatively spliced Stat5a and/or a JAK2 transcript or message, determines or predicts that the treatment, drug, therapy or diet will be effective for the treatment, prevention or amelioration of a leukemic stem cell (LSC) or cells, or eliminating, killing or reducing the amounts of a leukemic stem cell (LSC) or cells.

In alternative embodiments, the invention provides compositions and methods for determining or predicting a positive response or monitoring a response (predicting a negative or positive response) to a selective JAK2 inhibition therapy, drug or treatment, comprising (a) applying, contacting or administering a diet, a treatment, a drug or a therapy to a LSC cell or a cell population or subpopulation, and (b)(i) determining or measuring the amount of an alternatively spliced phosphoStat5a and/or a phospho-JAK2;

(ii) determining or measuring the amount of an alternatively spliced Stat5a and/or a JAK2; or (iii) determining or measuring the amount of an alternatively spliced Stat5a and/or a JAK2 transcript or message;

wherein a decrease in the amount of the alternatively spliced phosphoStat5a and/or a phospho-JAK2, or alternatively spliced Stat5a and/or a JAK2 transcript or message, or alternatively spliced Stat5a and/or a JAK2 transcript or message, determines or predicts that the selective JAK2 inhibition therapy, drug or treatment will be (or is) effective for the treatment, prevention or amelioration of a leukemic stem cell (LSC) or cells, or eliminating, killing or reducing the amounts of a leukemic stem cell (LSC) or cells.

In alternative embodiments, the invention provides compositions and methods for assessing the resistance, or relative resistance, of a self-renewing leukemic stem cell (LSC) or cells to a selective JAK2 inhibition therapy, drug or treatment, comprising:

(i) determining or measuring the amount of an alternatively spliced phosphoStat5a and/or a phospho-JAK2;

(ii) determining or measuring the amount of an alternatively spliced Stat5a and/or a JAK2; or (iii) determining or measuring the amount of an alternatively spliced Stat5a and/or a JAK2 transcript or message;

wherein an increased amount of, or the presence of, the alternatively spliced phosphoStat5a and/or a phospho-JAK2, or alternatively spliced Stat5a and/or a JAK2 transcript or message, or alternatively spliced Stat5a and/or a JAK2 transcript or message, determines or predicts that the self-renewing leukemic stem cell (LSC) or cells will be resistant, or relatively resistant, to a selective JAK2 inhibition therapy, drug or treatment, or a decreased amount of, or lack of, the alternatively spliced phosphoStat5a and/or a phospho-JAK2, or alternatively spliced Stat5a and/or a JAK2 transcript or message, or alternatively spliced Stat5a and/or a JAK2 transcript or message, determines or predicts that the self-renewing leukemic stem cell (LSC) or cells will be sensitive or responsive to a selective JAK2 inhibition therapy, drug or treatment.

In alternative embodiments, the invention provides compositions and methods for distinguishing leukemic progenitors from their normal counterparts, comprising:

(i) determining or measuring the amount of an alternatively spliced phosphoStat5a and/or a phospho-JAK2;

(ii) determining or measuring the amount of an alternatively spliced Stat5a and/or a JAK2; or (iii) determining or measuring the amount of an alternatively spliced Stat5a and/or a JAK2 transcript or message;

wherein the presence of the alternatively spliced phosphoStat5a and/or a phospho-JAK2, or alternatively spliced Stat5a and/or a JAK2 transcript or message, or alternatively spliced Stat5a and/or a JAK2 transcript or message, distinguishes the leukemic progenitors from their normal counterparts.

In alternative embodiments of methods of the invention, the method detects a cancer stem cell specific JAK/STAT signaling pathway splice isoforms by RNA sequencing qRT-PCR and/or nanoproteomics.

In alternative embodiments of methods of the invention, the LSC is a chronic myelogenous or myeloid leukemia (CML) stem cell, or a cancer stem cell in a primary or metastatic niche, or a cancer stem cell in a setting of inflammatory cytokines and interleukins as elaborated in a cancer.

In alternative embodiments of methods of the invention, the presence, absence and/or amount of the alternatively spliced phosphoStat5a and/or a phospho-JAK2, or alternatively spliced Stat5a and/or a JAK2 transcript or message, or alternatively spliced Stat5a and/or a JAK2 transcript or message, is measured by a procedure or device comprising (or comprising use of): a fluorescent activated cell sorter (FACS), an array, an immunoassay, an immunoprecipitation, a kit, a polymerase chain reaction (PCR), a qRT-PCR, a nanofluidic assay or device, a nanofluidic proteome assay, a chromatography, a nanoproteomics quantification, or an isoelectric focusing assay, or any combination thereof.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The patent or application file contains at least one drawing executed in color. Copies of this patent or patent application publication with color drawing(s) will be provided by the Office upon request and payment of the necessary fee.

RNA Editing as a Novel Cancer Stem Cell Target

FIG. 7 graphically illustrates data showing that ADAR1 expression is significantly positively and negatively correlated with PU1 and GATA1, respectively; FIG. 7A: mRNA from individual colony formed from sorted CD24+38+Lin− CML patient was measured for expression of ADAR1, PU1, and GATA1 using qRT-PCR; FIG. 7B: cord blood sorted CD34+38+Lin− cells were transduced with either ORF control or ADAR1 overexpression lentivirus; the expression levels of ADAR1, PU1, and GATA1 were analyzed; as described in detail in Example 1, below.

Figure 1B:
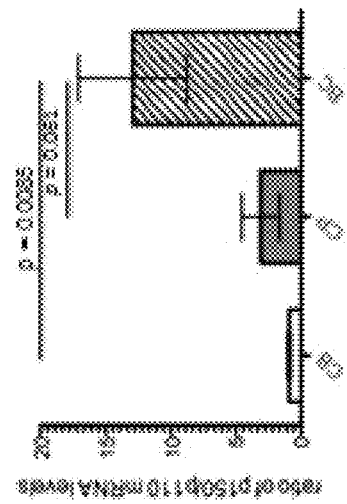
FIG. 1B graphically illustrates data showing the ratio of ADAR1 isoforms (p150/p110) increases from normal cord blood; qRT-PCR of ADAR1 isoform mRNA in FACS sorted CD34+38+lin− cells from normal cord blood (n=8), CML CP (n=6) and CML BC (n=7); as described in detail in Example 1, below.

Compositions and Methods for Dormant Cancer Stem Cell Detection and Elimination

Sonic Hedgehog Targets as Biomarkers of Prognosis and Response for Human Chronic Myelogenous Leukemia FIG. 8a graphically illustrates data where GLI1 and GLI2 transcripts were compared by TaqMan RT-PCR in FACS-purified human cord blood and peripheral blood CD34$^+$CD38$^+$Lin$^-$PI$^-$ progenitor cells, chronic phase CML and in blast crisis CML patient samples; and comparative qRT-PCR analysis of GLI3 transcript levels was performed on normal, chronic phase and blast crisis CML cells; FIG. 8b graphically illustrates data from a FACS analysis that showed a reduction in leukemic progenitor survival following 7 days of PF-04449913 compared with vehicle (DMSO) treatment in SL/M2 co-cultures; FIG. 8c graphically illustrates data from the down regulation of GLI expression, as analyzed by TaqMan RT-PCR in human LSC engrafted bone marrow derived from PF-04449913 and vehicle treated mice; FIG. 8d graphically illustrates data showing spleen size in blast crisis CML LSC engrafted mice after 14 days of treatment with vehicle or PF-04449913; FIG. 8e illustrates images of an immunofluorescence analysis of splenic sections from no transplant or LSC engrafted mice treated with vehicle or PF-04449913: Photomicrographs of sections stained with DAPI (upper panel) and antibodies specific for human CD45 (upper middle panel), human GLI (lower middle panel) and the merged image (lower panel); FIG. 8f graphically illustrates data from isoform-level transcriptome measurements of Shh pathway genes in vehicle-treated and PF-04449913-treated CML BC LSC and in normal $CD34^+CD38^+Lin^-$ FACS-purified progenitors; FIG. 8g in tabular format presents data showing a significant concordance was observed in the relative expression of the 50 isoforms in PF-0449913-treated and in normal cells relative to vehicle treated cells; FIG. 8h graphically illustrates data of nanoproteomic (CB1000) traces of total GLI protein after vehicle and PF-04449913 treatment; and, FIG. 8i graphically illustrates the quantification of GLI protein expression in splenic $CD34^+$ cells derived from vehicle (n=3) or PF-04449913 treated LSC engrafted mice; all figures are also further described, below.

FIG. 9a graphically illustrates data showing the frequency of $CD45^+$ cells in hematopoietic tissues of blast crisis CML engrafted mice; FIG. 9b graphically illustrates data from a FACS quantitation of common myeloid progenitors (CMP), granulocyte-macrophage progenitors (GMP) and megakaryocyte-erythroid progenitors (MEP) populations within each hematopoietic tissue; FIG. 9c graphically illustrates data showing a comparison of cell cycle status of human $CD45^+$ blast crisis CML progenitors engrafted mice in the bone marrow and spleen; FIG. 9d illustrates representative FACS plots comparing Ki67 and 7AAD in bone marrow engrafted viable human $CD45^+$ cells after 14 days of vehicle or PF-04449913 treatment; FIG. 9c graphically illustrates data from a gene set enrichment analysis for the significantly down-regulated pathway "Regulators of Cell Cycle"; FIG. 9f graphically illustrates data showing isoform-level transcriptome measurements of cell cycle genes in vehicle-treated and PF-04449913-treated blast crisis CML LSC and in normal $CD34^+CD38^+Lin^-$ FACS-purified progenitors; and, FIG. 9g graphically illustrates data showing the relative expression of the 75 isoforms in PF-0449913-treated and in normal cells relative to vehicle treated cells; all figures are also further described, below.

FIG. 10a graphically illustrates data showing: Left, Differentiation into CFU-Mix (black), BFU-E (red), CFU-G (orange), CFU-M (yellow), CFU-GM (blue) of normal cord blood HSPC was assessed in hematopoietic progenitor assays (n=3) after PF-04449913 (1 µM) or vehicle treatment for 12 days, Right, illustration of representative photomicrographs of cord blood colonies after 12 days of treatment with vehicle (DMSO) or PF-04449913 (1 µM); FIG. 10b graphically illustrates FACS analysis data from experiments where human cord blood (n=3), $CD34^+38^+Lin^-PI^-$ cells were plated on SL/M2 stroma and treated with vehicle (DMSO) or PF-04449913 (1 µM) for 7 days followed by FACS analysis; FIG. 10c illustrates representative FACS plots depicting HSPC, myeloid and lymphoid differentiation in human cord blood engrafted mice after 14 days of treatment with vehicle (n=3) or PF-04449913 100 mg/kg (n=4), after staining with murine CD45, CD34, CD13 and CD4; FIG. 10d graphically illustrates data from a FACS analysis used to determine the total human CD45+, HSPC, myeloid and lymphoid cell count in bone marrow after 14 days of treatment with vehicle (n=3, green) or 100 mg/kg of PF-04449913 (n=4, purple); FIG. 10e graphically illustrates data summarizing a FACS quantification of G0 (green), G1 (light blue) and G2/S (navy) human $CD45^+$ cells in cord blood engrafted marrow after 14 days of treatment with vehicle (n=3) or PF-4449913 100 mg/kg (n=4); all figures are also further described, below.

Figure 11A:
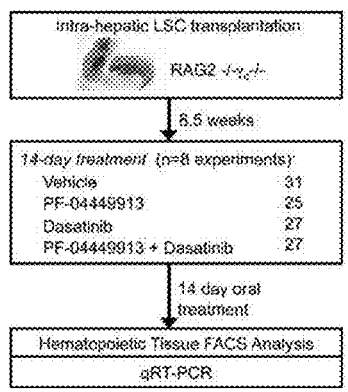
Figure 11B:
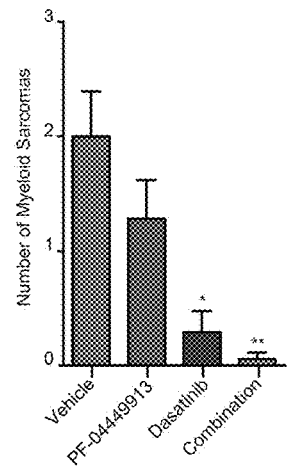
Figure 11C:
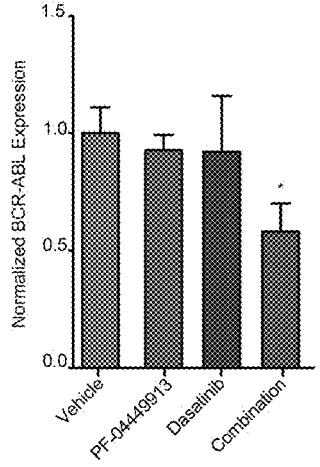
Figure 11D:
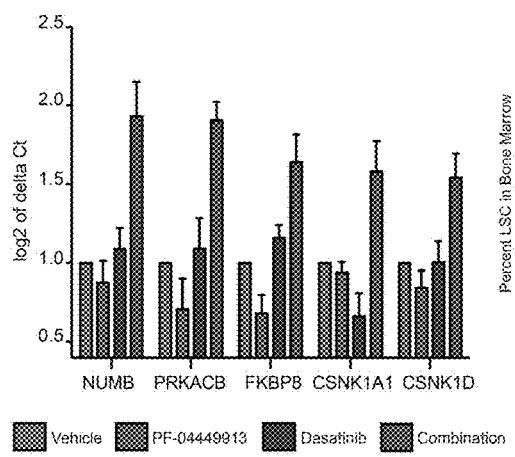
Figure 11E:
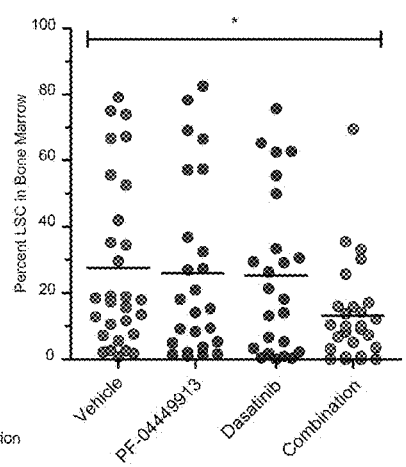
Figure 11F:
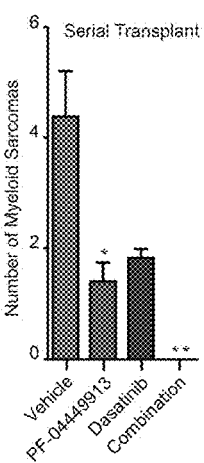

FIG. 11a schematically illustrates in vivo experiments where $RAG2^{-/-}\gamma_c^{-/-}$ pups were transplanted intrahepatically with 50,000 $CD34^+$ cells within 48 hours of birth; and after 8 to 10 weeks, blast crisis CML engrafted mice were treated daily for 14 days by oral gavage with vehicle, PF-04449913 (100 mg/kg), Dasatinib (50 mg/kg) or combination (PF-04449913 100 mg/kg and Dasatinib 50 mg/kg); and then hematopoietic tissues were FACS analyzed for leukemia engraftment and qRT-PCR for BCR-ABL1 transcripts; FIG. 11b graphically illustrates a myeloid sarcoma count of blast crisis CML engrafted mice in each treatment group vehicle (n=13, green), PF-04449913 (n=7, purple), dasatinib (n=6, red) and combination (n=3, black) after 14 days of treatment; FIG. 11c graphically illustrates BCR-ABL1 transcripts in the spleens of blast crisis CML engrafted mice after 14 days of treatment with vehicle (green, n=9), PF-04449913 (purple, n=11), dasatinib (n=8, red) or combination (n=5, black); FIG. 11d graphically illustrates Shh gene expression in FACS purified human progenitor cells from blast crisis LSC engrafted mouse marrow treated with vehicle (n=3, green), PF-04449913 (n=4, purple) dasatinib (n=4, maroon), combination (n=3, dark grey) was analyzed via qPCR array (SA Biosciences); FIG. 11e graphically illustrates FACS analysis of percentage of marrow engrafted blast crisis LSC (n=3 patients) after 14-day treatment with vehicle (n=31, green), PF-04449913 (n=25, purple), dasatinib (n=27, maroon) and combination (n=27, grey); FIG. 11f graphically illustrates myeloid sarcoma counts in mice serially transplanted with vehicle (n=12, green), PF-04449913 (n=12, purple), dasatinib (n=8, maroon) or combination (n=3, grey) treated human progenitors; all figures are also further described, below.

Figure 12A:
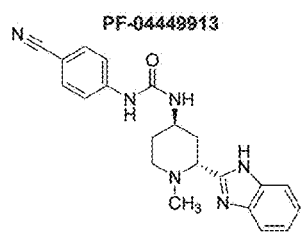
Figure 12B:
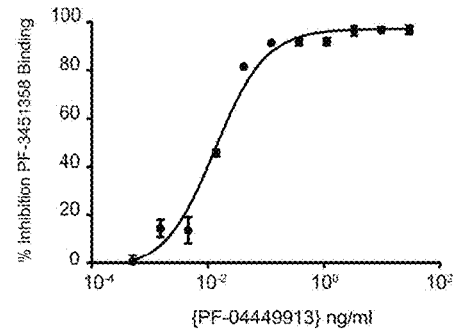
Figure 12C:
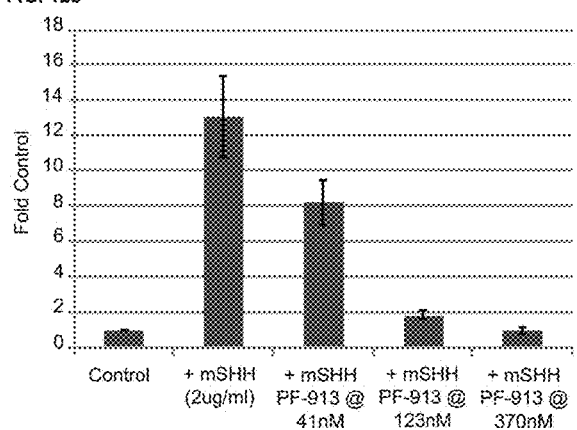
Figure 12D:
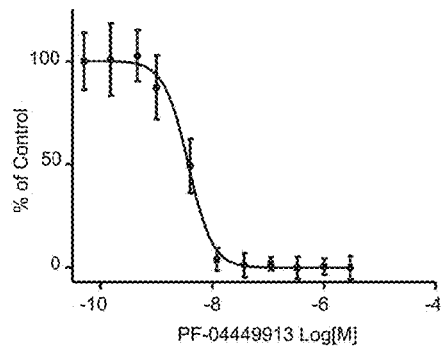

FIG. 12a schematically illustrates the chemical structure of PF-04449913, a selective smoothened (SMO) antagonist; FIG. 12b graphically illustrates data from a competition-binding assay using a characterized cyclopamine-competitive SMO antagonist. PF-04449913 competes with the radiolabeled SMO antagonist for binding to human SMO (amino acids 181-787) with an IC50 of 4 nM; FIG. 12c graphically illustrates data from a study inhibiting Shh-stimulated luciferase expression using mouse embryonic fibroblasts expressing luciferase under control of an 8× Gli-response element (Gli-Luc MEFs); FIG. 12d graphically illustrates data from a study showing dose-dependent inhibition by PF-04449913 in the Gli-Luc MEF reporter assay; PF-04449913 inhibits Shh stimulated reporter activity with an IC50 of 6.8 nM (n=5); all figures are also further described, below.

FIG. 13a graphically illustrates data from a study showing anti-tumor activity of PF-04449913 against Ptch+/−p53+/− medulloblastoma; FIG. 13b graphically illustrates data from a study showing dose dependent anti-tumor efficacy of PF-04449913 against Ptch+/−p53+/− medulloblastoma allografts; FIG. 13c graphically illustrates data from a study showing Hh pathway inhibition in PF-04449913 treated Ptch+/−p53+/− medulloblastoma allografts; FIG. 13d graphically illustrates data from a study showing which genes are significantly down-regulated by PF-04449913 treatment in $Ptch^{+/-}p53^{-/-}$ mice; FIG. 13e graphically illustrates data from a study showing gene signatures are enriched for within the top 31 PF-04449913-downregulated genes in Ptch+/−p53−/− mice; all figures are also further described, below.

Figure 14A:
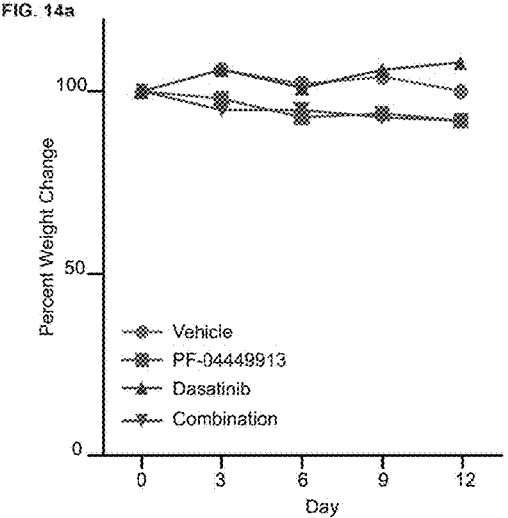
Figure 14B:
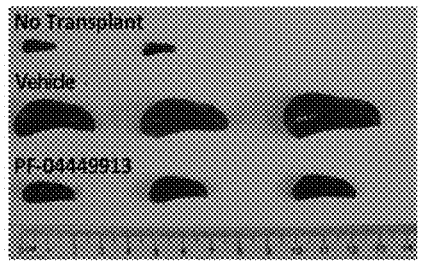
Figure 14C:
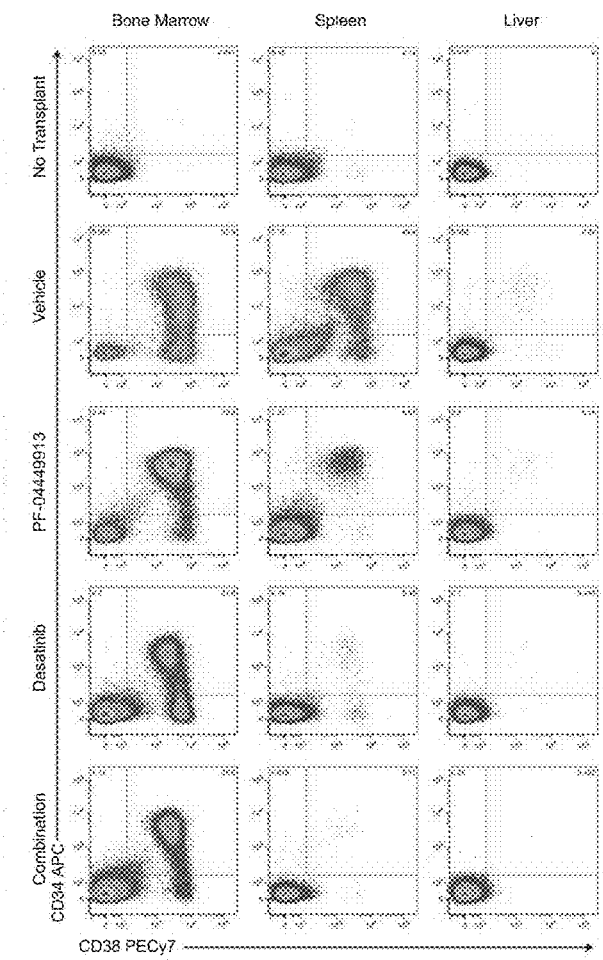
Figure 14D:
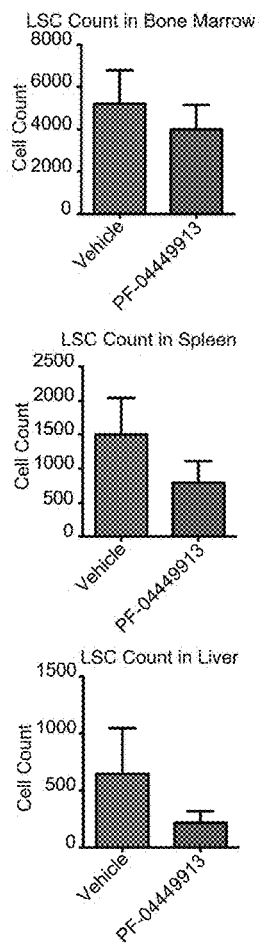

FIG. 14a graphically illustrates data from a study showing the percentage of weight changes in groups of mice over the course of 14 days of treatment with vehicle, PF-04449913, dasatinib, or a combination thereof; FIG. 14b illustrates representative photographs of spleens from no transplant, blast crisis CML engrafted mice treated with vehicle or PF-04449913; FIG. 14c graphically illustrates representative FACS plots of blast crisis CML engrafted mice treated with vehicle, PF-04449913, dasatinib, or combination; FIG. 14d graphically illustrates total blast LSC count in bone marrow, spleen and liver after 14 days of treatment with vehicle (n=15) or PF-04449913 (n=14); all figures are also further described, below.

FIG. 15a graphically illustrates heat-map of normalized expression values on log 2 scale for 10,573 highly expressed genes in FACS-purified primary blast crisis CML $CD34^+CD38^-Lin^-$ and $CD34^+CD38^+Lin^-$; $RAG2^{-/-}g\text{-}c^{-/-}$ marrow engrafted blast crisis CML $CD34^+CD38^-Lin^-$ and $CD34^+CD38^+Lin^-$; and normal cord blood $CD34^+CD38^-Lin^-$ and $CD34^+CD38^+Lin^-$ samples; FIG. 15b graphically illustrates a gene set enrichment analysis (GSEA) summary table obtained from SOLiD RNAseq data comparing PF-04449913 treated mice (n=4) to control (n=4) (average 24.7-58.0 million mapped reads/sample); FIG. 15c graphically illustrates a GSEA enrichment plot for the significantly down-regulated pathway (regulation of Cell Cycle); FIG. 15d graphically illustrates a cell cycle analysis of bone marrow from blast crisis CML engrafted mice after 14 days of vehicle (n=8) or PF-04449913 (n=8), *p<0.05 for both $G_0$ and $G_1$ population compared with vehicle treatment; all figures are also further described, below.

FIG. 16a schematically illustrates a heatmap from unsupervised agglomerative hierarchical clustering of sonic hedgehog (SHH) pathway genes using RNA Seq data from FACS-purified progenitors ($CD34^+CD38^+lin^-PI^-$) from 8 chronic phase (CP) and 9 blast crisis (BC) patients, 3 normal cord blood (CB) and 3 normal peripheral blood (NPB) sample; FIG. 16b graphically illustrates a principal components plot derived from RNA Seq data for 41 genes in the SHH pathway, from 8 chronic phase (CP; black triangles) and 9 basic crisis (BC; red circles) subjects, as well as 3 cord blood normal samples (CB; blue diamonds) and 3 normal peripheral blood (NPB; blue circles); FIG. 16c graphically illustrates box plots for GLI2 expression of 7 chronic phase (CP) and 6 blast crisis (BC) non-treated subjects, as well as 3 cord blood normal samples (CB) and 3 normal peripheral blood (NPBc); FIG. 16d graphically illustrates quantitative RT-PCR data where GLI1 and GLI2 transcripts were compared using quantitative RT-PCR in FACS-purified human cord blood and normal peripheral blood $CD34^+CD38^+Lin^-PI^-$ progenitor cells (n=9, black), chronic phase CML (n=7, blue) and in blast crisis CML (n=10, red) patients samples; all figures are also further described, below.

FIG. 17a schematically illustrates the chemical structure of PF-04449913, a selective smoothened (SMO) antagonist; FIG. 17b graphically illustrates a FACS analysis, which revealed a significant reduction in blast crisis leukemic progenitor survival (n=4 patients) following 7 days of PF-04449913 (1 mM, purple) compared with vehicle (DMSO, blue) treatment in SL/M2 co-cultures; FIG. 17c graphically illustrates data from a Colony forming unit (CFU) survival experiment where cord blood (n=3) or AML (n=4 patients) $CD34^+$ cells were plated on SL/M2 co-cultures and treated with vehicle (DMSO) or PF-04449913 (1 uM) for 7 days, and colony forming unit (CFU) survival was determined and compared to vehicle treatment; FIG. 17d graphically illustrates spleen weight in blast crisis CML LSC engrafted mice after 14 days of treatment with vehicle (n=16, blue) or PF-04449913 (n=12; 100 mg/kg daily, purple); FIG. 17e graphically illustrates nanoproteomic (CB1000) traces of total GLI2 protein after vehicle (blue) and PF-04449913 (green) treatment; FIG. 17f graphically illustrates a quantification of GLI2 protein expression in sorted progenitors derived from vehicle (n=3) or PF-04449913 (n=3) treated LSC engrafted mice. GLI2 expression was determined after normalizing the area under the curve (AUC) to a β2-microglobulin ($b_2M$) loading control (Student's t-test *p=0.001); FIG. 17g illustrates photomicrographs of confocal fluorescence microscopic images of an analysis of spleen sections from no transplant or LSC engrafted mice treated with vehicle or PF-04449913; all figures are also further described, below.

FIG. 18a graphically illustrates a heatmap from unsupervised agglomerative hierarchical clustering of cell cycle pathway genes using RNA Seq data from FACS-purified progenitors ($CD34^+CD38^+lin^-PI^-$) from 8 chronic phase (CP) and 9 blast crisis (BC) patients sample; FIG. 18b schematically illustrates a network analysis performed on differentially expressed genes between BC and CP revealed CDKN1A as a key hub for cell cycle difference; FIG. 18c graphically illustrates representative FACS plots comparing Ki67 and 7AAD in bone marrow engrafted viable human $CD45^+$ cells after 14 days of vehicle or PF-04449913 treatment; FIG. 18c graphically illustrates data from a cell cycle analysis of bone marrow from blast crisis CML engrafted mice after 14 days of vehicle (n=8) or PF-04449913 (n=8); FIG. 18e schematically and graphically illustrates a GSEA enrichment plot for the significantly down-regulated pathway; FIG. 18f graphically illustrates normalized gene expression values for the 18 genes in the core enrichment subset from the "Regulation of Cell Cycle" pathway; all figures are also further described, below.

FIG. 19a summarizes the characteristics of patients enrolled in clinical trial NCT01546038; FIG. 19b graphically illustrates the clinical response to PF-04449913 in the bone marrow of AML patient samples; FIG. 19c illustrates representative FACS cell cycle plots of Ki67 and 7AAD staining of human CD34+CD38− and CD34+ CD38+ cells derived from primary patient samples after 4 weeks (C1D28) of treatment with PF-04449913 (40 mg) on the Phase I clinical trial; FIG. 19d graphically illustrates cell cycle analysis (peripheral blood-CD45+PI−) from a secondary AML patient that was treated with PF-04449913 (40 mg) for 4 weeks on the Phase I clinical trial; FIG. 19e summarizes the characteristics of patient samples analyzed for their cell cycle study; all figures are also further described, below.

FIG. 20a schematically illustrates in vivo experiments using $RAG2^{-/-}\gamma_c^{-/-}$ pups that were transplanted intrahepatically with 50,000 $CD34^+$ cells within 48 hours of birth, as discussed in detail, below; FIG. 20b graphically illustrates a myeloid sarcoma count in blast crisis CML engrafted mice in each treatment group vehicle (n=13, blue), PF-04449913 (n=7, purple), dasatinib (n=6, red) and combination (n=3, black) after 14 days of treatment; FIG. 20c graphically illustrates a FACS analysis of percentage of marrow engrafted blast crisis progenitor LSC (n=3 patients) after 14-day treatment with vehicle (n=31, blue), PF-04449913 (n=25, purple), dasatinib (n=27, maroon) and combination (n=27, grey), Graph shows percentage of CD34+CD38+lin− cells in the bone marrow; *p<0.05 by ANOVA and Tukey post-hoc analysis; FIG. 20d graphically illustrates data showing the amount of BCR-ABL transcripts in the blast crisis CML engrafted marrow mice after 14 days of treatment with vehicle (blue, n=9), PF-04449913 (purple, n=11), dasatinib (n=8, red) or combination (n=5, black); FIG. 20e graphically illustrates a qPCR array assay showing Hedgehog pathway gene expression in FACS purified human progenitor cells from blast crisis LSC engrafted mouse marrow treated with vehicle (n=3, blue), PF-04449913 (n=4, purple) dasatinib (n=4, maroon), combination (n=3, dark grey) was analyzed by hedgehog (SHH) (SAbiosciences); FIG. 20e graphically illustrates data of myeloid sarcoma count from mice serially transplanted with FACS purified human progenitors from LSC engrafted mice treated with vehicle (n=12, green), PF-04449913 (n=12, purple), dasatinib (n=8, maroon) or combination (n=7, grey); all figures are also further described, below.

FIG. 21a graphically illustrates data from a competition-binding assay using a characterized cyclopamine-competitive SMO antagonist; FIG. 21b graphically illustrates data showing that the inhibition of Shh stimulated luciferase expression using mouse embryonic fibroblasts expressing luciferase under control of an 8× GLI-response element (GLI-LUC MEFs); FIG. 21c graphically illustrates data showing the dose dependent inhibition by PF-04449913 in the GLI-Luc MEF reporter assay; FIG. 21d graphically illustrates data showing anti-tumor activity of PF-04449913 against Ptch+/−p53+/− medulloblastoma; FIG. 21e graphically illustrates data showing the dose dependent anti-tumor efficacy of PF-04449913 against Ptch+/−p53+/− medulloblastoma allografts; FIG. 21f graphically illustrates data showing genes significantly down-regulated by PF-04449913 treatment in Ptch$^{+/-}$p53$^{-/-}$ mice; FIG. 21g graphically illustrates data showing Hh pathway inhibition in PF-04449913 treated Ptch+/−p53+/− medulloblastoma allografts; FIG. 21g summarizes the gene signatures enriched for within the top 31 PF-04449913-downregulated genes in Ptch+/−p53−/− mice); all figures are also further described, below.

FIG. 22a is a GSEA analysis summary table obtained from RNA sequencing data comparing PF-0449913 treated engrafted mice (n=4) to control (n=4) (average 24.7-58.0 million mapped reads/sample); FIG. 22b summarizes the characteristics of patients enrolled and sequenced using the gene expression profile by Affymetrix GENECHIP 1.0 ST™ after PF-04449913 treatment for 28 days (C1D28); FIG. 21c summarizes a GSEA analysis summary table obtained from patients (n=8) sequenced after PF-04449913 treatment (C1D28); all figures are also further described, below.

FIG. 23a graphically illustrates data showing the differentiation into CFU-Mix (purple), BFU-E (red), CFU-G (orange), CFU-M (yellow), CFU-GM (blue) of normal cord blood progenitors, as assessed in hematopoietic progenitor assays (n=3) after PF-04449913 (1 mM) or vehicle treatment for 14 days; FIG. 23b graphically illustrates data from a FACS analysis used to determine the total human CD45$^+$, hematopoietic stem and progenitor cell (HSPC), myeloid and lymphoid cell count in bone marrow after 14 days of treatment with vehicle (n=3, green) or 100 mg/kg of PF-04449913 (n=4, purple); FIG. 23c graphically illustrates data from a FACS quantification of G0 (green), G1 (light blue) and G2/S (navy) human CD45$^+$ cells in cord blood engrafted marrow after 14 days of treatment with vehicle (n=3) or PF-04449913 100 mg/kg (n=4); FIG. 23c illustrates representative FACS plots depicting HSPC, myeloid and lymphoid differentiation (panel B) in human cord blood engrafted mice after 14 days of treatment with vehicle or 100 mg/kg of PF-04449913; all figures are also further described, below.

Figure 24:
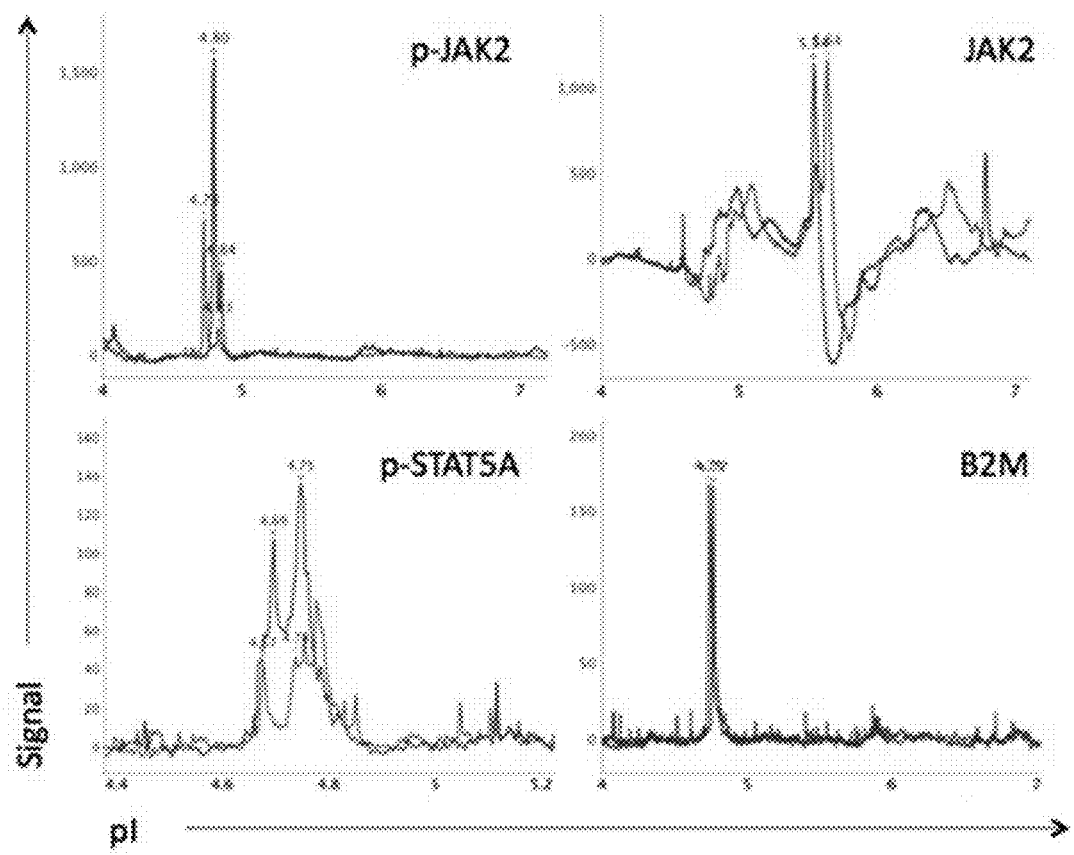

Spliced Isoform Biomarkers to Assess Responses to Cancer Stem Cell Targeted Therapies FIG. 24 illustrates a mechanism of action analysis using nanoproteonomics (CB1000) technology to show the nanoproteomics of SAR302503, panels show phospho-JAK2 protein (upper left); total JAK2 protein (upper right); phospho-STAT5A protein (lower right) and β2-microblobulin (lower right) status after vehicle (blue) or selective JAK2 inhibitor (SAR302503; green) treatment; all figures are also further described, below.

Figures 25A, 25B:
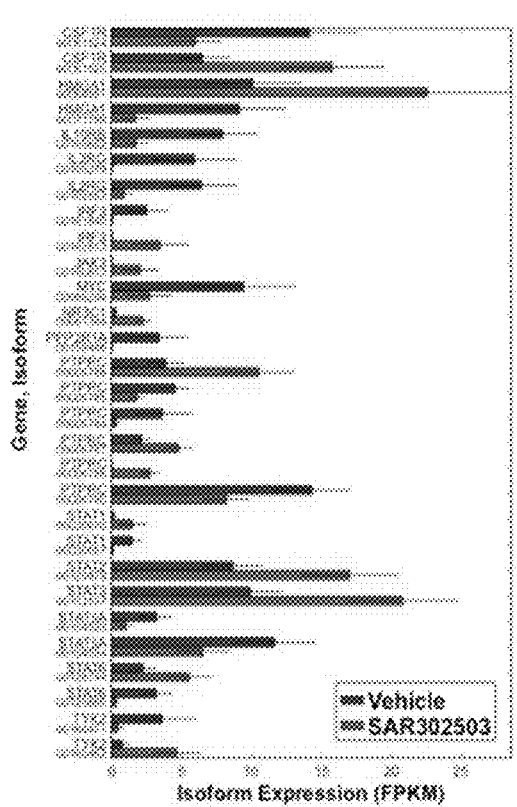

FIG. 25A graphically illustrates RNA-seq-based expression levels of isoforms involved in the Jak/Stat pathway, in vehicle-treated (blue) and SAR302503-treated (red) blast crisis CML sorted progenitors; FIG. 25B graphically illustrates specific isoform expression after treatment with SAR302503 (JAK2 inhibitor) and dasatinib (BCR-ABL inhibitor), relative to vehicle treatment; all figures are also further described, below.

Like reference symbols in the various drawings indicate like elements.

DETAILED DESCRIPTION

RNA Editing as a Novel Cancer Stem Cell Target

The invention provides compositions and methods for treating, ameliorating or preventing diseases and conditions responsive to the inhibition or slowing of cell differentiation and/or self-renewal of dysfunctional cells, cancer cells, leukemia cells, hematopoietic stem cells or cancer stem cells, e.g., leukemia or Chronic Myeloid Leukemia (CML). While the invention is not limited by any particular mechanism of action, compositions and methods of the invention can slow or inhibit RNA editing by, e.g., inhibiting or slowing the expression of or the activity of an ADAR1 gene (adenosine deaminase acting on RNA 1), an ADAR1 gene product, an ADAR1 transcript, and/or an ADAR1 polypeptide.

Unlike many known treatments for CML, which focus directly on the Bcr-abl protein pathway, this invention targets the RNA editing events that lead to Chronic Myeloid Leukemia (CML) progression. ADAR1 is an RNA editing enzyme, required for hematopoiesis; and levels of ADAR1 were assessed in isolated human normal and cancer stem cells (CSC) at various times during the progression of CML. Data described herein demonstrates a crucial role for ADAR1 in both cell differentiation and self-renewal of hematopoietic stem cells. Hence, in alternative embodiments, the invention provides compositions and methods that target, or inhibit ADAR1, and treat or ameliorate diseases and conditions responsive to the inhibition of cell differentiation and/or self-renewal of hematopoietic stem cells, such as cancer, e.g., CML. In alternative embodiments, the invention provides a model for the development of therapeutics for treating CML patients, as well as for diagnosing and monitoring CML patients.

Experiments described herein using cells isolated from normal cord blood, CML chronic phase (noted as "CP" in figures), and CML blast crisis (noted as "BC" in figures) indicate that the expression of ADAR1 p150 is increasing as CML progresses from Chronic to Blast phase. Results include: qRT-PCR data that show that blast crisis leukemia stem cells harbor higher levels of ADAR1 p150 isoform, (vs. chronic phase or normal); increased ADAR1 expression (in vitro transduction of lentiviral ADAR1 p150) changes normal and chronic phase progenitors to a preferred differentiation to a GMP (Granulocyte-macrophage progenitor) population found in the leukemia stem cells in CML; and ADAR1 knockdown (shRNA) leads to a universal (blast and chronic phase) decrease of self-renewal capacity.

ADAR1 is significantly upregulated in cancer stem cell population as CML progresses from chronic phase to blast crisis, the final phase of the disease, and because ADAR1 deletion in CML patient sample reduces cancer stem cell renewal capacity, the compositions and methods of the invention are effective for diagnosing, treating and ameliorate diseases and conditions responsive to the inhibition of cell differentiation and/or self-renewal of hematopoietic stem cells, such as cancer, e.g., CML.

Polypeptides and Peptides

In alternative embodiments, the invention provides compositions and methods for treating, ameliorating or preventing diseases and conditions responsive to the inhibition or slowing of cell differentiation and/or self-renewal of dysfunctional cells, cancer cells, leukemia cells, hematopoietic stem cells or cancer stem cells, e.g., leukemia or Chronic Myeloid Leukemia (CML), comprising use of polypeptides, e.g., antibodies, and/or peptides, e.g., aptamers, that inhibit or slow the expression of or the activity of: an ADAR1 gene (adenosine deaminase acting on RNA 1), and ADAR1 gene product, an ADAR1 transcript, and/or an ADAR1 enzyme.

Polypeptides and peptides used to practice the invention (e.g., an ADAR1 enzyme-inhibiting peptide or polypeptide) can comprise a recombinant protein, a synthetic protein, a peptidomimetic, a non-natural peptide, or a combination thereof. Peptides and proteins used to practice the invention can be recombinantly expressed in vitro or in vivo. The peptides and polypeptides used to practice the invention can be made and isolated using any method known in the art. Polypeptide and peptides used to practice the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289: 3-13) including any automated polypeptide synthesis process known in the art.

Antibodies

In alternative embodiments, compositions and methods of the invention comprise use of antibodies to inhibit or slow the expression of or the activity of: an ADAR1 gene (adenosine deaminase acting on RNA 1), and ADAR1 gene product, an ADAR1 transcript, and/or an ADAR1 enzyme.

In alternative embodiments, an antibody for practicing the invention can comprise a peptide or polypeptide derived from, modeled after or substantially encoded by an ADAR1 gene (SEQ ID NO:1) or transcript (SEQ ID NO:2), or a peptide or polypeptide derived from, modeled after a protein as set forth in SEQ ID NO:3, or subsequences thereof, or immunogenic fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97.

In alternative embodiments, an antibody for practicing the invention includes antigen-binding portions, i.e., "antigen binding sites," (e.g., fragments, subsequences, complementarity determining regions (CDRs)) that retain capacity to bind antigen (e.g., a Bcl-2 family protein, or immunogenic fragments thereof) including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

In alternative embodiments, antibodies used to practice this invention comprise "affinity matured" antibodies, e.g., antibodies comprising with one or more alterations in one or more hypervariable regions which result in an improvement in the affinity of the antibody for antigen; e.g., an ADAR1 protein, or immunogenic fragments thereof. In alternative embodiments, antibodies used to practice this invention are matured antibodies having nanomolar or even picomolar affinities for the target antigen, e.g., a targeted transcriptional activating factor. Affinity matured antibodies can be produced by procedures known in the art.

For example, one embodiment, antibodies used to practice this invention are designed to bind to, or affinity matured to bind to, a polypeptide encoded by SEQ ID NO:1, or subsequences thereof:

```
                                                        (SEQ ID NO: 1)
  1    gaccagacca ttgattcccg actgaaggta gagaaggcta cgtggtgggg gagggtgggg 61    ggagggtcgc ggccgcactg gcagoctccg ggtgtccggc cgtgtcccga ggaagtgcaa 121    gacccggtaa gagcctccgt ccttctcggc tacacctgcc tgggctggaa cgcgcggccc 181    atgcggcctc tccagtctct ggcgccgatg ttagaggaag cgtggggcg ccccggcagg 241    gcactgaggg tggccgcagg gctgggtggg gacgcagctg gtaggggcac agtggccggt
```

-continued

```
 301   ctcggcagcc ttccaggagg cggacgcccg ggccggtgta cttttgtgcg tgtgtgcgcg
 361   cccgtgtgtg cgcgagtgtg ggcggcagag gctgcgcacg gatgctccgg cgctcgtgcc
 421   agccggagcc cagcagctgg gtaccaaagg cccaacagct gggtaccaaa ggcccttgtt
 481   tccctctcgc cggctccccc gcctcggaga gtgactggag agtgagctgc ctgggactcg
 541   ccgcggtagg cgcttttgct gcgccttcta coacaaactg cgttaggacc ggcccttat
 601   cccagagata acatcgccgc cctggcgtgc cttccacagg gaaggcgtag gaggccactg
 661   tggaaagctc actgcggggt cacgccgcc gcgctcagcc tgtctggcct ggtgcaggag
 721   gcctagttgc gtcacctcct cttccttctc tgtttagctt gatttggggg ccccactaga
 781   gggtaatccg gccccaggtg tttcgtgttg gtatcagagt ttgggaaact tgccttccaa
 841   aaagggatac ctgtcattgg atttttgaatg ttgtgtggag gagcccaagt atgcaattag
 901   cggagggagc agagtctagg ctgccacggg aggagacttg caaacagagg cctacacagt
 961   gtcttgttgc tagagaggga ggcaggattg ctagagcggg tcattggggg cagagaaggc
1021   agggcgtca aactgtcagc agttgtgatg ccaacttctt tctccaccag agaagccttg
1081   ttcccatcct tttaaagatc tcttgaaata tcttggtcgt tatttacaaa cagttagtgc
1141   ttgctatatg ggaaaaaggg aaatagagtg gaaagggggac atgaactttg gagtcaggtc
1201   tgccactttg cagctgtttg acattgaatg agttatttaa cctccccact cctacttggg
1261   cttatctaca aaatgaagat aattatatct accttgcccg aggtgtcaga attcgaagtg
1321   tctagctatt attagtaagg gcccagtacc caggagcttg gacttgctcc cttgctgaag
1381   gtttcctatt ggtacagctg cttgagaagc aggggaactt tttgctattt tagatgtttg
1441   ctattctgcc agatatgata tgcagacttg ggggtggtag tggagggggaa atctcaaaat
1501   ccataatctc tctgctgtac acttcattaa attctagaac tgcaaagagg tgaagatctc
1561   actttaggcc gggtgcagtg gctcatgcct gtaatcccag cactttggga ggccgaggca
1621   ggtggatcat gtgaggtcag gagttcgaga ccagcctggc caacatggtg aaaccccgtc
1681   tctactaaaa atacaaaaat tagaccagca tgatggtgca catctgtgat cccagctact
1741   tgggaggctg aggcaggacc atctctcaaa cccaggtggt ggaggttgca gtgagccaat
1801   atccaccatt gcaccccagc ctggacgaca gcgaaactgt atctcaaaaa aaaaaaaact
1861   cactttatta attatagctt ctcattttat tttattattt ttcaattta tcccgagtag
1921   ctgggatcac agatgtgcac caccatgcct ggctaatttt tttttttttt ttttttgag
1981   acagagtctc actccatcgc gcaggctgga gtgcaatgat gcgatctcag ctcactgcaa
2041   actctacctc ccgggttcaa gtgagtctcc ctcctcagcc tcccgagtag ctgggattac
2101   aggagcatgc caccatgcct ggctaatttt tgtatttta gtaagacagg gtttcaccat
2161   gttggccagg ctggtctcga actcctgacc tcaggtgatc cacctgcctc ggcctcccaa
2221   actgctggga ttacaggtat gagccaccgt gcctggccta tgcccggcta atttttgtat
2281   ttttagtaga gatggggttt caccatgttg gccaggctgg tctcgaactc ctgacctcaa
2341   gtgatctgcg cactaggcc tcccagagtg atgggattac aggcatgagc caccgcgcca
2401   ggcctttcgc ttctctttag cacttgctat gtacctgaca cggtgttgag cactttacat
2461   atactaactt atttcatccc tctaacaact gagtgcacta aatattatcc ccattttata
2521   gatgcagaag tgaatcttgg ctaaggtcct gacattaatt aacggcaaag ctggaacttg
2581   aagccagctg tgtggtttga gtcttgctct ttctcagtgt ctagcaagtc ttgctcttgc
2641   ccttgctcat caggctatgt ggtttgagtc ttgctctttc tcagtgacta gtatcccagc
2701   aatgtaaacc tggtgcagtg ggggaaagga ggcccagaca gagtttagtg ggccaggatt
```

-continued

```
2761  ggctgcaaga ataacatctc aaattgtcta atgatacatt atctttttatt ttacattttt 2821  tactcagcat tgtccagata tgaaccaagg tttggccttt tcacccagag aaaaaggaca 2881  ggctcatggg tacactgtgc tgggatgacg ggcacaaagt aggtattcgg aaaatgcttg 2941  tggaaaaaag aaatcctgag gcattgttat ttctgccaga aggaggccca gtgcttatta 3001  cacacaggct ccttaagcca gctattttta tactataaca cactgtaata tgagcatttt 3061  tctgattcat ggatttaaag atttgaagcc ctgtttcaga ccaagattgg tagtattatc 3121  tgtgaccaac tgattagagt tctcaaatat gtgaacaaca gaatctgagc ttttgggctt 3181  ctgtagtaat ctcttgagat agagcaattt gttttgctat aacatctgtt agacttggac 3241  cttaatgggt acaactgctt gagttttctg gagaacactg gatgattgtt tgacatcagg 3301  gataaagagt tcaaatatt aagtttgtct caaattaaa tatttgggaa agacctgtga 3361  ttgatgtgca ttcattgtag gaatagtaca ctagttttaa acagatgata ttcctggtat 3421  ttttgatgag ctattctgtg tcttaaagat gtttaaagat gacttgtagt tgtatagtga 3481  actattagga acatacaaaa tttatataac ccatccatat agactgtgac ttacaccccc 3541  ctcagttcct ccacccaagg aggtctagtt gctgcttcta taccctctgt ttaccttgaa 3601  tctacctatt tcaccatctt tatcagactt tatcagactt aataggtgag accctctgac 3661  atcagcctcc ctttccttct gtaccacccc ttgccacatg cacacagaat gaagctcttc 3721  tccaaaagga ctgtatatta atctacttgc aagtggcaca aacccagtgt aaattaactt 3781  aagcaaaaaa aggttttttc ctccctttga ttatttaact agaaagtcca aaggcaagct 3841  tcaggcatgg ctggatcctg gggctaaaat gatgtcatga gggctttctt ggcccttcct 3901  ttttcggctc cgttttcttt attgacttca ttctctcttg ctgctttctt tttctttttt 3961  ttttttttgag atggagtctt gctcgtcttg ctctgtcgcc cccaggctgg agtgcagtgg 4021  cacgatcttg gctggcggca acctccacct cccaggttca agtgattctc ctgcctcagc 4081  ctcccgggta gctaggatta caggagcccg tcactacccc cggctaattt ttgtatttt 4141  agtagaaatg gggtttcact atgttggcca ggctggtctt gaactcctga cctcaggtga 4201  tccacccgcc tcagcctccc aaagtgctgg gattacaggc atgagctact gtgcccggcc 4261  ttcttgctgc tttctctatg catactgaaa aagctccctg tcagcaaccc caagcctatg 4321  acctgatggc tgtcttttag cgttgtaaat taaccattgc tgacaaggaa atagggagac 4381  cacaattgga gaggtctaca tcataggctc actcttggga tgaggaagta aactgcccgt 4441  ccataacctt atgggatggg gaagttcaga ggtcctaggc aggcagaaac agcacatgac 4501  tactgcaggg gtgtgtgtat gcacacatgt gtgcttacat gtgtgctctt atctcacttc 4561  tttggggtcc ttctagagcc ttccaactgg aatgaatcca gtgggttgtg tttgtccatc 4621  aaactttgac tcccactgtg gcatccatta tgtgctctcc gtcctttctg tacctttgca 4681  tctgctgttt gggttgccct tccccattgc ttcatctggc tgatccttct agattcaggt 4741  catgcttctc ccagaagcct tccttgacac cttccttaat gagctaggca tcccttctct 4801  ctgctcccat aaacacctga gcacaacccc cttgtagatg ttatttctgt ttgataatta 4861  tctgtttatt ggtcatgtct ccactagacg gagagcccct tgaggacaga gtgtcctttg 4921  ctttgtattc cttatctcct acccttagct agtattattt gtcttcatag cactcataac 4981  tgacattgta tatttatttg tttatttatt gcctgtctct cctcattgac tgtctttcat 5041  tagcttcatg agaacaatgt ggaaaggaat tttctttgat caaagcaaaa caaaactacc 5101  ttgaggccta ggacagtgcc tcatactggc atatagtata tgttcagtaa atgtttatta
```

-continued

```
5161  aatgaatgaa tggaaatctt cccacaggaa gaaaacactg gcattatgtt gatgaacatt
5221  ccagtctgca tgatagatac acttctcact gtaaagatct gaaacttgag taccatggca
5281  tcccaggaag gtagcacacc tcttcccata tgtgtttgaa cctgcagagg tcaggcccaa
5341  ggagcctcca gctggaaatt ctaccctgtg tgatgtttca ctcctctcaa acttttctga
5401  actttgatag gttgtatatt aaggccttct ccatattttg gggccctttc cttggagtat
5461  ttattttaa aacatttatt taagcactta caaggtgaca ggcactgttc ttagtccttt
5521  ataaatagca actcactctt ggactggagt tggggaccaa agggttgtca actttaaaac
5581  ttttttcttt ttaagtacca aaacactcaa gaacagaaat aagactactc tgcatctagt
5641  ccatcttgcc ctccagaagt agagctatct aacagcctga tacaggtctt gtccctgccc
5701  tttcctcagg tttttacagc catagctagt aaatataaca tactgcatct catcgccttt
5761  gtttggtctt cacccaaacg cagccacgct ctgccgcagg atatgtggca gagccaggtg
5821  gggaatcagt ggctcagagc ccactctgct tttcaggaca taggctgctc aagcatctgt
5881  cttcagccct ctcccaggga gggcctaaac ccacatcctc aggccctgc agagcacatc
5941  catcttcctg gttacatgtt atgccttatc tgtgggaacc ctagccacgc cacacccaca
6001  cctcaacaca tgaagaaagg gaaaaaatac ccctttcttt cttttgacaa caacaaaaaa
6061  gtacttctcc tacaaataga gacttgaaat gacagggtta ttatttaacc ccgctcttac
6121  tccaaacatc caagcggcag tttcagccta gctgcagtac tctgttgtag tgcttagtcc
6181  tgatttgctt cctaagaagt gaataccagt ttccactgcc atcagcaatg cctgagtact
6241  tactgtgcct ctccctcacc ctaccctcct ctccagaact gagtatttta ctaaaaaagg
6301  aaaatcttag ctaaatttga aatagcatct cattttaatt tgcatttttt attataattg
6361  tttgagccct ttttacccat actgagccat tttatttct acttttttaa tttttggtta
6421  atgttttgtc tattcactta ttgtgtttaa gtgattttta aaatatacaa atattctgaa
6481  aaacatgagt ttatcctcat ggtaaaaagc aaacaatttt atttgcagtt aattctttt
6541  agtttattgt ttgccatcta attttggctt tatcattaaa aatacaaatc tatttttcat
6601  tcttttttag acaaatttta ttcttttga tttcttttgc ttgtgagcat aaaaaggttt
6661  ttttccttat tctatattct agttttttt atggtttgca tttttacata tgacttttaa
6721  aaagctagca ttcagtttta tttcagattt taataagata tttgatgaaa atagtgtaat
6781  attttaaata aaatcagttt taattaaagg tctatgtttt gttttaagga tgtttatatt
6841  actgtactta tatttttct ttttaaataa tttatcagaa tagcgaacag cttgcttgac
6901  aaaactaaga ttcacatata tagataatca taattttagt gttcttagcg tttccataaa
6961  ttgctgcatg aaaagatatt tatgtgtggc tgtctggttt aaagaggcac tcgtgcttgg
7021  caacagcttt tcagcatgta gccaagatga caaattcagc ctcttccagt tcctcttcct
7081  cactatttcc ctaagatttt tttcatggga gcataactat gtgtatctct gtgcacagat
7141  tttatgtgta cctttcaatg tattttaaca aaaatatatc catttaacta tccaaatcaa
7201  gaaataaaac attttcatta cctcagaaag ctcccctgtg gtagtcacca ctaccccaa
7261  aggccaacac tattgatgtc tgatatctat cactatagat tagattagtt ttgcctgttc
7321  taaaatttca tgtcagtatg tgcttttgtt tgtggcttct ttcagtgagg atcaaccatg
7381  ttgcatgtgt cagtatccat tgtgtgaata tgcatcaagt tatttattca ttagttgatt
7441  gacatttggg ttattccagt ttggggctat taagaagaat aaagctctat gaacagtttt
7501  ttttcctgtt ttttattgta gtaaaatcaa caacataaaa tttaccatct taaaccattg
7561  tttgtttttt tttttgagac ggagccttgc tctgttaccc aggctggagt gcagtggcac
```

-continued

```
7621  gatcttggct ccctgcaacc tccacctccc aggttcaagc aattctctgc cttagcctcc
7681  caagtagctg ggattacagg cacccaccac catgcccagc taatgtttgt attttaata
7741  gagacggagt ttcatcacct tggccaggct ggtcttgaac tcctgacctt gtggtccacc
7801  cgccttggcc tcccaaagtg ctgggattac aggcatgagc caccgcgcct ggcccgtaaa
7861  ccatttttaa gtgtatagtt cagtagtgtt aggtatagtc acattgttgt gcaacaaatc
7921  tccagaactt tttcatcttg cagatctaaa actatattca ttaacaactc ctcttttccc
7981  ccatcctcca gccctggtt ctatggacat tcttgtacaa gtcttttgt ggccattttt
8041  cttgggtaag tacccaggag tataaatgct gggtctagcc ttagaagaaa ctgccttaca
8101  gttttctcga atagttagtc gtaccatttt atgttccac agtatacaaa aatgctagtt
8161  tgcttcatat cctcaccaac attaggtatt gtgagtcttt ttttatttta gccattctgt
8221  agctgtgaag cggcatccca ttgtggtttt attacatgtt ctagtcagtt atttacatgt
8281  ctgttcccat tactagactg tgaacttcat aagggaaggt tcatgcagta agtagttttg
8341  ttttttttgt tgttgttctt attaaccttc ctcttcttat tttgagggtg atacatgctt
8401  tattattaaa aagaacttaa aaattataga aagctattaa aaagccaata aaatcacagg
8461  ttagcccacc tctcagacat catcaggagt attttggtct ttcaggcagt gctgtgttgg
8521  ttcgtacaga cagaacagtt cccatgatgg ttgattcagc aacccagcat tgttccagcc
8581  cactgccttg ctatcctctg gacatcactt attcccagcg aggagccctt ttctcagaca
8641  gccccagaca gattgttttt gtggtttgct ggccacaaat gtatcacatg tatcactgac
8701  aaaagaagta gaatcctcaa tactggatta aattagatta attaacatcc ttcctctggg
8761  gctggggagg gaacctggcc ttcttaggaa agtggacaga atcagggcac tctcagaaag
8821  ggaggcatag ttctagcgta ggccactaac attatctgcc tctttttttt tgagatggag
8881  tctcactctg ttgcccaggc tggagtgcag tggcacaatc tcagctcact gcaacctctg
8941  cttcccaggt tcaagcgatc ctcctgcctc tgccccacta gtagctggga ttacaagtac
9001  ctgccaccac gcccggctaa tgtttgtatt tttagtagag acggggtttc gccatgttgg
9061  ccaggctggt ctcaaactcg tgacctcagg tgatccacct gcctcggact tccaaagtgc
9121  tgagattaca ggcataagcc accacggccg gcctgcttct ggtgtttttt atttaatttt
9181  tttacactta gtctgtcaat acatttgcaa tttgttttgg cttattaata taaggctaga
9241  ctctagactt tttttttttc caaatagcca ttcagttggc ccagctccat ctgttgaata
9301  acgcttttc tcactgctgt ttttggttcc tcatcatgca ttggattct gcacatacta
9361  ggctctgttt ggagggaggt ggttcttttc tgttagtctg aagctctacc cttgctttat
9421  accagtgctg ccttggttta attagcgtag ctgtcttctt tttaaaaaac tgttttgttt
9481  gttcttgtac ttgaacttta tttattccca tccaatgacc tattaattgc atctgaactt
9541  tagagtaatc attttgtcag gtatccactc cttactgccc caacctcata gtatttgcag
9601  taaatcgtta tttaatttga tattaattag tattcataaa gtattctgcc atcacatttg
9661  agactggtat gtccttctat ttaagacata tattcctcag cagagttttg taattttcca
9721  catgtaagct cttcacattt cttagggtta gtcctagata cttctttttt ttaatttaat
9781  gttttatttg ctattaagaa tatggtattc ttaatagcaa ataaaacatt aaagtatata
9841  aagaatatat acttactata tgaagaaggt atacttatat attactatag taatgtatat
9901  attactatat aaagaatata actttagat gcatatatac atatgcatat aaagaagcta
9961  ttgtgtttta tatgtttctc ttatattcaa ccatattcct tgactggtat tggttctaag
```

-continued

```
10021  agtttttcag ttgatcctct tgaatcaact agggttatga tgatatcatc tgcaaataat
10081  ctattttct ttttaatagt ttatctctta tttttgtttc ataatgtaga atatgtaaga
10141  atttccatag gtagaaaaga tattaaatat atatatttaa catgtgttaa ataccatatt
10201  tgttttaaga ccactgagca taaagacttg ctattgattt aataacagat ttgggggggca
10261  ctatattaaa tgtatactta cactgtaatt catattccaa tatcagaaat gttaggatgt
10321  aaaaagcagt gcatcttaga attaaggaaa ataacaatgg taatggtagc cctccttttt
10381  ctcgtttgag tggtagtgtc taactgttcc attctacata tgatattggc tgttgattta
10441  tgatagacag tctttattat taagggtcc tcacacatct tcctgtttgg aagaggtttt
10501  gtgttggttt aatcagctta ggagggaaag gtgatcatca gggtcacttt cgtgcagaat
10561  cccacctctg cccacaattc ctgccttctt tgaactttct ttgttaaagt aagaatctag
10621  actctggcat caaagattga tatgctaagc agaagtttac tgcccagcag agaaccagtt
10681  gagtgcaaaa gttaggctct gagatctaag ccttgagggt ggcaatgagg gatgaggtag
10741  gtttttaaaa ctcatggtct ccatcccata ttaggaaatc aaagtctcca aatgctactt
10801  attggccagt gttatctgga ctaggcattg tctaagcaac aagcaggaca ggacgcttgc
10861  aggggttttt gataagttat ctctcactat gtctatgagt caggataata gtgccccagt
10921  cattgttttg gtagaagtcc agtccactgg ctaggcagcc atgttgggat tcatcacttt
10981  gtagtttcta acttttttact gtattccata ttggaaagtt cagccctcct ctgagatacc
11041  cattgtccac tagaactcca gacagaagtg ctggagaggg cagtgggcca ggtcaggaag
11101  acataagcca gagttgaagt acaacagtgg aaagaacaaa gtctttggag cagtgcctct
11161  taaccttcgt tctgggtaca cagatctatc tgggagtctg aaagctatgg gctgtctctt
11221  gagggaaatg cgcatgttgc gttttttcagt aaatattttt gagcacgctg aaagcaaaac
11281  acttgtatag ccctagcttc ttggaacttg tagtaagaga cacagatatt taccaaaaaa
11341  ccacatgaag aaatgtaaaa ttacaagtgt aaatatgctc caaagagag gagggggtct
11401  tgaaatcatg cgatgggagg gggtagggggt tagagctcaa gctcttcctc cagaagtgtt
11461  gactaccctg agatctgaag ggcaaatcat aggatagtgg aaaggaggag aaataatcca
11521  gagagagggg caagtatgtg gcaggaggga gcatggcaat ctagagggag gaaaagaagg
11581  ctcagggagg ctgggggaca gagagatggg gcatggtcca acagaaggga gaaggatggc
11641  agggctaggc cacgtaaggc tttggagcca tcgtgtaaag atgtttgcct ttatcttaag
11701  agcattagga agccatcaaa gtatttttg ttaataatgt aaatatttga tatgcataaa
11761  agattcctgc agcatatatg tatcactgaa atacaacaat gaaacgaatg cacgtgaacc
11821  taacaccttc ccctgaatga gaaccttatc tgtattgctg aagcctccct tgtcgcctct
11881  tggatcccat ctgcctgtgt tcccctccc ccttaattg ctaggttaga attttcttga
11941  attccatgca tgacatgatc agatttggt tttcagagat cacacaagct gtgtcgagaa
12001  gactggatag aaaagaggcc aaagtacatg cggggaaacc agtttggagg ttgtaatcac
12061  aaaacacaat cttactaaaa gtttgtctgc attttatttt attgccttgg aaatttattt
12121  ctttcacaga tgatttattt tcatcatttt aaaatataa attaatggta tcttcctaga
12181  aaaaaataaa atcagataaa actaaaagct ctaattctgt tggacaataa tgagaaggct
12241  gtactgtttg gcttaactaa aaaatgtggt gaggcatggt ggctcacgcc tgtaattcca
12301  gcactcaggg aggccaaggc aggcagattg cttgagccca ggagttcgtg actggcctgg
12361  gcaacatagt gcggccctat ttctacgaaa aaaattttt ttaattagcc aagcatggtg
12421  gtatgtgcct gtagtcccag ctgcttaaga agctgaggca ggaggattgc ttgagcccag
```

```
-continued 12481  gagtttgaga ttgcagtgag acatgactgt accactgcac tctggcctgg gtgacagaga
12541  ccttgtcttt taaaaaataa ataaaggaca tcatggctgt gcataagtac atctatgaca
12601  gctagtctgt tttggccttt tccctttgat gtacccaaat gcagaaactc ctatctcgcc
12661  tagcaaagcc tctggcagcc ctggacttgg agctccctgg tttgtattgt ccagcaaaga
12721  tgctgtagta gtttcccgtg gctgtctgct gtaaaaaaat aaccacaaac taggtggctt
12781  aaaacaatgg aaatttatta tctgacagtg ctggaggcca gaaatctgaa atcagtatca
12841  ctgggccatg ttggcagggc tgtgctccct ccagaggctg taggggagaa tccattcctt
12901  gcctctccca acctctggtg ggtgctggca tcgcttgtgt tgcggctgcg tcgctctagt
12961  cttcaaggct agcatcttcg aatcattctc tactctgtct tcacatggcc ttttcctctg
13021  tgtgtgtagg tggaaatttt tttgaacttg ccaacactaa agaaacact tttaaagacc
13081  agtgttcact tgaaaatggc tctctgtcaa attccaagaa accagttca ctgaaagtca
13141  gttctacaaa agcccctcca tcctacccct ttgcctcctc agtttcctcc tcaatcttct
13201  gctctacagc agcagggaga cagcagagca tatttcctct aaattctatt aagaagacag
13261  aataaaaact ggtcaattaa gactagggag atttaagaaa aaagtaaatg caacatattg
13321  gttgtttcgt aaattggtta tccaaggaat tgaccatttg gcaaactgac tttcggcaaa
13381  ttggctgttg gtgaaatcag cctatttccc tgagaaacac tgcagaaggc agggcagtgg
13441  ctgccttgag cctgcccagg acaggactgt gactgtcccc tcctgctttc tacaagccat
13501  ggagataggg gcattgctct tgcatgaggc tggggctgag agcagccccc tacaggctgg
13561  atctggatcc tagggaagaa gaagatggga gatctcccc tttgggtcct gactcaatag
13621  aacccaaatg taggccagta gcggaacctc tgtgctagcc agagtcaggc cagaagtcag
13681  tcaggtgctg catccaagaa caatctagca tcggagaagc ggcttaaggg tgtcagaata
13741  taatgtataa aaccacaagt tgtataaggt caccccgtgg ggtagttatc cgactgaatg
13801  tacatttatt agttatacat acttgcaaaa gattgcacac aggcctgtta gtcattatta
13861  ttagtattat tttacatatg taatattatt gcaaatgtta tatctttatt atataatact
13921  taagcctggc acatatagct agttgataaa taccactttt tttctttgtt actagataac
13981  ttactggagt ggataaatgc acttaatagc ttttggagac ctcttttct tctgggggta
14041  cctgaggcat ttcttgcttt ctttttttt tttttgaga tggagtttcg ctcttgttgc
14101  tcagggtgga gtgcagtggt gcgatctcgg ctcactgcaa cctccgcctc ccaggttcaa
14161  gtgattctcc tgcctcagcc tccctagtag ctaggattac aggcatgtgc caccacaccc
14221  ggctaatttt gtattttag taaagacgga gtttctctat gttagtcagg cgggtctcga
14281  actcccgacc tcaggtgatc cacccacctc ggtgtcccaa agtgctggga ttacaggcat
14341  gagccaccgc gcctggccac atttcttgct ttcttgtaac ttcaaaagcc agttttagct
14401  gggagcaatg gttcacgcct gtaatcccag cattttgga ggccgaggca ggcggatcac
14461  ctgagatcag gagtttgcga ccagcctggc caacatggtg agaccccacc tctactaaaa
14521  atataaaaat tagccaggca tgatagcgcg tgcctgtagt cccagctact tgggaggctg
14581  aggcaggaga atcacttgta cctgggaggt ggaggttgca gtgagccgag atcatgccac
14641  tgcactggag cctggataac agagtgagat tctggctcaa aaaaaaaaa aaaaaaaag
14701  ccatttgtga tcattaacat caatagaata tatgtcagca taaatactgc cacagagcac
14761  tactcagcca gttgggcaac tcactcttct ctaccaaaag ctttacaggt tatcaaagca
14821  agtgggttta ctgtgggagg ctactgtgaa ttttggaaat taatgttgag ggactagcgc
```

```
-continued
14881  agtggctcac acctgtaatc ccaacatttt gggaggccga ggcaggcgga tcacgaagtc
14941  aggagattga gaccatcctg gctaacacgg tgaaacgccg tctctactaa aaatacaaaa
15001  aattacccag gcatggtggc atgtgcctgt agtcccagct actcgggagg ctgagacagg
15061  agaatcactt gaacctggga ggtggaggtt gcagtgagct gagatcgcac cactgcactc
15121  caacctgggc aacagagcga gactctatct caaaaaaaga aagaaagaaa gaaaattaat
15181  gttgttagga actgttgtag tggaataaaa actcagtgat aaagaattga ggagaaacaa
15241  cgataacaaa aaaggagggc aataaatttg tgcctagcaa ctctgaattg cttactatac
15301  atttcctaag agttattcta aaatgatgcc ctggtactta aaataactga agcaggctgg
15361  gcgtggtggc tcacacctgt aatcccagca ctttgggagg ccaagaccgg cagatgacga
15421  ggtcaggaga tcgagaccat cctggctaac acagtgaaac cccgtctcta ataaaaatac
15481  aaaaaaatag ccgggtgtgg tggcaggcac ctgtagtccc agccactcgg gaggctgagg
15541  caggagaatg gcgtgaaccc aggaggcgga gcttgcagtg agccaagatt gcaccactgc
15601  actccagcct gggtgacaga gccagactcc atctcaaaaa aaaaaaaaaa aaaaaaaaa
15661  aactgagtaa tttattactt tctttgataa tatgttgcaa attgtttaga atacattcac
15721  aggcagtaca tttctgtccc agtatcactg tatgagcaaa tactgaagga gtttgcagac
15781  atctgcttta cagtagacag gagatagatg ttccaattgg atatagccca tgtgtgtagt
15841  aaagtctggt tataggaaat tacagattaa aaaagactgt tgttgtaaac atgtatccct
15901  gcacgcagta aggttaaaca gaagatccac aacaaaccaa attaacaatt actaagtcag
15961  actaacagtt acttatagtt aaaaagcaag aatagcaggg attggaaaac aaaaccaact
16021  caggagccct gataatagca tgtcctttcc tataggtggg gaagtctcac cccctgaatg
16081  cacctataga gctagagctt ggcactgcta tgtggaagcc agacttctga gaatactgag
16141  tttctgagta cttcattttt agacagtaac tcttaatcat ttaggtggtt tttaataagt
16201  agacctaggt ggtatagata catctgggt catttcacag gcccctgggg aggtgagcca
16261  ttctttatag gaagagctcc tcccttgaga ggactgacca cccatgtgtt ggcagtgccg
16321  ttacgcacgg ggaagttacg cacagggaaa atgctcgaag ggtaggcacg gatgaatgat
16381  gaattaacaa tgggtgattt ttattgtgtt tgcttgtctg tattttctga aataaaccta
16441  ttattttggg ttaattttt taaagacttt catccaactc gtcaagttcc tacaatagaa
16501  cagttaaaaa aaaaaagaca tcatcacctc acaaccatgg gggagttaaa acaattactg
16561  aggggagga gatgaaacgt ttatgaataa gactgtctgc agttacttga gctgctaaga
16621  ttaaatgaca ataggagttg ttgttctttc aaggcataaa ctgaccttct gttgaggaaa
16681  gttcactgct ttgccactgt gtcctatgtt agattaaaag gggtgggggg agcagcggtg
16741  cagcttccct cggacagtag ttgtgattaa agcttttctg gatcatttct gaagaagggt
16801  aaaggctttc agattgtctt gcctgaagac aagaaagcag aggtaagata taactcctgt
16861  tacttaaacg gaggaaaaaa aacatgggga agtggactgg aattgcaaca gcaagagttt
16921  gttgtggttc ttgtttgttt ttacctttta aatttgtgaa atacagcata tatatacaga
16981  aacatgaata aaacgtaaat gtataatgaa attattggaa agcaaacata tgtagccact
17041  acccaagtca agagctagaa catcaccggt acccaaaaga tttcttccca gtcaaaactc
17101  ccacctttct ccctagaagt gattaaccac aattttgtct tttttttttt ttttttcttt
17161  ttttttttttt ttgagacggt gtcttgctct gtctccaggc tggagtgcaa tggcacaatc
17221  ttggctcact gcaacctccg actccctgct tcaagcgttt ctaccacgtc agcctcccca
17281  gtagctggga ctacaggcac acgccaccat gcccagctaa ttttttgtac ttttagtaga
```

-continued

| | |
|---|---|
| 17341 | gatggggttt cactatgttg gccaggatgg tctcgatccc ctgacctcgt gatccgccca |
| 17401 | cctcggcctc ccaaagtgct gggattacag gcatgagcca ctgcgcccgg cctcatttg |
| 17461 | tcttttatgc agagcatact atagtttggt tttgcctggc ttgggacttt ctgtaagtgg |
| 17521 | gatcatatag tatacatatg gcttttccca ctcagtatca tatttagata attagctacc |
| 17581 | ttgttgcatg cgtagatctt tcattttgt tgctgtattg tattccatca tgggcatatg |
| 17641 | ccaccattta tccatttac ttttgatgga catttgggtt gtttccagtt tggggctat |
| 17701 | taattacaaa taatgcaacc atgaacttct tggggtttac cattacctt ctagataatg |
| 17761 | gtaaactggt ttcctgtagt gactaagagc tgctctgcat ccttgctgcc acctggtcta |
| 17821 | atcagatggc taatgctgtc tgtctggtga atggacagta gctcactgta gctatactgt |
| 17881 | gcatttctct gatgtgatgg ggttgagaac cttttcatat gtttgatatt ttttatctcc |
| 17941 | tgtgaagttg tctttcgatt gttttgccc attgttatac ctactgaggg gtctgttatt |
| 18001 | ctttcaacta accagccctc tgaaggcgaa ataaggata caaaacatgc ttcctgcccc |
| 18061 | cgaggagatg acttgacaat tctagaggca gatatatgaa caagaagtac atgataattg |
| 18121 | tgattactga gcatccatc ttccctagca gactagctaa aggatggcgc tcttatttgt |
| 18181 | gtcatatcct gggtgcttaa cacagtatct gccacataat taggtgctta gtaaagtttt |
| 18241 | gttaaatgat cgaatggggc gttttagcg cagtgtgcaa gtgcccatt aggggtaggc |
| 18301 | gcccagtaac tcgagaagca tggagtagga aaccacaaac agcacctgct ccccctcctc |
| 18361 | tcccctacc tgctgtgggg aaggcctccc ttgtaaattt gaaaggttga ttcacgggaa |
| 18421 | gccgtggagg aggtgcatgc taggccaacg aatagaatgt gcaaaggccc agaaggaaga |
| 18481 | cagagcccag cctgcaaggg aatgttaatt tggagtgact aacaccatga aagggcatca |
| 18541 | gctggagata ctgctataaa gggactgcct tgtaatttca taagcatggg ggtaaaatta |
| 18601 | agattaaaca cagggaaaga acattctcac aggtgaggat ggtgttgaac cctagaataa |
| 18661 | tcgtttccca gataccttga acaaaaatcc agcagttaga gaagcctgac catgaagcaa |
| 18721 | atttgacttt tgtccctcta gataacaaaa gttatctttt tgaaagtaat ggtgtaattt |
| 18781 | gaatgagtgt agagaagcgc tgaagactga gctttactaa agccttcaga cctggatttg |
| 18841 | gcagcagcgt ggccttagtc aagcctcggt ttctacacct gcaaagtggg aataatgcct |
| 18901 | accttggagg gctgttgtga agattaaggg agataataca tgtaaagtac ttaaccattt |
| 18961 | gcctggtggg gtagtttta tgacctagat cctaaattgt tcactgctgc tgttgctact |
| 19021 | cttggtactt tttactggct ggcatctgct tgcttaagtt tataacatag taggagcatt |
| 19081 | aacaaggtcc cacggtgggg accttggtcg tttgacgaga tctgcgctcc cgcccatccc |
| 19141 | ctcccccccc cctccacatt ggagacgcgg ccaccaccgc gctggcgcgg agagagggag |
| 19201 | gaccgggcgt catgctgttt ctggcctgag gttttgtgtg cctttgtttt ccttttgctc |
| 19261 | tattcgtgta ttcctgccta cggcctgtgc ggggaattag gagctcagta ctgaaacggc |
| 19321 | ggttttccta aacagtaccg gacgggcgcg ggggctgacg cctgtaatcc caacactttg |
| 19381 | ggaggccgag gtgggcggat ctcttgaagc cgggagttcg agaccaccct ggctaacgtg |
| 19441 | gtgaaaccct gttcttacta aaatacaaa aaaaaaaaa aaaaaaagc caggagtgat |
| 19501 | ggcgctcgcc tgtaatccca gctactccgt aggctgaggc aggagaatcg cttgaacccg |
| 19561 | gggggcagag gttgcagtga gccgagattg cgccattgca ctccagcctg gcaaaaaga |
| 19621 | gcgagactcc gcctcaaaaa aaaaaaaaa agtaccttcc gtagttctca tgcagcggag |
| 19681 | gggttcgact tgtaaccggc ctgaaaccaa gcgtggcgca agatttgctc aagcccctcc |

-continued

| | | | | | |
|---|---|---|---|---|---|
| 19741 | tcttggccaa | actttccgga | ggggaaggct | ttccgaggaa | acgaaagcga | aattgaaccg |
| 19801 | gagccatctt | gggcccggcg | cgcagacccg | cggagtttcc | cgtgccgacg | ccccggggcc |
| 19861 | acttccagtg | cggagtagcg | gaggcgtggg | ggcctcgagg | ggctggcgcg | gcccagcggt |
| 19921 | cgggccaggg | tcgtgccgcc | ggcgggtcgg | gccgggcaat | gcctcgcggg | cgcaatgaat |
| 19981 | ccgcggcagg | taagccgggc | cggccttgga | ccttcgccgc | cgtctgggtt | ctgggacaac |
| 20041 | ctcacaggct | tgtgttgca | gtgcgtagcg | tgtgcgtctt | gtgagtgtta | gagtgtgtgt |
| 20101 | gtgtgtgtcg | tcttgccaag | cagcattgct | ggtttaggaa | tttgtgcgtc | ttgtgagtgt |
| 20161 | gtgtgtgtgg | gtgtgtgtcg | tcttgccaag | cagcattgct | ggtttaggaa | tttgtgcgtc |
| 20221 | ttgtgagagt | gtgtgtgtgt | gtgtgtgcgt | gtgtgtgtag | tcttgccaag | cagcattgct |
| 20281 | ggtttaggaa | tttgtgaatt | tgtatcctgc | tcattaattc | tgcagaatga | agcagtgcgt |
| 20341 | gaagagggct | tgggggaaaa | tgcgcccccg | tctgagtagg | aaggcctgag | cccatgtcaa |
| 20401 | ggcagacaca | tcgtctccct | ttctgctagg | gcccttgtg | aacccccta | ccccgcttt |
| 20461 | agccccactt | gaacaacgtt | cggactttga | gcagcgcaca | ctatcctcag | ctcaccttat |
| 20521 | ccacctcctg | aaggccttct | gggagttaaa | aatggcactt | aagctgtagg | agaaagcttg |
| 20581 | ttaaccactt | tatagctaaa | aactgggaaa | acacaaatgg | ccttcagcag | gttaacagat |
| 20641 | aaactgaaat | acatccacat | aatgggatac | tgcttagtag | tgaagaggaa | atactgttac |
| 20701 | aagtaacaac | acgggtgact | cgcaagtgcg | ttatgctaag | cacgagaagc | cagactcaaa |
| 20761 | aggctgcata | ctgtatgagt | ccatttatat | gacattctgg | aaaaaaaaaa | ccacagttat |
| 20821 | agggatggaa | agtggatccg | tgggtgccag | ggactgggta | tcgtggaaga | aattgattgt |
| 20881 | tgagtggcat | gaaaaagctt | tttagggaaa | tagaaatgtt | ctatatcttg | attgtggtgg |
| 20941 | cgattgtcga | aattcataga | tttatacact | taaaaggata | aattttactg | tatctaaatt |
| 21001 | atatacctca | attttgttaa | gatatatata | tattttttt | ttttaagca | ctcctttgaa |
| 21061 | aggattaagg | acgcctaact | tgaaggaaaa | gcatttctgc | acaggtgtca | gtgtattgca |
| 21121 | ctgtggaacc | tgtgtggtaa | aggcaaaggg | ggtagtgctt | atctcttgat | cctaaatatg |
| 21181 | tgagaccaga | ttaaagtgaa | atctgggagg | caatgaatgt | taaatgagtt | gttatgtaat |
| 21241 | ttgcatagag | gtgatgctga | gagatttaga | aaggatcact | gtgggttgct | tgctcacttt |
| 21301 | cttgctctcc | tattccgtag | ctttccaaat | ggctgtactc | aacggtggct | tggtgtttag |
| 21361 | gggatttaag | gggggcaaaa | agaaagatta | ataatctcct | cctctccctc | taaccctact |
| 21421 | gccctaagat | atccttagca | aacttacatc | tcctttcttt | tctctgtgtt | cattccattg |
| 21481 | tgcgcacaca | tacacattca | tggattttct | ctttttgttt | agggaaaaaa | attataatgt |
| 21541 | acatactatt | ctacaacttt | ttgttgtttt | attgaacatt | atatgattcc | taaattatcc |
| 21601 | ccaggtgaat | acaaatagat | atgacacatt | ttaaaaaat | aaaataactg | gccgggcgtg |
| 21661 | gtagctcatg | cctgtaatcc | cagcactttg | ggaggccgag | gagggcggat | caggagatcg |
| 21721 | acaccatcct | ggccagcatg | gtgaaacccc | atctctacta | aaaatacaaa | aattagctgg |
| 21781 | gtgtggtggc | gtgcgcctgt | aatcccagct | actccggagg | ctgaggcagg | agaatcactt |
| 21841 | gaacccggga | ggcggagatt | gcagtgagct | gagatcacac | tgcactccag | cctgattgca |
| 21901 | gtgagccgag | atcatgccac | tgcactccag | cttggcaaca | gagcgagact | ccgtctcaca |
| 21961 | agaaaaaaaa | taaccgtgtg | agtactattc | catagaatga | atgtttcata | atttaattct |
| 22021 | tctatagaca | gacattaaaa | tattttccag | atttgggcca | agagtagcag | tttaaaaaac |
| 22081 | atttagcttt | taactgactc | tagccacttt | gaaacacaat | ttttttttcc | caaggtcact |
| 22141 | caaagagcta | ataggagaac | ccctaagtcc | cataattcag | ctctgggagc | cagcactcac |

```
22201   tctgtacaca catttgcctc tgtccctagc aatatggtgg gcgtgagggt gcagcaagag
22261   gaacaagaaa gaaatgattg cttgcatagt ggcgtcttgt tcatgcagtc attaattcaa
22321   caaatgtttg ttgagaatca gctttgtgcc aagtgctaga gaggttgaga tgattgaagc
22381   atagtccttg accccaaga gctcaccatg gaatcaactg aagcccctca tcagtactgt
22441   gttgggaata ttgagagtgg agagttgagt ataacttata ggacacctaa tgttaattac
22501   ctttcagaca ctgcaatgtg tgtgtgccat aaaaaaaaaa aaaatccagt agctctgata
22561   cgagggaaag taaatggttt aacaggtgct gagtaggaga agctcaagga gaggaaaccc
22621   caagggctga agaaggtggg agtcaggagt ctcctgaagc aagtggcatt taaggagctc
22681   tataaggaaa gggtcagagt tgtgataggt ggctgtggag ggagatgtgc cacctggatt
22741   ggcatgtaga gggatagaaa gattataggc ctttgcaatg cccagtaag aggtaatgag
22801   gggctggaac tggaagaaaa cacatttaag acacagtaca gaggtggcag acaaggtggg
22861   acttggcaac tacctgatga gatccaggag atgaggccag gaggcgggca gcaaagatga
22921   cgcaggtttc tagccttaat aggctaggag gagagtgatg ccattagcaa taagaactac
22981   aggagaagga gctgagtttg agggaactat taatttggtt cagaatatgt gctgtttgag
23041   ttatggcagg atatttaagt ggacagactg tcgacatagt tggaaattca gatcttaagc
23101   tcccacacaa ggtagtggct ggacatagta gatttgagtg ctcttgcttc agagggctag
23161   tttaggttgg ggcagtgatt aaagcaacct aggaaataaa ttataaagga agaagaggtc
23221   cttaaaacct tggagactga ttatataaag ggtggatccg ttaatacagt agctattaaa
23281   aaattataag gggtgggaaa aagggacaaa gaagaaaaaa gaggtgaaag acctttgctg
23341   tgtcaccaaa ccctggggagg agaatttttt aaaagaagag tactcaatcc acagtgaact
23401   aaggcatgtt tggttaacac aattgaccac cacacagcga agacccaaat gaggttcaag
23461   agaaggaatt tttatggacc ctgttagcac aagtcaaggt ccttctccag taccactggg
23521   aagctttgga gaagaaaagg gggacagtgg gccttgggtg gagaagggaa ctgaccatga
23581   gatccaggtg gggtgaggag gtgtgtgaag tcagagtggg gaagaatcag ggtggcttac
23641   tggcagcttc accggggtca tgcgaggagc aggttccacc agagtaagga gtgaagttgt
23701   agaaacacag ggaagtcacc atcagaaaag agcaggagtc aagaaactat ggcccacagg
23761   tacaaactac ctgtttttat aaataaagct tcatggtaaa tgaattgtaa ataaagtttt
23821   gcatattgtg tgaggctgtt tttgtgctac agtggcagag ctgtctggcc ctttatagaa
23881   aaagtttatc agccactgga aaagagttgc aggatttgag gtcttggtgt gatggcctag
23941   gttagagtca tagtgagatt gaaggagtag ctagacaagc caattgtgtg gcagaaaggt
24001   agggatggag atcactgggt taaggatcct tgtagccagg acaccatgag agtgattgac
24061   aagaatgctg aaatcccta agtgtgtcag gatgtggaag agtagaaggc tagagttatg
24121   gaagaaaggg tcccacctct acctgtgcag cctccaggag agtctgagga ggggcggtg
24181   agtgtgagta aatgttgtca gaatccctcc tcccagtcta caagccccag ggaaaggaag
24241   caaggtgttt actgacaccc ccaggcttat aagtacttcc tggctccatc accctccagt
24301   gaacagccct ggggagaaga cagtactggt ttgcaggtgg gtgggtgggg aaagggtca
24361   caggtgcttg gtgttctggt aaatgtgcat atgagaacat ggggttgctt gtgccctgtc
24421   cttcagggtt cagaagaacg tgcagtggaa gcagctatgg ggaagtagct agggaaggta
24481   ggactggtct gaggtggtga ggagcagatg ctgccagctc cacacatcca ggagagcctg
24541   ggtggtttgg gcaaaagtct ctggcatccc ttctgagcct gggtaccaca ctgaagagtg
```

```
24601  aggacagtgt gccatttta tcaggaaacc ctccagctcc ctgaagacca aattctgatc
24661  ctcctgggat ggcagtgaag agccacagag atgactctga ggtcccgtgg ccttttccca
24721  cctggagatt gttttcgtta ctgcgctgtt acagccttgg aggactgggg ttcagtttca
24781  tccaatcaca tttcttcttt tgtcatagtc atctaaacga tagatcttag agacaggtgg
24841  gcaaggggtg cactggtgag cctgacttaa ggagaggtca tctcgtccct tccctagtcc
24901  catctccctt ggttattgtt atttcatgtg attgttctgg ttatttcagg ttattctgtt
24961  tttgttttca aaacaataac atatatttgt tgttctgatt ttaaaggggt aattgttttg
25021  gtaactagaa aattaccttc tcaactccct taaattctgt caaagggaaa agtaagttag
24081  gttgctggag aggctatgct gaggcctcag aacctctgta ttcctggaag ttctgcgtgc
25141  tttgcctcct gctcccctct ctgtgttcct gttggcaggc cctaggcag gatttaggag
25201  gtaggcaagt caccctagcc aagtcataag cccatggctc aattgccttc tcagcccttc
25261  aagggctgtt ccacaggcag caaagggagg ggcctccaca ggttcaccac tgcagcccta
25321  attcattttc tttttccact gtcttattct gcaggggtat tccctcagcg gatactacac
25381  ccatccattt caaggctatg agcacagaca gctcaggtac cagcagcctg ggccaggatc
25441  ttcccccagt agtttcctgc ttaagcaaat agaatttctc aagggggcagc tcccagaagc
25501  accggtgatt ggaaagcaga caccgtcact gccaccttcc ctcccaggac tccggccaag
25561  gtttccagta ctacttgcct ccagtaccag aggcaggcaa gtggacatca ggggtgtccc
25621  caggggcgtg catctcggaa gtcaggggct ccagagaggg ttccagcatc cttcaccacg
25681  tggcaggagt ctgccacaga gaggtgttga ttgcctttcc tcacatttcc aggaactgag
25741  tatctaccaa gatcaggaac aaaggatctt aaagttcctg gaagagcttg gggaagggaa
25801  ggccaccaca gcacatgatc tgtctgggaa acttgggact ccgaagaaag aaatcaatcg
25861  agttttatac tccctggcaa agaagggcaa gctacagaaa gaggcaggaa cacccccttt
25921  gtggaaaatc gcggtctcca ctcaggcttg gaaccagcac agcggagtgg taagaccaga
25981  cggtcatagc caaggagccc caaactcaga cccgagtttg gaaccggaag acagaaactc
26041  cacatctgtc tcagaagatc ttcttgagcc ttttattgca gtctcagctc aggcttggaa
26101  ccagcacagc ggagtggtaa gaccagacag tcatagccaa ggatcccaa actcagaccc
26161  aggtttggaa cctgaagaca gcaactccac atctgccttg gaagatcctc ttgagttttt
26221  agacatggcc gagatcaagg agaaaatctg cgactatctc ttcaatgtgt ctgactcctc
26281  tgccctgaat ttggctaaaa atattggcct taccaaggcc cgagatataa atgctgtgct
26341  aattgacatg gaaaggcagg gggatgtcta tagacaaggg acaacccctc ccatatggca
26401  tttgacagac aagaagcgag agaggatgca aatcaagaga aatacgaaca gtgttcctga
26461  aaccgctcca gctgcaatcc ctgagaccaa aagaaacgca gagttcctca cctgtaatat
26521  acccacatca aatgcctcaa ataacatggt aaccacagaa aaagtggaga atgggcagga
26581  acctgtcata aagttagaaa acaggcaaga ggccagacca gaaccagcaa gactgaaacc
26641  acctgttcat tacaatggcc cctcaaaagc agggtatgtt gactttgaaa atggccagtg
26701  ggccacagat gacatcccag atgacttgaa tagtatccgc gcagcaccag gtgagtttcg
26761  agccatcatg gagatgcccc ccttctacag tcatggcttg ccacggtgtt caccctacaa
26821  gaaactgaca gagtgccagc tgaagaaccc catcagcggg ctgttagaat atgcccagtt
26881  cgctagtcaa acctgtgagt tcaacatgat agagcagagt ggaccacccc atgaacctcg
26941  gtaagagacc acccaggaac tgtacctagg gttggggtca ggtgcttttg ctcctgacgc
27001  agtcttggct gatttgtgag cagtgctgtt tggtggcgcc tatctttcc tccttcccctt
```

-continued

```
27061   ctgccttta  gctaaattcc  ccttgattgg  ccctttctcc  agatattgag  cagggaatat
27121   agaccttgga  ccagccagaa  tcttggctga  acaaggggga  ggttgactct  gttggctgta
27181   atgaagcttc  tttagaaatg  attggttttg  gccgtacgcg  gtggctcatg  cctgtaatcc
27241   cagcactttt  tgaggccgag  gcaggcatat  cacgaggtca  ggagtttgag  accagcctgg
27301   ccaacatggt  gaaaccctgt  ctctactaaa  aatacaaaaa  ttagctgggc  gtggtggcgt
27361   gcacctgtag  tcccagctac  tcaggaagct  gagacaggag  aatcacttga  acccaggagg
27421   cagaggttgc  agtgaactga  gattgcgcca  ctgcactcca  gcctgggcca  cagagcaaga
27481   ctccatctca  aaaaaaaaaa  agaaagaaat  gattggtctt  gggggccggg  gcggtggctt
27541   acgactgtaa  tcccagcact  ttgggaggcc  aaggcaggca  gatcatgagg  tgaggaattc
27601   gagaccagcc  tggccaacat  ggtgaaaccc  catctctact  aaaaatacaa  aaattagctg
27661   ggggtggtgg  tgcttgcctg  taatcccagc  tactcgggag  gctgaggcag  gagaatcact
27721   tgaacccagg  aggtggaggt  tgtagtgagc  cgagattggc  gccactgcac  tccagcctgg
27781   gcgacagagt  gagactccat  cttggaaaaa  gaaagaaaaa  agaaaaacat  gattgatctc
27841   catgcatcaa  tatcatgcct  gcctcctaag  gcagaggtaa  tgaagactta  attcccttct
27901   gtaggccttc  ccctcctccc  taagccgttt  tctgagagag  gtgcaggagc  aggtgggttg
27961   gggcaggctg  catacacagt  gggggtgggt  tgtgctgcta  agcagcagca  ggtccacaat
28021   ccccctctg  catagctcct  gggggaaag  gatggaggag  cgtgtgcacg  gctgcctgcc
28081   tgttgaaggt  ggtggttcta  attttataaa  cctcctctgc  acagatgggg  aggctagcac
28141   ttgctgccac  tcctgagctg  tgaagtcagc  ctttacctca  ctcagatagc  tggtcaggcc
28201   ctgcactgta  ggtcctaata  ggccagtgga  cagattgagg  aaaacaggag  cttctgaagg
28261   gcataacaga  gagcaaaacc  actgaagctg  agtggctgca  gctgcagcca  gggaaagagc
28321   cagtaggatg  ggggagaatt  ccactgacct  ttatgtttac  ctagcctggt  ttctaggggt
28381   gtagattcct  ggctagggcc  cttattcctt  gtcttgactg  tcttcatgac  accaatttgg
28441   catttcagga  gagcggttaa  gaaaaggagt  tgtgtctgtc  caaaagctgg  caaggccaga
28501   gctggattgt  ttgggtaga  gactggatgg  ccgtcattct  cttttgcctc  catccctcct
28561   ccccagagtt  ggaggaaagc  agtggatttt  gtggttagtc  attctttgga  ctcacactaa
28621   aagaaacatt  ggtgccatgt  tcaaatatat  cagaagacct  aggaaataag  aaatttgacc
28681   tacttttcta  aatgaaatcc  cagactgagc  aaagagctca  ccacatttga  aagcttgaac
28741   aaaggggcc  taggctaagt  ccagaggcct  agaacaaatg  cttttttatt  ttctacataa
28801   caaggggaaa  ttccttgtta  tgtagaaaat  agctggagac  aaatggtgct  atagagtgac
28861   tcataacaaa  ctacggtgat  ataggtctag  ggacaaaagc  aggccactga  taagtggcag
28921   atgcctgatc  ccctaggta  gtggggagtg  tgagactggg  ttataagaag  ccttcactat
28981   cttttaggac  cctcccttga  ggaggccagt  ctaccacaat  tgctttagaa  tgaaggtctt
29041   ttggttgctc  acaagactat  aatggtaatt  tttggctcat  cattttttgtg  tgtgtgggtt
29101   ttatcttaat  tcattgttaa  agagatagtg  ggtttcccct  gagctagttt  cctatcatct
29161   gtgcctatgt  ttgcttcact  gagctatggg  gaaagagtca  ctggctgctt  tgtttacaaa
29221   aagaaaggac  aggctgagcc  ttaaggagta  ggaaggagtt  ccttggccta  cccttcatct
29281   ccacaagtga  aaagccccctt  agcgtagcag  aaaattccag  gttgaaggtc  tctttggaga
29341   aggcagaagg  agtgacctag  actcctgttc  acacatctaa  tcactttccg  tcaagattta
29401   aattccaggt  tgtcatcaat  ggccgagagt  ttccccagc  tgaagctgga  agcaagaaag
```

-continued

| | | | | | |
|---|---|---|---|---|---|
| 29461 | tggccaagca | ggatgcagct | atgaaagcca | tgacaattct | gctagaggaa | gccaaagcca |
| 29521 | aggacagtgg | aaaatcagaa | gaatcatccc | actattccac | agagaaagaa | tcagagaagg |
| 29581 | taggtgtcct | cctgccatct | gggaggatca | gttccctgtc | agtgtctgga | ttgtaactga |
| 29641 | ctcccttgag | gcaatcccag | cctaaacaac | tgacaccatc | tcggagtcag | cttcccactc |
| 29701 | ttccctctac | cctatctcgc | cagcccacct | ttcctcctct | catacccagc | tcctctgtct |
| 29761 | gctcctgtcc | caacataatt | ggatttacag | aatttcggac | ttgaaagaga | cctgaaagtt |
| 29821 | tattgaggcc | aatctcctct | cttggaagat | gcggaatgag | agctccagca | gcccctttaa |
| 29881 | ctttgggaag | ccaacccctt | gacaggtggt | gggaataaag | tcccccatcc | catcccttc |
| 29941 | ttctgtgatg | gactaaccag | tgttttctta | gttttgtttt | cttcttgtct | ctcattttct |
| 30001 | ctagactgca | gagtcccaga | ccccaccc | ttcagccaca | tccttctttt | ctgggaagag |
| 30061 | cccgtcacc | acactgcttg | agtgtatgca | caaattgggg | aactcctgcg | aattccgtct |
| 30121 | cctgtccaaa | gaaggccctg | cccatgaacc | caagtatgtc | ctacgtgtcc | tctgtccagc |
| 30181 | tgaggttttc | tcagaaagaa | aaagagacac | atttcttcc | ttgcctcctc | agggatggca |
| 30241 | gattgaccaa | tttctcctgt | ttcaaaatgg | ggaaaggagg | gctctgaggt | cctggttgct |
| 30301 | gcttgtgagg | cagacaatta | gggattagga | attcaaaggg | aattcctggc | ccaccctcta |
| 30361 | tctcctctat | aagcactagg | gaggttcacg | gcttggaggt | cactcactgt | tggtgggaca |
| 30421 | gaaaggtaca | ggacctgaga | agctctctgc | ctgtgggtct | atagactcac | atgttcaaga |
| 30481 | gaagtgttcc | tggaagaggt | gaaactaggt | tgatgcttaa | atgttgaaag | cggtcagcca |
| 30541 | ggctaagaga | cactggctgt | tcaaggcaga | agtgactgca | tgagatgtga | ctgcacagag |
| 30601 | gtgatgtgtt | caaggaaatt | accagtagtg | gaggatggca | gcctggcaga | ggctaggtca |
| 30661 | ggctcctcag | tcaaaaccat | tttaatcctt | ctacgtgctt | catctcctgt | caggttccaa |
| 30721 | tactgtgttg | cagtgggagc | ccaaactttc | cccagtgtga | gtgctcccag | caagaaagtg |
| 30781 | gcaaagcaga | tggccgcaga | ggaagccatg | aaggccctgc | atggggaggc | gaccaactcc |
| 30841 | atggcttctg | ataaccaggt | agggcgtttt | cctactcaaa | agatacaggt | catttttagc |
| 30901 | aactgagtgg | tttaagattg | ccagtgactc | cctcaacatt | tcctgaagtg | tttatggctc |
| 30961 | ctctgtttga | tggattctcc | tttagcctga | aggtatgatc | tcagagtcac | ttgataactt |
| 31021 | ggaatccatg | atgcccaaca | aggtcaggaa | gattggcgag | ctcgtgagat | acctgaacac |
| 31081 | caaccctgtg | ggtggccttt | tggagtacgc | ccgctcccat | ggctttgctg | ctgaattcaa |
| 31141 | gttggtcgac | cagtccggac | ctcctcacga | gcccaagtga | gtgtcctagt | cctggctaat |
| 31201 | gcatgtgtca | ccagttgggg | atggtctgta | acccagggaa | aacaagggtg | tgctttagct |
| 31261 | gtgtaggaca | gaaggggcga | gttgagggaa | acaagtccag | ccctgtctcc | acgcctctt |
| 31321 | agaagacaat | agacctgcca | agagtgaatg | cgttcactct | tccagtaagc | atgatccttt |
| 31381 | ttaattttt | gactagtttt | aattttaaa | gaaatgtata | ggtacattaa | aaaatcattc |
| 31441 | aggccagaca | tggtggctca | cgcctgtaat | cccagcactt | tgggaagttg | aggcaggtag |
| 31501 | attacctgag | gtcgggagtt | caagaccagc | cggaccatat | gaggaaaccc | tgtctctact |
| 31561 | aaaaatacaa | aaattagctg | ggcgtggcag | cgggtgcctg | taatcccagc | tactcgggag |
| 31621 | gcagacagga | gaattgattg | aagctgggag | gcggaggttg | cagtgagctg | agatcgcacc |
| 31681 | actgcactcc | agcctgagca | acagagcaag | actccatctt | gaaaaaaatc | attcaagctg |
| 31741 | attgaaaaag | tagtcatttc | aatgaaaagt | ctcatttccg | tctcagactt | ctagtttccc |
| 31801 | tccctagacc | catatattac | tatagccctg | cattagcaac | tgggatgcgg | tctgagaagc |
| 31861 | atggttttgt | tgttgtgaga | acatcagtgt | gtatttacat | aaacctagat | ggcatgggct |

```
31921  cctacacacg tacaggctgt atggtatggc cggttgctcc taggctacaa acctgtacag
31981  catgtaactg tagtgaatac tgtgggcagc tgcaacacac tggtaagtat tggtgtctat
32041  ctaaacagca aaagataca gtaaaaagac agcataaagg attaaaaaaa tactacacct
32101  gtatagggcg cctgccatga atggagcttg caggactaga agttgctgtg ggtgagtcag
32161  ccagtgagtg gagaatgaat atgagggcct aggacatgac tgtacactaa tgtaggcttt
32221  gtaaacactg ttcacttagg ctaactacat ttatttaaaa tattttttctt taataaatta
32281  accttagctt actgtaactt ttttactttta tttttacttt attttttact ttattaactt
32341  ttttatttttt tgttccttttt gtaataatac ttagcttaaa acacaaacat gttgtactgc
32401  tatccaaaaa tatttccttt gtttatatcc ttaattctat agtctttttt ctgtttgtaa
32461  attttttat tttttttaact ttttaaactt ttttgttgaa agctaagatg aatatacatt
32521  agctgttagc ctaggcctac acagggtcag gatcctcagt atcactgtct tccacctcca
32581  cgtcttgtcc cactgtaagg tgttcagggg caataacatg catgggggcc gtcatctcct
32641  atggtaacag tgctttctgg aatacctgcc tgaggctttt tttagttact tattttttcta
32701  gaagtagaag gagtatacgc tgaaataatg ataaaaatat agtaaacaca taaggagcgt
32761  gtagcctaga tccctcgcat tcacagttca cagtcgagtt cacactccta caagaatctc
32821  atgctgctgc tgatcccaca ggaggcggag ctcggaccag aatgctttct tgctcgccac
32881  tcacctcttc ctgtgtgccc aggttcctaa caggttacag agccctgcac ttggtgataa
32941  gaatttttca gctccatcat aatcttacgg ggcccctgtc atatgtgtga tttatcattg
33001  aacaaaacac tgttatgcag tacatgacta taccagtttc ttgagtcctt ctagaaattg
33061  ctgtgcataa ctagcacatt ttcccttttg tctttttaaa caagtatatc ttctgtttta
33121  tacgttgact cctttactta ccagacttct tgcatagctg catagtattt cattgaatag
33181  aagctgacaa attcagtttc tcagaagtaa acatttaata gggacttagg aacagaaatg
33241  atgtcttggg tggctgcaag atggtggatc cctgcactta ccctccagaa agtatgcttt
33301  ctatagaggc ttttttggtt aaacatgcag ctggtcacac attatacttt cttgtgaaac
33361  ttatgagcac tagctggtgg ggaggcttgg tagacatctt tgtgtggaat tatttatgct
33421  acccaacact ttgggatgcg ggagtcagat attggtggtc atagtggttt tgcatcaaga
33481  tggcatcact cttgccatgc aaccggcatg ttttcttaat ctctaaggtc tatcacaaag
33541  tggaaaagca aggtgtaaag tgaggggaga ggtgaagatt gtctgtatat gtctagaata
33601  ttttcttgaa ggatcgaaaa aactggcaac tgtgtttgct tctggggaag gagggacact
33661  tttattgtac actcttaact gtttgaattt tcacatgttt ggcatccaac ttgtccattt
33721  taaagtcatt aaggaaaaaa gcttataaaa atgctatctt gttactttaa atttgtctct
33781  ccttaataga agtaatgtca gccgggcgca gtggcttacg cctataatcc cagcactttg
33841  ggaggccgag gtgggtggat catttgagct cagtaatttg agaccagcct ggccaacatg
33901  gtaaaacccc atctctacta aaaatacaaa aaatagctga gcatggtggt atgccctgt
33961  atgccagcta ctccggaggc tgagcaggag aattacttga acccaggagg cggaagttgc
34021  agtgacctga gattgtgcca ctgcactcca gcctgggtga tggagtgaga ctccgtctca
34081  aaaaaaaaaa caaaaaaatc agaagtaatg gcatttcatt tattcatatt tatgtgttat
34141  ttgcatttcc ttttctgtga accacctgtt cttgtccttt tccagttttc tttcagattg
34201  ttactctcat ggatatgtaa gaacttttaa cataatttttt aaaagtagcc ctttgcccaa
34261  catgacccaa tttagaacac acatctgccc actgtttaag ccatctggaa aaggagaggc
```

-continued

```
34321  ccagtctccc tccagctgct cttctactaa ttcatatcct tcatctcaat aagcacctcc
34381  ttatctttaa gcacagtcct tcagatgata ggttcagtgc atttcctctt tctcttctgt
34441  gaaatcttct gtgaaatcct ttctaggact tcaagtcagc cattcattga gaatgtaaga
34501  acttactatg aactagatgg aagatacaaa aaattgctgc ccctgagtgt gtagcagaca
34561  tatagccata gcagtattga aatgtgccat tggaggtgaa tgcagagtgc tgtggggaca
34621  cagaggacac tgctgccact gtctgccagg gagctgagga aggttgcata gagaggggaa
34681  atgctaattg agtaactacg tttattaact atctcgtaca ataatatact ttagttgctt
34741  cttaatgtga attatgctgg gtctttttttt cctttctgtc tactgtggct ggtgacgtta
34801  actaattta tgacttcttt tctgtttttt tttttttttt ttttggaga tggagtctca
34861  ctctgtcacc caggctggag tgcagtggcg cagtctcagc tcactgcaac ctccgcctcc
34921  tgggttcaaa caattctctt gcctcagctc ctcgagtagc tgggattaca ggcatctgcc
34981  accacatctg actattttg tattttagt agagacagag tttcaccatg ttggccaggc
35041  tggtcttcaa ctcctgacct cagatgatcc acccgcctca gcctcccaaa gtgctgggat
35101  tacaggcatg aaccaccgcg acagccatga cctttaatat ctaaatgctg gagaccactc
35161  agagctcccg attcctccat ctagttgctt acttgtcacc tctgtttgga ttaacatccc
35221  taatatgaca tgtccaaagc agaactcttg ggttttgccc ccttcgcttc atttccccca
35281  agtctttccc agcttagtaa gtgataccac tgtctaccca gtggctcaag tcagaaacct
35341  gaggatcatc ttttcctcta tctcctttac ctccttcgtc aactcatcct taagtcctat
35401  tggttatact tagaatttct atcccaaatc ccttcctctt ctttccacct ccagcgtcag
35461  cactctaatc caagccactg tctcatctag actgtcacaa tagcctccta actgatcttt
35521  atactttatt tactcaacac ttatttatgg agtatcttct attttttta gaacaggaac
35581  caaacattaa ccaatagtca cctaaagaaa tgtaagatct catatttgat aagtattcca
35641  aagggctgga gttgcagcga gaatcaatta tagcacagtt tgacttagga aggagagggg
35701  gaagggcttc cccaagaagt actgcctgag ctgagacttt aaggatgatg aagagagaaa
35761  gactgagggt tctaggcgaa ggacactgtt aaatcctgtg gtgggagaag cgcagagctg
35821  gcaaagaggc tgagaggagg cacttatggc aatagcccca tttggctagt ggctaccata
35881  ttggatagca cagctctaaa ggattctagt tgcataatta acaaacttta tcatatatgt
35941  aaatatatca gtataaaact ttgcacgtaa gagttcatat tcttttcaaa cacatggggc
36001  agtcatgaaa ttctcctgga tccctgaggt aaagatacta cacaatctgt ccctcctgac
36061  cgccttcacc atcttctttt catgccactg tccctctcat tctgaactta agcccactgg
36121  cctgcacggg cctgccagca tggacaaaga aaagagtgaa ggcatttagt tgcttcggat
36181  catcaaggaa cagtgagaaa ctccatgtgg ttgaacataa acgttgattc cttttactgc
36241  ctgagctgct aagtcttgaa actgaagcct ctgttatatg cagttagagt atccaaagct
36301  gggttctcag ccagtagatt aggatctggt tgaaagctag gattcttgat gccttgtctg
36361  gtacatttcc aagctgtttt gctccaccat gctcttccct ctgtgtttgg aaattaccag
36421  ccggagcggt agaagccacc tccctgctcc acttgggcac tttattgtca gcgcagctca
36481  tgcgcccaag atccattcct taccccagag ttagcttaag cctgccagga gtcaaaaaaa
36541  caactcccag caaaacctgg gtccctggcc taaggccgac cttgacctaa tgacctctcc
36601  aggtcaagtc cccttgagct aataggaagt aaatgaggga atggagttgg gcgctttaaa
36661  aatcagacag tgtatgaagt aacagtgact tgtggggaga aaggtagtcc cttctgattt
36721  ctgcttaaga agagagtcca agttggtgct agcatttcgt taagccttcc tcatacttca
```

```
36781  taatcttcct ttatagtaag gacgggctca gagcctttgc aggtaacagt atctagtcag
35841  aattttataa catgatttta tcatattctg ttttacagcc accttcaata tgtggcaagt
36901  gatactggtt ttccatttac agtagtgaaa caaagtttcc tatttcagtg tgtttacatt
36961  tttatctctt ttttcatacc tagtattacg gatatttaca ttttttagagt ctgtttgttt
37021  attttagaga tggggatctt gctgtctcgc gcaggctgga gtgcagtgat atggtcatag
37081  ctcactgcag ccttgacctc cagggctcaa gtgatcctct caccccagcc tcccaagtag
37141  ctgagactat aggcacagac caccgtgccc agctaaattt tttttttttt ttttaagaga
37201  caggggtctc gctatgttgc ctgggggatt actatgttgc ccaggctggt cttgaactcc
37261  tggcctcaag tgatctccca ccttagctcc tcaagttgct gggattacag gtgtgagcca
37321  caatggctgg ctctaagaag tcaatttaga gaaaaatatt aattaatagt ccaagtaata
37381  cctggatgtg gcacaaatca tgtggtgatt catgaatgac caaaatctag gaaatgctgc
37441  cttagaaaca gcttctgttt gacgggtcca tatgtttgca agactggcca catcttcagc
37501  aaaactaacc cttccttgga acaatgtcag ggtctggcac ttgtcttcat tctctgtttc
37561  tcatcccaaa ggttcgttta ccaagcaaaa gttgggggtc gctggttccc agccgtctgc
37621  gcacacagca agaagcaagg caagcaggaa gcagcagatg cggctctccg tgtcttgatt
37681  ggggagaacg agaaggcaga acgcatgggt ttcacagagg taaccccagt gacaggggcc
37741  agtctcagaa gaactatgct cctcctctca aggtccccag aagcacagcc aaagacagtt
37801  aagacgtcta cttttggtgc cttttttggg gcgggggggt cctcctaact cctaagtgga
37861  ggtggctctt gctgtcatgc gagttattcc taggctttac tcttagcctc gagagagcag
37921  taactgggac actagatgta agaaggaaaa gatgactcac acgacaagta gagcttgatc
37981  tccctgccca cggtgaatat ggtggacaca gcctcagctt tgtggtgctg acacagcctc
38041  ttttccccac agctccctct cactggcagc accttccatg accagatagc catgctgagc
38101  caccggtgct tcaacactct gactaacagc ttccagccct ccttgctcgg ccgcaagatt
38161  ctggccgcca tcattatgaa aaaagactct gaggacatgg gtgtcgtcgt cagcttggga
38221  acaggtgagt gaggctctga gacatgccgc ctcccatggc gcctgaaagc gggtgcctct
38281  catcctcccc tggagtccat gcatgtaagt ccaaggcagg gagaagagac ttcatttag
38341  ctacagtcaa ttcagagtga ggaatgagtt cttagttcct agaggagaga atatgggagt
38401  ctaggatctg agaaactgag gctgtttctg ccttgaagct ttcagaacaa atagccttca
38461  tcctgttttc catcggtttc cttccattat tctatttctg ttttaaacac cttcctaggg
38521  aatcgctgtg tgaaaggaga ttctctcagc ctaaaaggag aaactgtcaa tgactgccat
38581  gcagaaataa tctcccggag aggcttcatc aggtgagcga ggtcagagct gtggcccggc
38641  tgcccggctg tggagagctc cagttccctg ccccacatgg ctctgacacg gcctctgaat
38701  cccctcaga cagacgggtc atgatgtggc agtggcagcc tttgcttttc acccgtccat
38761  ttgaacctgt ctgatggaat ccatcccctc tgtgagctga gctgcctccc actgctcggc
38821  ctgtttttaa atgctgtcct ttttctgct aactctgctg cttcatgttc ttttctaaaa
38881  acacaaaatg acctttagt cctcagggcc ttgaggatga ggcagctttc catttccgtt
38941  tgaggaccta cacaaccttg atgcccctgc cagcttttctc ctctagctca ccttttcttt
39001  aatttatgaa gggagagact tagaaaggag caacagcttc ctgtagtcct tgaatcagtt
39061  tgctctgctc tagaatccct gtagccgcca tagcgaggag ccctcagcag aaatgaagga
39121  gaccaaaaag gctaactatg ctttatgaaa tgctgaggtc tccctggag aatttccacc
```

-continued

```
39181   tgataaactg tgaaacgtct gcaacattga gacttttcct tactttctca tttggaggtc
39241   agattataga aacaactgct tttcccagaa ttgaacctgc cttcctaacc agactttctt
39301   tttgtaggtt tctctacagt gagttaatga aatacaactc ccagactgcg aaggatagta
39361   tatttgaacc tgctaaggga ggagaaaagc tccaaataaa aaagactgtg tcattccatc
39421   tgtatatcag gtctgtacag ttcctgttgc tgccagggtg ggccctgcca ggctgttaga
39481   attgggtatc caaatgctct cctggcctgt aaatcgaacc tgatacaata agccacactc
39541   cactgtgggt ttgaggtcca tattcaggtg tagatgactc acatgtactg ctgtccacct
39601   ccagtctccc atggtaggcc ttagaaaaca tcccttgctt ctgtcacatc tgactgtttt
39661   ggagccccac gaaattgcag atttcccaca ggtgagtttt aacagccacc cctgtttttc
39721   agcactgctc cgtgtggaga tggcgccctc tttgacaagt cctgcagcga ccgtgctatg
39781   gaaagcacag aatcccgcca ctaccctgtc ttcgagaatc ccaaacaagg aaagctccgc
39841   accaaggtgg agaacggtga gtgatacatg cccccgcctc ctttcctcaa aaggctctgc
39901   aaggtccagg gaccccaagt ctctacaagc tgctaggat tttaccatta gtcactgggc
39961   acagaggtgc tgtttacagg aaagggaaga cctgggtcag ggagctgtgt ggtaagatca
40021   gggttctatt ttgaatgtgt tagtttggga gatctgggag atccccaagt caaataggag
40081   gtgggggttc ccatgtggag ctcagaggag ggagcttggc tggaaataga aatatgggag
40101   tcatccccct atagggtctt catggccatg agaatgcata ggattacctc aagaaagcgg
40201   ggaggaaatg aagagtgcgg cacaaccaag ccctgaggag ttgacagatg aggatgccaa
40261   atgctggggt cccctcctgt ctagctggca gttgactctg ccttgtccac tggctccttc
40321   tctcctatcc tctcctgtct ccttactgtc tcttcgcatc cactccattg cgttcaggcc
40381   acgtcagcag tcatcatggt ggtcctgaaa ccttgctaaa taccctaaag tatagacaca
40441   gttaccatgg agccggtgct ccactcctag gtatatgctg cagagagatg gagatctgtg
40501   tccacacgga aactaatatg tgaatgttca tggcagcatt actcacaaga gccaaaaaag
40561   tggaaacaac ccagacgtcc atcagctgat ggattcataa ataaaacatc aaatatatcc
40621   ataaattgaa tattattttg gccataaaaa gaagtgaagt gctgatacat gcttacaata
40681   tggatgcact tgaaaacttg atgccaaatg aaaaaagcca gtcacaaaag atcacatatt
40741   gtatgattcc atttatatga aatgtccaga atagacaaat ccatagagac agaaagtaga
40801   tgagtggttg ccagggccag gagtgggaga gttggagaga tgaggagtga ctgcgccaat
40861   gggtagaagg tttcttttttg gagcgatgaa atgttctaaa attgactgtg tgacagttg
40921   cagaactctg tgaatatact aaaaatgact gaattgtatg ctttaaatgg gtgaactgta
40981   tggcatatga actatatctc agtaaagcat ttttttttgt tttttttaa acccgatagt
41041   ggtttcccac tgcactgcat atacaagcaa aacctgctgt gatcacccgg cctcctctca
41101   tgccactttc cccatccctc gcatatgctc tgtccacact ggctctctgt caggcgcctg
41161   aacagccaat ccgctggctg ccttgggcc tttgcttttg tcctgtgtgc ctgaaacact
41221   tactccagct gtcctcctcc atgtctgggc tcccctgctg ctgctgtccc aggaggtgtc
41281   ccctgtggtc ctccgtcata gctgcctcag agcttcagaa gcactgtcag catctggaat
41341   tcttccgtat gtactggcta ctggtttagt gtctattctc ttcccttttca atctcctcac
41401   caccatagat gttttaagag cacaaagatc ttacttggtt ttgctcaccg ttctttccca
41461   gcaccaagca tagtgcctgg cgcatagcag gggctgtgaa atatgtgaag aatgaatgaa
41521   tgtagcctgt ggcccaagct aaggaggat agaaaccacg ccagggagtg gtttggtcca
41581   ttggcgcctg tgggtctgac ccaagtctct cacacaggag aaggcacaat ccctgtggaa
```

-continued

```
41641   tccagtgaca ttgtgcctac gtgggatggc attcggctcg gggagagact ccgtaccatg
41701   tcctgtagtg acaaatcct acgctggaac gctctgggcc tgcaaggggc actgttgacc
41761   cacttcctgc agcccattta tctcaaatct gtcacattgg gtaagggcc tgccttggga
41821   tctggaactg gtctgtcctt cttgtgccca gatcccaaac tgcatgcttt attgccaggt
41881   gttttgtctc ccttatcaaa gtgagcatga ttcactcctc agtaattgat tgagtgtcca
41941   gtctgctgtg gtaggaagat cctggtagcc ccagtcagaa ggtgcttcct aacaaggcag
42001   ctgtttctct ttcttgacaa ctatatcttg tacctccaaa atccccacat gcttctgcct
42061   cttaacagca tttggtgcaa acacaggtat atatgtttct ctttttttgta ctcaggttac
42121   cttttcagcc aagggcatct gacccgtgct atttgctgtc gtgtgacaag agatgggagt
42181   gcatttgagg atggactacg acatcccttt attgtcaacc accccaaggt gctataaccc
42241   ccttctattt tccctgacat tttcctcctt ttcaagcagt catgtaaaca gaggaaaaat
42301   gtacactgtg ggcaaggggga acattgccca cagtggtagc ccacaaggga acattgccca
42361   cagtggccca ccaccaacat tggttggtct cccaagaact taaactttct tccttttgga
42421   tgccaagggc ttttcttctc ttagtctgga attaatctga atcgaggtgg agttagtatg
42481   tctagagggt gctcagtctt agccaaacag aaccctaaat acaggggaaa gatcatgacc
42541   ccacacttcc tctctcctat gagtcttgag tccctgcttc agaatcttat tcctgaaagg
42601   tttccatctt tctcccgttg cttctgggat tcctaggttg gcagagtcag catatatgat
42661   tccaaaaggc aatccgggaa gactaaggag acaagcgtca actggtgtct ggctgatggc
42721   tatgacctgg agatcctgga cggtaccaga ggcactgtgg atgggtaagg agacaggaga
42781   gcgcagtgag gaccaagcct ctgccctgac ttgcaagggt gcatcatacc tctgcagtct
42841   cagggcttga gagccgcctc ccctcccacg gtgtctccac tgtgagctcc ttatcttaca
42901   ggtcccaggt gaataatgag tgctttttgtt tctctaggcc acggaatgaa ttgtcccggg
42961   tctccaaaaa gaacatttttt cttctattta agaagctctg ctccttccgt taccgcaggg
43021   atctactgag actctcctat ggtgaggcca agaaagctgc ccgtgactac gagacggcca
43081   agaactactt caaaaaaggc ctgaaggata tgggctatgg gaactggatt agcaaacccc
43141   aggaggaaaa gaactttttat ctctgcccag tatagtatgc tccagtgaca gatggattag
43201   ggtgtgtcat actagggtgt gagagaggta ggtcgtagca ttcctcatca catggtcagg
43261   ggatttttttt ttctccttttt ttttttcttttt taagccataa ttggtgatac tgaaaactttt
43321   gggttccat ttatcctgct ttctttggga ttgctaggca aggtctggcc aggcccccct
43381   tttttccccc aagtgaagag gcagaaacct aagaagttat cttttcttttc tacccaaagc
43441   atacatagtc actgagcacc tgcggtccat ttcctcttaa aagttttgtt ttgatttgtt
43501   tccatttcct ttccctttgt gtttgctaca ctgacctctt gcggtcttga ttaggtttca
43561   gtcaactctg gatcatgtca gggactgata atttcatttg tggattacg agacccctct
43621   acttcccctc tttcccttct gagattcttt ccttgtgatc tgaatgtctc cttttccccc
43681   tcagagggca aagaggtgaa cataaaggat ttggtgaaac atttgtaagg gtaggagttg
43741   aaaactgcag ttcccagtgc cacggaagtg tgattggagc ctgcagataa tgcccagcca
43801   tcctcccatc ctgcacttta gccagctgca gggcgggcaa ggcaaggaaa gctgcttccc
43861   tggaagtgta tcactttctc cggcagctgg gaagtctaga accagccaga ctgggttaag
43921   ggagctgctc aagcaatagc agaggtttca cccggcagga tgacacagac cacttcccag
43981   ggagcacggg catgccttgg aatattgcca agcttccagc tgcctcttct cctaaagcat
```

```
44041   tcctaggaat attttccccg ccaatgctgg gcgtacaccc tagccaacgg gacaaatcct
44101   agagggtata aaatcatctc tgctcagata atcatgactt agcaagaata agggcaaaaa
44161   atcctgttgg cttaacgtca ctgttccacc cggtgtaata tctctcatga cagtgacacc
44221   aagggaagtt gactaagtca catgtaaatt aggagtgttt taaagaatgc catagatgtt
44281   gattcttaac tgctacagat aacctgtaat tgagcagatt taaaattcag gcatactttt
44341   ccatttatcc aagtgctttc attttccag atggcttcag aagtaggctc gtgggcaggg
44401   cgcagacctg atctttatag ggttgacata gaaagcagta gttgtgggtg aaagggcagg
44461   ttgtcttcaa actctgtgag gtagaatcct ttgtctatac ctccatgaac attgactcgt
44521   gtgttcagag cctttggcct ctctgtggag tctggctctc tggctcctgt gcattctttg
44581   aatagtcact cgtaaaaact gtcagtgctt gaaactgttt cctttactca tgttgaaggg
44641   actttgttgg cttttagagt gttggtcatg actccaagag cagagcaggg aagagcccaa
44701   gcatagactt ggtgccgtgg tgatggctgc agtccagttt tgtgatgctg cttttacgtg
44761   tccctcgata acagtcagct agacacactc aggaggacta ctgaggctct gcgaccttca
44821   ggagctgagc ctgcctctct cctttagatg acagaccttc atctgggaac gtgctgagcc
44881   agcaccctca gatgatttcc ctccaaactg ctgactaggt catcctctgt ctggtagaga
44941   cattcacatc tttgctttta ttctatgctc tctgtacttt tgaccaaaaa ttgaccaaag
45001   taagaaaatg caagttctaa aaatagacta aggatgcctt tgcagaacac caaagcatcc
45061   caaggaactg gtagggaagt ggcgcctgtc tcctggagtg gaagaggcct gctccctggc
45121   tctgggtctg ctgggggcac agtaaatcag tcttggcacc cacatccagg gcagagaggt
45181   ctgtggttct cagcatcaga aggcagcgca gcccctctcc tcttcaggct acagggttgt
45241   cacctgctga gtcctcaggt tgtttggcct ctctggtcca tcttgggcat taggttctcc
45301   agcagagctc tggccagctg cctcttcttt aactgggaac acaggctctc acaagatcag
45361   aaccccact cacccccaag atcttatcta gcaagcctgt agtattcagt ttctgttgta
45421   ggaagagagc gaggcatccc tgaattccac gcatctgctg gaaacgagcc gtgtcagatc
45481   gcacatccct gcgcccccat gcccctctga gtcacacagg acagaggagg cagagcttct
45541   gcccactgtt atcttcactt tctttgtcca gtcttttgtt tttaataagc agtgaccctc
45601   cctactcttc tttttaatga tttttgtagt tgatttgtct gaactgtggc tactgtgcat
45661   tccttgaata atcacttgta aaaattgtca gtgcttgaag ctgtttcctt tactcacatt
45721   gaagggactt cgttggtttt ttggagtctt ggttgtgact ccaagagcag agtgaggaag
45781   accccaagc atagactcgg gtactgtgat gatggctgca gtccagtttt atgattctgc
45841   ttttatgtgt cccttgataa cagtgactta acaatataca ttcctcataa ataaaaaaaa
45901   aacaagaatc tgaattctta gaaa
```

In another embodiment, antibodies used to practice this invention are designed to bind to, or affinity matured to bind to, a polypeptide encoded by SEQ ID NO:2, or subsequences thereof:

```
                                                            (SEQ ID NO: 2)
  1   gaccagacca ttgattcccg actgaaggta gagaaggcta cgtggtgggg gagggtgggg
 61   ggagggtcgc ggccgcactg gcagcctccg ggtgtccggc cgtgtcccga ggaagtgcaa
121   gacccggggt attccctcag cggatactac acccatccat ttcaaggcta tgagcacaga
181   cagctcaggt accagcagcc tgggccagga tcttccccca gtagtttcct gcttaagcaa
```

-continued

```
 241   atagaatttc tcaaggggca gctcccagaa gcaccggtga ttggaaagca gacaccgtca
 301   ctgccacctt ccctcccagg actccggcca aggtttccag tactacttgc ctccagtacc
 361   agaggcaggc aagtggacat caggggtgtc cccaggggcg tgcatctcgg aagtcagggg
 421   ctccagagag ggttccagca tccttcacca cgtggcagga gtctgccaca gagaggtgtt
 481   gattgccttt cctcacattt ccaggaactg agtatctacc aagatcagga acaaaggatc
 541   ttaaagttcc tggaagagct tggggaaggg aaggccacca cagcacatga tctgtctggg
 601   aaacttggga ctccgaagaa agaaatcaat cgagttttat actccctggc aaagaagggc
 661   aagctacaga aagaggcagg aacacccct tgtggaaaa tcgcggtctc cactcaggct
 721   tggaaccagc acagcggagt ggtaagacca gacggtcata gccaaggagc cccaaactca
 781   gacccgagtt tggaaccgga agacagaaac tccacatctg tctcagaaga tcttcttgag
 841   ccttttattg cagtctcagc tcaggcttgg aaccagcaca gcggagtggt aagaccagac
 901   agtcatagcc aaggatcccc aaactcagac ccaggtttgg aacctgaaga cagcaactcc
 961   acatctgcct tggaagatcc tcttgagttt ttagacatgg ccgagatcaa ggagaaaatc
1021   tgcgactatc tcttcaatgt gtctgactcc tctgccctga atttggctaa aatattggc
1081   cttaccaagg cccgagatat aaatgctgtg ctaattgaca tggaaaggca gggggatgtc
1141   tatagacaag ggacaacccc tcccatatgg catttgacag acaagaagcg agagaggatg
1201   caaatcaaga gaaatacgaa cagtgttcct gaaaccgctc cagctgcaat ccctgagacc
1261   aaaagaaacg cagagttcct cacctgtaat atacccacat caaatgcctc aaataacatg
1321   gtaaccacag aaaaagtgga gaatgggcag gaacctgtca taagttaga aaacaggcaa
1381   gaggccagac cagaaccagc aagactgaaa ccacctgttc attacaatgg cccctcaaaa
1441   gcagggtatg ttgactttga aaatggccca tgggccacag atgacatccc agatgacttg
1501   aatagtatcc gcgcagcacc aggtgagttt cgagccatca tggagatgcc ctccttctac
1561   agtcatggct tgccacggtg ttcaccctac aagaaactga cagagtgcca gctgaagaac
1621   cccatcagcg ggctgttaga atatgcccag ttcgctagtc aaacctgtga gttcaacatg
1681   atagagcaga gtggaccacc ccatgaacct cgatttaaat tccaggttgt catcaatggc
1741   cgagagtttc ccccagctga agctggaagc aagaaagtgg ccaagcagga tgcagctatg
1801   aaagccatga caattctgct agaggaagcc aaagccaagg acagtggaaa atcagaagaa
1861   tcatcccact attccacaga gaaagaatca gagaagactg cagagtccca gaccccacc
1921   ccttcagcca catccttctt ttctgggaag agccccgtca ccacactgct tgagtgtatg
1981   cacaaattgg ggaactcctg cgaattccgt ctcctgtcca agaaggccc tgcccatgaa
2041   cccaagttcc aatactgtgt tgcagtggga gcccaaactt tccccagtgt gagtgctccc
2101   agcaagaaag tggcaaagca gatggccgca gaggaagcca tgaaggccct gcatggggag
2161   gcgaccaact ccatggcttc tgataaccag cctgaaggta tgatctcaga gtcacttgat
2221   aacttggaat ccatgatgcc caacaaggtc aggaagattg cgagctcgt gagatacctg
2281   aacaccaacc ctgtgggtgg cctttttggag tacgcccgct cccatggctt tgctgctgaa
2341   ttcaagttgg tcgaccagtc cggacctcct cacgagccca gttcgtttta ccaagcaaaa
2401   gttggggtc gctggttccc agccgtctgc gcacacagca agaagcaagg caagcaggaa
2461   gcagcagatg cggctctccg tgtcttgatt ggggagaacg agaaggcaga acgcatgggt
2521   ttcacagagg taaccccagt gacaggggcc agtctcagaa gaactatgct cctcctctca
2581   aggtccccag aagcacagcc aaagacactc cctctcactg gcagcacctt ccatgaccag
2641   atagccatgc tgagccaccg gtgcttcaac actctgacta acagcttcca gccctccttg
```

-continued

```
2701  ctcggccgca agattctggc cgccatcatt atgaaaaaag actctgagga catgggtgtc
2761  gtcgtcagct tgggaacagg gaatcgctgt gtgaaggag attctctcag cctaaaagga
2821  gaaactgtca atgactgcca tgcagaaata atctcccgga gaggcttcat caggtttctc
2881  tacagtgagt taatgaaata caactcccag actgcgaagg atagtatatt tgaacctgct
2941  aagggaggag aaaagctcca aataaaaaag actgtgtcat tccatctgta tatcagcact
3001  gctccgtgtg gagatggcgc cctctttgac aagtcctgca gcgaccgtgc tatggaaagc
3061  acagaatccc gccactaccc tgtcttcgag aatcccaaac aaggaaagct ccgcaccaag
3121  gtggagaacg gagaaggcac aatccctgtg gaatccagtg acattgtgcc tacgtgggat
3181  ggcattcggc tcggggagag actccgtacc atgtcctgta gtgacaaaat cctacgctgg
3241  aacgtgctgg gcctgcaagg ggcactgttg acccacttcc tgcagcccat ttatctcaaa
3301  tctgtcacat tgggttacct tttcagccaa gggcatctga cccgtgctat tgctgtcgt
3361  gtgacaagag atgggagtgc atttgaggat ggactacgac atcccttat tgtcaaccac
3421  cccaaggttg gcagagtcag catatatgat tccaaaaggc aatccgggaa gactaaggag
3481  acaagcgtca actggtgtct ggctgatggc tatgacctgg agatcctgga cggtaccaga
3541  ggcactgtgg atgggccacg gaatgaattg tcccgggtct ccaaaaagaa cattttcttc
3601  ctatttaaga agctctgctc cttccgttac cgcagggatc tactgagact ctcctatggt
3661  gaggccaaga aagctgcccg tgactacgag acggccaaga actacttcaa aaaaggcctg
3721  aaggatatgg gctatgggaa ctggattagc aaaccccagg aggaaaagaa cttttatctc
3781  tgcccagtat agtatgctcc agtgacagat ggattagggt gtgtcatact agggtgtgag
3841  agaggtaggt cgtagcattc ctcatcacat ggtcagggga ttttttttc tccttttttt
3901  ttcttttaa gccataattg gtgatactga aaactttggg ttcccattta tcctgctttc
3961  tttgggattg ctaggcaagg tctggccagg ccccccttt tccccccaag tgaagaggca
4021  gaaacctaag aagttatctt ttcttttctac ccaaagcata catagtcact gagcacctgc
4081  ggtccatttc ctcttaaaag ttttgtttttg atttgtttcc atttccttttc cctttgtgtt
4141  tgctacactg acctcttgcg gtcttgatta ggtttcagtc aactctggat catgtcaggg
4201  actgataatt tcatttgtgg attacgcaga cccctctact tcccctcttt cccttctgag
4261  attctttcct tgtgatctga atgtctcctt ttccccctca gagggcaaag aggtgaacat
4321  aaaggatttg gtgaaacatt tgtaagggta ggagttgaaa actgcagttc ccagtgccac
4381  ggaagtgtga ttggagcctg cagataatgc ccagccatcc tcccatcctg cactttagcc
4441  agctgcaggg cgggcaaggc aaggaaagct gcttccctgg aagtgtatca ctttctccgg
4501  cagctgggaa gtctagaacc agccagactg ggttaaggga gctgctcaag caatagcaga
4561  ggtttcaccc ggcaggatga cacagaccac ttcccaggga gcacgggcat gccttggaat
4621  attgccaagc ttccagctgc ctcttctcct aaagcattcc taggaatatt tccccgcca
4681  atgctgggcg tacaccctag ccaacgggac aaatcctaga gggtataaaa tcatctctgc
4741  tcagataatc atgacttagc aagaataagg gcaaaaaatc ctgttggctt aacgtcactg
4801  ttccacccgg tgtaatatct ctcatgacag tgacaccaag ggaagttgac taagtcacat
4861  gtaaattagg agtgttttaa agaatgccat agatgttgat tcttaactgc tacagataac
4921  ctgtaattga gcagatttaa aattcaggca tactttccca tttatccaag tgctttcatt
4981  tttccagatg gcttcagaag taggctcgtg gcagggcgc agacctgatc tttatagggt
5041  tgacatagaa agcagtagtt gtgggtgaaa gggcaggttg tcttcaaact ctgtgaggta
```

```
-continued
5101  gaatcctttg tctatacctc catgaacatt gactcgtgtg ttcagagcct ttggcctctc
5161  tgtggagtct ggctctctgg ctcctgtgca ttctttgaat agtcactcgt aaaaactgtc
5221  agtgcttgaa actgtttcct ttactcatgt tgaagggact tgttggctt ttagagtgtt
5281  ggtcatgact ccaagagcag agcagggaag agcccaagca tagacttggt gccgtggtga
5341  tggctgcagt ccagttttgt gatgctgctt ttacgtgtcc ctcgataaca gtcagctaga
5401  cacactcagg aggactactg aggctctgcg accttcagga gctgagcctg cctctctcct
5461  ttagatgaca gaccttcatc tgggaacgtg ctgagccagc accctcagat gatttccctc
5521  caaactgctg actaggtcat cctctgtctg gtagagacat tcacatcttt gcttttattc
5581  tatgctctct gtacttttga ccaaaaattg accaaagtaa gaaaatgcaa gttctaaaaa
5641  tagactaagg atgcctttgc agaacaccaa agcatcccaa ggaactggta gggaagtggc
5701  gcctgtctcc tggagtggaa gaggcctgct ccctggctct gggtctgctg ggggcacagt
5761  aaatcagtct tggcacccac atccagggca gagaggtctg tggttctcag catcagaagg
5821  cagcgcagcc cctctcctct tcaggctaca gggttgtcac ctgctgagtc ctcaggttgt
5861  ttggcctctc tggtccatct tgggcattag gttctccagc agagctctgg ccagctgcct
5941  cttctttaac tgggaacaca ggctctcaca agatcagaac ccccactcac ccccaagatc
6001  ttatctagca agcctgtagt attcagtttc tgttgtagga agagagcgag gcatccctga
6061  attccacgca tctgctggaa acgagccgtg tcagatcgca catccctgcg cccccatgcc
6121  cctctgagtc acacaggaca gaggaggcag agcttctgcc cactgttatc ttcactttct
6181  ttgtccagtc tttgttttt aataagcagt gaccctccct actcttcttt ttaatgattt
6241  ttgtagttga tttgtctgaa ctgtggctac tgtgcattcc ttgaataatc acttgtaaaa
6301  attgtcagtg cttgaagctg tttcctttac tcacattgaa gggacttcgt tggttttttg
6361  gagtcttggt tgtgactcca agagcagagt gaggaagacc cccaagcata gactcgggta
6421  ctgtgatgat ggctgcagtc cagttttatg attctgcttt tatgtgtccc ttgataacag
6481  tgacttaaca atatacattc ctcataaata aaaaaaaaac aagaatctga attcttagaa
6541  aaaaaaaaaa aaaaaaaaa a
```

In another embodiment, antibodies used to practice this invention are designed to bind to, or affinity matured to bind to, a polypeptide SEQ ID NO:3, or subsequences thereof:

```
                                                             (SEQ ID NO: 3)
  1  mnprqgysls gyythpfggy ahrqlryqqp gpgsspssfl lkqieflkgg lpeaprigkq
 61  tpslppslpg lrprfpvlla sstrgrqvdi rgvprgvhlg sgglqrgfqh psprgrslpq
121  rgvdclsshf qelsiyqdge qrilkfleel gegkattahd lsgklgtpkk einrvlysla
181  kkgklqkaeg tpplwkiavs tqawnqhsgv yrpdghsqga pssdpslepe drnstsvsed
241  llepfiavsa qawnqhsgvv rpdshsqqsp nsdpgleped snstsatedp lefldmaeik
301  ekicdylfnv sdssalnlak nigltkardi navlidmerq gdvyrqgttp piwhltdkkr
361  ermqikrntn svpetapaai petkrnaefl tcniptsnas ssmvttekve ngqepvikle
421  srqearpepa rlkppvhysg pskagyvdfe ngqwatddip ddlnsiraap gefraimemp
481  sfyshglprc spykkltecg lknpisglle yaqfasqtce frmieqsgpp heprfkfqvv
541  ingrefppae agskkvakqd aamkamtill eeakakdsgk seesshyste kesektaesq
601  tptpsatsff sgkspvttll ecmhklgnsc efrllskegp ahepkfqyev avgaqtfpsv
661  sapskkvakq maaeeamkal hgeatnsmas dngpegmise sldnlesmmp nkvrkigelv
```

```
 721    rylntnpvgg lleyarshgf aaefklvdqs qpphepkfvy qakvggrwfp avcahskkqg 781    kqeaadaalr vligenekae rmgftevtpv tgaslrrtml llsrspeaqp ktlpltgstf 841    hdqiamlshr efntltnsfq psllgrkila aiimkkdsed mgyvyslgtg nrcvkgdsls 901    lkgetvndch aeiisrrgfi rflyselmky nsqtakdsif epakggeklq ikktvsfhly 961    istapcgdga lfdkscsdra mestesrhyp vfenpkqgkl rtkvengegt ipvessdivp 1021    twdgirlger lrtmscsdki lrwnvlglqg allthflqpi ylksvtlgyl fsqghltrai 1081    ccrvtrdgsa fedglrhpfi vnhpkvgrvs iydskrgsqk tketsvnwcl adgydleild 1141    gtrgtvdgpr nelsrvskkn ifllfkkles fryrrdllrl sygaekkaar dyetaknyfk 1201    kglkdmgygn wiskpqeekn fylcpv
```

Generating and Manipulating Nucleic Acids

In alternative embodiments, compositions and methods of the invention use nucleic acids for treating, ameliorating or preventing diseases and conditions responsive to the inhibition or slowing of cell differentiation and/or self-renewal of hematopoietic stem cells or cancer stem cells. In alternative embodiments, compositions and methods of the invention comprise use of an inhibitory nucleic acid molecule or an antisense oligonucleotide inhibitory to expression of the ADAR1 gene (e.g., SEQ ID NO:1) or an ADAR1 gene transcript (e.g., SEQ ID NO:2). In alternative embodiments, compositions and methods of the invention comprise use of an inhibitory nucleic acid molecule or antisense oligonucleotide inhibitory to expression of the ADAR1 gene or ADAR1 gene transcript comprises: an RNAi inhibitory nucleic acid molecule, a double-stranded RNA (dsRNA) molecule, a small interfering RNA (siRNA), a microRNA (miRNA) and/or a short hairpin RNA (shRNA), or a ribozyme.

In alternative embodiments, nucleic acids of the invention are made, isolated and/or manipulated by, e.g., cloning and expression of cDNA libraries, amplification of message or genomic DNA by PCR, and the like.

The nucleic acids used to practice this invention, whether RNA, iRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including e.g. bacterial, fungal, mammalian, yeast, insect or plant cell expression systems.

Alternatively, nucleic acids used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I, Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

Nucleic acids or nucleic acid sequences used to practice this invention can be an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. Compounds use to practice this invention include "nucleic acids" or "nucleic acid sequences" including oligonucleotide, nucleotide, polynucleotide, or any fragment of any of these; and include DNA or RNA (e.g., mRNA, rRNA, tRNA, iRNA) of genomic or synthetic origin which may be single-stranded or double-stranded; and can be a sense or antisense strand, or a peptide nucleic acid (PNA), or any DNA-like or RNA-like material, natural or synthetic in origin, including, e.g., iRNA, ribonucleoproteins (e.g., double stranded iRNAs, e.g., iRNPs). Compounds use to practice this invention include nucleic acids, i.e., oligonucleotides, containing known analogues of natural nucleotides. Compounds use to practice this invention include nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. Compounds use to practice this invention include "oligonucleotides" including a single stranded polydeoxynucleotide or two complementary polydeoxynucleotide strands that may be chemically synthesized. Compounds use to practice this invention include synthetic oligonucleotides having no 5' phosphate, and thus will not ligate to another oligonucleotide without adding a phosphate with an ATP in the presence of a kinase. A synthetic oligonucleotide can ligate to a fragment that has not been dephosphorylated.

In alternative aspects, compounds used to practice this invention include genes or any segment of DNA or RNA involved in producing a polypeptide chain; it can include regions preceding and following the coding region (leader and trailer) as well as, where applicable, intervening sequences (introns) between individual coding segments (exons). "Operably linked" can refer to a functional relationship between two or more nucleic acid (e.g., DNA or RNA) segments. In alternative aspects, it can refer to the functional relationship of transcriptional regulatory sequence to a transcribed sequence. For example, a promoter can be operably linked to a coding sequence, such as a nucleic acid used to practice this invention, if it stimulates or modulates the transcription of the coding sequence in an appropriate host cell or other expression system. In alternative aspects, promoter transcriptional regulatory sequences can be operably linked to a transcribed sequence where they can be physically contiguous to the transcribed sequence, i.e., they can be cis-acting. In alternative aspects, transcriptional regulatory sequences, such as enhancers, need not be physically contiguous or located in close proximity to the coding sequences whose transcription they enhance.

In alternative aspects, the invention comprises use of "expression cassette" comprising a nucleotide sequence used to practice this invention, which can be capable of affecting expression of the nucleic acid, e.g., a structural gene or a transcript (e.g., encoding a DRP or antibody) in a host compatible with such sequences. Expression cassettes can include at least a promoter operably linked with the polypeptide coding sequence or inhibitory sequence; and, in one aspect, with other sequences, e.g., transcription termination signals. Additional factors necessary or helpful in effecting expression may also be used, e.g., enhancers.

In alternative aspects, expression cassettes used to practice this invention also include plasmids, expression vectors, recombinant viruses, any form of recombinant "naked DNA" vector, and the like. In alternative aspects, a "vector" used to practice this invention can comprise a nucleic acid that can infect, transfect, transiently or permanently transduce a cell. In alternative aspects, a vector used to practice this invention can be a naked nucleic acid, or a nucleic acid complexed with protein or lipid. In alternative aspects, vectors used to practice this invention can comprise viral or bacterial nucleic acids and/or proteins, and/or membranes (e.g., a cell membrane, a viral lipid envelope, etc.). In alternative aspects, vectors used to practice this invention can include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and can include both the expression and non-expression plasmids. In alternative aspects, the vector used to practice this invention can be stably replicated by the cells during mitosis as an autonomous structure, or can be incorporated within the host's genome.

In alternative aspects, "promoters" used to practice this invention include all sequences capable of driving transcription of a coding sequence in a cell, e.g., a mammalian cell such as a brain cell. Thus, promoters used in the constructs of the invention include cis-acting transcriptional control elements and regulatory sequences that are involved in regulating or modulating the timing and/or rate of transcription of a gene. For example, a promoter used to practice this invention can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

"Constitutive" promoters used to practice this invention can be those that drive expression continuously under most environmental conditions and states of development or cell differentiation. "Inducible" or "regulatable" promoters used to practice this invention can direct expression of the nucleic acid of the invention under the influence of environmental conditions or developmental conditions.

Antisense Inhibitory Nucleic Acid Molecules

In alternative embodiments, compositions and methods of the invention comprise use of an inhibitory nucleic acid molecule or an antisense oligonucleotide inhibitory to expression of the ADAR1 gene (e.g., SEQ ID NO:1) or an ADAR1 gene transcript (e.g., SEQ ID NO:2). In alternative embodiments, compositions and methods of the invention comprise use of an inhibitory nucleic acid molecule or antisense oligonucleotide inhibitory to expression of the ADAR1 gene or ADAR1 gene transcript comprises: an RNAi inhibitory nucleic acid molecule, a double-stranded RNA (dsRNA) molecule, a small interfering RNA (siRNA), a microRNA (miRNA) and/or a short hairpin RNA (shRNA), or a ribozyme.

Naturally occurring or synthetic nucleic acids can be used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol. Appl. Pharmacol. 144:189-197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene(methylimino), 3'-N-carbamate, and morpholino carbamate nucleic acids.

RNA Interference (RNAi)

In one aspect, the invention provides RNAi inhibitory nucleic acid molecules capable of decreasing or inhibiting expression of one or a set of ADAR1 transcripts or proteins, e.g., the transcript (mRNA, message) SEQ ID NO:2 or isoform or isoforms thereof. In one aspect, the RNAi molecule comprises a double-stranded RNA (dsRNA) molecule. The RNAi molecule can comprise a double-stranded RNA (dsRNA) molecule, e.g., siRNA, miRNA (microRNA) and/or short hairpin RNA (shRNA) molecules.

In alternative aspects, the RNAi is about 11, 12, 13, 14, 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi, e.g., siRNA for inhibiting transcription and/or miRNA to inhibit translation, is the breaking of a double-stranded RNA (dsRNA) matching a specific gene sequence into short pieces called short interfering RNA, which trigger the degradation of mRNA that matches its sequence.

In one aspect, intracellular introduction of the RNAi (e.g., miRNA or siRNA) is by internalization of a target cell specific ligand bonded to an RNA binding protein comprising an RNAi (e.g., microRNA) is adsorbed. The ligand can be specific to a unique target cell surface antigen. The ligand can be spontaneously internalized after binding to the cell surface antigen. If the unique cell surface antigen is not naturally internalized after binding to its ligand, internalization can be promoted by the incorporation of an arginine-rich peptide, or other membrane permeable peptide, into the structure of the ligand or RNA binding protein or attachment of such a peptide to the ligand or RNA binding protein. See, e.g., U.S. Patent App. Pub. Nos. 20060030003; 20060025361; 20060019286; 20060019258. In one aspect, the invention provides lipid-based formulations for delivering, e.g., introducing nucleic acids of the invention as nucleic acid-lipid particles comprising an RNAi molecule to a cell, see e.g., U.S. Patent App. Pub. No. 20060008910.

Methods for making and using RNAi molecules, e.g., siRNA and/or miRNA, for selectively degrade RNA are well known in the art, see, e.g., U.S. Pat. Nos. 6,506,559; 6,511,824; 6,515,109; 6,489,127.

Methods for making expression constructs, e.g., vectors or plasmids, from which an inhibitory polynucleotide (e.g., a duplex siRNA of the invention) is transcribed are well known and routine. A regulatory region (e.g., promoter, enhancer, silencer, splice donor, acceptor, etc.) can be used to transcribe an RNA strand or RNA strands of an inhibitory polynucleotide from an expression construct. When making a duplex siRNA inhibitory molecule, the sense and antisense strands of the targeted portion of the targeted IRES can be transcribed as two separate RNA strands that will anneal together, or as a single RNA strand that will form a hairpin loop and anneal with itself. For example, a construct targeting a portion of a gene, e.g., an NADPH oxidase enzyme coding sequence or transcriptional activation sequence, is inserted between two promoters (e.g., mammalian, viral, human, tissue specific, constitutive or other type of promoter) such that transcription occurs bidirectionally and will result in complementary RNA strands that may subsequently anneal to form an inhibitory siRNA of the invention.

Alternatively, a targeted portion of a gene, coding sequence, promoter or transcript can be designed as a first and second antisense binding region together on a single expression vector; for example, comprising a first coding region of a targeted gene in sense orientation relative to its controlling promoter, and wherein the second coding region of the gene is in antisense orientation relative to its controlling promoter. If transcription of the sense and antisense coding regions of the targeted portion of the targeted gene occurs from two separate promoters, the result may be two separate RNA strands that may subsequently anneal to form a gene-inhibitory siRNA used to practice this invention.

In another aspect, transcription of the sense and antisense targeted portion of the targeted gene is controlled by a single promoter, and the resulting transcript will be a single hairpin RNA strand that is self-complementary, i.e., forms a duplex by folding back on itself to create a gene-inhibitory siRNA molecule. In this configuration, a spacer, e.g., of nucleotides, between the sense and antisense coding regions of the targeted portion of the targeted gene can improve the ability of the single strand RNA to form a hairpin loop, wherein the hairpin loop comprises the spacer. In one embodiment, the spacer comprises a length of nucleotides of between about 5 to 50 nucleotides. In one aspect, the sense and antisense coding regions of the siRNA can each be on a separate expression vector and under the control of its own promoter.

Inhibitory Ribozymes

The invention provides ribozymes capable of binding and inhibiting, e.g., decreasing or inhibiting, expression of one or a set of ADAR1 transcripts or proteins, e.g., SEQ ID NO:1 or SEQ ID NO:2, or isoform or isoforms thereof.

These ribozymes can inhibit a gene's activity by, e.g., targeting a genomic DNA or an mRNA (a message, a transcript). Strategies for designing ribozymes and selecting a gene-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

Kits and Instructions

The invention provides kits comprising compositions and/or instructions for practicing methods of the invention. As such, kits, cells, vectors and the like can also be provided. In alternative embodiments, the invention provides kits comprising: a composition used to practice a method of any of the invention, or a composition, a pharmaceutical composition or a formulation of the invention, and optionally comprising instructions for use thereof.

Compositions and Methods for Dormant Cancer Stem Cell Detection and Elimination

In alternative embodiments, the invention provides compositions and methods to detect dormant cancer stem cells, e.g., Chronic Myelogenous Leukemia (CML) stem cells. In alternative embodiments, the invention provides compositions and methods for use to, e.g., therapeutically, initiate, stimulate or force a dormant cancer stem cell, e.g., a Chronic Myelogenous Leukemia (CML) stem cell, into cycle so that it can be targeted by a therapeutic agent or procedure, e.g., chemotherapy, radiation therapy or targeted tyrosine kinase inhibitors, or any agent or procedure that targets dividing cells.

In alternative embodiments, the invention provides compositions and methods comprising or comprising use of sonic hedgehog inhibitors, e.g., inhibitors of Smoothened (SMO), an integral membrane protein mediator of Hedgehog signaling (see e.g., Shi et al. (2011) Development, Epub 2011 Aug. 18; Su, et al. (2011) Sci. Signal. July 5; 4(180): ra43), which activate, stimulate or initiate in a stem cell, e.g., a cancer stem cell, a transition from G0 to G1 of the cell cycle, thereby sensitizing the stem cells to agents that target dividing cells.

Here we investigated the role of Shh signaling in maintenance of dormancy. We show that, compared to chronic phase CML and normal progenitors, human blast crisis LSC harbor enhanced expression of the Shh transcriptional activator, GLI2, and decreased expression of a transcriptional repressor, GLI3. Treatment of human blast crisis LSC engrafted RAG2$^{-/-}$γc$^{-/-}$ mice with a novel selective Shh inhibitor, designated PF-04449913 (see Supplementary FIG. 1a for structure), reduced leukemic burden in a niche-dependent manner commensurate with GLI downregulation.

Full transcriptome RNA sequencing performed on FACS-purified human progenitors from PF-04449913 treated blast crisis LSC engrafted mice demonstrated greater Shh gene splice isoform concordance with normal progenitors than vehicle treated controls. In addition, RNA sequencing revealed significantly decreased cell cycle regulatory gene expression and splice isoform analysis demonstrated reversion toward a normal splice isoform signature for many cell cycle regulatory genes.

Moreover, cell cycle FACS analysis showed that selective Shh inhibition permitted dormant blast crisis LSC to enter the cell cycle while normal progenitor cell cycle status was unaffected.

Finally, PF-04449913 synergized with BCR-ABL inhibition to reduce blast crisis LSC survival and self-renewal in concert with increased expression of Shh pathway regulators.

Our findings demonstrate that selective Shh antagonism induces cycling of dormant human blast crisis LSC, rendering them susceptible to BCR-ABL inhibition, while sparing normal progenitors.

The invention also provides novel stem cell, e.g., LSC, splice isoform detection platforms, e.g., as kits of the invention, to assess the efficacy of Shh inhibitor-mediated sensitization. In alternative embodiments, stem cell splice isoform detection platforms and compositions (e.g., kits) of the invention are used to identify "conversion" of a stem cell to a "normal cell", or to determine or define a molecularly targeted therapy for dormant cancer stem cell elimination strategies that ultimately avert relapse. In alternative embodiments, stem cell splice isoform detection platforms and compositions (e.g., kits) of the invention are used to identify compounds or treatments that can successfully inhibit Shh expression.

In alternative embodiments, compositions and methods of the invention can be used synergistically to sensitize dormant stem cells, e.g., LSC, to therapeutic agents that target dividing cells including e.g., tyrosine kinase inhibitors, chemotherapy. In alternative embodiments, compositions and methods of the invention can be used sensitize, e.g., radiosensitize, a cancer stem cell, e.g., a LSC and other cancer stem cell populations, through cell cycle induction or stimulation.

When CML stem cells were treated with a Smoothened (SMO) protein inhibitor (SMO being a key component of the Hedgehog signaling pathway), dormant stem cells entered the cell cycle, as evidenced by the RNA isoform pattern of a leukemic cancer stem cell reverting to the pattern of a normal cell. Hence, in alternative embodiments, this RNA isoform pattern can be used as a biomarker of response to chemotherapy and a target for drug development, e.g., successful or effective inhibition of Shh give a particular, detectable RNA isoform pattern.

Our findings demonstrate that selective Shh antagonism induces cycling of dormant human blast crisis LSC, rendering them susceptible to BCR-ABL inhibition, while sparing normal progenitors. Implementation of novel cancer stem cell, e.g., a LSC, splice isoform detection platforms of this invention can assess the efficacy of Shh inhibitor-mediated sensitization to molecularly targeted therapies. Implementation of novel LSC splice isoform detection platforms of this invention can identify and determine the effectiveness of dormant cancer stem cell elimination strategies that ultimately avert relapse.

In alternative embodiments, the invention provides splice isoform detection kits or arrays for stem cells, e.g., LSC stem cells. In alternative embodiments, the invention provides nanoproteomic detection kits or arrays for stem cells (to determine an altered proteome caused by an altered RNA splicing pattern, or alternatively spliced transcripts) to determine a response to a stem cell therapy, e.g., a LSC targeted therapy.

Kits and Instructions

The invention provides kits comprising compositions and/or instructions for practicing methods of the invention. As such, kits, cells, vectors and the like can also be provided. In alternative embodiments, the invention provides kits comprising: a composition used to practice a method of any of the invention, or a composition, a pharmaceutical composition or a formulation of the invention, and optionally comprising instructions for use thereof.

Antisense Inhibitory Nucleic Acid Molecules

In alternative embodiments, compositions and methods of the invention comprise use of an inhibitory nucleic acid molecule or an antisense oligonucleotide inhibitor to expression of the Shh or a Shh gene transcript. In alternative embodiments, compositions and methods of the invention comprise use of an inhibitory nucleic acid molecule or antisense oligonucleotide inhibitory to expression of the Shh gene or Shh gene transcript comprises: an RNAi inhibitory nucleic acid molecule, a double-stranded RNA (dsRNA) molecule, a small interfering RNA (siRNA), a microRNA (miRNA) and/or a short hairpin RNA (shRNA), or a ribozyme.

Naturally occurring or synthetic nucleic acids can be used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol. Appl. Pharmacol. 144:189-197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene(methylimino), 3'-N-carbamate, and morpholino carbamate nucleic acids.

RNA Interference (RNAi)

In one aspect, the invention provides RNAi inhibitory nucleic acid molecules capable of decreasing or inhibiting expression of one or a set of Shh transcripts or proteins, e.g., the transcript (mRNA, message) or isoform or isoforms thereof. In one aspect, the RNAi molecule comprises a double-stranded RNA (dsRNA) molecule, e.g., siRNA, miRNA (microRNA) and/or short hairpin RNA (shRNA) molecules.

In alternative aspects, the RNAi is about 11, 12, 13, 14, 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi, e.g., siRNA for inhibiting transcription and/or miRNA to inhibit translation, is the breaking of a double-stranded RNA (dsRNA) matching a specific gene sequence into short pieces called short interfering RNA, which trigger the degradation of mRNA that matches its sequence.

In one aspect, intracellular introduction of the RNAi (e.g., miRNA or siRNA) is by internalization of a target cell specific ligand bonded to an RNA binding protein comprising an RNAi (e.g., microRNA) is adsorbed. The ligand can be specific to a unique target cell surface antigen. The ligand can be spontaneously internalized after binding to the cell surface antigen. If the unique cell surface antigen is not naturally internalized after binding to its ligand, internalization can be promoted by the incorporation of an arginine-rich peptide, or other membrane permeable peptide, into the structure of the ligand or RNA binding protein or attachment of such a peptide to the ligand or RNA binding protein. See, e.g., U.S. Patent App. Pub. Nos. 20060030003; 20060025361; 20060019286; 20060019258. In one aspect, the invention provides lipid-based formulations for delivering, e.g., introducing nucleic acids of the invention as nucleic acid-lipid particles comprising an RNAi molecule to a cell, see e.g., U.S. Patent App. Pub. No. 20060008910.

Methods for making and using RNAi molecules, e.g., siRNA and/or miRNA, for selectively degrade RNA are well known in the art, see, e.g., U.S. Pat. Nos. 6,506,559; 6,511,824; 6,515,109; 6,489,127.

Methods for making expression constructs, e.g., vectors or plasmids, from which an inhibitory polynucleotide (e.g., a duplex siRNA of the invention) is transcribed are well known and routine. A regulatory region (e.g., promoter, enhancer, silencer, splice donor, acceptor, etc.) can be used to transcribe an RNA strand or RNA strands of an inhibitory polynucleotide from an expression construct. When making a duplex siRNA inhibitory molecule, the sense and antisense strands of the targeted portion of the targeted IRES can be transcribed as two separate RNA strands that will anneal together, or as a single RNA strand that will form a hairpin loop and anneal with itself. For example, a construct targeting a portion of a gene, e.g., a Shh coding sequence or transcriptional activation sequence, is inserted between two promoters (e.g., mammalian, viral, human, tissue specific, constitutive or other type of promoter) such that transcription occurs bidirectionally and will result in complementary RNA strands that may subsequently anneal to form an inhibitory siRNA of the invention.

Alternatively, a targeted portion of a gene, coding sequence, promoter or transcript can be designed as a first and second antisense binding region together on a single expression vector; for example, comprising a first coding region of a targeted gene in sense orientation relative to its controlling promoter, and wherein the second coding region of the gene is in antisense orientation relative to its controlling promoter. If transcription of the sense and antisense coding regions of the targeted portion of the targeted gene occurs from two separate promoters, the result may be two separate RNA strands that may subsequently anneal to form a gene-inhibitory siRNA used to practice this invention.

In another aspect, transcription of the sense and antisense targeted portion of the targeted gene is controlled by a single promoter, and the resulting transcript will be a single hairpin RNA strand that is self-complementary, i.e., forms a duplex by folding back on itself to create a gene-inhibitory siRNA molecule. In this configuration, a spacer, e.g., of nucleotides, between the sense and antisense coding regions of the targeted portion of the targeted gene can improve the ability of the single strand RNA to form a hairpin loop, wherein the hairpin loop comprises the spacer. In one embodiment, the spacer comprises a length of nucleotides of between about 5 to 50 nucleotides. In one aspect, the sense and antisense coding regions of the siRNA can each be on a separate expression vector and under the control of its own promoter.

Inhibitory Ribozymes

In alternative embodiment, compositions and methods of the invention comprise use of ribozymes capable of binding and inhibiting, e.g., decreasing or inhibiting, expression of one or a set of Shh transcripts or proteins, or isoform or isoforms thereof.

These ribozymes can inhibit a gene's activity by, e.g., targeting a genomic DNA or an mRNA (a message, a transcript). Strategies for designing ribozymes and selecting a gene-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

Bioisosteres of Compounds Used to Practice the Invention

In alternative embodiments, the invention also provides bioisosteres of compounds used to practice the invention, e.g., compounds having a structure as set forth in FIG. 17a, or PF-04449913. In alternative embodiments, the invention provides compositions that inhibit or slow the expression of a Shh gene, a Shh gene product, a Shh transcript, and/or a Shh polypeptide comprising a PF-04449913, or an equivalent thereof, or a bioisostere thereof.

In alternative embodiments, bioisosteres of the invention are compounds of the invention comprising one or more substituent and/or group replacements with a substituents and/or group having substantially similar physical or chemical properties which produce substantially similar biological properties to a compound of the invention, or stereoisomer, racemer or isomer thereof. In one embodiment, the purpose of exchanging one bioisostere for another is to enhance the desired biological or physical properties of a compound without making significant changes in chemical structures.

For example, in one embodiment, bioisosteres of compounds of the invention are made by replacing one or more hydrogen atom(s) with one or more fluorine and/or deuterium atom(s), e.g., at a site of metabolic oxidation; this may prevent metabolism (catabolism) from taking place. Because the fluorine atom or deuterium is similar in size to the hydrogen atom the overall topology of the molecule is not significantly affected, leaving the desired biological activity unaffected. However, with a blocked pathway for metabolism, the molecule may have a longer half-life or be less toxic, and the like.

Sonic Hedgehog Targets as Biomarkers of Prognosis and Response for Human Chronic Myelogenous Leukemia In alternative embodiments, this invention compositions and methods to analyze or measure biomarkers in human leukemia cells to predict the amount of blastic transformation, the severity of the disease, the progress (e.g., regression) of the disease in light of a particular treatment or drug administration. In alternative embodiments, this invention compositions and methods to analyze or measure biomarkers which are predictors of response to selective Sonic Hedgehog (Shh) inhibition.

This invention is the first to analyze Shh gene expression in human leukemic versus normal progenitors and to identify an increase in GLI2 and commensurate decrease in GLI3 as predictor of blastic transformation. In alternative embodiments, compositions and methods of the invention measure GLI1 and GLI2 transcript and/or GLI1 and GLI2 protein levels to predict a response to selective Shh inhibition, where GLI1 and GLI2 presence is a positive predictor of a response to selective Shh inhibition. In alternative embodiments, GLI1 and/or GLI2 are used as predictive biomarkers, individually or together, of a response to an inhibitor of the Sonic Hedgehog (shh) pathway, including inhibitors of Smoothened (SMO), an integral membrane protein mediator of Hedgehog signaling (see e.g., Shi et al. (2011) Development, Epub 2011 Aug. 18; Su, et al. (2011) Sci. Signal, July 5; 4(180):ra43). Both qRT-PCR and nanoproteomics confirmed these functional biomarkers.

In alternative embodiments, compositions and methods of the invention measure (determine) levels of GLI2 (increasing) and/or GLI3 (decreasing) as prognostic biomarkers (individually or together) for chronic myelogenous leukemia (CML) progression, Leukemic Stem Cell (LSC) generation and tyrosine kinase inhibitor resistance. Both qRT-PCR and nanoproteomics confirmed these functional biomarkers.

In alternative embodiments, the invention provides compositions and methods comprising or comprising use of sonic hedgehog inhibitors, e.g., inhibitors of Smoothened (SMO), which activate, stimulate or initiate in a stem cell, e.g., a cancer stem cell, a transition from G0 to G1 of the cell cycle, thereby sensitizing the stem cells to agents that target dividing cells.

Here we investigated the role of Shh signaling in maintenance of dormancy. We show that, compared to chronic phase CML and normal progenitors, human blast crisis LSC harbor enhanced expression of the Shh transcriptional activator, GLI2, and decreased expression of a transcriptional repressor, GLI3. Treatment of human blast crisis LSC engrafted RAG2$^{-/-}$γc$^{-/-}$ mice with a novel selective Shh inhibitor, designated PF-04449913 (see Supplementary FIG. 1a for structure), reduced leukemic burden in a niche-dependent manner commensurate with GLI downregulation.

Full transcriptome RNA sequencing performed on FACS-purified human progenitors from PF-04449913 treated blast crisis LSC engrafted mice demonstrated greater Shh gene splice isoform concordance with normal progenitors than vehicle treated controls. In addition, RNA sequencing revealed significantly decreased cell cycle regulatory gene expression and splice isoform analysis demonstrated reversion toward a normal splice isoform signature for many cell cycle regulatory genes.

Moreover, cell cycle FACS analysis showed that selective Shh inhibition permitted dormant blast crisis LSC to enter the cell cycle while normal progenitor cell cycle status was unaffected.

Finally, PF-04449913 synergized with BCR-ABL inhibition to reduce blast crisis LSC survival and self-renewal in concert with increased expression of Shh pathway regulators.

Our findings demonstrate that selective Shh antagonism induces cycling of dormant human blast crisis LSC, rendering them susceptible to BCR-ABL inhibition, while sparing normal progenitors.

The invention also provides novel stem cell, e.g., LSC, splice isoform detection platforms, e.g., as kits of the invention, to assess the efficacy of Shh inhibitor-mediated sensitization. In alternative embodiments, stem cell splice isoform detection platforms and compositions (e.g., kits) of the invention are used to identify "conversion" of a stem cell to a "normal cell", or to determine or define a molecularly targeted therapy for dormant cancer stem cell elimination strategies that ultimately avert relapse. In alternative embodiments, stem cell splice isoform detection platforms and compositions (e.g., kits) of the invention are used to identify compounds or treatments that can successfully inhibit Shh expression.

In alternative embodiments, compositions and methods of the invention can be used synergistically to sensitize dormant stem cells, e.g., LSC, to therapeutic agents that target dividing cells including e.g., tyrosine kinase inhibitors, chemotherapy. In alternative embodiments, compositions and methods of the invention can be used sensitize, e.g., radiosensitize, a cancer stem cell, e.g., a LSC and other cancer stem cell populations, through cell cycle induction or stimulation.

When CML stem cells were treated with a Smoothened (SMO) protein inhibitor (SMO being a key component of the Hedgehog signaling pathway), dormant stem cells entered the cell cycle, as evidenced by the RNA isoform pattern of a leukemic cancer stem cell reverting to the pattern of a normal cell. Hence, in alternative embodiments, this RNA isoform pattern can be used as a biomarker of response to chemotherapy and a target for drug development, e.g., successful or effective inhibition of Shh give a particular, detectable RNA isoform pattern.

Our findings demonstrate that selective Shh antagonism induces cycling of dormant human blast crisis LSC, rendering them susceptible to BCR-ABL inhibition, while sparing normal progenitors. Implementation of novel cancer stem cell, e.g., a LSC, splice isoform detection platforms of this invention can assess the efficacy of Shh inhibitor-mediated sensitization to molecularly targeted therapies. Implementation of novel LSC splice isoform detection platforms of this invention can identify and determine the effectiveness of dormant cancer stem cell elimination strategies that ultimately avert relapse.

In alternative embodiments, the invention provides splice isoform detection kits or arrays for stem cells, e.g., LSC stem cells. In alternative embodiments, the invention provides nanoproteomic detection kits or arrays for stem cells (to determine an altered proteome caused by an altered RNA splicing pattern, or alternatively spliced transcripts) to determine a response to a stem cell therapy, e.g., a LSC targeted therapy.

In alternative embodiments, biomarkers of the invention can be detected using arrays, microarrays, proteomic arrays and the like, e.g., as described by: Oehler, et al., (2009) Blood, "The derivation of diagnostic markers of chronic myeloid leukemia progression from microarray data", October 8; 114(15):3292-8. Epub 2009 Aug. 4; Fan, et al., Nature Medicine, May 2009, "Nanofluidic proteomic assay for serial analysis of oncoprotein activation in clinical specimens," Volume 15, Number 5: 566-571; O'Neill, et al., Proc. Natl. Acad. Sci. USA, October 2006, "Isoelectric focusing technology quantifies protein signaling in 25 cells", Volume 103, Number 44: 16153-161158.

Kits and Instructions

The invention provides kits comprising compositions and/or instructions for practicing methods of the invention. As such, kits, cells, vectors and the like can also be provided. In alternative embodiments, the invention provides kits comprising: a composition used to practice a method of any of the invention, or a composition, a pharmaceutical composition or a formulation of the invention, and optionally comprising instructions for use thereof.

Spliced Isoform Biomarkers to Assess Responses to Cancer Stem Cell Targeted Therapies In alternative embodiments, the invention provides compositions and methods for determining the pattern of alternatively spliced transcripts and their protein products to, e.g., distinguish leukemic progenitors from their normal counterparts, e.g., by determining the pattern of alternatively spliced Stat5a specific splice isoforms. In alternative embodiments, the pattern of alternatively spliced Stat5a specific splice isoforms is used as a novel leukemic stem cell (LSC) identification marker.

In alternative embodiments, the invention provides compositions and methods to assess LSC specific responses to targeted agents such as JAK2 inhibitors, e.g., Stat5a specific splice isoforms can be used as biomarkers of response to JAK2 inhibition.

In alternative embodiments, one or both phosphoStat5a and phospho-JAK2 are used as biomarker or biomarkers of a response to a selective JAK2 inhibition, e.g., when selective JAK2 inhibition is used as a clinical treatment or when selective JAK2 inhibitors are tested in in vitro, in animals, or in clinical trials. In alternative embodiments, both signatures of response (biomarker of response in clinical trial) are quantitatively measured; and if the alternative spliced forms do not decrease, the self-renewing LSC are resistant to treatment; and, if STAT5a isoforms are decreased or inhibited, LSC self-renewal capacity is decreased.

We have identified novel isoforms of phosphoStat5a and phospho-JAK2 via RNA-seq that will provide functional LSC markers and will help to determine if different therapies will target this specific population. Our invention is the first to analyze specific isoform expression of STAT5 as a paradigm for human leukemia stem cell identification and to identify splice isoforms that predict cancer stem cell response. In addition, reductions in phosphoStat5a and/or phosphoJAK2 proteins are positive predictors of response to selective JAK2 inhibition. Both qRT-PCR confirmed decreases in transcripts and nanoproteomics confirmed decreases in these alternatively spliced proteins as functional biomarkers of response.

In alternative embodiments, the invention provides compositions and methods that comprise use of splice isoform specific qPCR, and equivalents, and/or nanoproteomics, to detect isoforms that sustain LSC self-renewal, including Stat5a isoforms and other pathway LSC specific splice isoforms in a prognostic kit for cancer stem cells (CSC).

In alternative embodiments, the invention provides compositions and methods that comprise use of splice isoforms such as Stat5a isoforms as predictors of LSC response to selective JAK2 inhibition.

In alternative embodiments, the invention provides compositions and methods that comprise use of splice isoform patterns by qPCR and nanoproteomics to predict response to CSC targeted therapy.

In alternative embodiments, the invention provides compositions and methods to detect cancer stem cell specific JAK/STAT signaling pathway splice isoforms by RNA sequencing, qRT-PCR and nanoproteomics, validated in CML, but applicable to cancer stem cells in the primary and metastatic niches, particularly in the setting of inflammatory cytokines and interleukins elaborated in cancer.

In alternative embodiments, biomarkers, or alternatively spliced forms, used to practice the invention can be detected using e.g., arrays, microarrays, proteomic arrays and the like, e.g., as described by: Oehler, et al., (2009) Blood, "The derivation of diagnostic markers of chronic myeloid leukemia progression from microarray data", October 8; 114(15): 3292-8. Epub 2009 Aug. 4; Fan, et al., Nature Medicine, May 2009, "Nanofluidic proteomic assay for serial analysis of oncoprotein activation in clinical specimens," Volume 15, Number 5: 566-571; O'Neill, et al., Proc. Natl. Acad. Sci. USA, October 2006, "Isoelectric focusing technology quantifies protein signaling in 25 cells", Volume 103, Number 55: 16153-16158.

FIG. 24: Nanoproteomic SAR302503 mechanism of action analysis. Sorted progenitors from mice spleen that where treated where analyzed using nanoproteonomics (CB1000) technology. Panels shows phospho-JAK2 protein (upper left); total JAK2 protein (upper right); phospho-STAT5A protein (lower right) and β2-microblobulin (lower right) status after vehicle (blue) or selective JAK2 inhibitor (SAR302503; green) treatment.

FIG. 25: Identification and quantification of transcript isoforms in LSC treated with vehicle or a selective JAK2 inhibitor. A) RNA-seq-based expression levels of isoforms involved in the Jak/Stat pathway, in vehicle-treated (blue) and SAR302503-treated (red) blast crisis CML sorted progenitors. B) Specific isoform expression after treatment with SAR302503 (JAK2 inhibitor) and dasatinib (BCR-ABL inhibitor), relative to vehicle treatment demonstrating synergistic inhibition of self-renewal gene isoforms such as phosphoSTAT5a and increases in interferon response genes.

Kits and Instructions

The invention provides kits comprising compositions and/or instructions for practicing methods of the invention. As such, kits, cells, vectors and the like can also be provided. In alternative embodiments, the invention provides kits comprising: a composition used to practice a method of any of the invention, or a composition, a pharmaceutical composition or a formulation of the invention, and optionally comprising instructions for use thereof.

The invention will be further described with reference to the following examples; however, it is to be understood that the invention is not limited to such examples.

EXAMPLES

Example 1

Inhibiting ADAR Enzyme to Decrease in Self-Renewal Capacity or Stem Cells

RNA Editing as a Novel Cancer Stem Cell Target

This example provides data demonstrating that the methods and compositions of the invention are effective for treating, ameliorating or preventing diseases and conditions responsive to the inhibition or slowing of cell differentiation and/or self-renewal of dysfunctional cells, cancer cells, leukemia cells, hematopoietic stem cells or cancer stem cells.

Our research focused on dissecting the role of RNA editing in both normal HSC development and the progression of human chronic myeloid leukemia (CML) from chronic phase (CP) to blast crisis (BC). The qRT-PCR data shown here demonstrates that blast crisis LSCs harbor higher levels of IFN responsive ADAR1 p150 isoform than chronic phase progenitors and normal cord blood progenitors (p=0.014). An in vitro study of lentiviral ADAR1 p150 transduced progenitors from normal cord blood and chronic phase showed a significant change for preferred differentiation to GMP (Granulocyte-macrophage progenitor) population, which has been shown to be the leukemia stem cells in CML. A similar inclination was observed in lentiviral shRNA ADAR1 transducer progenitors from blast crisis phase and chronic phase. ADAR1 may also play a role in self-renewal, as a significant of decrease in self-renewal capacity was observed in shRNA transducer chronic phase progenitors. The data shown herein illustrates a crucial role for ADAR1 in both cell differentiation and self-renewal of hematopoietic stem cells.

Example 2

Inhibiting Shh and Breaking the Dormancy of Cancer Stem Cells/Biomarkers for Assessing Cancer Stem Cell Populations Compositions and Methods for Dormant Cancer Stem Cell Detection and Elimination This example provides data demonstrating that the methods and compositions of the invention are effective for: inducing in a stem cell susceptibility to BCR-ABL inhibition; activating, stimulating or initiating in a cancer stem cell a transition from G0 to G1 of the cell cycle; or initiating cell cycling in a cancer stem cell; or breaking dormancy in a cancer stem cell; or radiosensitizing of a cancer stem cell; or sensitizing a cancer stem cell to a treatment or protocol that targets dividing cells; or sensitizing a cancer stem cell to a chemotherapy, a radiation therapy or a targeted tyrosine kinase inhibitor.

Sonic Hedgehog Targets as Biomarkers of Prognosis and Response for Human Chronic Myelogenous Leukemia This example provides data demonstrating that the methods and compositions of the invention are effective for measuring or determining, or predicting, chronic myelogenous leukemia (CML) progression, Leukemic Stem Cell (LSC) generation and/or tyrosine kinase inhibitor resistance, and for measuring or determining, or predicting, a response to an inhibitor or inhibitors of a Sonic Hedgehog (Shh) pathway, or a targeted Shh inhibition, or a selective Shh inhibition, comprising measuring or determining, individually or together, levels or amounts of GLI1 and/or GLI2 transcript and/or protein.

Here we investigated the role of Shh signaling in maintenance of dormancy. We show that, compared to chronic phase CML and normal progenitors, human blast crisis LSC harbor enhanced expression of the Shh transcriptional activator, GLI2, and decreased expression of a transcriptional repressor, GLI3. Treatment of human blast crisis LSC engrafted $RAG2^{-/-}\gamma c^{-/-}$ mice with a novel selective Shh inhibitor, PF-04449913 (see FIG. 17a, Supplementary FIG. 1a), reduced leukemic burden in a niche-dependent manner commensurate with GLI downregulation. Full transcriptome RNA sequencing performed on FACS-purified human progenitors from PF-04449913 treated blast crisis LSC engrafted mice demonstrated greater Shh gene splice isoform concordance with normal progenitors than vehicle treated controls.

In addition, RNA sequencing after the Shh inhibition revealed significantly decreased cell cycle regulatory gene expression and splice isoform analysis demonstrated reversion toward a normal splice isoform signature for many cell cycle regulatory genes. Moreover, cell cycle FACS analysis showed that selective Shh inhibition permitted dormant blast crisis LSC to enter the cell cycle while normal progenitor cell cycle status was unaffected.

Finally, PF-04449913 synergized with BCR-ABL inhibition to reduce blast crisis LSC survival and self-renewal in concert with increased expression of Shh pathway regulators.

Our findings demonstrate that selective Shh antagonism induces cycling of dormant human blast crisis LSC, rendering them susceptible to BCR-ABL inhibition, while sparing normal progenitors. Implementation of novel LSC splice isoform detection platforms to assess efficacy of Shh inhibitor-mediated sensitization to molecularly targeted therapy may inform dormant cancer stem cell elimination strategies that ultimately avert relapse.

In this study, we investigated whether Shh signaling links human blast crisis LSC quiescence and self-renewal and whether these traits can be uncoupled with a therapeutic Shh antagonist, as a strategy to enhance sensitivity to BCR-ABL1 tyrosine kinase inhibitors (TKI).

First, to determine if Shh pathway activation fuels blastic transformation and LSC generation, chronic phase (n=7), blast crisis CML (n=21) and normal progenitor (n=15) samples (Supplementary Table 1, below) were analyzed by full transcriptome RNA sequencing (Supplementary Table 2, below), qRT-PCR and nanoparticles. Supplementary Table 1: shows CML patient and normal sample characteristics. Supplementary Table 2: shows Sample Characteristics for Full Transcriptome RNA Sequencing.

SUPPLEMENTARY TABLE 1

| | CML SAMPLES | | | | | |
|---|---|---|---|---|---|---|
| Sample ID | Date | Sex/Age | Sample Type | WBC Count (K/mm$^3$) | % Blasts, PB | Treatment |
| C001 | 26 Oct. 2007 | N/A | Chronic Phase CML | N/A | N/A | N/A |
| C002 | 09 Jan. 2007 | M | Chronic Phase CML | 689 | 4% | Imatinib |
| C003 | N/A | N/A | Chronic Phase CML | N/A | N/A | N/A |
| C004 | 05 Feb. 2007 | F | Chronic Phase CML | N/A | N/A | N/A |
| C01 | 13 Nov. 2006 | M/60 | Chronic Phase CML | 189 | 1.4% | none |

SUPPLEMENTARY TABLE 1-continued

CML SAMPLES

| Sample ID | Date | Sex/Age | Sample Type | WBC Count (K/mm$^3$) | % Blasts, PB | Treatment |
|---|---|---|---|---|---|---|
| C02 | 23 May 2008 | F/63 | Chronic Phase CML | 326 | 5% | none |
| C03 | 10 Dec. 1999 | M/57 | Chronic Phase CML | 49 | 4.1% | none |
| C04 | 14 Oct. 2006 | M/44 | Chronic Phase CML | 306 | 5.8% | none |
| C05 | 21 Sep. 2009 | M/26 | Chronic Phase CML | 231 | <1% | none |
| C06 | 25 Sep. 2009 | F/68 | Chronic Phase CML | 88 | <5% | Imatinib |
| C07 | 25 Mar. 2007 | F/33 | Chronic Phase CML | 37.1 | <1% | N/A |
| C08 | 29 Jan. 1999 | M/56 | Chronic Phase CML | 381 | <5% | Imatinib |
| C11 | 14 Jan. 2009 | F/44 | Chronic Phase CML | 9.5 | <1% | Hydroxyurea |
| C12 | 26 Aug. 2009 | N/A | Chronic Phase CML | 390 | N/A | N/A |
| C13 | 21 Sep. 2007 | F/50 | Chronic Phase CML | N/A | N/A | Imatinib |
| B001 | 15 May 2008 | M/50 | Blast Crisis CML | N/A | N/A | N/A |
| B002 | N/A | N/A | Blast Crisis CML | N/A | N/A | N/A |
| B04 | 29 Jul. 2008 | M/20 | Blast Crisis CML | 622 | 68% | Imatinib |
| B05 | 08 Dec. 2003 | M/51 | Blast Crisis CML | 82.4 | 32% | Imatinib |
| B06 | 26 Oct. 1993 | M/30 | Blast Crisis CML | 170 | 94.1% | Hydroxyurea |
| B07 | 29 Oct. 1993 | M/48 | Blast Crisis CML | 209 | 86.1% | Hydroxyurea |
| B08 | 27 Jul. 2000 | M/53 | Blast Crisis CML | 98 | 82.6% | Hydroxyurea |
| B09 | 17 Oct. 1991 | M/65 | Blast Crisis CML | 72 | 41.7% | none |
| B10 | 21 Sep. 1993 | M/40 | Blast Crisis CML | 133 | 82% | none |
| B11 | 16 Mar. 2006 | M/31 | Blast Crisis CML | 40.1 | 79% | Hydroxyurea |
| B12 | 26 Jul. 2009 | F/47 | Blast Crisis CML | 262 | 45% | Hydroxyurea |
| B13 | 16 May 2008 | M/49 | Blast Crisis CML | 8.4 | 15% | Imatinib |
| B14 | 16 Apr. 2004 | M/40 | Blast Crisis CML | 47.7 | 47% | none |
| B15 | 8 Mar. 2005 | F/31 | Blast Crisis CML | 11.4 | 55% | none |
| B16 | 22 Jul. 2002 | F/52 | Blast Crisis CML | 60.3 | 14% | none |
| B20 | N/A | ?/37 | Blast Crisis CML | N/A | N/A | N/A |
| B26 | N/A | ?/78 | Blast Crisis CML | N/A | N/A | N/A |

SUPPLEMENTARY TABLE 2

Cytogenetics on primary patient samples used for RNAseq

| Patient ID | Treatment | Cytogenetics | Immunophenotyping |
|---|---|---|---|
| CP-01 | None | t(9; 22)(q34; q11) | N/A |
| CP-02 | None | 46, XX, t(9; 22)(q34; q11.2)[20], nuc ish(ABL1x3), (BCRx3), (ABL1 con BCRx2)[194/200] | N/A |
| CP-04 | None | 46, XY, t(9; 22)(q34; q11.2)[20] | N/A |
| CP-05 | None | 46, XY, t(9; 22)(q34; q11.2)[20] | N/A |
| CP-06 | None | t(9; 22)(q34; q11.2) | N/A |
| CP-12 | None | N/A | N/A |
| CP-13 | Imatinib | 46, XX, t(9; 22)(q34; q11.2), add(17)(p11.2~13) & T315I | CD34+ 6% of CD45+ |
| CP-19 | None | t(9; 22)(q34; q11.2) | N/A |
| BC-02 | None | t(9; 22)(q34; q11.2) | CD11b 90%; CD13 99%; CD33 99%; CD34 88%; CD56 95%; HLA-DR 95%; CD10 21%; CD19 15% |
| BC-05 | None | t(9; 22)(q34; q11.2) | CD11b 95%; CD13 95%; CD33 95%; CD4 95%; CD117 48%; HLA-DR 90% |
| BC-06 | Hydroxyurea | 46, XY, t(9; 22)(q34; q11.2) | CD13 70%; CD14 .28; CD33 74%; CD19 48%; HLA-DR 49% |
| BC-07 | Hydroxyurea | t(9; 22)(q34; q11.2) abn 7 | CD13 76%; CD33 17%; CD19 90%; HLA-DR 88%; CD34 82%; CD10 84% |
| BC-08 | Hydroxyurea | 46, XY, t(9; 22)(q34; q11), add(18)(q?21).nuc ish 9q34(ABLx3), 22q11(BCRx2) | CD11 49%; CD13 100%; CD33 95%; CD56 91%; HLA-DR 92%; CD34 85% |
| BC-09 | None | 45, XY, −7, t(6; 17; 18)(p21.3; q23; p11.3), t(9; 22)(q34; q11) | CD13 45%; CD14 68%; CD33 67%; HLA-DR 58% |
| BC-17 | Imatinib | t(9; 22)(q34; q11.2) | CD34 46%; CD13 HLA-DR 83%; CD10 99%; CD19 99%; TdT 99% |
| BC-19 | Imatinib followed by dasatinib | t(9; 22)-T315I | CD34+, CD13+, HLA-DR+, CD117+, MPO+, CD33+, weak CD79a, aberrant CD7+ |
| BC-25 | Imatinib & Hydroxyurea | t(9; 22) and inv3(q21q26) | CD117−, HLA-DR−, CD33dim, CD38dim |

SUPPLEMENTARY TABLE 3

| Sample # | Mouse # | # Cells | Treatment | RNA (ng/ul) | Amount (ng) | # Reads (Millions) |
|---|---|---|---|---|---|---|
| 1 | 197 | 50k | Vehicle | 16.06 | 225.9 | 96.9 |
| 2 | 197 | 23k | Vehicle | 15.6 | 232.5 | 73 |
| 3 | 147 | 50k | Vehicle | 16.91 | 253.65 | 21.4 |
| 4 | 147 | 50k | Vehicle | 21.83 | 327.45 | 79.7 |
| 5 | 167 | 50k | Vehicle | 27.12 | 406.8 | 109.8 |
| 6 | 167 | 50k | Vehicle | 11.98 | 179.7 | 78.2 |

SUPPLEMENTARY TABLE 3-continued

| Sample # | Mouse # | # Cells | Treatment | RNA (ng/ul) | Amount (ng) | # Reads (Millions) |
|---|---|---|---|---|---|---|
| 7 | 176 | 50k | SMO | 16.46 | 246.9 | 88.3 |
| 8 | 176 | 30k | SMO | 12.69 | 190.35 | 150.2 |
| 9 | 189 | 50k | SMO | 13.54 | 203.1 | 157.9 |
| 10 | 191 | 50k | SMO | 14.09 | 211.35 | 162.5 |
| 11 | 182 | 50k | Vehicle | 14.05 | 210.75 | 187.1 |
| 12 | 187 | 50k | SMO | 13.39 | 200.85 | 196.7 |

Figure 1A:
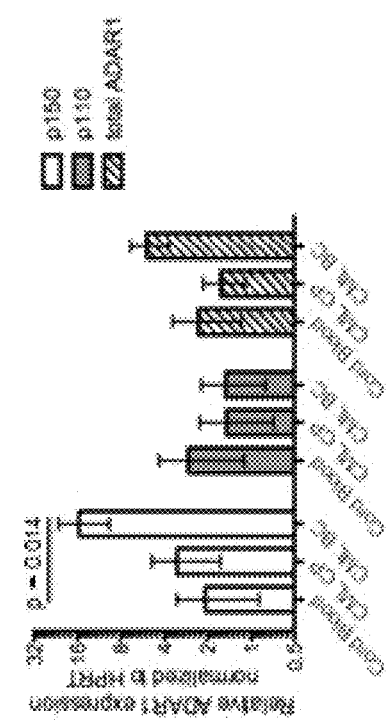
FIG. 1A graphically illustrates data showing that the expression of ADAR1 p150 is increasing as CML progresses from CP to BC; the values were normalized to HPRT; a significant increase of ADAR1 p150 expression was observed in CML BC comparing to CML CP.

Compared with normal progenitors, both chronic phase and blast crisis CML progenitors were typified by diminished expression of GLI3, a transcriptional repressor. Progression of chronic phase to blast crisis was marked by elevated GLI2, a critical Shh pathway activator (FIG. 1a). While seminal studies have linked Shh activation to cancer stem cell generation[4-6], others have shown that Shh signaling modulates the malignant niche[7].

However, the role of Shh signaling in niche dependent human LSC maintenance had not been established. To recapitulate extrinsic growth regulatory cues provided by the LSC niche, blast crisis LSC were co-cultured on human SCF, IL-3 and G-CSF (SL/M2) stromal layers. Then, a novel small molecules smoothened (SMO) antagonist, PF-04449913, shown to compete for binding to human SMO (amino acids 181-787) with an IC50 of 4 nM (Supplementary FIG. 1a); to inhibit Shh stimulated luciferase expression in mouse embryonic fibroblasts with an IC50 of 6.8 nM (n=5) (Supplementary FIG. 1b, c); and to significantly reduce medulloblastoma growth in a Ptch1$^{+/-}$p53$^{+/-}$ allograft model (Supplementary FIG. 2a, b) at doses that decreased Shh target gene expression (Supplementary FIG. 2c-e) was utilized to selectively inhibit Shh signaling in human LSC co-culture experiments. In these studies, LSC survival was significantly reduced by targeted SMO inhibition with PF-04449913 (p=0.047) (FIG. 1b).

Figure 3:
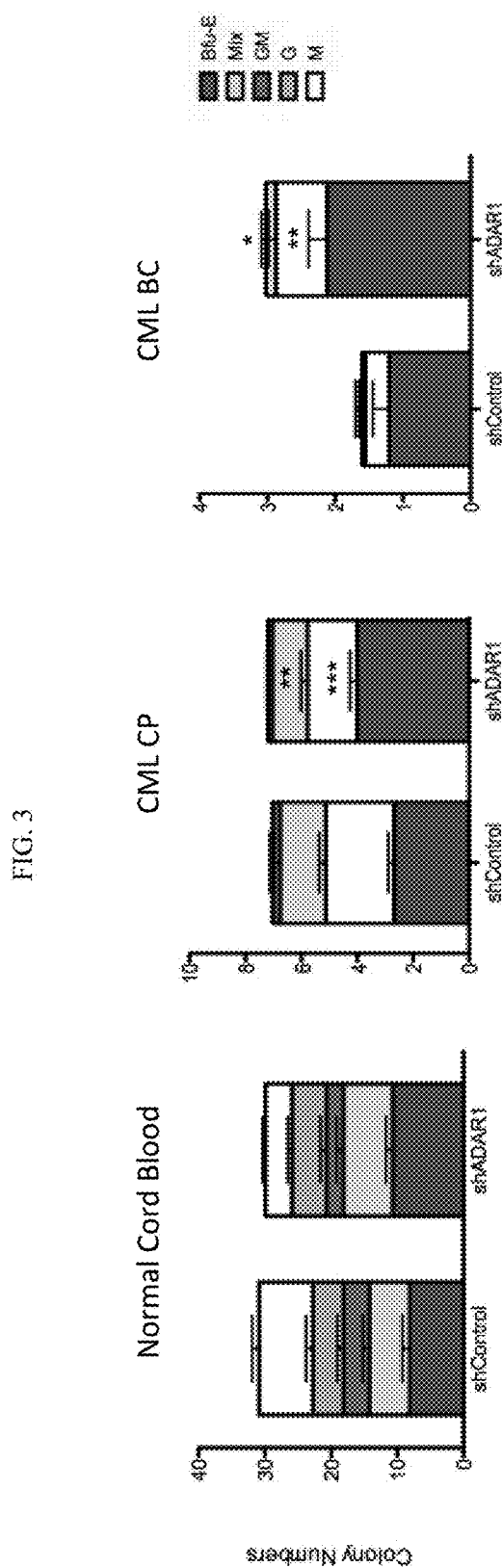
FIG. 3 graphically illustrates data showing that knock down of ADAR1 leads to increase of Bfu-E colonies and decrease of Macrophage (M) colonies in CML CP (n=3) and BC (n=1) but not in normal cord blood (n=3); sorted CD34+38+Lin− cells from normal cord blood, CML CP and BC patients were transduced with either shADAR1 or shControl lentivirus, *, $p<0.05$, , $p<0.005$; *, $p<0.0001$; for CML CP $p=0.0037$, $p=0.0001$, (n=3); for CML BC (n=1), $p=0.0167$, $p=0.0030$; as described in detail in Example 1, below.
Figure 4:
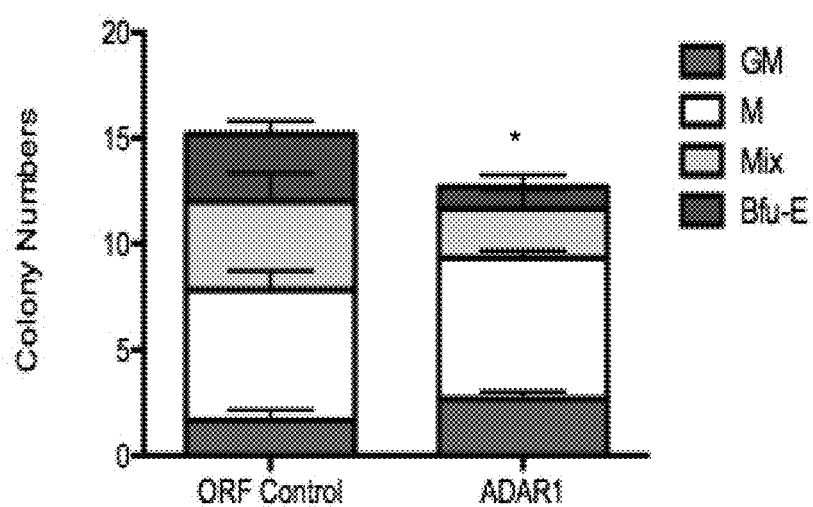
FIG. 4 graphically illustrates data showing lentiviral overexpression of ADAR1 leads to decrease of Bfu-E colonies in normal cord blood (n=3); sorted CD34+38+Lin− cells from normal cord blood were transduced with either ORF control or ADAR1 overexpression lentivirus. *, $p<0.05$, $p=0.029$; as described in detail in Example 1, below.
Figure 5:
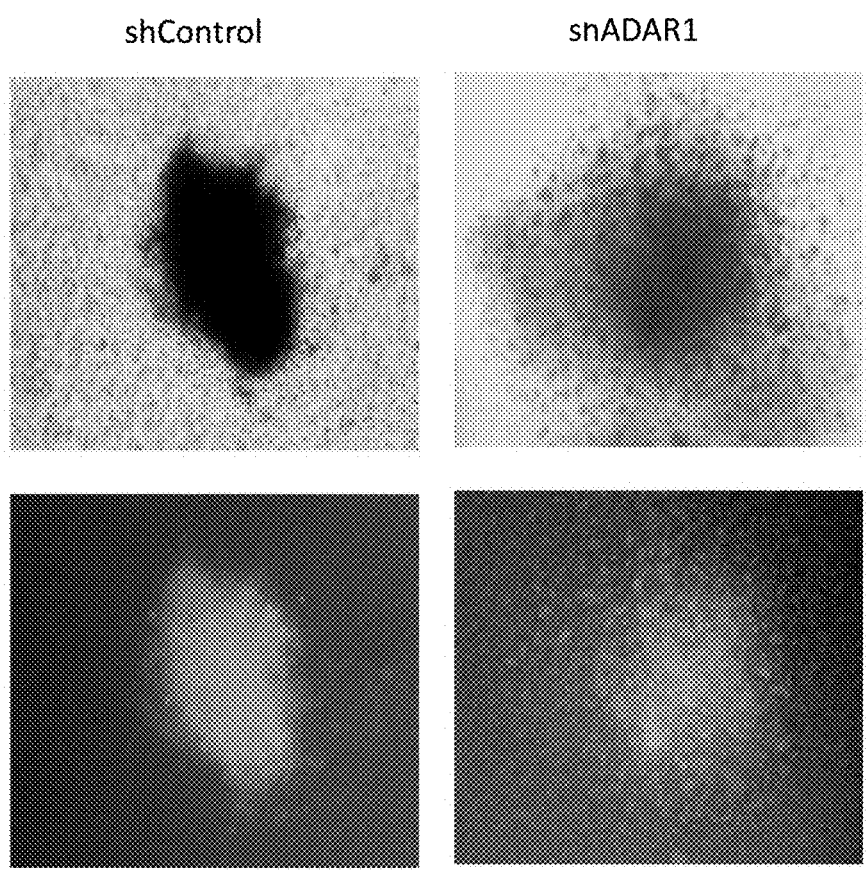
FIG. 5 illustrates representative pictures of GFP+ colonies; as described in detail in Example 1, below.
Figure 6:
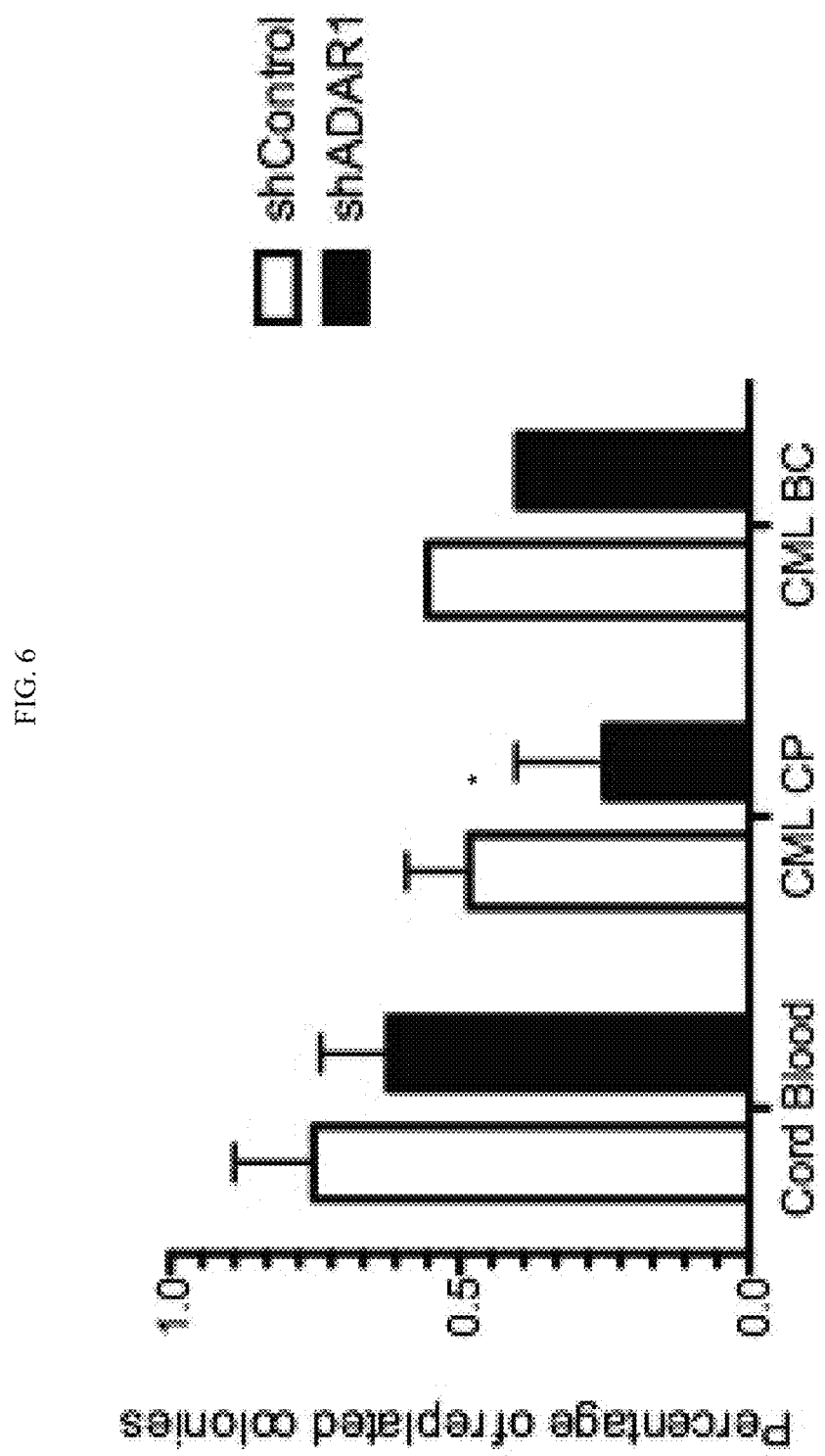
FIG. 6 graphically illustrates data showing that ADAR1 knockdown leads to a universal decrease of self-renewal capacity; individual colonies from FACS sorted CD34+38+ lin− cord Blood (n=4), CML CP (n=3), and CML BC (n=1) were replated in to 96 well-plates and replate efficiency was observed after 14 days. *, $p<0.05$; as described in detail in Example 1, below.

To delineate whether these LSC inhibitory effects could be recapitulated in vivo and if Shh driven LSC survival was niche dependent, human LSC engrafted immune deficient RAG2$^{-/-}\gamma_c^{-/-}$ mice were treated for 14 days with PF-0444913 (100 mg/kg) by oral gavage. Human LSC engrafted mice were able to sustain treatment with no evidence of weight loss (Supplementary FIG. 3a). Progenitors purified by FACS from PF-04449913 treated LSC engrafted mice displayed reductions in GLI1 (p=0.056) and GLI2 transcript levels (p=0.08) (FIG. 1c) in the splenic niche and a corresponding significant decrease (p=0.006) in spleen weight (FIG. 1d) and size (Supplementary FIG. 3b). Molecular mechanisms of response were investigated with full transcriptome RNA sequencing analysis which revealed marked differences in gene expression between primary and bone marrow engrafted CML indicative of niche specific effects on gene expression (Supplementary FIG. 4a). Following PF-044499913 treatment of mice engrafted with human leukemic progenitors, there was a reversion to a normal progenitor splice isoform pattern for 37 of 50 sonic hedgehog pathway genes in PF-04449913 (Fisher exact test, p=0.0048) (FIG. 1f, g). Of particular interest, Shh pathway gene isoforms that adopted a pattern similar to normal progenitors after Shh inhibitor treatment included pathway regulators such as SUFU, ARRB1, BTRC, CSKN1G1, FBXW11, and PRKACB. Moreover, PF-04449913 treatment of human blast crisis LSC engrafted RAG2$^{-/-}\gamma_c^{-/-}$ mice reduced human GLI protein expression compared with vehicle treated controls as demonstrated by both immunofluorescence (FIG. 1e) and nanoproteomics (p=0.001) analyses (FIG. 1h, i). However, FACS analysis revealed that Shh inhibitor responses were more robust in extramedullary than medullary niches (Supplementary FIG. 3c, d) suggesting that resistant LSC were more prominent in the marrow perhaps as a consequence of quiescence induction.

Figures 2A, 2B:
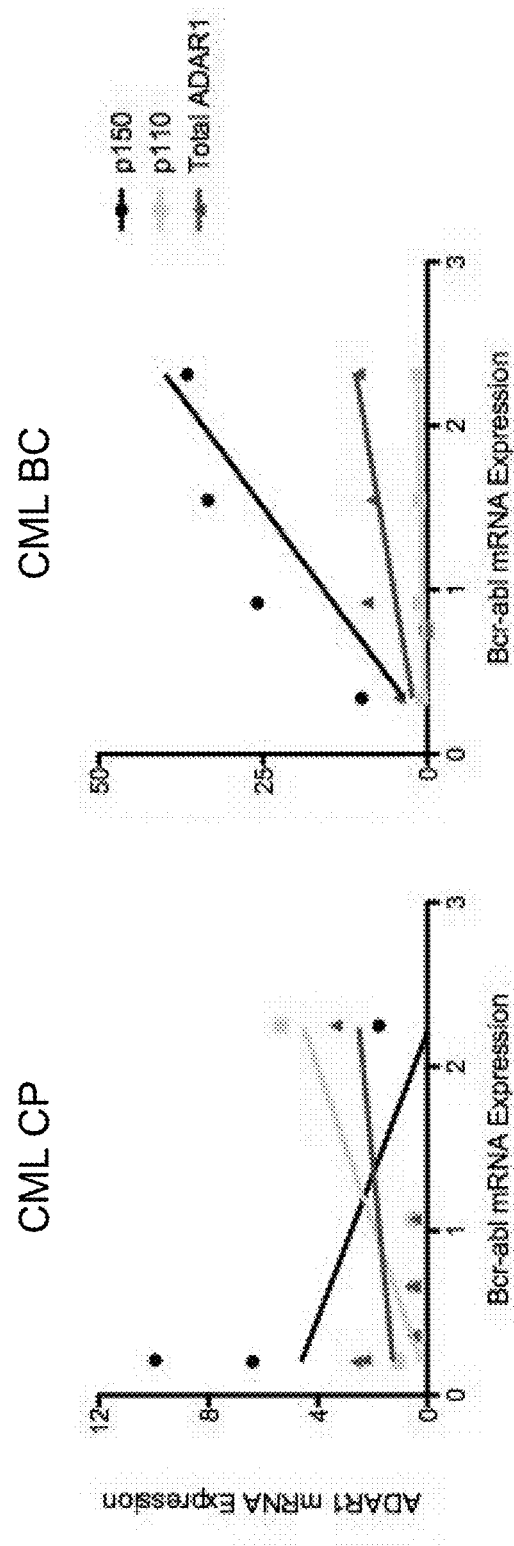
FIGS. 2A and 2B graphically illustrate data showing that an increase in ADAR1 expression is driven by Bcr-Abl in CML BC patients; Bcr-Abl and ADAR1 expression were analyzed in CML CP (n=6) and CML BC (n=4); a positive correlation is observed in only CML BC instead of CML CP; as described in detail in Example 1, below.

Because previous mouse model studies linked Shh signaling to modulation of stem cell cycle control[8], we investigated whether Shh signaling induced dormancy by employing cell cycle FACS and full transcriptome RNA sequencing analysis of blast crisis LSC engrafted in RAG2$^{-/-}\gamma_c^{-/-}$ mice. While human CD45$^+$ leukemic cells homed to liver, spleen, myeloid sarcomas (tumor) and marrow (FIG. 2a), FACS analysis revealed that blast crisis GMP (LSC) were more prevalent in the marrow than other niches (FIG. 2b). In addition, cell cycle FACS analysis demonstrated that a significantly (p=0.045) greater proportion of marrow resident human leukemic cells were dormant compared with those in the splenic niche (FIG. 2c). Full transcriptome RNA sequencing analysis of engrafted leukemic progenitors revealed repression of cell cycle regulators (family wise p-value 0.02) in response to PF-04449913 compared with vehicle treatment (FIG. 2c and Supplementary FIG. 4b, c) and a shift toward a normal progenitor cell cycle gene splice isoform expression pattern for 75 of 110 isoforms (Fisher exact test, p=0.0006) (FIG. 2f, g). Moreover, cell cycle FACS analysis demonstrated that PF-04449913 treatment of LSC engrafted mice reduced the fraction of leukemic progenitors in G0 commensurate with an increase in the G1 fraction (FIG. 2d and Supplementary FIG. 4d) suggesting that the dormant LSC population had been induced to enter the cell cycle through selective Shh inhibition potentially rendering them sensitive to agents that target dividing cells.

For Shh inhibition to be effective in LSC eradication, normal hematopoietic stem cells must be spared. While some mouse model studies suggest that Shh signaling is dispensable for adult hematopoiesis[9], others demonstrate that Gli1 regulates hematopoietic stem cell fate decisions[10].

However, the role of Shh signaling in normal human hematopoietic stem and progenitor cell (HSPC) maintenance had not been examined extensively in vitro or in primary sample xenograft (primagraft) models that permit robust engraftment. Thus, we examined the effects of PF-04449913 treatment on normal HSPC phenotype and function. Following, PF-04449913 treatment the differentiation capacity of normal human HSPC in hematopoietic progenitor assays (FIG. 3a) was unimpaired and the percentage of HSPC remained constant after 7 days of SL/M2 stromal co-culture period with PF-04449913 (FIG. 3b). When CD34$^+$ cord blood engrafted NSG mice were treated with PF-04449913 (100 mg/kg for 14 days), the frequency of HSPC as well as myeloid and lymphoid cell fate commitment remained comparable to vehicle treated controls (FIG. 3c, d). Moreover, human hematopoietic cell cycle status was unaltered (FIG. 3e). These data suggest that, unlike LSC, normal human HSPC survival, cell fate decisions and cell cycle regulation are Shh independent thus, explaining their resistance to Shh inhibition and providing a therapeutic window between normal HSC and LSC.

The reduced dormancy of blast crisis progenitors following Shh inhibition compared with their normal progenitor counterparts provided the impetus for determining if LSC were rendered sensitive to dasatinib, a potent TKI (FIG. 4a). Combination therapy with dasatinib and PF-04449913 reduced myeloid sarcoma (FIG. 4b) formation (p<0.0001) and BCR-ABL expression (p=0.0331) (FIG. 4c) in LSC engrafted marrow. Furthermore, Hedgehog PCR array analysis revealed that dasatinib synergized with PF-04449913 by significantly increasing expression of negative regulators of the Shh pathway (p<0.05), including NUMB, PRKACB, FKBP8, CSNK1A1 and CSNK1D (FIG. 4d). Combination therapy led to a marked reduction in marrow LSC (p=0.0016) (FIG. 4e) and LSC serial myeloid sarcoma transplantation potential (p=0.02) (FIG. 4f) providing the impetus for developing combination BCR-ABL and Shh inhibitor clinical trials for imatinib resistant and advanced phase CML patients.

While Ptc-1$^{+/-}$ mouse model experiments have linked Shh modulation of cell cycle regulators to hematopoietic stem cell regeneration[8], the role of Shh signaling in human normal progenitor and LSC dormancy had not been established. In robust primagraft assays, we show, for the first time, that marrow resident GLI expressing human blast crisis LSC become dormant thereby enabling them to evade therapy. Following treatment with a clinical Shh antagonist, PF-04449913, dormant LSC were activated to enter the cell cycle thereby rendering them susceptible to agents that target proliferating cells, such as dasatinib, and reducing LSC self-renewal potential. In contrast, normal hematopoietic progenitor cell cycle status and cell fate were unaffected. Together these data support clinical implementation of RNA sequencing derived predictive biomarkers of CSC response and selective Shh pathway inhibition as a strategy to invoke cycling of dormant LSC therapy sensitizing them to BCR-ABL inhibitors and obviating therapeutic resistance. This approach may also provide a viable strategy for CSC eradication in other refractory malignancies.

Methods

Patient Sample Preparation

Normal cord blood and adult peripheral blood samples were purchased from All Cells or obtained from the Cord Blood/Reproductive Sciences Core at UCLA. CML samples were obtained from consenting patients at the UC San Diego, Stanford University, and the University of Toronto Health Network according to Institutional Review Board approved protocols.

Transcriptome Analysis

The SOLiD™ total RNA-Seq kit (Applied Biosystems part #4445374) was used to prepare libraries from normal and blast crisis CML samples, which were sequenced on Solid v.3 plus instruments. Gene isoform models were developed by first combining the isoform models from June 2011 versions of REFSEQ™[11], UCSC Known Genes[12], and ENSEMBL™[13] and then creating a nonredundant set of models using the "CUFFCOMPARE™" program from version 0.9.3 of the CUFFLINKS™ software package[14]. Then, we mapped RNA-seq reads to the nucleotide sequences of the isoform models using BWA[15] with default parameters and then translated the alignment coordinates in hg19/GRCh37 human genome reference sequence coordinates using a custom script.

Stromal Co-Culture and in vitro Drug Treatment

Normal or blast crisis CML CD34$^+$ cells were plated on confluent mitomycin-C treated SL/M2 cells with different doses of PF-04449913, dasatinib, a combination of PF-04449913 and dasatinib, or vehicle for 14 days. After 1 week of culture, FACS was used to quantify human progenitors and progenitors were FACS sorted into hematopoietic progenitor assays. Colonies were scored after 2 weeks in culture.

Human Progenitor Primagrafts and Treatment

Equal numbers of primary normal or blast crisis CML CD34$^+$ cells were transplanted intrahepatically into neonatal RAG2$^{-/-}$γc$^{-/-}$ mice to form primagrafts, according to established methods[1,3]. At 8-12 weeks post-transplant, mice were treated with PF-04449913, Dasatinib, a combination of PF-04449913 and Dasatinib, or drug vehicle for 14 days followed by FACS analysis of human hematopoietic engraftment in hematopoietic tissues.

Quantitative RT-PCR Analysis of GLI Family Gene Expression

Normal or BC CML cells from patient samples at the University of California San Diego, Stanford University, MD Anderson Cancer Center and the University of Toronto Health Network according to Institutional Review Board approved protocols, were CD34$^+$ selected and FACS-sorted for analyses using a FACS Aria and FLOWJO™ software as described previously[19,20]. Quantitative PCR (qRT-PCR) was performed in duplicate on an ICYCLER™ using SYBR Greener Super Mix (Invitrogen, Carlsbad, Calif.), GLI primers were purchased from ABSciences-Catalog number 4331182: GLI 1 (HS00171790_ml), GLI 2 (HS00257977_ml) and GLI 3 (HS00609233_ml). The following primers were used in reactions run with SYBR: BCR-ABL Forward: ctccagactgtccacagcat (SEQ ID NO:4), BCR-ABL Reverse: ccctgaggctcaaagtcaga (SEQ ID NO:5), HPRT Forward: cgtcttgctcgagatgtgatg (SEQ ID NO:6), HPRT Reverse: tttatagccccccttgagcac (SEQ ID NO:7). Relative levels of mRNA were determined according to standard curves. All values were then normalized to HPRT or RPL27 values from the same sample.

TAQMAN™ primer/probe sets (ABI) for FoxM1 (Mm00514924_ml), Gli1 (Mm00494645_ml), Gli2 (Mm01293117_ml), Mycn (Mm00476449_ml), Ptch1 (Mm00436026_ml), Ptch2 (Mm00436047_ml), Sfrp1 (Mm00489161_ml), Smo (Mm01162710_ml) and mouse GAPDH (4352339E), on the ABI 7900HT instrument. Target gene expression levels were normalized to mouse GAPDH and calibrated to vehicle treated mice to yield the relative quantitation (RQ) value.

Confocal Fluorescence Microscopic Analyses

Spleens of xenografted mice that were subjected to 2 weeks of treatment were embedded in OCT freezing media (Sakura, Torrance, Calif.), frozen and sent off to histology core (UCSD Moores Cancer Center). For immunostaining, antibodies were used with MOM kit (Vector, Burlingame, Calif.). Primary antibodies used were anti-GLI2 (Abcam) and Alexa 647-conjugated anti-human CD45 (1:25, Serotec). Stained sections were mounted using PROLONG® Gold antifade with DAPI (Invitrogen). Confocal fluorescence images were acquired using Zeiss LSM510™ or Olympus FLUOVIEW FV10i™ microscopes and ADOBE PHOTOSHOP CS5™ software.

Nanoproteomic Immunoassay

Nanofluidic phospho-proteomic immunoassay (NPI) experiments were performed with the NANOPRO 1000™ instrument (Cell Biosciences) and all samples were run in triplicate at least. The FIREFLY™ system first performed a charge-based separation (isoelectric focusing). Predicted pIs were calculated with SCANSITE™. Each sample was run on a panel of different pH gradients (pH 5-8) to optimize the resolution of different peak patterns. After separation and photo-activated in-capillary immobilization, GLI-2 was detected using GLI2-specific antibody (Abcam). A β2-microglubulin-specific antibody (β$_2$M; Upstate) was used to normalize the amount of loaded protein. The peaks were quantified by calculating the area under the curve (AUC).

Primagrafts, in vivo Drug Treatment, and Engraftment Analysis

Immunocompromised RAG2$^{-/-}$γc$^{-/-}$ mice were bred and maintained in the UC San Diego Moores Cancer Center vivarium. Neonatal mice were transplanted intrahepatically with normal progenitors or LSC from primary patient samples according to our previously published methods[19]. Upon detection of tumor or peripheral blood engraftment, mice were treated daily by oral gavage with vehicle (50% 1,2 Propandiol, 50% HBSS or methylcellulose), PF-04449913 (100 mg/kg dissolved in vehicle), Dasatinib (50 mg/kg dissolved in vehicle), combination of PF-04449913 (100 mg/kg) and dasatinib (50 mg/kg). After treatment, mice were euthanized and single cell suspensions of hematopoietic tissues were analyzed for human engraftment by FACS as described previously[19, 20]. Similarly, NOD.

Cg-Prkdc^scid Il2rg^tm1Wjl/SzJ female mice at 7-10 weeks were irradiated sublethally and transplanted with 100K CD34$^+$ human cord blood cells via retro-orbital injection. Eight weeks after transplantation of cord blood cells, the mice were treated for 14 days with either vehicle, or PF-04449913 via oral gavage.

Stromal Co-Culture and in vitro Drug Treatment

The mouse bone marrow stromal cells lines M2-10B4 (M2) and SL/SL (SL) were provided by StemCell Technologies on behalf of Dr. Donna Hogge in the Terry Fox Laboratory (Vancouver, British Columbia). One day prior to co-culture, the cell lines were treated with mitomycin-C (1 mg/ml) and plated in a 1:1 mixture in total concentration of 100,000/ml. 10,000-20,000 CD34$^+$ blast crisis CML or normal cells were then plated on adherent SL/M2 stromal cells, cultured for 7 days, and analyzed by FACS as described previously[19]. To assess expansion of normal human HS/PCs, irradiated OP9 (M2 clone) stromal cells (20 Gray on a Saxon-Mark1 irradiator) were co-cultured with 50,000 human CD34$^+$ cord blood. OP9M2 stroma was grown in AlphaMem from Gibco with 20% Hyclone FBS, 1% pen strep glutamine and supplemented with cytokines: 50 ug/ml SCF, 10 ug/ml thrombopoietin, and 10 ug/ml Flt3.

Transcriptome Splice Isoform Analysis

Four vehicle-treated and four PF-04449913-treated samples constituting two sets of four technical replicates. The reads from the four RNA sequencing experiments under each treatment regimen were then combined for analysis of effects of vehicle and PF-04449913-treatment containing a total of 65M and 64M reads, respectively and compared with normal FACS purified cord blood CD34$^+$CD38$^+$Lin$^-$ progenitors.

Cell Cycle FACS Analysis

Single cell suspensions of bone marrow cells from mice treated with PF-0449913 or vehicle were immunostained with Alexa647-conjugated anti-human CD45 (BioLegend) in 2% fetal bovine serum/PBS followed by live cell staining using the LIVE/DEAD® Fixable Near-IR Dead Cell Stain Kit (Invitrogen). Surface stained cells were then fixed in 70% ethanol overnight. Fixed, surface stained cells were immunostained with FITC-conjugated anti-Ki-67 (Abcam, 1:100) in 0.15% saponin/2% fetal bovine serum/PBS, washed twice in saponin-containing staining media and incubated with 7-AAD (10 µg/mL in 0.1M sodium citrate/5 mM EDTA pH8.0/0.15M NaCl/0.5% BSA/0.02% saponin). Stained samples were analyzed using a FACSARIA™ and FLOWJO™[21].

SMO Radioligand Competition Binding Assay

Membranes were prepared from a stable cell line created in HEK293FlpIn-TetR cells (Invitrogen) using Flp recombinase-mediated insertion of the pSecTag-FRT/V5-His vector containing a cDNA encoding amino acids 181-787 of human Smo fused to the murine Igk leader sequence to produce a cell surface expressed Smo 181-781 protein. LacZ-negative cells were analyzed for binding a well characterized cyclopamine-competitive tritiated Smo antagonist[22]. The tritiated ligand was prepared using Crabtree's catalyst and tritium gas. The labeled material was purified by RP HPLC (53.1 Ci/mmol specific activity at 99% purity). For the binding competition assay, 100 µl of assay buffer was added to all the wells of a 96 well GF/B filter plate (Millipore MULTISCREEN-HTS-FB™ cat # MSFBN6B50). The plates were counted in a TOP-COUNT™ scintillation counter (Perkin Elmer). Data analysis uses EXCEL™ for % Inhibition and GRAPHPAD PRISM™ for IC$_{50}$ calculation.

Mouse Embryonic Fibroblast Gli-Luciferase Assay

Mouse Embryonic Fibroblasts expressing luciferase under control of an 8× Gli-response element (Gli-Luc MEFs)[23] were obtained from the Pfizer transgenic core facility. Luciferase activity was quantified with an ENVISION™ plate reader (Perkin Elmer). Graphpad Prism was used for data analysis and IC$_{50}$ calculation.

Selective Shh Inhibition in a Mouse Medulloblastoma Allograft Model

Primary medulloblastoma tumors were harvested from Ptch$^{+/-}$p53$^{+/-}$ or Ptch$^{+/-}$p53$^{-/-}$ mice and propagated as allografts in SCID-bg mice 6-8 weeks of age (20 grams). Freshly isolated tumor fragments of approximately 50 mm$^3$ were surgically implanted subcutaneously into the hind flank region. Body weights and tumor size (length and width) were measured at regular intervals using a caliper and tumor volume was calculated using the formula: length (mm)× width (mm)×width (mm)×0.4. For the tumor growth inhibition studies, cohorts of Ptch$^{+/-}$p53$^{+/-}$ medulloblastoma allograft bearing mice with tumors ranging from 200 mm$^3$ to 1000 mm$^3$ were dosed daily by oral gavage with vehicle (30% PEG 400/70% PBS) or with PF-04449913 formulated in vehicle.

Assessment of Target Gene Expression in Mouse Model; Microarray Processing

Microarray data were RMA normalized using BIOCONDUCTOR AFFY™ package. Differentially expressed genes were identified based on joint thresholds of t-test pvalue <0.01 and fold change >2. Their human orthologs were mapped using HOMOLOGENE BUILD 62™. They were compared with curated gene sets from a variety of pathway/signature databases and enrichment P-value was determined using hypergeometric statistics calculated with MATLAB™. More specifically, the probability of observing at least (k) genes from a gene set is given by $$P = 1 - \sum_{t=g}^{k-1} \frac{\binom{f}{t}\binom{g-f}{n-t}}{\binom{g}{n}}$$

where (f) is size of the gene set, (n) is the # of differentially expressed genes, (g) is the total number of unique human ortholog genes of mouse probes on the microarray. The obs/exp ratio was calculated as k/(f*n/g).

Statistical Analysis

Statistical analyses were performed with Microsoft Excel and Graphpad Prism software. Continuous variables for each comparison group were assessed for distribution through univariate statistics. If the assumption of normal distribution could be supported, then the Student's t test was performed for comparison of two samples with assessment of equality of variance with an F statistic. If the assumption of normal distribution was not supported, nonparametric testing was performed with the two samples Wilcoxon test using the t approximation for samples with N of less than 20.
Figure Legends FIG. 8. Blast Crisis LSC Activate Sonic Hedgehog in Selective Niches: FIG. 8a. GLI1 and GLI2 transcripts were compared by TaqMan RT-PCR in FACS-purified human cord blood and peripheral blood CD34$^+$CD38$^+$Lin$^-$PI$^-$ progenitor cells (n=9, black), chronic phase CML (n=7, blue) and in blast crisis CML (n=10, red) patient samples. Comparative qRT-PCR analysis of GLI3 transcript levels was performed on normal (n=7, black), chronic phase (n=6, blue) and blast crisis CML (n=7, red) cells. Values were normalized to RPL27 or HPRT housekeeping genes, and set to 1 for the normal progenitors. b. FACS analysis revealed a reduction in leukemic progenitor survival following 7 days of PF-04449913 (1 µM, purple) compared with vehicle (DMSO, blue) treatment in SL/M2 co-cultures. c. Down regulation of GLI expression analyzed by TaqMan RT-PCR in human LSC engrafted bone marrow derived from PF-04449913 and vehicle treated mice. d. Spleen size in blast crisis CML LSC engrafted mice after 14 days of treatment with vehicle (n=16, blue) or PF-04449913 (n=6; 100 mg/kg daily, purple), e. Immunofluorescence analysis of splenic sections from no transplant or LSC engrafted mice treated with vehicle or PF-04449913. Photomicrographs of sections stained with DAPI (upper panel) and antibodies specific for human CD45 (upper middle panel), human GLI (lower middle panel) and the merged image (lower panel). f. Isoform-level transcriptome measurements of Shh pathway genes in vehicle-treated (blue) and PF-04449913-treated (purple) CML BC LSC and in normal CD34$^+$CD38$^+$Lin$^-$ FACS-purified progenitors (black). Of the 87/249 genes/ isoforms in the Shh pathway, 50 isoforms of 18 genes were significantly differentially expressed in either PF-04449913- treated or normal cells when compared to vehicle-treated cells. In 37 of 50 instances (bold), the expression level of treated and normal isoforms followed the same directional change (concordant) when compared to vehicle-treated cells. g. A significant concordance was observed in the relative expression of the 50 isoforms in PF-0449913-treated and in normal cells relative to vehicle treated cells. h. Nanoproteomic (CB1000) traces of total GLI protein after vehicle (blue) and PF-04449113 (green) treatment. i. Quantification of GLI protein expression in splenic CD34$^+$ cells derived from vehicle (n=3) or PF-04449913 (n=3) treated LSC engrafted mice. GLI expression was determined after normalizing the area under the curve (AUC) to a β2-microglobulin (β$_2$M) loading control.

FIG. 9. Induction of Blast Crisis LSC Cycling with Sonic Hedgehog Inhibition: FIG. 9a. Frequency of CD45$^+$ cells in hematopoietic tissues (liver n=4, spleen n=3, bone marrow n=6, tumor n=3) of blast crisis CML engrafted mice. b. FACS quantitation of common myeloid progenitors (CMP), granulocyte-macrophage progenitors (GMP) and megakaryocyte-erythroid progenitors (MEP) populations within each hematopoietic tissue. c. Comparison of cell cycle status (G0, green; G1, light blue; G2/S, navy) of human CD45$^+$ blast crisis CML progenitors engrafted mice in the bone marrow and spleen. More human CD45$^+$ blast crisis cells in the marrow were in G0 than those in the splenic niche (n=8) d. Representative FACS plots comparing Ki67 and 7AAD in bone marrow engrafted viable human CD45$^+$ cells after 14 days of vehicle or PF-04449913 treatment. e. Gene set enrichment analysis for the significantly down-regulated pathway "Regulators of Cell Cycle" (please see methods for details). The core enrichment subset shows the 18 most down regulated genes among the 41 genes in the pathway. f. Isoform-level transcriptome measurements of cell cycle genes in vehicle-treated (blue) and PF-04449913-treated (purple) blast crisis CML LSC and in normal CD34$^+$CD38$^+$ Lin$^-$FACS-purified progenitors (black). Of the 84/454 genes/isoforms in the cell cycle, 110 isoforms of 51 genes were significantly differentially expressed in either PF-04449913-treated or normal cells when compared to vehicle-treated cells. In 75 of 110 instances (bold), the expression level of treated and normal isoforms followed the same directional change (concordant) when compared to vehicle-treated cells. g. A significant concordance was observed in the relative expression of the 75 isoforms in PF-0449913-treated and in normal cells relative to vehicle treated cells.

FIG. 10. Shh Inhibition Spares Normal Human Hematopoietic Stem and Progenitor cells: FIG. 10a. Left, Differentiation into CFU-Mix (black), BFU-E (red), CFU-G (orange), CFU-M (yellow), CFU-GM (blue) of normal cord blood HSPC was assessed in hematopoietic progenitor assays (n=3) after PF-04449913 (1 M) or vehicle treatment for 12 days. Right, Representative photomicrographs of cord blood colonies after 12 days of treatment with vehicle (DMSO) or PF-04449913 (1 M). b. Human cord blood (n=3), CD34$^+$38$^+$Lin$^-$PI$^-$ cells, plated on SL/M2 stroma and treated with vehicle (DMSO) or PF-04449913 (1 µM) for 7 days followed by FACS analysis. c. Representative FACS plots depicting HSPC, myeloid and lymphoid differentiation in human cord blood engrafted mice after 14 days of treatment with vehicle (n=3) or PF-04449913 100 mg/kg (n=4). d. FACS analysis was used to determine the total human CD45+, HSPC, myeloid and lymphoid cell count in bone marrow after 14 days of treatment with vehicle (n=3, green) or 100 mg/kg of PF-04449913 (n=4, purple). e. FACS quantification of G0 (green), G1 (light blue) and G2/S (navy) human CD45$^+$ cells in cord blood engrafted marrow after 14 days of treatment with vehicle (n=3) or PF-04449913 100 mg/kg (n=4).

FIG. 11. Combined BCR-ABL and Shh Inhibition Reduces LSC Survival in the Niche: FIG. 11a. Schematic of in vivo experiments. RAG2$^{-/-}$γ$_c^{-/-}$ pups were transplanted intrahepatically with 50,000 CD34$^+$ cells within 48 hours of birth. After 8 to 10 weeks, blast crisis CML engrafted mice were treated daily for 14 days by oral gavage with vehicle, PF-04449913 (100 mg/kg), Dasatinib (50 mg/kg) or combination (PF-04449913 100 mg/kg and Dasatinib 50 mg/kg). Hematopoietic tissues were FACS analyzed for leukemia engraftment and qRT-PCR for BCR-ABL1 transcripts. b. Myeloid sarcoma count of blast crisis CML engrafted mice in each treatment group vehicle (n=13, green), PF-04449913 (n=7, purple), dasatinib (n=6, red) and combination (n=3, black) after 14 days of treatment. c. BCR-ABL1 transcripts in the spleens of blast crisis CML engrafted mice after 14 days of treatment with vehicle (green, n=9), PF-04449913 (purple, n=11), dasatinib (n=8, red) or combination (n=5, black) d. Shh gene expression in FACS purified human progenitor cells from blast crisis LSC engrafted mouse marrow treated with vehicle (n=3, green), PF-04449913 (n=4, purple) dasatinib (n=4, maroon), combination (n=3, dark grey) was analyzed via qPCR array (SA Biosciences). Expression levels of 5 Shh regulatory genes (NUMB, PRKABC, CTNNB1, FKBP8, CSNK1A1, CSNK1D and STK36) were significantly upregulated by the synergistic effects of PF-04449913 and dasatinib treatment after performing limma test. e. FACS analysis of percentage of marrow engrafted blast crisis LSC (n=3 patients) after 14-day treatment with vehicle (n=31, green), PF-04449913

(n=25, purple), dasatinib (n=27, maroon) and combination (n=27, grey). f. Myeloid sarcoma counts in mice serially transplanted with vehicle (n=12, green), PF-04449913 (n=12, purple), dasatinib (n=8, maroon) or combination (n=3, grey) treated human progenitors.

FIG. 12 (Supplementary FIG. 1): PF-04449913 structure and chemical properties: FIG. 12a. Chemical structure of PF-04449913, a selective smoothened (SMO) antagonist. b. Competition-binding assay using a characterized cyclopamine-competitive SMO antagonist, PF-04449913 competes with the radiolabeled SMO antagonist for binding to human SMO (amino acids 181-787) with an IC50 of 4 nM (4.3 nM+/−5.2 nM, N=5). c. Inhibition of Shh stimulated luciferase expression using mouse embryonic fibroblasts expressing luciferase under control of an 8× Gli-response element (Gli-Luc MEFs). d. Dose dependent inhibition by PF-04449913 in the Gli-Luc MEF reporter assay; PF-04449913 inhibits Shh stimulated reporter activity with an IC50 of 6.8 nM (n=5).

FIG. 13 (Supplementary FIG. 2): PF-04449913 Inhibits Shh Signaling in Ptch$^{+/-}$p53$^{+/-}$ Tumor model: FIG. 13a. Anti-tumor activity of PF-04449913 against Ptch+/−p53+/− medulloblastoma. Allograft (~700 mm$^3$) bearing SCID-bg female mice were dosed orally once a day for six days with 100 mg/kg of PF-04449913 or vehicle. Tumor size (length and width) was measured using a caliper at regular intervals and tumor volume was calculated by standard procedure. Results are mean+/−standard error of the mean (n=3 animals per group). b. Dose dependent anti-tumor efficacy of PF-04449913 against Ptch+/−p53+/− medulloblastoma allografts. Cohorts of allograft (~100 mm$^3$ to 1000 mm$^3$) bearing SCID-bg female mice were dosed orally once a day for six days with different dose levels of PF-04449913. Tumor size (length and width) was measured using a caliper at regular intervals and tumor volume was calculated by standard procedure. The percent change of an individual tumor volume was calculated from the tumor volume on the first day of dosing to the sixth day. Results are expressed as mean+/−standard deviation (n=3 to 12 animals per group; p<0.01 for 1 mg/kg group and p<0.001 for all other groups). c. Hh pathway inhibition in PF-04449913 treated Ptch+/−p53+/− medulloblastoma allografts. Ptch+/−p53+/− allograft bearing SCID-bg female mice were dosed orally once a day for six days with 100 mg/kg of PF-04449913 or vehicle. Expression levels of FoxM1, Gli1, Gli2, Mycn, Ptch1, Ptch2, Sfrp1 and Smo were determined by real time PCR. The vehicle-treated levels for each gene were normalized to 100%. d. Genes significantly down-regulated by PF-04449913 treatment in Ptch$^{+/-}$p53$^{-/-}$ mice. Hierarchical clustering was performed on Z-score transformed data using correlation similarity metric and centroid linkage method. e. Gene signatures enriched for within the top 31 PF-04449913-downregulated genes in Ptch+/−p53−/− mice. Statistical significance of over-representation and observed/expected ratio were calculated as described in supplementary methods.

FIG. 14 (Supplementary FIG. 3): LSC Responses to Shh Inhibition are Niche Dependent: FIG. 14a. Percentage of weight changes in each treatment group of mice over the course of 14 days of treatment. b. Representative photographs of spleens from no transplant, blast crisis CML engrafted mice treated with vehicle or PF-04449913. c. Representative FACS plots of blast crisis CML engrafted mice treated with vehicle, PF-04449913, dasatinib, or combination. d. Total blast LSC count in bone marrow, spleen and liver after 14 days of treatment with vehicle (n=15) or PF-04449913 (n=14).

FIG. 15 (Supplementary FIG. 4): Decreased Cell Cycle Regulator Expression Enhances LSC Cycling: FIG. 15a. Heat-map of normalized expression values on log 2 scale for 10,573 highly expressed genes in FACS-purified primary blast crisis CML CD34$^+$CD38$^-$Lin$^-$ and CD34$^+$CD38$^+$Lin$^-$ (SOLiD RNAseq gene count per million reads >1 in all the 6 samples); RAG2$^{-/-}$g-c$^{-/-}$ marrow engrafted blast crisis CML CD34$^+$CD38$^-$Lin$^-$ and CD34$^+$CD38$^+$Lin$^-$; and normal cord blood CD34$^+$CD38$^-$Lin$^-$ and CD34$^+$CD38$^+$Lin$^-$ samples. Hierarchical cluster analysis based on Euclidean distance measure was performed to check the similarities between the samples. b. Gene set enrichment analysis (GSEA) summary table obtained from SOLiD RNAseq data comparing PF-04449913 treated mice (n=4) to control (n=4) (average 24.7-58.0 million mapped reads/sample). In this analysis, 13,850 protein-coding genes with >10 reads in at least one sample were included. Read counts were normalized[16] and genes ranked by Significance Analysis of Microarrays (SAM)[17]. Eight a priori cell cycle pathways were considered in the GSEA analysis[18], with significance assessed by gene-wise permutation. The "Regulation of Cell Cycle" pathway was significantly down-regulated in human progenitors from PF-04449913 treated mice; 7 of 8 investigated pathways decreased. Table columns are pathway name, number of genes (pathway size), nominal p-value; FDR adjusted q-value and adjusted p-value controlling for the family-wise error rate. c. GSEA enrichment plot for the significantly down-regulated pathway (Regulation of Cell Cycle). The horizontal heatmap shows SAM score in descending order for all 13,850 genes. The GSEA enrichment score for the pathway (genes indicated as vertical bars) is indicated as the maximal excursion of the green line. Because the pathway is down regulated, the core enrichment subset consists of the right-most 18 among the 41 genes in the pathway. d. Cell cycle analysis of bone marrow from blast crisis CML engrafted mice after 14 days of vehicle (n=8) or PF-04449913 (n=8), *p<0.05 for both $G_0$ and $G_1$ population compared with vehicle treatment.

FIG. 16: SHH Pathway Gene Expression Pattern Portends BC Transformation. Using the SHH pathway allowed us to distinguish CML CP from BC and normal counterparts, demonstrating that this pathway is activated with disease progression.

a. Heatmap from unsupervised agglomerative hierarchical clustering of sonic hedgehog (SHH) pathway genes using RNA Seq data from FACS-purified progenitors (CD34$^+$CD38$^+$lin$^-$PI$^-$) from 8 chronic phase (CP) and 9 blast crisis (BC) patients, 3 normal cord blood (CB) and 3 normal peripheral blood (NPB) sample. Red indicates over- and green, under-expression relative to the median RPKM (log 2 scale). Grey represent not expressed (RPKM=0). b. Principal components plots derived from RNA Seq data for 41 genes in the SHH pathway, from 8 chronic phase (CP; black triangles) and 9 blast crisis (BC; red circles) subjects, as well as 3 cord blood normal samples (CB; blue diamonds) and 3 normal peripheral blood (NPB; blue circles). c. Box plots for GLI2 expression of 7 chronic phase (CP) and 6 blast crisis (BC) non-treated subjects, as well as 3 cord blood normal samples (CB) and 3 normal peripheral blood (NPB). Two-sided Jonckheere-Terpstra trend test: p=0.014. d. GLI1 and GLI2 transcripts were compared using quantitative RT-PCR in FACS-purified human cord blood and normal peripheral blood CD34$^+$CD38$^+$Lin$^-$PI$^-$ progenitor cells (n=9, black), chronic phase CML (n=7, blue) and in blast crisis CML (n=10, red) patient samples. Values were normalized to RPL27 or HPRT housekeeping genes, and set to 1 for the normal progenitors. (Student's t-test *p<0.05).

FIG. 17: FIG. 2. Selective SHH Inhibition Reduces BC LSC Burden in Selective Niches. In our preclinical model that utilized human samples, we tested a SHH pathway inhibitor on AML and CML samples and observed a decrease in survival after treatment. We also identified GLI2 as a biomarker of response.

a. Chemical structure of PF-04449913, a selective smoothened (SMO) antagonist. b. FACS analysis revealed a significant (Student's t-test, *p=0.047) reduction in blast crisis leukemic progenitor survival (n=4 patients) following 7 days of PF-04449913 (1 mM, purple) compared with vehicle (DMSO, blue) treatment in SL/M2 co-cultures. c. Cord blood (n=3) or AML (n=4 patients) CD34$^+$ cells were plated on SL/M2 co-cultures and treated with vehicle (DMSO) or PF-04449913 (1 uM) for 7 days. Colony forming unit (CFU) survival was determined and compared to vehicle treatment. (Student's t-test, **p=0.001). d. Spleen weight in blast crisis CML LSC engrafted mice after 14 days of treatment with vehicle (n=16, blue) or PF-04449913 (n=12; 100 mg/kg daily, purple). A significant (Student t-test, *p=0.006) reduction is observed after PF-044449913 treatment. e. Nanoproteomic (CB1000) traces of total GLI2 protein after vehicle (blue) and PF-04449913 (green) treatment. f. Quantification of GLI2 protein expression in sorted progenitors derived from vehicle (n=3) or PF-04449913 (n=3) treated LSC engrafted mice. GLI2 expression was determined after normalizing the area under the curve (AUC) to a b2-microglobulin ($b_2M$) loading control (Student's t-test *p=0.001) g. Confocal fluorescence microscopic analysis of spleen sections from no transplant or LSC engrafted mice treated with vehicle of PF-04449913. Photomicrographs of sections stained with DAPI and antibodies specific for human CD45, human GLI2 and the merged image.

FIG. 18: SHH PATHWAY Inhibition Induces Cycling of Dormant BC LSC.

a. Heatmap from unsupervised agglomerative hierarchical clustering of cell cycle pathway genes using RNA Seq data from FACS-purified progenitors (CD34$^+$CD38$^+$lin$^-$PI$^-$) from 8 chronic phase (CP) and 9 blast crisis (BC) patients sample. Red indicates over- and green, under-expression relative to the median RPKM (log 2 scale). Grey represent not expressed (RPKM=0). b. Network analysis performed on differentially expressed genes between BC and CP revealed CDKN1A as a key hub for cell cycle difference. c. Representative FACS plots comparing Ki67 and 7AAD in bone marrow engrafted viable human CD45$^+$ cells after 14 days of vehicle or PF-04449913 treatment. d. Cell cycle analysis of bone marrow from blast crisis CML engrafted mice after 14 days of vehicle (n=8) or PF-04449913 (n=8). Student's t-test *p<0.05 for both $G_0$ and $G_1$ population compared with vehicle treatment. e. GSEA enrichment plot for the significantly down-regulated pathway (Regulation of Cell Cycle). The horizontal heatmap shows SAM score in descending order for all 13,850 genes (SHH pathway genes indicated as vertical black bars). The GSEA enrichment score for the pathway (0-45) is indicated as the maximal excursion of the green line. f. Normalized gene expression values for the 18 genes in the core enrichment subset from the "Regulation of Cell Cycle" pathway. All the genes had a negative SAM score and are sorted in order of descending SAM score along the x-axis. This order agrees with the order in the GSEA enrichment plot, where expression levels for these genes are significantly reduced in the PF-04449913 treated mice.

FIG. 19: SHH Inhibition in clinical samples. We tested the effects of SHH pathway inhibition in a clinical study and observed similar results to what we observed in our preclinical model.

a. Characteristics of patients enrolled in clinical trial NCT01546038. b. Clinical response to PF-04449913 in the bone marrow of AML patient samples. c. Representative FACS cell cycle plots of Ki67 and 7AAD staining of human CD34+CD38− and CD34+CD38+ cells derived from primary patient samples after 4 weeks (C1D28) of treatment with PF-04449913 (40 mg) on the Phase I clinical trial. d. Cell cycle analysis (peripheral blood-CD45+PI−) from a secondary AML patient (AML-4, Supplementary table 1) that was treated with PF-04449913 (40 mg) for 4 weeks on the Phase I clinical trial. Student's t-test *p<0.05 for both $G_0$ and $G_1$ population compared with pre-treatment. e. Characteristics of patient samples analyzed for their cell cycle study. Patients in red represent clinical responders.

FIG. 20: SHH inhibitor Induced cell cycle activation Enhances BC LSC TKI Sensitivity. Using our preclinical model, we demonstrated that using SHH pathway inhibitor in combination with current therapy is the best possible route for curative treatment.

a. Schematic of in vivo experiments. RAG2$^{-/-}\gamma_c^{-/-}$ pups were transplanted intrahepatically with 50,000 CD34$^+$ cells within 48 hours of birth. After 8 to 10 weeks, blast crisis CML engrafted mice were treated daily for 14 days by oral gavage with vehicle, PF-04449913 (100 mg/kg), Dasatinib (50 mg/kg) or combination (PF-04449913 100 mg/kg and Dasatinib 50 mg/kg). Hematopoietic tissues were FACS analyzed for human leukemic engraftment and qRT-PCR for BCR-ABL1 transcripts. b. Myeloid sarcoma count in blast crisis CML engrafted mice in each treatment group vehicle (n=13, blue), PF-04449913 (n=7, purple), dasatinib (n=6, red) and combination (n=3, black) after 14 days of treatment. Graph shows mean+/−SEM; *p<0.05 and *p<0.01 by ANOVA and Tukey post-hoc analysis c. FACS analysis of percentage of marrow engrafted blast crisis progenitor LSC (n=3 patients) after 14-day treatment with vehicle (n=31, blue), PF-04449913 (n=25, purple), dasatinib (n=27, maroon) and combination (n=27, grey). Graph shows percentage of CD34+CD38+lin− cells in the bone marrow; *p<0.05 by ANOVA and Tukey post-hoc analysis d. BCR-ABL transcripts in the blast crisis CML engrafted marrow mice after 14 days of treatment with vehicle (blue, n=9), PF-04449913 (purple, n=11), dasatinib (n=8, red) or combination (n=5, black). Graph shows normalized BCR-ABL expression (HPRT)+/−SEM; *p<0.05 by ANOVA and Tukey post-hoc analysis e. Hedgehog pathway gene expression in FACS purified human progenitor cells from blast crisis LSC engrafted mouse marrow treated with vehicle (n=3, blue), PF-04449913 (n=4, purple) dasatinib (n=4, maroon), combination (n=3, dark grey) was analyzed by hedgehog (SHH) qPCR array (SAbiosciences). The limma method was used to test for main effects of PF-04449913 and Dasatinib, and their synergistic interaction among 41 genes. Null hypotheses were rejected at p=0.05 significance level without adjusting for multiple comparisons. Expression levels of seven genes were significantly altered by synergistic effect of PF-04449913 and Dasatinib (NUMB, PRKACB, CTNNB1, FKBP8, CSNK1A1, CSNK1D and STK36), where five represent SHH regulatory genes (graphed). f. Mice serially transplanted with FACS purified human progenitors from LSC engrafted mice treated with vehicle (n=12, green), PF-04449913 (n=12, purple), dasatinib (n=8, maroon) or combination (n=7, grey) were examined for myeloid sarcomas. Graph shows mean myeloid sarcoma count+/−SEM; *p<0.05 and *p<0.01 by ANOVA and Tukey post-hoc analysis.

FIG. 21 (supplementary FIG. 1): PF-04449913 chemical properties and Inhibition of Shh Signaling in a Ptch$^{+/-}$p53$^{+/-}$ Tumor model. This figure summarizes the effect of inhibiting the SHH pathway in a different preclinical mouse model.

a. Competition-binding assay using a characterized cyclopamine-competitive SMO antagonist. PF-04449913 competes with the radiolabeled SMO antagonist for binding to human SMO (amino acids 181-787) with an IC50 of 4 nM (4.3 nM+/−5.2 nM, N=5). b. Inhibition of Shh stimulated luciferase expression using mouse embryonic fibroblasts expressing luciferase under control of an 8× GLI-response element (GLI-LUC MEFs). c. Dose dependent inhibition by PF-04449913 in the GLI-Luc MEF reporter assay; PF-04449913 inhibits Shh stimulated reporter activity with an IC50 of 6.8 nM (n=5). d. Anti-tumor activity of PF-04449913 against Ptch+/−p53+/− medulloblastoma. Allograft (~700 mm$^3$) bearing SCID-bg female mice were dosed orally once a day for six days with 100 mg/kg of PF-04449913 or vehicle. Tumor size (length and width) was measured using a caliper at regular intervals and tumor volume was calculated by standard procedure. Results are mean+/−standard error of the mean (n=3 animals per group). e. Dose dependent anti-tumor efficacy of PF-04449913 against Ptch+/−p53+/− medulloblastoma allografts. Cohorts of allograft (~200 mm$^3$ to 1000 mm$^3$) bearing SCID-bg female mice were dosed orally once a day for six days with different dose levels of PF-04449913. Tumor size (length and width) was measured using a caliper at regular intervals and tumor volume was calculated by standard procedure. The percent change of an individual tumor volume was calculated from the tumor volume on the first day of dosing to the sixth day. Results are expressed as mean+/−standard deviation (n=3 to 12 animals per group; p<0.01 for 1 mg/kg group and p<0.001 for all other groups). f. Genes significantly down-regulated by PF-04449913 treatment in Ptch$^{+/-}$p53$^{-/-}$ mice. Hierarchical clustering was performed on Z-score transformed data using correlation similarity metric and centroid linkage method. g. Hh pathway inhibition in PF-04449913 treated Ptch+/−p53+/− medulloblastoma allografts. Ptch+/−p53+/− allograft bearing SCID-bg female mice were dosed orally once a day for six days with 100 mg/kg of PF-04449913 or vehicle. Expression levels of FoxM1, Gli1, Gli2, Mycn, Ptch1, Ptch2, Sfrp1 and Smo were determined by qRT-PCR. The vehicle-treated levels for each gene were normalized to 100%. h. Gene signatures enriched for within the top 31 PF-0449913-downregulated genes in Ptch+/−p53−/− mice. Statistical significance of over-representation and observed/expected ratio were calculated as described in supplementary methods.

FIG. 22 (supplementary FIG. 2): Cell cycle analysis in clinical samples—this data supports the effect of these clinical study.

a. GSEA analysis summary table obtained from RNA sequencing data comparing PF-04449913 treated engrafted mice (n=4) to control (n=4) (average 24.7-58.0 million mapped reads/sample). In total, 13,850 protein-coding genes with >10 reads in at least one sample were included. Read counts were normalized[16] and genes ranked by Significance Analysis of Microarrays (SAM).[17] Eight cell cycle pathways were considered in the GSEA analysis[18], with significance assessed by gene-wise permutation. The "Regulation of Cell Cycle" pathway was significantly down-regulated in PF-04449913 purified human progenitors derived from treated mice (family-wise p value=0.02). Table columns show pathway name, number of genes (pathway size), nominal p-value, FDR adjusted q-value. b. Characteristics of patients enrolled and sequenced using the gene expression profile by Affymetrix GeneChip 1.0 ST after PF-04449913 treatment for 28 days (C1D28), Clinical trial Gov.NTC00953758. c. GSEA analysis summary table obtained from patients (n=8) sequenced after PF-04449913 treatment (C1D28). GSEA was performed at FDR=5% and data compared pre-treatment (screening) v/s, PF-04449913 treated. Table columns show pathway name, number of genes (ES), nominal p-value and FDR adjusted q-value.

FIG. 23 (supplementary FIG. 3): SHH Inhibition Spares Normal Human Hematopoietic Progenitors. We did not observe a toxic effect on the normal counterparts analyzed; thus, a clear therapeutic index for the use of SHH inhibition was demonstrated.

a. Differentiation into CFU-Mix (purple), BFU-E (red), CFU-G (orange), CFU-M (yellow), CFU-GM (blue) of normal cord blood progenitors was assessed in hematopoietic progenitor assays (n=3) after PF-04449913 (1 mM) or vehicle treatment for 14 days. b. FACS analysis was used to determine the total human CD45$^+$, hematopoietic stem and progenitor cell (HSPC), myeloid and lymphoid cell count in bone marrow after 14 days of treatment with vehicle (n=3, green) or 100 mg/kg of PF-04449913 (n=4, purple). c. FACS quantification of G0 (green), G1 (light blue) and G2/S (navy) human CD45$^+$ cell in cord blood engrafted marrow after 14 days of treatment with vehicle (n=3) or PF-04449913, 100 mg/kg (n=4). d. Representative FACS plots depicting HSPC, myeloid and lymphoid differentiation (panel B) in human cord blood engrafted mice after 14 days of treatment with vehicle or 100 mg/kg of PF-04449913.

REFERENCES

1 Essers, M. A. & Trumpp, A. Targeting leukemic stem cells by breaking their dormancy. Molecular oncology 4, 443-450, doi:10.1016/j.molonc.2010.06.001 (2010).

2 Zhao, C. et al. Hedgehog signalling is essential for maintenance of cancer stem cells in myeloid leukaemia. Nature 458, 776-779, doi:10.1038/nature077737 (2009).

3 Dierks, C. et al. Expansion of Bcr-Abl-positive leukemic stem cells is dependent on Hedgehog pathway activation. Cancer cell 14, 238-249, doi:10.1016/j.ccr.2008.08.003 (2008).

4 Radich, J. P. et al. Gene expression changes associated with progression and response in chronic myeloid leukemia. Proceedings of the National Academy of Sciences of the United States of America 103, 2794-2799, doi: 10.1073/pnas.0510423103 (2006).

5 Nagao, H. et al. Role of GLI2 in the growth of human osteosarcoma. The Journal of pathology 224, 169-179, doi:10.1002/path.2880 (2011).

6 Buczkowicz, P., Ma, J. & Hawkins, C. GLI2 is a potential therapeutic target in pediatric medulloblastoma. Journal of neuropathology and experimental neurology 70, 430-437, doi:10.1097/NEN.0b013e31821b94db (2011).

7 Olive, K. P. et al. Inhibition of Hedgehog signaling enhances delivery of chemotherapy in a mouse model of pancreatic cancer. Science 324, 1457-1461, doi:10.1126/science.1171362 (2009).

8 Trowbridge, J. J., Scott, M. P. & Bhatia, M. Hedgehog modulates cell cycle regulators in stem cells to control hematopoietic regeneration. Proceedings of the National Academy of Sciences of the United States of America 103, 14134-14139, doi:10.1073/pnas.0604568103 (2006).

9. Gao, J. et al. Hedgehog signaling is dispensable for adult hematopoietic stem cell function. Cell stem cell 4, 548-558, doi:10.1016/j.stem.2009.03.05 (2009).
10. Merchant, A. Joseph, G., Wang, Q., Brennan, S. & Matsui, W. Gli1 regulates the proliferation and differentiation of HSCs and myeloid progenitors. Blood 115, 2391-2396, doi:10.1182/blood-2009-09-241703 (2010).
11. Pruitt, K. D., Tatusova, T. & Maglott, D. R. NCBI reference sequences (RefSeq): a curated non-redundant sequence database of genomes, transcripts and proteins. Nucleic acids research 35, D61-65, doi:10.1093/nar/gkl842 (2007).
12. Hsu, F. et al. The UCSC Known Genes. Bioinformatics 22, 1036-1046, doi:10.1093/bioinformatics/bt1048 (2006).
13. Flicek, P. et al. Ensembl 2011. Nucleic acids research 39, D800-806, doi:10.1093/nar/gkq1064 (2011).
14. Li, H. & Durbin, R. Fast and accurate short read alignment with Burrows-Wheeler transform. Bioinformatics 25, 1754-1760, doi:10.1093/bioinformatics/btp324 (2009).
15. Trapnell, C. et al. Transcript assembly and quantification by RNA-Seq reveals unannotated transcripts and isoform switching during cell differentiation. Nature biotechnology 28, 511-515, doi:10.1038/nbt.1621 (2010).
16. Bullard, J. H., Purdom, E., Hansen, K. D & Dudoit, S. Evaluation of statistical methods for normalization and differential expression in mRNA-Seq experiments. BMC bioinformatics 11, 94, doi:10.1186/1471-2105-11-94 (2010).
17. Tusher, V. G., Tibshirani, R. & Chu, G. Significance analysis of microarrays applied to the ionizing radiation response. Proceedings of the National Academy of Sciences of the United States of America 98, 5116-5121, doi:10.1073/pnas.091062498 (2001).
18. Subramanian, A. et al. Gene set enrichment analysis: a knowledge-base approach for interpreting genome-wide expression profiles. Proceedings of the National Academy of Sciences of the United States of America 102, 15545-15550, doi:10.1073/pnas.0506580102 (2005).
19. Abrahamsson, A. E. et al. Glycogen synthase kinase 3beta missplicing contributes to leukemia stem cell generation. Proceedings of the National Academy of Sciences of the United States of America 106, 3925-3929, doi:10.1073/pnas.0900189106 (2009).
20. Geron, I. et al. Selective inhibition of JAK2-driven erythroid differentiation of polycythemia vera progenitors. Cancer cell 13, 321-330, doi:10.1016/j.ccr.2008.02.017 (2008).
21. Jamieson, C. H. et al. Granulocyte-macrophage progenitors as candidate leukemic stem cells in blast-crisis CML. The New England journal of medicine 351, 657-667, doi:10.1056/NEJMoa040258 (2004).
22. Frank-Kamenetsky, M. et al. Small-molecule modulators of Hedgehog signaling: identification ad characterization of Smoothened agonists and antagonists. Journal of biology 1, 10 (2002).
23. Kimura, H., Ng, J. M. & Curran, T. Transient inhibition of the Hedgehog pathway in young mice causes permanent defects in bone structure. Cancer cell 13, 249-260, doi:10:1016/j.ccr.2008.01.027 (2008).

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating, ameliorating or preventing diseases and conditions responsive to the inhibition or slowing of cell differentiation, or self-renewal or self-renewal capacity of a dysfunctional cell, a cancer cell, or a hematopoietic stem cell, comprising,
   (a) providing a composition that inhibits or slows the expression of or the activity of: an ADAR1 gene (adenosine deaminase acting on RNA 1) comprising a sequence as set forth in (SEQ ID NO:1) and/or an ADAR1 transcript comprising a sequence as set forth in (SEQ ID NO:2)
   and the composition that inhibits or slows the expression of the ADAR1 gene or the ADAR1 transcript comprises an inhibitory nucleic acid molecule or an antisense oligonucleotide inhibitory to expression of the ADAR1 gene or ADAR1 gene transcript; and
   (b) administering a sufficient amount of the composition to an individual in need thereof, wherein a sufficient amount comprises the inhibition or slowing of cell differentiation, or self-renewal or self-renewal capacity of the dysfunctional cell the cancer cell, or the hematopoietic stem cell.

2. The method of claim 1, wherein the method treats, ameliorates or prevents conditions responsive to the inhibition or slowing of the self-renewal or self-renewal capacity of a hematopoietic stem cell.

3. The method of claim 1, wherein the inhibitory nucleic acid molecule or antisense oligonucleotide inhibitory to expression of the ADAR1 gene or ADAR1 gene transcript comprises: a ribozyme; an RNAi inhibitory nucleic acid molecule, a double-stranded RNA (dsRNA) molecule, a small interfering RNA (sRNA), a microRNA (miRNA) and/or a short hairpin RNA (shRNA).

4. The method of claim 1, wherein the inhibitory nucleic acid molecule or antisense oligonucleotide inhibitory to expression of the ADAR1 gene or ADAR1 gene transcript comprises a single or doublestranded and/or sense or antisense sequence or subsequence comprising or complementary to SEQ ID NO:1 or SEQ ID NO:2.

5. The method of claim 1, wherein the method treats, ameliorates or prevents diseases and conditions responsive to the inhibition or slowing of cell differentiation.

6. The method of claim 1, wherein the method treats, ameliorates or prevents conditions responsive to the inhibition or slowing of the self-renewal or self-renewal capacity of a dysfunctional cell or a cancer cell.

7. The method of claim 6, wherein the cancer cell is a cancer stem cell.

8. The method of claim 7, wherein the cancer stem cell is a leukemia stem cell or a Chronic Myeloid Leukemia (CML) stem cell.

9. The method of claim 6, wherein the cancer cell is a leukemia cell.

10. The method of claim 9, wherein the leukemia cell is a Chronic Myeloid Leukemia (CML) cell.

11. The method of claim 1, wherein the method treats or ameliorates diseases and conditions responsive to the inhibition or slowing of cell differentiation.

12. The method of claim 1, wherein the method treats or ameliorates diseases and conditions responsive to the self-renewal or self-renewal capacity of dysfunctional cells, cancer cells.

13. The method of claim 1, wherein the method treats or ameliorates diseases and conditions responsive to the self-renewal or self-renewal capacity of hematopoietic stem cells.

14. The method of claim 1, wherein the cancer cell is a leukemia cell.

15. The method of claim 1, wherein the composition formulated as a pharmaceutical composition, optionally a lipid-based formulation.

16. The method of claim 1, wherein the inhibitory nucleic acid molecule or antisense oligonucleotide inhibitory to expression of the ADAR1 gene or ADAR1 gene transcript is contained in an expression construct, or optionally a vector or a plasmid.

17. A method for treating or ameliorating a cancer, comprising:
   administering a sufficient amount of a composition to an individual in need thereof,
   wherein a sufficient amount of the composition inhibits or slows the self-renewal or self-renewal capacity of a cancer cell or a cancer stem cell,
   and the composition inhibits or slows the expression of or the activity of: an ADAR1 gene (adenosine deaminase acting on RNA 1) comprising a sequence as set forth in (SEQ ID NO:1) and/or an ADAR1 transcript comprising a sequence as set forth in (SEQ ID NO:2),
   and the composition that inhibits or slows the expression of the ADAR1 gene or the ADAR1 transcript comprises an inhibitory nucleic acid molecule or an antisense oligonucleotide inhibitory to expression of the ADAR1 gene or ADAR1 gene transcript.

18. The method of claim 17, wherein the cancer stem cell is a leukemia stem cell or a Chronic Myeloid Leukemia (CML) stem cell.

19. The method of claim 17, wherein the cancer cell is a leukemia cell.

20. The method of claim 17, wherein the leukemia cell is a Chronic Myeloid Leukemia (CML) cell.

* * * * *

SEQUENCE LISTING

```
<160> NUMBER OF SEQ ID NOS: 7

<210> SEQ ID NO 1
<211> LENGTH: 45924
<212> TYPE: DNA
<213> ORGANISM: Homo sapiens

<400> SEQUENCE: 1
gaccagacca ttgattcccg actgaaggta gagaaggcta cgtggtgggg gagggtgggg      60
ggagggtcgc ggccgcactg gcagcctccg ggtgtccggc cgtgtcccga ggaagtgcaa     120
gacccggtaa gagcctctgt ccttctcggc tacacctgcc tgggctggaa cgcgcggccc     180
atgcggcctc tccagtctct ggcgttgatg ttagaggaag cgtgggggcg ccccggcagg     240
gcactgaggg tggccgcagg gctgggtggg gacgcagctg gtagggcac agtggccggt      300 ctcggcagcc ttccaggagg cggacgcccg ggccggtgta cttttgtgcg tgtgtgcgcg     360
cccgtgtgtg cgcgagtgtg ggcggcagag gctgcgcacg gatgctccgg cgctcgtgcc     420
agccggagcc cagcagctgg gtaccaaagg cccaacagct gggtaccaaa ggcccttgtt     480
tccctctcgc cggctccccc gcctcggaga gtgactggag agtgagctgc ctggactcg      540 ccgcggtagg cgcttttgct gcgccttcta ccacaaactg cgttaggacc ggcccttttat    600 cccagagata acatcgccgc cctggcgtgc cttccacagg gaaggcgtag gaggccactg     660
tggaaagctc actgcggggt cacggccgcc gcgctcagcc tgtctggcct ggtgcaggag     720
gcctagttgc gtcacctcct cttccttctc tgtttagctt gatttggggg ccccactaga     780
gggtaatccg gccccaggtg tttcgtgttg gtatcagagt ttgggaaact tgccttccaa     840
```

```
aaagggatac ctgtcattgg attttgaatg ttgtgtggag gagcccaagt atgcaattag     900
cggagggagc agagtctagg ctgccacggg aggagacttg caaacagagg cctacacagt     960
gtcttgttgc tagagaggga ggcaggattg ctagagcggg tcattggggg cagagaaggc    1020
aggggcgtca aactgtcagc agttgtgatg ccaacttctt tctccaccag agaagccttg    1080
ttcccatcct tttaaagatc tcttgaaata tcttggtcgt tatttacaaa cagttagtgc    1140
ttgctatatg ggaaaaaggg aaatagagtg aaaggggac atgaactttg gagtcaggtc     1200
tgccactttg cagctgtttg acattgaatg agttatttaa cctctccact cctacttggg    1260
cttatctaca aaatgaagat aattatatct accttgcccg aggtgtcaga attcgaagtg    1320
tctagctatt attagtaagg gcccagtacc caggagcttg gacttgctcc cttgctgaag    1380
gtttcctatt ggtacagctg cttgagaagc aggggaactt tttgctattt tagatgtttg    1440
ctattctgcc agatatgata tgcagacttg ggggtggtag tggaggggaa atctcaaaat    1500
ccataatctc tctgctgtac acttcattaa attctagaac tgcaaagagg tgaagatctc    1560
actttaggcc gggtgcagtg gctcatgcct gtaatcccag cactttggga ggccgaggca    1620
ggtggatcat gtgaggtcag gagttcgaga ccagcctggc caacatggtg aaacccegtc    1680 tctactaaaa atacaaaaat tagaccagca tgatggtgca catctgtgat cccagctact    1740
tgggaggctg aggcaggaca atctctcaaa cccaggtggt ggaggttgca gtgagccaat    1800
atccaccatt gcaccccagc ctggacgaca gcgaaactgt atctcaaaaa aaaaaaaact    1860
cactttatta attatagctt ctcattttat tttattattt ttcaatttta tcccgagtag    1920
ctgggatcac agatgtgcac caccatgcct ggctaatttt ttttttttt ttttttgag     1980 acagagtctc actccatcgc gcaggctgga gtgcaatgat gcgatctcag ctcactgcaa    2040
actctacctc ccgggttcaa gtgagtctcc ctcctcagcc tcccgagtag ctgggattac    2100
aggagcatgc caccatgcct ggctaatttt tgtatttta gtaagacagg gtttcaccat    2160
gttggccagg ctggtctcga actcctgacc tcaggtgatc cacctgcctc ggcctcccaa    2220
actgctggga ttacaggtat gagccaccgt gcctggccta tgcccggcta attttgtat    2280 ttttagtaga gatggggttt caccatgttg gccaggctgg tctcgaactc ctgacctcaa    2340
gtgatctgcg cacttaggcc tcccagagtg atgggattac aggcatgagc caccgcgcca    2400
ggcctttcgc ttctctttag cacttgctat gtacctgaca cggtgttgag cactttacat    2460
atactaactt atttcatccc tctaacaact gagtgcacta aatattatcc ccattttata    2520
gatgcagaag tgaatcttgg ctaaggtcct gacattaatt aacggcaaag ctggaacttg    2580
aagccagctg tgtggtttga gtcttgctct ttctcagtgt ctagcaagtc ttgctcttgc    2640
ccttgctcat caggctatgt ggtttgagtc ttgctctttc tcagtgacta gtatcccagc    2700
aatgtaaacc tggtgcagtg ggggaaagga gcccagaca gagtttagtg ggccaggatt    2760
ggctgcaaga ataacatctc aaattgtcta atgatacatt atcttttatt ttacatttt     2820 tactcagcat tgtccagata tgaaccaagg tttggccttt tcacccagag aaaaaggaca    2880
ggctcatggg tacactgtgc tgggatgacg ggcacaaagt aggtattcgg aaaatgcttg    2940
tggaaaaaag aaatcctgag gcattgttat ttctgccaga aggaggccca gtgcttatta    3000
cacacaggct ccttaagcca gctattttta tactataaca cactgtaata tgagcatttt    3060
tctgattcat ggatttaaag atttgaagcc ctgtttcaga ccaagattgg tagtattatc    3120
tgtgaccaac tgattagagt tctcaaatat gtgaacaaca gaatctgagc ttttgggctt    3180
```

```
ctgtagtaat ctcttgagat agagcaattt gttttgctat aacatctgtt agacttggac    3240
cttaatgggt acaactgctt gagttttctg gagaacactg gatgattgtt tgacatcagg    3300
gataaagagt tcaaaatatt aagtttgtct caaaattaaa tatttgggaa agacctgtga    3360
ttgatgtgca ttcattgtag gaatagtaca ctagttttaa acagatgata ttcctggtat    3420
ttttgatgag ctattctgtg tcttaaagat gtttaaagat gacttgtagt tgtatagtga    3480
actattagga acatacaaaa tttatataac ccatccatat agactgtgac ttacacccc     3540 ctcagttcct ccacccaagg aggtctagtt gctgcttcta taccctctgg ttaccttgaa    3600
gctacctatt tcaccatctt tatcagactt tatcagactt aataggtgag accctctgac    3660
atcagcctcc ctttccttct gtaccacccc ttgccacatg cacacagaat gaagctcttc    3720
tccaaaagga ctgtatatta atctacttgc aagtggcaca aacccagtgt aaattaactt    3780
aagcaaaaaa aggttttttc ctcccttga ttatttaact agaaagtcca aaggcaagct     3840
tcaggcatgg ctggatcctg gggctaaaat gatgtcatga gggctttctt ggcccttcct    3900
ttttcggctc cgttttcttt attgacttca ttctctcttg ctgcttcctt tttctttttt    3960
tttttttgag atggagtctt gctcgtcttg ctctgtcgcc cccaggctgg agtgcagtgg    4020
cacgatcttg gctggcggca acctccacct cccaggttca agtgattctc ctgcctcagc    4080
ctcccgggta gctaggatta caggagcccg tcactacccc cggctaattt ttgtattttt    4140
agtagaaatg gggtttcact atgttggcca ggctggtctt gaactcctga cctcaggtga    4200
tccacccgcc tcagcctccc aaagtgctgg gattacaggc atgagctact gtgcccggcc    4260
ttcttgctgc tttctctatg catactgaaa aagctccctg tcagcaaccc caagcctatg    4320
acctgatggc tgtcttttag cgttgtaaat taaccattgc tgacaaggaa atagggagac    4380
cacaattgga gaggtctaca tcataggctc actcttggga tgaggaagta aactgcccgt    4440
ccataacctt atgggatggg gaagttcaga ggtcctaggc aggcagaaac agcacatgac    4500
tactgcaggg gtgtgtgtat gcacacatgt gtgcttacat gtgtgctctt atctcacttc    4560
tttggggtcc ttctagagcc ttccaactgg aatgaatcca gtgggttgtg tttgtccatc    4620
aaactttgac tcccactgtg gcatccatta tgtgctctcc gtccttctg taccttttgca    4680 tctgctgttt gggttgccct tccccattgc ttcatctggc tgatccttct agattcaggt    4740
catgcttctc ccagaagcct tccttgacac cttccttaat gagctaggca tcccttctct    4800
ctgctcccat aaacacctga gcacaacccc cttgtagatg ttatttctgt ttgataatta    4860
tctgtttatt ggtcatgtct ccactagacg gagagcccct tgaggacaga gtgtcctttg    4920
ctttgtattc cttatctcct acccttagct agtattattt gtcttcatag cactcataac    4980
tgacattgta tatttatttg tttatttatt gcctgtctct cctcattgac tgtctttcat    5040
tagcttcatg agaacaatgt ggaaaggaat tttctttgat caaagcaaaa caaaactacc    5100
ttgaggccta ggacagtgcc tcatactggc atatagtata tgttcagtaa atgtttatta    5160
aatgaatgaa tggaaatctt cccacaggaa gaaaacactg gcattatgtt gatgaacatt    5220
ccagtctgca tgatagatac acttctcact gtaaagatct gaaacttgag taccatggca    5280
tcccaggaag gtagcacacc tcttcccata tgtgtttgaa cctgcagagg tcaggcccaa    5340
ggagcctcca gctggaaatt ctaccctgtg tgatgtttca ctcctctcaa acttttctga    5400
actttgatag gttgtatatt aaggccttct ccatattttg gggcccttc cttggagtat     5460 ttattttaa aacatttatt taagcactta caaggtgaca ggcactgttc ttagtccttt     5520
ataaatagca actcactctt ggactggagt ttggggacca agggttgtca actttaaaac    5580
```

```
tttttttcttt ttaagtacca aaacactcaa gaacagaaat aagactactc tgcatctagt   5640
ccatcttgcc ctccagaagt agagctatct aacagcctga tacaggtctt gtccctgccc   5700
tttcctcagg ttttacagc catagctagt aaatataaca tactgcatct catcgccttt   5760
gtttggtctt cacccaaacg cagccacgct ctgccgcagg atatgtggca gagccaggtg   5820
gggaatcagt ggctcagagc ccactctgct tttcaggaca taggctgctc aagcatctgt   5880
cttcagcccct ctcccaggga gggcctaaac ccacatcctc aggcccctgc agagcacatc   5940
catcttcctg gttacatgtt atgccttatc tgtgggaacc ctagccacgc cacacccaca   6000
cctcaacaca tgaagaaagg gaaaaaatac cccttctttt cttttgacaa caacaaaaaa   6060
gtacttctcc tacaaataga gacttgaaat gacagggtta ttatttaacc ccgctcttac   6120
tccaaacatc caagcggcag tttcagccta gctgcagtac tctgttgtag tgcttagtcc   6180
tgatttgctt cctaagaagt gaataccagt ttccactgcc atcagcaatg cctgagtact   6240
tactgtgcct ctccctcacc ctaccctcct ctccagaact gagtatttta ctaaaaaagg   6300
aaaatcttag ctaaatttga aatagcatct cattttaatt tgcatttttt attataattg   6360
tttgagcccct tttacccat actgagccat ttttatttct acttttttaaa ttttttggtta   6420
atgttttgtc tattcactta ttgtgtttaa gtgatttta aaatatacaa atattctgaa   6480
aaacatgagt ttatcctcat ggtaaaaagc aaacaatttt atttgcagtt aattcttttt   6540
agtttattgt ttgccatcta atttgggcttt tatcattaaa aatacaaatc tatttttcat   6600
tctttttag acaaattta ttcttttga tttcttttgc ttgtgagcat aaaaaggttt   6660
ttttccttat tctatattct agtttttttt atggtttgca ttttacata tgacttttaa   6720
aaagctagca ttcagttta tttcagattt taataagata tttgatgaaa atagtgtaat   6780
attttaaata aaatcagttt taattaaagg tctatgtttt gttttaagga tgtttatatt   6840
actgtactta tattttttct ttttaaataa tttatcagaa tagcgaacag cttgcttgac   6900
aaaactaaga ttcacatata tagataatca taattttagt gttcttagcg tttccataaa   6960
ttgctgcatg aaaagatatt tatgtgtggc tgtctggttt aaagaggcac tcgtgcttgg   7020
caacagcttt tcagcatgta gccaagatga caaattcagc ctcttccagt tcctcttcct   7080
cactatttcc ctaagatttt tttcatggga gcataactat gtgtatctct gtgcacagat   7140
tttatgtgta cctttcaatg tatttaaca aaaatatatc catttaacta tccaaatcaa   7200
gaaataaaac attttcatta cctcagaaag ctcccctgtg gtagtcacca ctaccccaa   7260
aggccaacac tattgatgtc tgatatctat cactatagat tagattagtt ttgcctgttc   7320
taaaatttca tgtcagtatg tgcttttgtt tgtggcttct ttcagtgagg atcaaccatg   7380
ttgcatgtgt cagtatccat tgtgtgaata tgcatcaagt tatttattca ttagttgatt   7440
gacatttggg ttattccagt ttggggctat taagaagaat aaagctctat gaacagtttt   7500
ttttcctgtt ttttattgta gtaaaataca caacataaaa tttaccatct taaaccattg   7560
tttgtttttt ttttgagac ggagccttgc tctgttaccc aggctggagt gcagtggcac   7620
gatcttggct ccctgcaacc tccacctccc aggttcaagc aattctctgc cttagcctcc   7680
caagtagctg ggattacagg cacccaccac catgcccagc taatgtttgt atttttaata   7740
gagacggagt ttcatcacct tggccaggct ggtcttgaac tcctgacctt gtggtccacc   7800
cgccttggcc tccaaagtg ctgggattac aggcatgagc caccgcgcct ggcccgtaaa   7860
ccattttttaa gtgtatagtt cagtagtgtt aggtatagtc acattgttgt gcaacaaatc   7920
```

```
tccagaactt tttcatcttg cagatctaaa actatattca ttaacaactc ctcttttccc      7980
ccatcctcca gccccctggtt ctatggacat tcttgtacaa gtcttttttgt ggccatttttt    8040
cttgggtaag tacccaggag tataaatgct gggtctagcc ttagaagaaa ctgccttaca      8100
gttttctcga atagttagtc gtaccatttt atgttcccac agtatacaaa aatgctagtt      8160
tgcttcatat cctcaccaac attaggtatt gtgagtcttt tttatttta gccattctgt      8220
agctgtgaag cggcatccca ttgtggtttt attacatgtt ctagtcagtt atttacatgt      8280
ctgttcccat tactagactg tgaacttcat aagggaaggt tcatgcagta agtagttttg      8340
ttttttttgt tgttgttctt attaaccttc ctcttcttat tttgagggtg atacatgctt      8400
tattattaaa aagaacttaa aaattataga aagctattaa aaagccaata aaatcacagg      8460
ttagcccacc tctcagacat catcaggagt attttggtct ttcaggcagt gctgtgttgg      8520
ttcgtacaga cagaacagtt cccatgatgg ttgattcagc aacccagcat tgttccagcc      8580
cactgccttg ctatcctctg gacatcactt attcccagcg aggagcccctt ttctcagaca      8640
gccccagaca gattgttttt gtggtttgct ggccacaaat gtatcacatg tatcactgac      8700
aaaagaagta gaatcctcaa tactggatta aattagatta attaacatcc ttcctctggg      8760
gctggggagg gaacctggcc ttcttaggaa agtggacaga atcagggcac tctcagaaag      8820
ggaggcatag ttctagcgta ggccactaac attatctgcc tctttttttt tgagatggag      8880
tctcactctg ttgcccaggc tggagtgcag tggcacaatc tcagctcact gcaacctctg      8940
cttcccaggt tcaagcgatc tcctgcctc tgccccacta gtagctggga ttacaagtac      9000
ctgccaccac gcccggctaa tgtttgtatt tttagtagag acggggtttc gccatgttgg      9060
ccaggctggt ctcaaactcg tgacctcagg tgatccacct gcctcggact tccaaagtgc      9120
tgagattaca ggcataagcc accacggccg gcctgcttct tggtgttttt atttaatttt      9180
tttacactta gtctgtcaat acatttgcaa tttgttttgg cttattaata taaggctaga      9240
ctctagactt tttttttttc caaatagcca ttcagttggc ccagctccat ctgttgaata      9300
acgcttttttc tcactgctgt ttttggttcc tcatcatgca ttggatttct gcacatacta      9360
ggctctgttt ggagggaggt ggttcttttc tgttagtctg aagctctacc cttgctttat      9420
accagtgctg ccttggttta attagcgtag ctgtcttctt tttaaaaaac tgttttgttt      9480
gttcttgtac ttgaaccttta tttattccca tccaatgacc tattaattgc atctgaactt      9540
tagagtaatc attttgtcag gtatccactc cttactgccc caacctcata gtatttgcag      9600
taaatcgtta tttaatttga tattaattag tattcataaa gtattctgcc atcacatttg      9660
agactggtat gtccttctat ttaagacata tattcctcag cagagttttg taattttcca      9720
catgtaagct cttcacattt cttagggtta gtcctagata cttcttttttt ttaatttaat      9780
gttttatttg ctattaagaa tatggtattc ttaatagcaa ataaaacatt aaagtatata      9840
aagaatatat acttactata tgaagaaggt atacttatat attactatag taatgtatat      9900
attactatat aaagaatata tactttagat gcatatatac atatgcatat aaagaagcta      9960
ttgtgtttta tatgtttctc ttatattcaa ccatattcct tgactggtat tggttctaag      10020
agttttcag ttgatcctct tgaatcaact agggttatga tgatatcatc tgcaaataat      10080
ctattttttct ttttaatagt ttatctctta tttttgtttc ataatgtaga atatgtaaga      10140
atttccatag gtagaaaaga tattaaatat atatatttaa catgtgttaa ataccatatt      10200
tgttttaaga ccactgagca taaagacttg ctattgattt aataacagat ttgggggggca      10260
ctatattaaa tgtatactta cactgtaatt catattccaa tatcagaaat gttaggatgt      10320
```

```
aaaaagcagt gcatcttaga attaaggaaa ataacaatgg taatggtagc cctccttttt   10380
ctcgtttgag tggtagtgtc taactgttcc attctacata tgatattggc tgttgattta   10440
tgatagacag tctttattat taaggggtcc tcacacatct tcctgtttgg aagaggtttt   10500
gtgttggttt aatcagctta ggagggaaag gtgatcatca gggtcacttt cgtgcagaat   10560
cccacctctg cccacaattc ctgccttctt tgaactttct tgttaaagt aagaatctag    10620
actctggcat caaagattga tatgctaagc agaagtttac tgcccagcag agaaccagtt   10680
gagtgcaaaa gttaggctct gagatctaag ccttgagggt ggcaatgagg gatgaggtag   10740
gtttttaaaa ctcatggtct ccatcccata ttaggaaatc aaagtctcca aatgctactt   10800
attggccagt gttatctgga ctaggcattg tctaagcaac aagcaggaca ggacgcttgc   10860
aggggttttt gataagttat ctctcactat gtctatgagt caggataata gtgccccagt   10920
cattgttttg gtagaagtcc agtccactgg ctaggcagcc atgttgggat tcatcacttt   10980
gtagtttcta acttttttact gtattccata ttggaaagtt cagccctcct ctgagatacc   11040
cattgtccac tagaactcca gacagaagtg ctggagaggg cagtgggcca ggtcaggaag   11100
acataagcca gagttgaagt acaacagtgg aaagaacaaa gtctttggag cagtgcctct   11160
taaccttcgt tctgggtaca cagatctatc tgggagtctg aaagctatgg gctgtctctt   11220
gagggaaatg cgcatgttgc gttttttcagt aaatattttt gagcacgctg aaagcaaaac   11280
acttgtatag ccctagcttc ttggaacttg tagtaagaga gacagatatt taccaaaaaa   11340
ccacatgaag aaatgtaaaa ttacaagtgt aaatatgctc caaaagagag gaggggtct    11400
tgaaatcatg cgatgggagg gggtaggggt tagagctcaa gctcttcctc cagaagtgtt   11460
gactaccctg agatctgaag ggcaaatcat aggatagtgg aaaggaggag aaataatcca   11520
gagagagggg caagtatgtg gcaggaggga gcatggcaat ctagagggag gaaaagaagg   11580
ctcaggagg ctgggggaca gagagatggg gcatggtcca acagaaggga gaaggatggc    11640
agggctaggc cacgtaaggc tttggagcca tcgtgtaaag atgtttgcct ttatcttaag   11700
agcattagga agccatcaaa gtattttttg ttaataatgt aaatatttga tatgcataaa   11760
agattcctgc agcatatatg tatcactgaa atacaacaat gaaacgaatg cacgtgaacc   11820
taacaccttc ccctgaatga gaaccttatc tgtattgctg aagcctccct tgtcgcctct   11880
tggatcccat ctgcctgtgt tcccctccc cccttaattg ctaggttaga attttcttga    11940
attccatgca tgacatgatc agattttggt tttcagagat cacacaagct gtgtcgagaa   12000
gactggatag aaaagaggcc aaagtacatg cggggaaacc agtttggagg ttgtaatcac   12060
aaaacacaat cttactaaaa gtttgtctgc attttatttt attgccttgg aaatttattt   12120
ctttcacaga tgatttatt tcatcatttt aaaaatataa attaatggta tcttcctaga     12180
aaaaaataaa atcagataaa actaaaagct ctaattctgt tggacaataa tgagaaggct   12240
gtactgtttg gcttaactaa aaaatgtggt gaggcatggt ggctcacgcc tgtaattcca   12300
gcactcaggg aggccaaggc aggcagattg cttgagccca ggagttcgtg actggcctgg   12360
gcaacatagt gcggcctat ttctacgaaa aaaaatttt ttaattagcc aagcatggtg     12420
gtatgtgcct gtagtcccag ctgcttaaga agctgaggca ggaggattgc ttgagcccag   12480
gagtttgaga ttgcagtgag acatgactgt accactgcac tctggcctgg gtgacagaga   12540
ccttgtcttt taaaaataa ataaaggaca tcatggctgt gcataagtac atctatgaca    12600
gctagtctgt tttggccttt tccctttgat gtacccaaat gcagaaactc ctatctcgcc   12660
```

```
tagcaaagcc tctggcagcc ctggacttgg agctccctgg tttgtattgt ccagcaaaga    12720
tgctgtagta gtttcccgtg gctgtctgct gtaaaaaaat aaccacaaac taggtggctt    12780
aaaacaatgg aaatttatta tctgacagtg ctggaggcca gaaatctgaa atcagtatca    12840
ctgggccatg ttggcagggc tgtgctccct ccagaggctg tagggagaa tccattcctt     12900 gcctctccca acctctggtg ggtgctggca tcgcttgtgt tgcggctgcg tcgctctagt    12960
cttcaaggct agcatcttcg aatcattctc tactctgtct tcacatggcc ttttcctctg    13020
tgtgtgtagg tggaaatttt tttgaacttg ccaacactaa agaaacact tttaaagacc     13080 agtgttcact tgaaaatggc tctctgtcaa attccaagaa aaccagttca ctgaaagtca    13140
gttctacaaa agcccctcca tcctacccct ttgcctcctc agtttcctcc tcaatcttct    13200
gctctacagc agcagggaga cagcagagca tatttcctct aaattctatt aagaagacag    13260
aataaaaact ggtcaattaa gactagggag atttaagaaa aaagtaaatg caacatattg    13320
gttgtttcgt aaattggtta tccaaggaat tgaccatttg gcaaactgac tttcggcaaa    13380
ttggctgttg gtgaaatcag cctatttccc tgagaaacac tgcagaaggc agggcagtgg    13440
ctgccttgag cctgcccagg acaggactgt gactgtcccc tcctgctttc tacaagccat    13500
ggagataggg gcattgctct tgcatgaggc tggggctgag agcagccccc tacaggctgg    13560
atctggatcc tagggaagaa gaagatggga gatctccccc tttgggtcct gactcaatag    13620
aacccaaatg taggccagta gcggaacctc tgtgctagcc agagtcaggc cagaagtcag    13680
tcaggtgctg catccaagaa caatctagca tcggagaagc ggcttaaggg tgtcagaata    13740
taatgtataa aaccacaagt tgtataggg cacccgtgg ggtagttatc cgactgaatg       13800
tacatttatt agttatacat acttgcaaaa gattgcacac aggcctgtta gtcattatta    13860
ttagtattat tttacatatg taatattatt gcaaatgtta tatctttatt atataatact    13920
taagcctggc acatatagct agttgataaa taccactttt tttctttgtt actagataac    13980
ttactggagt ggataaatgc acttaatagc ttttggagac ctctttttct tctgggggta    14040
cctgaggcat ttcttgcttt cttttttttt tttttgaga tggagtttcg ctcttgttgc     14100
tcagggtgga gtgcagtggt gcgatctcgg ctcactgcaa cctccgcctc ccaggttcaa    14160
gtgattctcc tgcctcagcc tccctagtag ctaggattac aggcatgtgc caccacaccc    14220 ggctaattt gtattttag taaagacgga gtttctctat gttagtcagg cgggtctcga      14280
actcccgacc tcaggtgatc cacccacctc ggtgtcccaa agtgctggga ttacaggcat    14340
gagccaccgc gcctggccac atttcttgct ttcttgtaac ttcaaaagcc agttttagct    14400
gggagcaatg gttcacgcct gtaatcccag cattttgga ggccgaggca ggcggatcac     14460
ctgagatcag gagtttgcga ccagcctggc caacatggtg agaccccacc tctactaaaa    14520
atataaaaat tagccaggca tgatagcgcg tgcctgtagt cccagctact ggggaggctg    14580
aggcaggaga atcacttgta cctgggaggt ggaggttgca gtgagccgag atcatgccac    14640
tgcactccag cctgggataac agagtgagat tctggctcaa aaaaaaaaaa aaaaaaaag    14700 ccatttgtga tcattaacat caatagaata tatgtcagca taaatactgc cacagagcac    14760
tactcagcca gttgggcaac tcactcttct ctaccaaaag ctttacaggt tatcaaagca    14820
agtgggttta ctgtgggagg ctactgtgaa ttttggaaat taatgttgag ggactagcgc    14880
agtggctcac acctgtaatc ccaacatttt gggaggccga ggcaggcgga tcacgaagtc    14940
aggagattga gaccatcctg gctaacacgg tgaaacgccg tctctactaa aaatacaaaa    15000
aattacccag gcatggtggc atgtgcctgt agtcccagct actcgggagg ctgagacagg    15060
```

```
agaatcactt gaacctggga ggtggaggtt gcagtgagct gagatcgcac cactgcactc    15120
caacctgggc aacagagcga gactctatct caaaaaaaga aagaaagaaa gaaaattaat    15180
gttgttagga actgttgtag tggaataaaa actcagtgat aaagaattga ggagaaacaa    15240
cgataacaaa aaggagggc aataaatttg tgcctagcaa ctctgaattg cttactatac    15300
atttcctaag agttattcta aaatgatgcc ctggtactta aaaataactg agcaggctgg    15360
gcgtggtggc tcacacctgt aatcccagca ctttgggagg ccaagaccgg cagatgacga    15420
ggtcaggaga tcgagaccat cctggctaac acagtgaaac cccgtctcta ataaaaatac    15480
aaaaaaatag ccgggtgtgg tggcaggcac ctgtagtccc agccactcgg gaggctgagg    15540
caggagaatg gcgtgaaccc aggaggcgga gcttgcagtg agccaagatt gcaccactgc    15600
actccagcct gggtgacaga gccagactcc atctcaaaaa aaaaaaaaaa aaaaaaaaa    15660 aactgagtaa tttattactt tctttgataa tatgttgcaa attgtttaga atacattcac    15720
aggcagtaca tttctgtccc agtatcactg tatgagcaaa tactgaagga gtttgcagac    15780
atctgcttta cagtagacag gagatagatg ttccaattgg atatagccca tgtgtgtagt    15840
aaagtctggt tataggaaat tacagattaa aaaagactgt tgttgtaaac atgtatccct    15900
gcacgcagta aggttaaaca gaagatccac aacaaaccaa attaacaatt actaagtcag    15960
actaacagtt acttatagtt aaaaagcaag aatagcaggg attggaaaac aaaaccaact    16020
caggagccct gataatagca tgtcctttcc tataggtggg gaagtctcac cccctgaatg    16080
cacctataga gctagagctt ggcactgcta tgtggaagcc agacttctga gaatactgag    16140
tttctgagta cttcattttt agacagtaac tcttaatcat ttaggtggtt tttaataagt    16200
agacctaggt ggtatagata catctggggt catttcacag gcccctgggg aggtgagcca    16260
ttctttatag gaagagctcc tcccttgaga ggactgacca cccatgtgtt ggcagtgccg    16320
ttacgcacgg ggaagttacg cacagggaaa atgctcgaag ggtaggcacg gatgaatgat    16380
gaattaacaa tgggtgattt ttattgtgtt tgcttgtctg tattttctga aataaaccta    16440 ttattttgg ttaattttt taaagacttt catccaactc gtcaagttcc tacaatagaa    16500
cagttaaaaa aaaaaagaca tcatcacctc acaaccatgg gggagttaaa acaattactg    16560
agggggagga gatgaaacgt ttatgaataa gactgtctgc agttacttga gctgctaaga    16620
ttaaatgaca ataggagttg ttgttctttc aaggcataaa ctgaccttct gttgaggaaa    16680
gttcactgct ttgccactgt gtcctatgtt agattaaaag gggtggggg agcagcggtg    16740 cagcttccct cgcacagtag ttgtgattaa agcttttctg gatcatttct gaagaaggg    16800 aaaggctttc agattgtctt gcctgaagac aagaaagcag aggtaagata taactcctgt    16860
tacttaaacg gaggaaaaaa aacatgggga agtggactgg aattgcaaca gcaagagttt    16920
gttgtggttc ttgtttgttt ttaccttta aatttgtgaa atacagcata tatatacaga    16980
aacatgaata aaacgtaaat gtataatgaa attattggaa agcaaacata tgtagccact    17040
acccaagtca agagctagaa catcaccggt acccaaaaga tttcttccca gtcaaaactc    17100
ccacctttct ccctagaagt gattaaccac aattttgtct tttttttttt tttttctttt    17160
tttttttttt ttgagacggt gtcttgctct gtctccaggc tggagtgcaa tggcacaatc    17220
ttggctcact gcaacctccg actccctgct tcaagcgttt ctaccacgtc agcctcccca    17280
gtagctggga ctacaggcac acgccaccat gcccagctaa ttttttgtac ttttagtaga    17340
gatgggtttt cactatgttg gccaggatgg tctcgatccc ctgacctcgt gatccgccca    17400
```

```
cctcggcctc ccaaagtgct gggattacag gcatgagcca ctgcgcccgg cctcatttg    17460 tcttttatgc agagcatact atagtttggt tttgcctggc ttgggacttt ctgtaagtgg    17520
gatcatatag tatacatatg gcttttccca ctcagtatca tatttagata attagctacc    17580
ttgttgcatg cgtagatctt tcattttgt tgctgtattg tattccatca tgggcatatg     17640
ccaccattta tccattttac ttttgatgga catttgggtt gtttccagtt tgggggctat    17700
taattacaaa taatgcaacc atgaacttct tggggtttac cattacctt ctagataatg     17760 gtaaactggt ttcctgtagt gactaagagc tgctctgcat ccttgctgcc acctggtcta    17820
atcagatggc taatgctgtc tgtctggtga atggacagta gctcactgta gctatactgt    17880
gcatttctct gatgtgatgg ggttgagaac cttttcatat gtttgatatt ttttatctcc    17940
tgtgaagttg tctttcgatt gttttgccc attgttatac ctactgaggg gtctgttatt     18000
ctttcaacta accagccctc tgaaggcgaa tataaggata caaaacatgc ttcctgcccc    18060
cgaggagatg acttgacaat tctagaggca gatatatgaa caagaagtac atgataattg    18120
tgattactga ggcatccatc ttccctagca gactagctaa aggatggcgc tcttatttgt    18180
gtcatatcct gggtgcttaa cacagtatct gccacataat taggtgctta gtaaagtttt    18240
gttaaatgat cgaatgggc gtttttagcg cagtgtgcaa gtgccctatt aggggtaggc    18300
gcccagtaac tcgagaagca tggagtagga aaccacaaac agcacctgct cccccctcctc   18360 tccccctacc tgctgtgggg aaggcctccc ttgtaaattt gaaaggttga ttcacgggaa    18420
gccgtggagg aggtgcatgc taggccaacg aatagaatgt gcaaaggccc agaaggaaga    18480
cagagcccag cctgcaaggg aatgttaatt tggagtgact aacaccatga aagggcatca    18540
gctggagata ctgctataaa gggactgcct tgtaatttca taagcatggg ggtaaaatta    18600
agattaaaca cagggaaaga acattctcac aggtgaggat ggtgttgaac cctagaataa    18660
tcgtttccca gataccttga acaaaaatcc agcagttaga aagcctgac catgaagcaa    18720 atttgacttt tgtccctcta gataacaaaa gttatctttt tgaaagtaat ggtgtaattt    18780
gaatgagtgt agagaagcgc tgaagactga gctttactaa agccttcaga cctggatttg    18840
gcagcagcgt ggcctagtc aagcctcggt ttctacacct gcaaagtggg aataatgcct     18900
accttggagg gctgttgtga agattaaggg agataataca tgtaaagtac ttaaccattt    18960
gcctggtggg gtagttttta tgacctagat cctaaattgt tcactgctgc tgttgctact    19020
cttggtactt tttactggct ggcatctgct tgcttaagtt tataacatag taggagcatt    19080
aacaaggtcc cacggtgggg accttggtcg tttgacgaga tctgcgctcc cgcccatccc    19140 ctccccccccc cctccacatt ggagacgcgg ccaccaccgc gctggcgcgg agagagggag    19200
gaccgggcgt catgctgttt ctggcctgag gttttgtgtg cctttgtttt ccttttgctc    19260
tattcgtgta ttcctgccta cggcctgtgc ggggaattag gagctcagta ctgaaacggc    19320
ggttttccta aacagtaccg gacgggcgcg gggctgacg cctgtaatcc caacactttg     19380
ggaggccgag gtgggcggat ctcttgaagc cgggagttcg agaccaccct ggctaacgtg    19440
gtgaaaccct gttcttacta aaaatacaaa aaaaaaaaa aaaaaaagc caggagtgat     19500 ggcgctcgcc tgtaatccca gctactccgt aggctgaggc aggagaatcg cttgaacccg    19560
gggggcagag gttgcagtga gccgagattg cgccattgca ctccagcctg gcaaaaaga    19620 gcgagactcc gcctcaaaaa aaaaaaaaaa agtaccttcc gtagttctca tgcagcggag    19680
gggttcgact tgtaaccggc ctgaaaccaa gcgtggcgca agatttgctc aagcccctcc    19740
tcttggccaa actttccgga ggggaaggct ttccgaggaa acgaaagcga aattgaaccg    19800
```

```
gagccatctt gggcccggcg cgcagacccg cggagtttcc cgtgccgacg ccccggggcc    19860
acttccagtg cggagtagcg gaggcgtggg ggcctcgagg ggctggcgcg gcccagcggt    19920
cgggccaggg tcgtgccgcc ggcgggtcgg gccgggcaat gcctcgcggg cgcaatgaat    19980
ccgcggcagg taagccgggc cggccttgga ccttcgccgc cgtctgggtt cgtttacaac    20040
ctcacaggct ttgtgttgca gtgcgtagcg tgtgcgtctt gtgagtgtta gagtgtgtgt    20100
gtgtgtgtcg tcttgccaag cagcattgct ggtttaggaa tttgtgcgtc ttgtgagtgt    20160
gtgtgtgtgg gtgtgtgtcg tcttgccaag cagcattgct ggtttaggaa tttgtgcgtc    20220
ttgtgagagt gtgtgtgtgt gtgtgtgcgt gtgtgtgtag tcttgccaag cagcattgct    20280
ggtttaggaa tttgtgaatt tgtatcctgc tcattaattc tgcagaatgg agcagtgcgt    20340
gaagagggct tgggggaaaa tgcgcccccg tctgagtagg aaggcctgag cccatgtcaa    20400
ggcagacaca tcgtctccct ttctgctagg gccccttgtg gaaccccta cccccgcttt    20460 agccccactt gaacaacgtt cggactttga gcagcgcaca ctatcctcag ctcaccttat    20520
ccacctcctg aaggccttct gggagttaaa aatggcactt aagctgtagg agaaagcttg    20580
ttaaccactt tatagctaaa aactgggaaa acacaaatgg ccttcagcag gttaacagat    20640
aaactgaaat acatccacat aatgggatac tgcttagtag tgaagaggaa atactgttac    20700
aagtaacaac acgggtgact cgcaagtgcg ttatgctaag cacgagaagc cagactcaaa    20760
aggctgcata ctgtatgagt ccatttatat gacattctgg aaaaaaaaaa ccacagttat    20820
agggatggaa agtggatccg tgggtgccag ggactgggta tcgtggaaga aattgattgt    20880
tgagtggcat gaaaaagctt tttagggaaa tagaaatgtt ctatatcttg attgtggtgg    20940
cgattgtcga aattcataga tttatacact taaaaggata aattttactg tatctaaatt    21000
atatacctca attttgttaa gatatatata tatttttttt tttttaagca ctcctttgaa    21060
aggattaagg acgcctaact tgaaggaaaa gcatttctgc acaggtgtca gtgtattgca    21120
ctgtggaacc tgtgtggtaa aggcaaaggg ggtagtgctt atctcttgat cctaaatatg    21180
tgagaccaga ttaaagtgaa atctgggagg caatgaatgt taaatgagtt gttatgtaat    21240
ttgcatagag gtgatgctga gagatttaga aaggatcact gtgggttgct tgctcacttt    21300
cttgctctcc tattccgtag cttttccaaat ggctgtactc aacggtggct tggtgtttag    21360
gggatttaag gggggcaaaa agaaagatta ataatctcct cctctccctc taaccctact    21420
gccctaagat atccttagca aacttacatc tcctttcttt tctctgtgtt cattccattg    21480
tgcgcacaca tacacattca tggattttct cttttgttt agggaaaaaa attataatgt    21540
acatactatt ctacaacttt ttgttgtttt attgaacatt atatgattcc taaattatcc    21600
ccaggtgaat acaaatagat atgacacatt ttaaaaaaat aaaataactg gccgggcgtg    21660
gtagctcatg cctgtaatcc cagcactttg ggaggccgag gagggcggat caggagatcg    21720
acaccatcct ggccagcatg gtgaaacccc atctctacta aaaatacaaa aattagctgg    21780
gtgtggtggc gtgcgcctgt aatcccagct actccggagg ctgaggcagg agaatcactt    21840
gaacccggga ggcggagatt gcagtgagct gagatcacac tgcactccag cctgattgca    21900
gtgagccgag atcatgccac tgcactccag cttggcaaca gagcgagact ccgtctcaca    21960
agaaaaaaaa taaccgtgtg agtactattc catagaatga atgtttcata atttaattct    22020
tctatagaca gacattaaaa tattttccag atttgggcca agagtagcag tttaaaaaac    22080
atttagcttt taactgactc tagccacttt gaaacacaat ttttttttcc caaggtcact    22140
```

```
caaagagcta ataggagaac ccctaagtcc cataattcag ctctgggagc cagcactcac    22200
tctgtacaca catttgcctc tgtccctagc aatatggtgg gcgtgagggt gcagcaagag    22260
gaacaagaaa gaaatgattg cttgcatagt ggcgtcttgt tcatgcagtc attaattcaa    22320
caaatgtttg ttgagaatca gctttgtgcc aagtgctaga gaggttgaga tgattgaagc    22380
atagtccttg acccccaaga gctcaccatg gaatcaactg aagcccctca tcagtactgt    22440
gttgggaata ttgagagtgg agagttgagt ataacttata ggacacctaa tgttaattac    22500 cttttcagaca ctgcaatgtg tgtgtgccat aaaaaaaaaa aaaatccagt agctctgata    22560
cgagggaaag taaatggttt aacaggtgct gagtaggaga agctcaagga gaggaaaccc    22620
caagggctga agaaggtggg agtcaggagt ctcctgaagc aagtggcatt taaggagctc    22680
tataaggaaa gggtcagagt tgtgataggt ggctgtggag ggagatgtgc cacctggatt    22740
ggcatgtaga gggatagaaa gattataggc cttttgcaatg gcccagtaag aggtaatgag    22800
gggctggaac tggaagaaaa cacatttaag acacagtaca gaggtggcag acaaggtggg    22860
acttggcaac tacctgatga gatccaggag atgaggccag gaggcgggca gcaaagatga    22920
cgcaggtttc tagccttaat aggctaggag gagagtgatg ccattagcaa taagaactac    22980
aggagaagga gctgagtttg agggaactat taatttggtt cagaatatgt gctgtttgag    23040
ttatggcagg atatttaagt ggacagactg tcgacatagt tggaaattca gatcttaagc    23100
tcccacacaa ggtagtggct ggacatagta gatttgagtg ctcttgcttc agagggctag    23160
tttaggttgg ggcagtgatt aaagcaacct aggaaataaa ttataaagga agaagaggtc    23220
cttaaaacct tggagactga ttatataaag ggtggatccg ttaatacagt agctattaaa    23280
aaattataag gggtgggaaa aagggacaaa gaagaaaaaa gaggtgaaag acctttgctg    23340
tgtcaccaaa ccctggggagg agaatttttt aaaagaagag tactcaatcc acagtgaact    23400
aaggcatgtt tgttaaacac aattgaccac cacacagcga agacccaaat gaggttcaag    23460
agaaggaatt tttatggacc ctgttagcac aagtcaaggt ccttctccag taccactggg    23520
aagctttgga gaagaaaagg gggacagtgg gccttgggtg gagaagggaa ctgaccatga    23580
gatccaggtg gggtgaggag gtgtgtgaag tcagagtggg gaagaatcag ggtggcttac    23640
tggcagcttc accggggtca tgcgaggagc aggttccacc agagtaagga gtgaagttgt    23700
agaaacacag ggaagtcacc atcagaaaag agcaggagtc aagaaactat ggcccacagg    23760
tacaaactac ctgttttttat aaataaagct tcatggtaaa tgaattgtaa ataaagtttt    23820
gcatattgtg tgaggctgtt tttgtgctac agtggcagag ctgtctggcc ctttatagaa    23880
aaagtttatc agccactgga aaagagttgc aggatttgag gtcttggtgt gatggcctag    23940
gttagagtca tagtgagatt gaaggagtag ctagacaagc caattgtgtg gcagaaaggt    24000
agggatggag atcactgggt taaggatcct tgtagccagg acaccatgag agtgattgac    24060
aagaatgctg aaatccccta agtgtgtcag gatgtggaag agtagaaggc tagagttatg    24120
gaagaaaggg tccacctct  acctgtgcag cctccaggag agtctgagga gggggcggtg    24180
agtgtgagta atgttgtca gaatccctcc tcccagtcta caagccccag ggaaaggaag    24240
caaggtgttt actgacaccc ccaggcttat aagtacttcc tggctccatc accctccagt    24300
gaacagccct ggggagaaga cagtactggt ttgcaggtgg gtgggtgggg aaaggggtca    24360
caggtgcttg gtgttctggt aaatgtgcat atgagaacat ggggttgctt gtgccctgtc    24420
cgtcagggtt cagaagaacg tgcagtggaa gcagctatgg ggaagtagct agggaaggta    24480
ggactggtct gaggtggtga ggagcagatg ctgccagctc cacacatcca ggagagcctg    24540
```

```
ggtggtttgg gcaaaagtct ctggcatccc ttctgagcct gggtaccaca ctgaagagtg   24600
aggacagtgt gccatttta tcaggaaacc ctccagctcc ctgaagacca aattctgatc    24660
ctcctgggat ggcagtgaag agccacagag atgactctga ggtcccgtgg ccttttccca   24720
cctggagatt gttttcgtta ctgcgctgtt acagccttgg aggactgggg ttcagtttca   24780
tccaatcaca tttcttcttt tgtcatagtc atctaaacga tagatcttag agacaggtgg   24840
gcaaggggtg cactggtgag cctgacttaa ggagaggtca tctcgtccct tccctagtcc   24900
catctccctt ggttattgtt atttcatgtg attgttctgg ttatttcagg ttattctgtt   24960
tttgttttca aaacaataac atatatttgt tgttctgatt ttaaaggggt aattgttttg   25020
gtaactagaa aattaccttc tcaactccct taaattctgt caagggaaa agtaagttag    25080 gttgctggag aggctatgct gaggcctcag aacctctgta ttcctggaag ttctgcgtgc   25140
tttgcctcct gctccctct  ctgtgttcct gttggcaggc ccctaggcag gatttaggag   25200
gtaggcaagt caccctagcc aagtcataag cccatggctc aattgccttc tcagcccttc   25260
aagggctgtt ccacaggcag caaagggagg ggcctccaca ggttcaccac tgcagcccta   25320 attcatttc  tttttccact gtcttattct gcagggtat  tccctcagcg gatactacac    25380
ccatccattt caaggctatg agcacagaca gctcaggtac cagcagcctg gccaggatc    25440 ttcccccagt agtttcctgc ttaagcaaat agaattctc  aaggggcagc tcccagaagc    25500
accggtgatt ggaaagcaga caccgtcact gccaccttcc ctcccaggac tccggccaag   25560
gtttccagta ctacttgcct ccagtaccag aggcaggcaa gtggacatca ggggtgtccc   25620
caggggcgtg catctcggaa gtcaggggct ccagagaggg ttccagcatc cttcaccacg   25680
tggcaggagt ctgccacaga gaggtgttga ttgccttcc  tcacatttcc aggaactgag    25740
tatctaccaa gatcaggaac aaaggatctt aaagttcctg gaagagcttg gggaagggaa   25800
ggccaccaca gcacatgatc tgtctgggaa acttgggact ccgaagaaag aaatcaatcg   25860
agttttatac tccctggcaa agaagggcaa gctacagaaa gaggcaggaa cacccccttt   25920
gtggaaaatc gcggtctcca ctcaggcttg gaaccagcac agcggagtgg taagaccaga   25980
cggtcatagc caaggagccc caaactcaga cccgagtttg gaaccggaag acagaaactc   26040
cacatctgtc tcagaagatc ttcttgagcc ttttattgca gtctcagctc aggcttggaa   26100
ccagcacagc ggagtggtaa gaccagacag tcatagccaa ggatcccaa  actcagaccc    26160 aggtttggaa cctgaagaca gcaactccac atctgccttg aagatcctc  ttgagttttt    26220 agacatggcc gagatcaagg agaaaatctg cgactatctc ttcaatgtgt ctgactcctc   26280
tgccctgaat ttggctaaaa atattggcct taccaaggcc cgagatataa atgctgtgct   26340
aattgacatg gaaaggcagg gggatgtcta tagacaaggg acaacccctc ccatatggca   26400
tttgacagac aagaagcgag agaggatgca aatcaagaga aatacgaaca gtgttcctga   26460
aaccgctcca gctgcaatcc ctgagaccaa agaaacgca  gagttcctca cctgtaatat    26520
acccacatca aatgcctcaa ataacatggt aaccacagaa aaagtggaga atgggcagga   26580
acctgtcata aagttagaaa acaggcaaga ggccagacca gaaccagcaa gactgaaacc   26640
acctgttcat tacaatggcc cctcaaaagc agggtatgtt gactttgaaa atggccagtg   26700
ggccacagat gacatcccag atgacttgaa tagtatccgc gcagcaccag gtgagtttcg   26760
agccatcatg gagatgccct ccttctacag tcatggcttg ccacggtgtt cacccctacaa 26820 gaaactgaca gagtgccagc tgaagaaccc catcagcggg ctgttagaat atgcccagtt   26880
```

```
cgctagtcaa acctgtgagt tcaacatgat agagcagagt ggaccacccc atgaacctcg    26940
gtaagagacc acccaggaac tgtacctagg gttggggtca ggtgcttttg ctcctgacgc    27000
agtcttggct gatttgtgag cagtgctgtt tggtggcgcc tatcttttcc tccttccctt    27060
ctgcctttta gctaaattcc ccttgattgg ccctttctcc agatattgag cagggaatat    27120
agaccttgga ccagccagaa tcttggctga acaaggggga ggttgactct gttggctgta    27180
atgaagcttc tttagaaatg attggttttg gccgtacgcg gtggctcatg cctgtaatcc    27240
cagcactttt tgaggccgag gcaggcatat cacgaggtca ggagtttgag accagcctgg    27300
ccaacatggt gaaaccctgt ctctactaaa aatacaaaaa ttagctgggc gtggtggcgt    27360
gcacctgtag tcccagctac tcaggaagct gagacaggag aatcacttga acccaggagg    27420
cagaggttgc agtgaactga gattgcgcca ctgcactcca gcctgggcca cagagcaaga    27480
ctccatctca aaaaaaaaaa agaaagaaat gattggtctt gggggccggg gcggtggctt    27540
acgactgtaa tcccagcact ttgggaggcc aaggcaggca gatcatgagg tgaggaattc    27600
gagaccagcc tggccaacat ggtgaaaccc catctctact aaaaatacaa aaattagctg    27660
ggggtggtgg tgcttgcctg taatcccagc tactcgggag gctgaggcag gagaatcact    27720

tgaacccagg aggtggaggt tgtagtgagc cgagattggc gccactgcac tccagcctgg    27780
gcgacagagt gagactccat cttggaaaaa gaagaaaaa agaaaaacat gattgatctc    27840
catgcatcaa tatcatgcct gcctcctaag gcagaggtaa tgaagactta attcccttct    27900
gtaggccttc ccctcctccc taagccgttt tctgagagag gtgcaggagc aggtgggttg    27960
gggcaggctg catacacagt gggggtgggt tgtgctgcta agcagcagca ggtccacaat    28020
cccccctctg catagctcct gggggaaag gatggaggag cgtgtgcacg gctgcctgcc    28080

tgttgaaggt ggtggttcta atttataaa cctcctctgc acagatgggt aggctagcac    28140

ttgctgccac tcctgagctg tgaagtcagc ctttacctca ctcagatagc tggtcaggcc    28200
ctgcactgta ggtcctaata ggccagtgga cagattgagg aaaacaggag cttctgaagg    28260
gcataacaga gagcaaaacc actgaagctg agtggctgca gctgcagcca gggaagagc    28320 cagtaggatg ggggagaatt ccactgacct ttatgtttac ctagcctggt ttctaggggt    28380
gtagattcct ggctagggcc cttattcctt gtcttgactg tcttcatgac accaatttgg    28440
catttcagga gagcggttaa gaaaaggagt tgtgtctgtc caaagctggc caaggccaga    28500 gcтggaтттgт ttggggtaga gactggatgg ccgtcattct cttttgcctc catccctcct    28560
ccccagagtt ggaggaaagc agтggaттттt gtggttagtc atttctttga ctcacactaa    28620
aagaaacatt ggtgccatgt tcaaatatat cagaagacct aggaaataag aaatttgacc    28680 tactттттcтa atgaaatcc cagactgagc aaagagctca ccacаттттga agcttgaac    28740 aaaggggggcc taggctaagt ccagaggcct agaacaaatg cttttttatt ttctacataa    28800
caaggggaaa ttccttgtta tgtagaaaat agctggagac aaatggtgct атagaгтgac    28860 tcataacaaa ctacggtgat ataggtctag gacaaaagc aggccactga таагтggcag    28920

atgcctgatc ccctaggta gtggggagtg tgagactggg ttataagaag ccttcactat    28980
cttttaggac cctcccttga ggaggccagt ctaccacaat tgctttagaa tgaaggtctt    29040

ttggttgctc acaagactat aatggtaatt tttggctcat catttttgtg tgtgtgggtt    29100

ttatcttaat tcattgttaa agagatagtg ggtttcccct gagctagttt cctatcatct    29160
gtgcctatgt ttgcttcact gagctatggg gaaagagtca ctggctgctt tgtttacaaa    29220
aagaaaggac aggctgagcc ttaaggagta ggaaggagtt ccttggccta cccttcatct    29280
```

```
ccacaagtga aaagcccctt agcgtagcag aaaattccag gttgaaggtc tctttggaga    29340
aggcagaagg agtgacctag actcctgttc acacatctaa tcactttccg tcaagattta    29400
aattccaggt tgtcatcaat ggccgagagt ttcccccagc tgaagctgga agcaagaaag    29460
tggccaagca ggatgcagct atgaaagcca tgacaattct gctagaggaa gccaaagcca    29520
aggacagtgg aaaatcagaa gaatcatccc actattccac agagaaagaa tcagagaagg    29580
taggtgtcct cctgccatct ggaggatca gttccctgtc agtgtctgga ttgtaactga    29640
ctcccttgag gcaatcccag cctaaacaac tgacaccatc tcggagtcag cttcccactc    29700
ttccctctac cctatctcgc cagcccacct ttcctcctct catacccagc tcctctgtct    29760
gctcctgtcc caacataatt ggatttacag aatttcggac ttgaaagaga cctgaaagtt    29820
tattgaggcc aatctcctct cttggaagat gcggaatgag agctccagca gccccttaa    29880 ctttgggaag ccaaccccctt gacaggtggt gggaataaag tcccccatcc ccatcccttc    29940
ttctgtgatg gactaaccag tgttttctta gttttgtttt cttcttgtct ctcattttct    30000
ctagactgca gagtcccaga ccccccacccc ttcagccaca tccttctttt ctgggaagag    30060
ccccgtcacc acactgcttg agtgtatgca caaattgggg aactcctgcg aattccgtct    30120
cctgtccaaa gaaggccctg cccatgaacc caagtatgtc ctacgtgtcc tctgtccagc    30180
tgaggttttc tcagaaagaa aaagagacac attttcttcc ttgcctcctc agggatggca    30240
gattgaccaa tttctcctgt ttcaaaatgg ggaaggagg gctctgaggt cctggttgct    30300
gcttgtgagg cagacaatta gggattagga attcaaaggg aattcctggc ccaccctcta    30360
tctcctctat aagcactagg gaggttcacg gcttggaggt cactcactgt tggtgggaca    30420
gaaaggtaca ggacctgaga agctctctgc ctgtgggtct atagactcac atgttcaaga    30480
gaagtgttcc tggaagaggt gaaactaggt tgatgcttaa atgttgaaag gggtcagcca    30540
ggctaagaga cactggctgt tcaaggcaga agtgactgca tgagatgtga ctgcacagag    30600
gtgatgtgtt caaggaaatt accagtagtg gaggatggca gcctggcaga ggctaggtca    30660
ggctcctcag tcaaaaccat tttaatcctt ctacgtgctt catctcctgt caggttccaa    30720
tactgtgttg cagtgggagc ccaaactttc cccagtgtga gtgctcccag caagaaagtg    30780
gcaaagcaga tggccgcaga ggaagccatg aaggccctgc atggggaggc gaccaactcc    30840
atggcttctg ataaccaggt agggcgtttt cctactcaaa agatacaggt catttttagc    30900
aactgagtgg tttaagattg ccagtgactc cctcaacatt tcctgaagtg tttatggctc    30960
ctctgtttga tggattctcc tttagcctga aggtatgatc tcagagtcac ttgataactt    31020
ggaatccatg atgcccaaca aggtcaggaa gattggcgag ctcgtgagat acctgaacac    31080
caaccctgtg gtggcctttt tggagtacgc ccgctcccat ggctttgctg ctgaattcaa    31140
gttggtcgac cagtccggac ctcctcacga gcccaagtga gtgtcctagt cctggctaat    31200
gcatgtgtca ccagttgggg atggtctgta acccaggaa aacaagggtg tgctttagct    31260
gtgtaggaca gaaggggcga gttgagggaa acaagtccag ccctgtctcc acggcctctt    31320
agaagacaat agacctgcca agagtgaatg cgttcactct tccagtaagc atgatccttt    31380 ttaattttt gactagtttt aattttaaa gaatgtata ggtacattaa aaaatcattc    31440
aggccagaca tggtggctca cgcctgtaat cccagcactt tgggaagttg aggcaggtag    31500
attacctgag gtcgggagtt caagaccagc cggaccatat gaggaaaccc tgtctctact    31560
aaaaatacaa aaattagctg gcgtggcag cgggtgcctg taatcccagc tactcgggag    31620
```

```
gcagacagga gaattgattg aagctgggag gcggaggttg cagtgagctg agatcgcacc   31680
actgcactcc agcctgagca acagagcaag actccatctt gaaaaaaatc attcaagctg   31740
attgaaaaag tagtcatttc aatgaaaagt ctcatttccg tctcagactt ctagttccc    31800 tccctagacc catatattac tatagccctg cattagcaac tgggatgcgg tctgagaagc   31860
atggttttgt tgttgtgaga acatcagtgt gtatttacat aaacctagat ggcatgggct   31920
cctacacacg tacaggctgt atggtatggc cggttgctcc taggctacaa acctgtacag   31980
catgtaactg tagtgaatac tgtgggcagc tgcaacacac tggtaagtat tggtgtctat   32040
ctaaacagca aaagataca gtaaaaagac agcataaagg attaaaaaaa tactacacct    32100
gtatagggcg cctgccatga atggagcttg caggactaga agttgctgtg ggtgagtcag   32160
ccagtgagtg gagaatgaat atgagggcct aggacatgac tgtacactaa tgtaggcttt   32220
gtaaacactg ttcacttagg ctaactacat ttatttaaaa tattttctt taataaatta    32280 accttagctt actgtaactt ttttactta ttttactt atttttact ttattaactt       32340 ttttattttt tgttcctttt gtaataatac ttagcttaaa acacaaacat gttgtactgc   32400
tatccaaaaa tatttccttt gtttatatc ttaattctat agtcttttt ctgtttgtaa     32460 attttttttat ttttttaact ttttaaactt ttttgttgaa agctaagatg aaaatacatt  32520
agctgttagc ctaggcctac acagggtcag gatcctcagt atcactgtct tccacctcca   32580
cgtcttgtcc cactgtaagg tgttcagggg caataacatg catgggggcc gtcatctcct   32640
atggtaacag tgcttctgg aataccgtcc tgaggctttt tttagttact tatttttcta    32700
gaagtagaag gagtatacgc tgaaataatg ataaaaatat agtaaacaca taaggagcgt   32760
gtagcctaga tccctcgcat tcacagttca cagtcgagtt cacactccta caagaatctc   32820
atgctgctgc tgatcccaca ggaggcgag ctcggaccag aatgctttct tgctcgccac    32880
tcacctcttc ctgtgtgccc aggttcctaa caggttacag agccctgcac ttggtgataa   32940 gaattttca gctccatcat aatcttacgg ggccctgtc atatgtgtga tttatcattg     33000
aacaaaacac tgttatgcag tacatgacta taccagtttc ttgagtcctt ctagaaattg   33060
ctgtgcataa ctagcacatt ttcccttttg tcttttaaa caagtatatc ttctgtttta    33120
tacgttgact cctttactta ccagacttct tgcatagctg catagtattt cattgaatag   33180
aagctgacaa attcagtttc tcagaagtaa acatttaata gggacttagg aacagaaatg   33240
atgtcttggg tggctgcaag atggtggatc cctgcactta ccctccagaa agtatgcttt   33300
ctatagaggc ttttttggtt aaacatgcag ctggtcacac attatacttt cttgtgaaac   33360
ttatgagcac tagctggtgg ggaggcttgg tagacatctt tgtgtggaat tatttatgct   33420
acccaacact tgggatgcg ggagtcgat attggtggtc atagtggttt tgcatcaaga     33480
tggcatcact cttgccatgc aaccggcatg ttttcttaat ctctaaggtc tatcacaaag   33540
tggaaaagca aggtgtaaag tgaggggaga ggtgaagatt gtctgtatat gtctagaata   33600
ttttcttgaa ggatcgaaaa aactggcaac tgtgtttgct tctggggaag gagggacact   33660
tttattgtac actcttaact gtttgaattt tcacatgttt ggcatccaac ttgtccattt   33720
taaagtcatt aaggaaaaaa gcttataaaa atgctatctt gttactttaa atttgtctct   33780
ccttaataga agtaatgtca gccgggcgca gtggcttacg cctataatcc cagcactttg   33840
ggaggccgag gtgggtggat catttgagct cagtaatttg agaccagcct ggccaacatg   33900
gtaaaacccc atctctacta aaaatacaaa aaatagctga gcatggtggt atgcccctgt   33960
atgccagcta ctccggaggc tgagcaggag aattacttga acccaggagg cggaagttgc   34020
```

```
agtgacctga gattgtgcca ctgcactcca gcctgggtga tggagtgaga ctccgtctca   34080
aaaaaaaaaa caaaaaaatc agaagtaatg gcatttcatt tattcatatt tatgtgttat   34140
ttgcatttcc ttttctgtga accacctgtt cttgtccttt tccagttttc tttcagattg   34200
ttactctcat ggatatgtaa gaacttttaa cataattttt aaaagtagcc ctttgcccaa   34260
catgacccaa tttagaacac acatctgccc actgtttaag ccatctggaa aaggagaggc   34320
ccagtctccc tccagctgct cttctactaa ttcatatcct tcatctcaat aagcacctcc   34380
ttatctttaa gcacagtcct tcagatgata ggttcagtgc atttcctctt tctcttctgt   34440
gaaatcttct gtgaaatcct ttctaggact tcaagtcagc cattcattga gaatgtaaga   34500
acttactatg aactagatgg aagatacaaa aaattgctgc ccctgagtgt gtagcagaca   34560
tatagccata gcagtattga aatgtgccat tggaggtgaa tgcagagtgc tgtggggaca   34620
cagaggacac tgctgccact gtctgccagg gagctgagga aggttgcata gagagggaa    34680
atgctaattg agtaactacg tttattaact atctcgtaca ataatatact ttagttgctt   34740
cttaatgtga attatgctgg gtcttttttt cctttctgtc tactgtggct ggtgacgtta   34800
actaatttta tgacttcttt tctgttttt ttttttttt tttttggaga tggagtctca    34860
ctctgtcacc caggctggag tgcagtggcg cagtctcagc tcactgcaac ctccgcctcc   34920
tgggttcaaa caattctctt gcctcagctc ctcgagtagc tgggattaca ggcatctgcc   34980
accacatctg actattttg tattttagt agagacagag tttcaccatg ttggccaggc    35040
tggtcttcaa ctcctgacct cagatgatcc acccgcctca gcctcccaaa gtgctgggat   35100
tacaggcatg aaccaccgcg acagccatga cctttaatat ctaaatgctg gagaccactc   35160
agagctcccg attcctccat ctagttgctt acttgtcacc tctgtttgga ttaacatccc   35220
taatatgaca tgtccaaagc agaactcttg ggttttgccc ccttcgcttc atttccccca   35280
agtctttccc agcttagtaa gtgataccac tgtctaccca gtggctcaag tcagaaacct   35340
gaggatcatc ttttcctcta tctcctttac ctccttcgtc aactcatcct taagtcctat   35400
tggttatact tagaatttct atcccaaatc ccttcctctt cttttccacct ccagcgtcag   35460
cactctaatc caagccactg tctcatctag actgtcacaa tagcctccta actgatcttt   35520
atactttatt tactcaacac ttatttatgg agtatcttct attttttta gaacaggaac    35580
caaacattaa ccaatagtca cctaaagaaa tgtaagatct catatttgat aagtattcca   35640
aagggctgga gttgcagcga gaatcaatta tagcacagtt tgacttagga aggagagggg   35700
gaagggcttc cccaagaagt actgcctgag ctgagacttt aaggatgatg aagagagaaa   35760
gactgagggt tctaggcgaa ggacactgtt aaatcctgtg gtgggagaag cgcagagctg   35820
gcaaagaggc tgagaggagg cacttatggc aatagcccca tttggctagt ggctaccata   35880
ttggatagca cagctctaaa ggattctagt tgcataatta acaaacttta tcatatatgt   35940
aaatatatca gtataaaact ttgcacgtaa gagttcatat tcttttcaaa cacatggggc   36000
agtcatgaaa ttctcctgga tccctgaggt aaagatacta cacaatctgt ccctcctgac   36060
cgccttcacc atcttctttt catgccactg tccctctcat tctgaactta agcccactgg   36120
cctgcacggg cctgccagca tggacaaaga aaagagtgaa ggcatttagt tgcttcgat    36180
catcaaggaa cagtgagaaa ctccatgtgg ttgaacataa acgttgattc cttttactgc   36240
ctgagctgct aagtcttgaa actgaagcct ctgttatatg cagttagagt atccaaagct   36300
gggttctcag ccagtagatt aggatctggt tgaaagctag gattcttgat gccttgtctg   36360
```

| | |
|---|---|
| gtacatttcc aagctgtttt gctccaccat gctcttccct ctgtgtttgg aaattaccag | 36420 |
| ccggagcggt agaagccacc tccctgctcc acttgggcac tttattgtca gcgcagctca | 36480 |
| tgcgcccaag atccattcct taccccagag ttagcttaag cctgccagga gtcaaaaaaa | 36540 |
| caactcccag caaaacctgg gtccctggcc taaggccgac cttgacctaa tgacctctcc | 36600 |
| aggtcaagtc cccttgagct aataggaagt aaatgaggga atggagttgg gcgctttaaa | 36660 |
| aatcagacag tgtatgaagt aacagtgact tgtggggaga aaggtagtcc cttctgattt | 36720 |
| ctgcttaaga agagagtcca agttggtgct agcatttcgt taagccttcc tcatacttca | 36780 |
| taatcttcct ttatagtaag gacaggctca gagcctttgc aggtaacagt atctagtcag | 36840 |
| aattttataa catgatttta tcatattctg ttttacagcc accttcaata tgtggcaagt | 36900 |
| gatactggtt ttccatttac agtagtgaaa caaagtttcc tatttcagtg tgtttacatt | 36960 |
| tttatctctt ttttcatacc tagtattacg gatatttaca tttttagagt ctgtttgttt | 37020 |
| attttagaga tggggatctt gctgtctcgc gcaggctgga gtgcagtgat atggtcatag | 37080 |
| ctcactgcag ccttgacctc cagggctcaa gtgatcctct caccccagcc tcccaagtag | 37140 |
| ctgagactat aggcacagac caccgtgccc agctaaattt tttttttttt tttaagaga | 37200 |
| caggggtctc gctatgttgc ctgggggatt actatgttgc ccaggctggt cttgaactcc | 37260 |
| tggcctcaag tgatctccca ccttagctcc tcaagttgct gggattacag gtgtgagcca | 37320 |
| caatggctgg ctctaagaag tcaatttaga gaaaaatatt aattaatagt ccaagtaata | 37380 |
| cctggatgtg gcacaaatca tgtggtgatt catgaatgac caaaatctag gaaatgctgc | 37440 |
| cttagaaaca gcttctgttt gacgggtcca tatgtttgca agactggcca catcttcagc | 37500 |
| aaaactaacc cttccttgga acaatgtcag ggtctggcac ttgtcttcat tctctgtttc | 37560 |
| tcatcccaaa ggttcgttta ccaagcaaaa gttgggggtc gctggttccc agccgtctgc | 37620 |
| gcacacagca agaagcaagg caagcaggaa gcagcagatg cggctctccg tgtcttgatt | 37680 |
| ggggagaacg agaaggcaga acgcatgggt ttcacagagg taaccccagt gacaggggcc | 37740 |
| agtctcagaa gaactatgct cctcctctca aggtccccag aagcacagcc aaagacagtt | 37800 |
| aagacgtcta cttttggtgc cttttttggg gcggggggt cctcctaact cctaagtgga | 37860 |
| ggtggctctt gctgtcatgc gagttattcc taggctttac tcttagcctc gagagagcag | 37920 |
| taactgggac actagatgta agaaggaaaa gatgactcac acgacaagta gagcttgatc | 37980 |
| tccctgccca cggtgaatat ggtggacaca gcctcagctt tgtggtgctg acacagcctc | 38040 |
| ttttccccac agctccctct cactggcagc accttccatg accagatagc catgctgagc | 38100 |
| caccggtgct tcaacactct gactaacagc ttccagcccc ccttgctcgg ccgcaagatt | 38160 |
| ctggccgcca tcattatgaa aaaagactct gaggacatgg gtgtcgtcgt cagcttggga | 38220 |
| acaggtgagt gaggctctga gacatgccgc ctcccatggc gcctgaaagc gggtgcctct | 38280 |
| catcctcccc tggagtccat gcatgtaagt ccaaggcagg gagaagagac ttcattttag | 38340 |
| ctacagtcaa ttcagagtga ggaatgagtt cttagttcct agaggagaga atatgggagt | 38400 |
| ctaggatctg agaaactgag gctgtttctg ccttgaagct ttcagaacaa atagccttca | 38460 |
| tcctgttttc catcggtttc cttccattat tctatttctg ttttaaacac cttcctaggg | 38520 |
| aatcgctgtg tgaaaggaga ttctctcagc ctaaaggag aaactgtcaa tgactgccat | 38580 |
| gcagaaataa tctcccggag aggcttcatc aggtgagcga ggtcagagct gtggccggc | 38640 |
| tgcccggctg tggagagctc cagttccctg ccccacatgg ctctgacacg gcctctgaat | 38700 |
| ccccctcaga cagacgggtc atgatgtggc agtggcagcc tttgcttttc acccgtccat | 38760 |

```
ttgaacctgt ctgatggaat ccatcccctc tgtgagctga gctgcctccc actgctcggc   38820
ctgtttttaa atgctgtcct tttttctgct aactctgctg cttcatgttc ttttctaaaa   38880
acacaaaatg accttttagt cctcagggcc ttgaggatga ggcagctttc catttccgtt   38940
tgaggaccta cacaaccttg atgccctgc cagctttctc ctctagctca ccttttcttt   39000
aatttatgaa gggagagact tagaaaggag caacagcttc ctgtagtcct tgaatcagtt   39060
tgctctgctc tagaatccct gtagccgcca tagcgaggag ccctcagcag aaatgaagga   39120
gacccaaaag gctaactatg ctttatgaaa tgctgaggtc tccctggag aatttccacc    39180 tgataaactg tgaaacgtct gcaacattga gacttttcct tactttctca tttggaggtc   39240
agattataga aacaactgct tttcccagaa ttgaacctgc cttcctaacc agactttctt   39300
tttgtaggtt tctctacagt gagttaatga aatacaactc ccagactgcg aaggatagta   39360
tatttgaacc tgctaaggga ggagaaaagc tccaaataaa aaagactgtg tcattccatc   39420
tgtatatcag gtctgtacag ttcctgttgc tgccagggtg ggccctgcca ggctgttaga   39480
attgggtatc caaatgctct cctggcctgt aaatcgaacc tgatacaata agccacactc   39540
cactgtgggt ttgaggtcca tattcaggtg tagatgactc acatgtactg ctgtccacct   39600
ccagtctccc atggtaggcc ttagaaaaca tcccttgctt ctgtcacatc tgactgtttt   39660
ggagccccac gaaattgcag atttcccaca ggtgagtttt aacagccacc cctgtttttc   39720
agcactgctc cgtgtggaga tggcgccctc tttgacaagt cctgcagcga ccgtgctatg   39780
gaaagcacag aatcccgcca ctaccctgtc ttcgagaatc ccaaacaagg aaagctccgc   39840
accaaggtgg agaacggtga gtgatacatg cccccgcctc ctttcctcaa aaggctctgc   39900
aaggtccagg gaccccaagt ctctacaagg ctgctaggat tttaccatta gtcactgggc   39960
acagaggtgc tgtttacagg aaagggaaga cctgggtcag ggagctgtgt ggtaagatca   40020
gggttctatt ttgaatgtgt tagtttggga gatctgggag atccccaagt caaataggag   40080
gtgggggttc ccatgtggag ctcagaggag ggagcttggc tggaaataga aatatgggag   40140 tcatcccct atagggtctt catggccatg agaatgcata ggattacctc aagaaagcgg    40200
ggaggaaatg aagagtgcgg cacaaccaag ccctgaggag ttgacagatg aggatgccaa   40260
atgctggggt cccctcctgt ctagctggca gttgactctg ccttgtccac tggctccttc   40320
tctcctatcc tctcctgtct ccttactgtc tcttcgcatc cactccattg cgttcaggcc   40380
acgtcagcag tcatcatggt ggtcctgaaa ccttgctaaa taccctaaag tatagacaca   40440
gttaccatgg agccggtgct ccactcctag gtatatgctg cagagagatg gagatctgtg   40500
tccacacgga aactaatatg tgaatgttca tggcagcatt actcacaaga gccaaaaaag   40560
tggaaacaac ccagacgtcc atcagctgat ggattcataa ataaacatc aaatatatcc    40620 ataaattgaa tattattttg gccataaaaa gaagtgaagt gctgatacat gcttacaata   40680
tggatgcact tgaaaacttg atgccaaatg aaaaagcca gtcacaaaag atcacatatt    40740
gtatgattcc atttatatga aatgtccaga atagacaaat ccatagagac agaaagtaga   40800
tgagtggttg ccagggccag gagtgggaga gttggagaga tgaggagtga ctgcgccaat   40860
gggtagaagg tttcttttg gagcgatgaa atgttctaaa attgactgtg gtgacagttg    40920
cagaactctg tgaatatact aaaaatgact gaattgtatg cttaaatgg gtgaactgta    40980 tggcatatga actatatctc agtaaagcat ttttttttgt ttttttttaa accgatagt    41040 ggtttcccac tgcactgcat atacaagcaa aacctgctgt gatcacccgg cctcctctca   41100
```

```
tgccactttc cccatccctc gcatatgctc tgtccacact ggctctctgt caggcgcctg    41160
aacagccaat ccgctggctg ccttggggcc tttgcttttg tcctgtgtgc ctgaaacact    41220
tactccagct gtcctcctcc atgtctgggc tcccctgctg ctgctgtccc aggaggtgtc    41280
ccctgtggtc ctccgtcata gctgcctcag agccttcaga gcactgtcag catctggaat    41340
tcttccgtat gtactggcta ctggtttagt gtctattctc ttccctttca atctcctcac    41400
caccatagat gttttaagag cacaaagatc ttacttggtt ttgctcaccg ttcttttccca   41460 gcaccaagca tagtgcctgg cgcatagcag gggctgtgaa atatgtgaag aatgaatgaa    41520
tgtagcctgt ggcccaagct taaggaggat agaaaccacg ccagggagtg gtttggtcca    41580
ttggcgcctg tgggtctgac ccaagtctct cacacaggag aaggcacaat ccctgtggaa    41640
tccagtgaca ttgtgcctac gtgggatggc attcggctcg gggagagact ccgtaccatg    41700
tcctgtagtg acaaaatcct acgctggaac gtgctgggcc tgcaaggggc actgttgacc    41760
cacttcctgc agcccattta tctcaaatct gtcacattgg gtaaggggcc tgccttggga    41820
tctggaactg gtctgtcctt cttgtgccca gatcccaaac tgcatgcttt attgccaggt    41880
gttttgtctc ccttatcaaa gtgagcatga ttcactcctc agtaattgat tgagtgtcca    41940
gtctgctgtg gtaggaagat cctggtagcc ccagtcagaa ggtgcttcct aacaaggcag    42000
ctgtttctct tcttgacaa ctatatcttg tacctccaaa atccccacat gcttctgcct     42060
cttaacagca tttggtgcaa acacaggtat atatgtttct ctttttttgta ctcaggttac   42120 cttttcagcc aagggcatct gacccgtgct atttgctgtc gtgtgacaag agatgggagt    42180
gcatttgagg atggactacg acatccctt attgtcaacc accccaaggt gctataaccc     42240 ccttctatt tccctgacat tttcctcctt ttcaagcagt catgtaaaca gaggaaaaat     42300
gtacactgtg ggcaagggga acattgccca cagtggtagc ccacaaggga acattgccca    42360
cagtggccca ccaccaacat tggttggtct cccaagaact taaactttct tccttttgga   42420
tgccaagggc ttttcttctc ttagtctgga attaatctga atcgaggtgg agttagtatg    42480
tctagagggt gctcagtctt agccaaacag aaccctaaat acaggggaaa gatcatgacc    42540
ccacacttcc tctctcctat gagtcttgag tccctgcttc agaatcttat tcctgaaagg    42600
tttccatctt tctcccgttg cttctgggat tcctaggttg gcagagtcag catatatgat    42660
tccaaaaggc aatccgggaa gactaaggag acaagcgtca actggtgtct ggctgatggc    42720
tatgacctgg agatcctgga cggtaccaga ggcactgtgg atgggtaagg agacaggaga    42780
gcgcagtgag gaccaagcct ctgccctgac ttgcaagggt gcatcatacc tctgcagtct    42840
cagggcttga gagccgcctc ccctcccacg gtgtctccac tgtgagctcc ttatcttaca    42900
ggtcccaggt gaataatgag tgcttttgtt tctctaggcc acggaatgaa ttgtcccggg    42960
tctccaaaaa gaacatttt cttctattta agaagctctg ctccttccgt taccgcaggg    43020
atctactgag actctcctat ggtgaggcca agaaagctgc ccgtgactac gagacgccca    43080
agaactactt caaaaaaggc ctgaaggata tgggctatgg aactggatt agcaaacccc     43140 aggaggaaaa gaactttat ctctgcccag tatagtatgc tccagtgaca gatggattag     43200
ggtgtgtcat actagggtgt gagagaggta ggtcgtagca ttcctcatca catggtcagg    43260 ggatttttt ttctccttt ttttctttt taagccataa ttggtgatac tgaaaacttt       43320
gggttcccat ttatcctgct ttctttggga ttgctaggca aggtctggcc aggccccct     43380 tttttccccc aagtgaagag gcagaaacct aagaagttat cttttctttc tacccaaagc    43440
atacatagtc actgagcacc tgcggtccat ttcctcttaa aagtttgtt ttgatttgtt    43500
```

```
tccatttcct ttcccttgt gtttgctaca ctgacctctt gcggtcttga ttaggtttca   43560
gtcaactctg gatcatgtca gggactgata atttcatttg tggattacgc agaccctct   43620 acttccctc tttcccttct gagattcttt ccttgtgatc tgaatgtctc cttttccccc   43680
tcagagggca aagaggtgaa cataaaggat ttggtgaaac atttgtaagg gtaggagttg   43740
aaaactgcag ttcccagtgc cacggaagtg tgattggagc ctgcagataa tgcccagcca   43800
tcctcccatc ctgcacttta gccagctgca gggcgggcaa ggcaaggaaa gctgcttccc   43860
tggaagtgta tcactttctc cggcagctgg gaagtctaga accagccaga ctgggttaag   43920
ggagctgctc aagcaatagc agaggtttca cccggcagga tgacacagac cacttcccag   43980
ggagcacggg catgccttgg aatattgcca agcttccagc tgcctcttct cctaaagcat   44040
tcctaggaat attttccccg ccaatgctgg gcgtacaccc tagccaacgg gacaaatcct   44100
agagggtata aaatcatctc tgctcagata atcatgactt agcaagaata agggcaaaaa   44160
atcctgttgg cttaacgtca ctgttccacc cggtgtaata tctctcatga cagtgacacc   44220
aagggaagtt gactaagtca catgtaaatt aggagtgttt taaagaatgc catagatgtt   44280
gattcttaac tgctacagat aacctgtaat tgagcagatt taaaattcag gcatactttt   44340
ccatttatcc aagtgctttc attttttccag atggcttcag aagtaggctc gtgggcaggg   44400
cgcagacctg atctttatag ggttgacata gaaagcagta gttgtgggtg aaagggcagg   44460
ttgtcttcaa actctgtgag gtagaatcct ttgtctatac ctccatgaac attgactcgt   44520
gtgttcagag cctttggcct ctctgtggag tctggctctc tggctcctgt gcattctttg   44580
aatagtcact cgtaaaaact gtcagtgctt gaaactgttt cctttactca tgttgaaggg   44640
actttgttgg cttttagagt gttggtcatg actccaagag cagagcaggg aagagcccaa   44700
gcatagactt ggtgccgtgg tgatggctgc agtccagttt tgtgatgctg cttttacgtg   44760
tccctcgata acagtcagct agacacactc aggaggacta ctgaggctct gcgaccttca   44820
ggagctgagc ctgcctctct cctttagatg acagaccttc atctgggaac gtgctgagcc   44880
agcaccctca gatgatttcc ctccaaactg ctgactaggt catcctctgt ctggtagaga   44940
cattcacatc tttgctttta ttctatgctc tctgtacttt tgaccaaaaa ttgaccaaag   45000
taagaaaatg caagttctaa aaatagacta aggatgcctt tgcagaacac caaagcatcc   45060
caaggaactg tagggaagt ggcgcctgtc tcctggagtg gaagaggcct gctccctggc   45120
tctgggtctg ctgggggcac agtaaatcag tcttggcacc cacatccagg gcagagaggt   45180
ctgtggttct cagcatcaga aggcagcgca gcccctctcc tcttcaggct acagggttgt   45240
cacctgctga gtcctcaggt tgtttggcct ctctggtcca tcttgggcat taggttctcc   45300
agcagagctc tggccagctg cctcttcttt aactgggaac acaggctctc acaagatcag   45360 aaccccact cacccccaag atcttatcta gcaagcctgt agtattcagt ttctgttgta   45420
ggaagagagc gaggcatccc tgaattccac gcatctgctg gaaacgagcc gtgtcagatc   45480
gcacatccct gcgcccccat gcccctctga gtcacacagg acagaggagg cagagcttct   45540
gcccactgtt atcttcactt tctttgtcca gtcttttgtt tttaataagc agtgaccctc   45600
cctactcttc tttttaatga ttttttgtagt tgatttgtct gaactgtggc tactgtgcat   45660
tccttgaata tcacttgta aaaattgtca gtgcttgaag ctgtttcctt tactcacatt   45720
gaagggactt cgttggtttt ttggagtctt ggttgtgact ccaagagcag agtgaggaag   45780 accccaagc atagactcgg gtactgtgat gatggctgca gtccagtttt atgattctgc   45840
```

```
ttttatgtgt cccttgataa cagtgactta acaatataca ttcctcataa ataaaaaaaa    45900
aacaagaatc tgaattctta gaaa                                           45924

<210> SEQ ID NO 2
<211> LENGTH: 6561
<212> TYPE: DNA
<213> ORGANISM: Homo sapiens

<400> SEQUENCE: 2
gaccagacca ttgattcccg actgaaggta gagaaggcta cgtggtgggg gagggtgggg      60
ggagggtcgc ggccgcactg gcagcctccg ggtgtccggc cgtgtcccga ggaagtgcaa     120
gacccggggt attccctcag cggatactac acccatccat ttcaaggcta tgagcacaga     180
cagctcaggt accagcagcc tgggccagga tcttccccca gtagtttcct gcttaagcaa     240
atagaatttc tcaaggggca gctcccagaa gcaccggtga ttggaaagca gacaccgtca     300
ctgccacctt ccctcccagg actccggcca aggtttccag tactacttgc ctccagtacc     360
agaggcaggc aagtggacat caggggtgtc cccaggggcg tgcatctcgg aagtcagggg     420
ctccagagag ggttccagca tccttcacca cgtggcagga gtctgccaca gagaggtgtt     480
gattgccttt cctcacattt ccaggaactg agtatctacc aagatcagga acaaaggatc     540
ttaaagttcc tggaagagct tggggaaggg aaggccacca cagcacatga tctgtctggg     600
aaacttggga ctccgaagaa agaaatcaat cgagttttat actccctggc aaagaagggc     660
aagctacaga aagaggcagg aacaccccct ttgtggaaaa tcgcggtctc cactcaggct     720
tggaaccagc acagcggagt ggtaagacca gacggtcata gccaaggagc cccaaactca     780
gacccgagtt tggaaccgga agacagaaac tccacatctg tctcagaaga tcttcttgag     840
ccttttattg cagtctcagc tcaggcttgg aaccagcaca gcggagtggt aagaccagac     900
agtcatagcc aaggatcccc aaactcagac ccaggtttgg aacctgaaga cagcaactcc     960
acatctgcct tggaagatcc tcttgagttt ttagacatgg ccgagatcaa ggagaaaatc    1020
tgcgactatc tcttcaatgt gtctgactcc tctgccctga atttggctaa aaatattggc    1080
cttaccaagg cccgagatat aaatgctgtg ctaattgaca tggaaaggca gggggatgtc    1140
tatagacaag ggacaacccc tcccatatgg catttgacag acaagaagcg agagaggatg    1200
caaatcaaga gaaatacgaa cagtgttcct gaaaccgctc cagctgcaat ccctgagacc    1260
aaaagaaacg cagagttcct cacctgtaat atacccacat caaatgcctc aaataacatg    1320
gtaaccacag aaaaagtgga gaatgggcag gaacctgtca taagttaga aaacaggcaa    1380 gaggccagac cagaaccagc aagactgaaa ccacctgttc attacaatgg cccctcaaaa    1440
gcagggtatg ttgactttga aaatggccag tgggccacag atgacatccc agatgacttg    1500
aatagtatcc gcgcagcacc aggtgagttt cgagccatca tggagatgcc ctccttctac    1560
agtcatggct tgccacggtg ttcaccctac aagaaactga cagagtgcca gctgaagaac    1620
cccatcagcg ggctgttaga atatgcccag ttcgctagtc aaacctgtga gttcaacatg    1680
atagagcaga gtggaccacc ccatgaacct cgatttaaat tccaggttgt catcaatggc    1740
cgagagtttc cccagctgaa gctggaagc aagaaagtgg ccaagcagga tgcagctatg    1800
aaagccatga caattctgct agaggaagcc aaagccaagg acagtggaaa atcagaagaa    1860
tcatcccact attccacaga gaagaatcag agaagactg cagagtccca gacccccacc    1920
ccttcagcca catccttctt ttctgggaag agccccgtca ccacactgct tgagtgtatg    1980
cacaaattgg ggaactcctg cgaattccgt ctcctgtcca agaaggccct tgccatgaa    2040
```

```
cccaagttcc aatactgtgt tgcagtggga gcccaaactt tccccagtgt gagtgctccc   2100
agcaagaaag tggcaaagca gatggccgca gaggaagcca tgaaggccct gcatggggag   2160
gcgaccaact ccatggcttc tgataaccag cctgaaggta tgatctcaga gtcacttgat   2220
aacttggaat ccatgatgcc caacaaggtc aggaagattg gcgagctcgt gagatacctg   2280
aacaccaacc ctgtgggtgg ccttttggag tacgcccgct cccatggctt tgctgctgaa   2340
ttcaagttgg tcgaccagtc cggacctcct cacgagccca gttcgtttta ccaagcaaaa   2400
gttgggggtc gctggttccc agccgtctgc gcacacagca agaagcaagg caagcaggaa   2460
gcagcagatg cggctctccg tgtcttgatt ggggagaacg agaaggcaga acgcatgggt   2520
ttcacagagg taaccccagt gacaggggcc agtctcagaa gaactatgct cctcctctca   2580
aggtccccag aagcacagcc aaagacactc cctctcactg gcagcacctt ccatgaccag   2640
atagccatgc tgagccaccg gtgcttcaac actctgacta acagcttcca gccctccttg   2700
ctcggccgca agattctggc cgccatcatt atgaaaaaag actctgagga catgggtgtc   2760
gtcgtcagct gggaacagg gaatcgctgt gtgaaggag attctctcag cctaaaagga   2820
gaaactgtca atgactgcca tgcagaaata atctcccgga gaggcttcat caggtttctc   2880
tacagtgagt taatgaaata caactcccag actgcgaagg atagtatatt tgaacctgct   2940
aagggaggag aaaagctcca ataaaaaag actgtgtcat tccatctgta tatcagcact   3000
gctccgtgtg gagatggcgc cctctttgac aagtcctgca gcgaccgtgc tatggaaagc   3060
acagaatccc gccactaccc tgtcttcgag aatcccaaac aaggaaagct ccgcaccaag   3120
gtggagaacg gagaaggcac aatccctgtg gaatccagtg acattgtgcc tacgtgggat   3180
ggcattcggc tcggggagag actccgtacc atgtcctgta gtgacaaaat cctacgctgg   3240
aacgtgctgg gcctgcaagg ggcactgttg acccacttcc tgcagcccat ttatctcaaa   3300
tctgtcacat tgggttacct tttcagccaa gggcatctga cccgtgctat ttgctgtcgt   3360
gtgacaagag atgggagtgc atttgaggat ggactacgac atcccttta tgtcaaccac   3420 cccaaggttg gcagagtcag catatatgat tccaaaaggc aatccgggaa gactaaggag   3480
acaagcgtca actggtgtct ggctgatggc tatgacctgg agatcctgga cggtaccaga   3540
ggcactgtgg atgggccacg gaatgaattg tcccgggtct ccaaaaagaa cattttttctt   3600 ctatttaaga agctctgctc cttccgttac cgcagggatc tactgagact ctcctatggt   3660
gaggccaaga agctgcccg tgactacgag acggccaaga actacttcaa aaaaggcctg   3720
aaggatatgg gctatgggaa ctggattagc aaacccagg aggaaaagaa cttttatctc   3780
tgcccagtat agtatgctcc agtgacagat ggattagggt gtgtcatact agggtgtgag   3840
agaggtaggc cgtagcattc ctcatcacat ggtcagggga ttttttttc tccttttttt   3900 ttcttttttaa gccataattg gtgatactga aaactttggg ttcccattta tcctgctttc   3960
tttgggattg ctaggcaagg tctggccagg ccccccttt ttcccccaag tgaagaggca   4020
gaaacctaag aagttatctt ttctttctac ccaaagcata catagtcact gagcacctgc   4080
ggtccatttc ctcttaaaag tttttgttttg atttgtttcc atttcctttc cctttgtgtt   4140
tgctacactg acctcttgcg gtcttgatta ggtttcagtc aactctggat catgtcaggg   4200
actgataatt tcatttgtgg attacgcaga cccctctact tcccctcttt cccttctgag   4260
attctttcct tgtgatctga atgtctcctt ttccccctca gagggcaaag aggtgaacat   4320
aaaggatttg gtgaaacatt tgtaagggta ggagttgaaa actgcagttc ccagtgccac   4380
```

```
ggaagtgtga ttggagcctg cagataatgc ccagccatcc tcccatcctg cactttagcc    4440
agctgcaggg cgggcaaggc aaggaaagct gcttccctgg aagtgtatca ctttctccgg    4500
cagctgggaa gtctagaacc agccagactg ggttaaggga gctgctcaag caatagcaga    4560
ggtttcaccc ggcaggatga cacagaccac ttcccaggga gcacgggcat gccttggaat    4620
attgccaagc ttccagctgc ctcttctcct aaagcattcc taggaatatt ttccccgcca    4680
atgctgggcg tacaccctag ccaacgggac aaatcctaga gggtataaaa tcatctctgc    4740
tcagataatc atgacttagc aagaataagg gcaaaaaatc ctgttggctt aacgtcactg    4800
ttccacccgg tgtaatatct ctcatgacag tgacaccaag ggaagttgac taagtcacat    4860
gtaaattagg agtgttttaa agaatgccat agatgttgat tcttaactgc tacagataac    4920
ctgtaattga gcagatttaa aattcaggca tactttccca tttatccaag tgctttcatt    4980
tttccagatg gcttcagaag taggctcgtg ggcagggcgc agacctgatc tttatagggt    5040
tgacatagaa agcagtagtt gtgggtgaaa gggcaggttg tcttcaaact ctgtgaggta    5100
gaatcctttg tctataccte catgaacatt gactcgtgtg ttcagagcct ttggcctctc    5160
tgtggagtct ggctctctgg ctcctgtgca ttctttgaat agtcactcgt aaaaactgtc    5220
agtgcttgaa actgtttcct ttactcatgt tgaagggact ttgttggctt ttagagtgtt    5280
ggtcatgact ccaagagcag agcagggaag agcccaagca tagacttggt gccgtggtga    5340
tggctgcagt ccagttttgt gatgctgctt ttacgtgtcc ctcgataaca gtcagctaga    5400
cacactcagg aggactactg aggctctgcg accttcagga gctgagcctg cctctctcct    5460
ttagatgaca gaccttcatc tgggaacgtg ctgagccagc accctcagat gatttccctc    5520
caaactgctg actaggtcat cctctgtctg gtagagacat tcacatcttt gcttttattc    5580
tatgctctct gtacttttga ccaaaaattg accaaagtaa gaaaatgcaa gttctaaaaa    5640
tagactaagg atgcctttgc agaacaccaa agcatcccaa ggaactggta gggaagtggc    5700
gcctgtctcc tggagtggaa gaggcctgct ccctggctct gggtctgctg ggggcacagt    5760
aaatcagtct tggcacccac atccagggca gagaggtctg tggttctcag catcagaagg    5820
cagcgcagcc cctctcctct tcaggctaca ggggttgtcac ctgctgagtc ctcaggttgt    5880
ttggcctctc tggtccatct tgggcattag gttctccagc agagctctgg ccagctgcct    5940
cttctttaac tgggaacaca ggctctcaca agatcagaac ccccactcac ccccaagatc    6000
ttatctagca agcctgtagt attcagtttc tgttgtagga agagagcgag gcatccctga    6060
attccacgca tctgctggaa acgagccgtg tcagatcgca catccctgcg cccccatgcc    6120
cctctgagtc acacaggaca gaggaggcag agcttctgcc cactgttatc ttcactttct    6180
ttgtccagtc ttttgttttt aataagcagt gaccctccct actcttcttt ttaatgattt    6240
ttgtagttga tttgtctgaa ctgtggctac tgtgcattcc ttgaataatc acttgtaaaa    6300
attgtcagtg cttgaagctg tttccttttac tcacattgaa gggacttcgt tggtttttg     6360 gagtcttggt tgtgactcca agagcagagt gaggaagacc cccaagcata gactcgggta    6420
ctgtgatgat ggctgcagtc cagttttatg attctgcttt tatgtgtccc ttgataacag    6480
tgacttaaca atatacattc ctcataaata aaaaaaaaac aagaatctga attcttagaa    6540
aaaaaaaaaa aaaaaaaaaa a                                              6561
```

<210> SEQ ID NO 3
<211> LENGTH: 1226
<212> TYPE: PRT
<213> ORGANISM: Homo sapiens -continued

```
<400> SEQUENCE: 3

Met Asn Pro Arg Gln Gly Tyr Ser Leu Ser Gly Tyr Tyr Thr His Pro
1               5                   10                  15

Phe Gln Gly Tyr Glu His Arg Gln Leu Arg Tyr Gln Gln Pro Gly Pro
                20                  25                  30

Gly Ser Ser Pro Ser Ser Phe Leu Leu Lys Gln Ile Glu Phe Leu Lys
            35                  40                  45

Gly Gln Leu Pro Glu Ala Pro Val Ile Gly Lys Gln Thr Pro Ser Leu
    50                  55                  60

Pro Pro Ser Leu Pro Gly Leu Arg Pro Arg Phe Pro Val Leu Leu Ala
65                  70                  75                  80

Ser Ser Thr Arg Gly Arg Gln Val Asp Ile Arg Gly Val Pro Arg Gly
                85                  90                  95

Val His Leu Gly Ser Gln Gly Leu Gln Arg Gly Phe Gln His Pro Ser
            100                 105                 110

Pro Arg Gly Arg Ser Leu Pro Gln Arg Gly Val Asp Cys Leu Ser Ser
        115                 120                 125

His Phe Gln Glu Leu Ser Ile Tyr Gln Asp Gln Glu Gln Arg Ile Leu
130                 135                 140

Lys Phe Leu Glu Glu Leu Gly Glu Gly Lys Ala Thr Thr Ala His Asp
145                 150                 155                 160

Leu Ser Gly Lys Leu Gly Thr Pro Lys Lys Glu Ile Asn Arg Val Leu
                165                 170                 175

Tyr Ser Leu Ala Lys Lys Gly Lys Leu Gln Lys Glu Ala Gly Thr Pro
            180                 185                 190

Pro Leu Trp Lys Ile Ala Val Ser Thr Gln Ala Trp Asn Gln His Ser
        195                 200                 205

Gly Val Val Arg Pro Asp Gly His Ser Gln Gly Ala Pro Asn Ser Asp
210                 215                 220

Pro Ser Leu Glu Pro Glu Asp Arg Asn Ser Thr Ser Val Ser Glu Asp
225                 230                 235                 240

Leu Leu Glu Pro Phe Ile Ala Val Ser Ala Gln Ala Trp Asn Gln His
                245                 250                 255

Ser Gly Val Val Arg Pro Asp Ser His Ser Gln Gly Ser Pro Asn Ser
            260                 265                 270

Asp Pro Gly Leu Glu Pro Glu Asp Ser Asn Ser Thr Ser Ala Leu Glu
        275                 280                 285

Asp Pro Leu Glu Phe Leu Asp Met Ala Glu Ile Lys Glu Lys Ile Cys
290                 295                 300

Asp Tyr Leu Phe Asn Val Ser Asp Ser Ser Ala Leu Asn Leu Ala Lys
305                 310                 315                 320

Asn Ile Gly Leu Thr Lys Ala Arg Asp Ile Asn Ala Val Leu Ile Asp
                325                 330                 335

Met Glu Arg Gln Gly Asp Val Tyr Arg Gln Gly Thr Thr Pro Pro Ile
            340                 345                 350

Trp His Leu Thr Asp Lys Lys Arg Glu Arg Met Gln Ile Lys Arg Asn
        355                 360                 365

Thr Asn Ser Val Pro Glu Thr Ala Pro Ala Ile Pro Glu Thr Lys
370                 375                 380

Arg Asn Ala Glu Phe Leu Thr Cys Asn Ile Pro Thr Ser Asn Ala Ser
385                 390                 395                 400

Asn Asn Met Val Thr Thr Glu Lys Val Glu Asn Gly Gln Glu Pro Val
```

-continued

```
                405                 410                 415
Ile Lys Leu Glu Asn Arg Gln Glu Ala Arg Pro Glu Pro Ala Arg Leu
            420                 425                 430

Lys Pro Pro Val His Tyr Asn Gly Pro Ser Lys Ala Gly Tyr Val Asp
            435                 440                 445

Phe Glu Asn Gly Gln Trp Ala Thr Asp Ile Pro Asp Asp Leu Asn
            450                 455                 460

Ser Ile Arg Ala Ala Pro Gly Glu Phe Arg Ala Ile Met Glu Met Pro
465                 470                 475                 480

Ser Phe Tyr Ser His Gly Leu Pro Arg Cys Ser Pro Tyr Lys Lys Leu
                485                 490                 495

Thr Glu Cys Gln Leu Lys Asn Pro Ile Ser Gly Leu Leu Glu Tyr Ala
            500                 505                 510

Gln Phe Ala Ser Gln Thr Cys Glu Phe Asn Met Ile Glu Gln Ser Gly
            515                 520                 525

Pro Pro His Glu Pro Arg Phe Lys Phe Gln Val Val Ile Asn Gly Arg
            530                 535                 540

Glu Phe Pro Pro Ala Glu Ala Gly Ser Lys Lys Val Ala Lys Gln Asp
545                 550                 555                 560

Ala Ala Met Lys Ala Met Thr Ile Leu Leu Glu Ala Lys Ala Lys
                565                 570                 575

Asp Ser Gly Lys Ser Glu Glu Ser Ser His Tyr Ser Thr Glu Lys Glu
            580                 585                 590

Ser Glu Lys Thr Ala Glu Ser Gln Thr Pro Thr Pro Ser Ala Thr Ser
            595                 600                 605

Phe Phe Ser Gly Lys Ser Pro Val Thr Thr Leu Leu Glu Cys Met His
            610                 615                 620

Lys Leu Gly Asn Ser Cys Glu Phe Arg Leu Leu Ser Lys Glu Gly Pro
625                 630                 635                 640

Ala His Glu Pro Lys Phe Gln Tyr Cys Val Ala Val Gly Ala Gln Thr
                645                 650                 655

Phe Pro Ser Val Ser Ala Pro Ser Lys Lys Val Ala Lys Gln Met Ala
            660                 665                 670

Ala Glu Glu Ala Met Lys Ala Leu His Gly Glu Ala Thr Asn Ser Met
            675                 680                 685

Ala Ser Asp Asn Gln Pro Glu Gly Met Ile Ser Glu Ser Leu Asp Asn
            690                 695                 700

Leu Glu Ser Met Met Pro Asn Lys Val Arg Lys Ile Gly Glu Leu Val
705                 710                 715                 720

Arg Tyr Leu Asn Thr Asn Pro Val Gly Gly Leu Leu Glu Tyr Ala Arg
                725                 730                 735

Ser His Gly Phe Ala Ala Glu Phe Lys Leu Val Asp Gln Ser Gly Pro
            740                 745                 750

Pro His Glu Pro Lys Phe Val Tyr Gln Ala Lys Val Gly Gly Arg Trp
            755                 760                 765

Phe Pro Ala Val Cys Ala His Ser Lys Lys Gln Gly Lys Gln Glu Ala
            770                 775                 780

Ala Asp Ala Ala Leu Arg Val Leu Ile Gly Glu Asn Glu Lys Ala Glu
785                 790                 795                 800

Arg Met Gly Phe Thr Glu Val Thr Pro Val Thr Gly Ala Ser Leu Arg
                805                 810                 815

Arg Thr Met Leu Leu Leu Ser Arg Ser Pro Glu Ala Gln Pro Lys Thr
            820                 825                 830
```

-continued

Leu Pro Leu Thr Gly Ser Thr Phe His Asp Gln Ile Ala Met Leu Ser
        835                 840                 845

His Arg Cys Phe Asn Thr Leu Thr Asn Ser Phe Gln Pro Ser Leu Leu
    850                 855                 860

Gly Arg Lys Ile Leu Ala Ala Ile Ile Met Lys Lys Asp Ser Glu Asp
865                 870                 875                 880

Met Gly Val Val Val Ser Leu Gly Thr Gly Asn Arg Cys Val Lys Gly
                885                 890                 895

Asp Ser Leu Ser Leu Lys Gly Glu Thr Val Asn Asp Cys His Ala Glu
            900                 905                 910

Ile Ile Ser Arg Arg Gly Phe Ile Arg Phe Leu Tyr Ser Glu Leu Met
            915                 920                 925

Lys Tyr Asn Ser Gln Thr Ala Lys Asp Ser Ile Phe Glu Pro Ala Lys
    930                 935                 940

Gly Gly Glu Lys Leu Gln Ile Lys Lys Thr Val Ser Phe His Leu Tyr
945                 950                 955                 960

Ile Ser Thr Ala Pro Cys Gly Asp Gly Ala Leu Phe Asp Lys Ser Cys
                965                 970                 975

Ser Asp Arg Ala Met Glu Ser Thr Glu Ser Arg His Tyr Pro Val Phe
            980                 985                 990

Glu Asn Pro Lys Gln Gly Lys Leu Arg Thr Lys Val Glu Asn Gly Glu
        995                 1000                1005

Gly Thr Ile Pro Val Glu Ser Ser Asp Ile Val Pro Thr Trp Asp
    1010                1015                1020

Gly Ile Arg Leu Gly Glu Arg Leu Arg Thr Met Ser Cys Ser Asp
    1025                1030                1035

Lys Ile Leu Arg Trp Asn Val Leu Gly Leu Gln Gly Ala Leu Leu
    1040                1045                1050

Thr His Phe Leu Gln Pro Ile Tyr Leu Lys Ser Val Thr Leu Gly
    1055                1060                1065

Tyr Leu Phe Ser Gln Gly His Leu Thr Arg Ala Ile Cys Cys Arg
    1070                1075                1080

Val Thr Arg Asp Gly Ser Ala Phe Glu Asp Gly Leu Arg His Pro
    1085                1090                1095

Phe Ile Val Asn His Pro Lys Val Gly Arg Val Ser Ile Tyr Asp
    1100                1105                1110

Ser Lys Arg Gln Ser Gly Lys Thr Lys Glu Thr Ser Val Asn Trp
    1115                1120                1125

Cys Leu Ala Asp Gly Tyr Asp Leu Glu Ile Leu Asp Gly Thr Arg
    1130                1135                1140

Gly Thr Val Asp Gly Pro Arg Asn Glu Leu Ser Arg Val Ser Lys
    1145                1150                1155

Lys Asn Ile Phe Leu Leu Phe Lys Lys Leu Cys Ser Phe Arg Tyr
    1160                1165                1170

Arg Arg Asp Leu Leu Arg Leu Ser Tyr Gly Glu Ala Lys Lys Ala
    1175                1180                1185

Ala Arg Asp Tyr Glu Thr Ala Lys Asn Tyr Phe Lys Lys Gly Leu
    1190                1195                1200

Lys Asp Met Gly Tyr Gly Asn Trp Ile Ser Lys Pro Gln Glu Glu
    1205                1210                1215

Lys Asn Phe Tyr Leu Cys Pro Val
    1220                1225

```
<210> SEQ ID NO 4
<211> LENGTH: 20
<212> TYPE: DNA
<213> ORGANISM: synthetic oligonucleotide

<400> SEQUENCE: 4
ctccagactg tccacagcat                                                20

<210> SEQ ID NO 5
<211> LENGTH: 20
<212> TYPE: DNA
<213> ORGANISM: synthetic oligonucleotide

<400> SEQUENCE: 5
ccctgaggct caaagtcaga                                                20

<210> SEQ ID NO 6
<211> LENGTH: 21
<212> TYPE: DNA
<213> ORGANISM: synthetic oligonucleotide

<400> SEQUENCE: 6
cgtcttgctc gagatgtgat g                                              21

<210> SEQ ID NO 7
<211> LENGTH: 21
<212> TYPE: DNA
<213> ORGANISM: synthetic oligonucleotide

<400> SEQUENCE: 7
tttatagccc cccttgagca c                                              21
```